US008114414B2

(12) United States Patent
Paterson et al.

(10) Patent No.: US 8,114,414 B2
(45) Date of Patent: Feb. 14, 2012

(54) COMPOSITIONS AND METHODS FOR TREATMENT OF CERVICAL CANCER

(75) Inventors: Yvonne Paterson, Philadelphia, PA (US); John Rothman, Lebanon, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 307 days.

(21) Appl. No.: 11/715,497

(22) Filed: Mar. 8, 2007

(65) Prior Publication Data

US 2009/0081250 A1 Mar. 26, 2009

Related U.S. Application Data

(63) Continuation-in-part of application No. 11/415,271, filed on May 2, 2006, which is a continuation-in-part of application No. 11/373,528, filed on Mar. 13, 2006, now Pat. No. 7,662,396, which is a continuation-in-part of application No. 10/835,662, filed on Apr. 30, 2004, now Pat. No. 7,588,930, which is a continuation-in-part of application No. 10/239,703, filed as application No. PCT/US01/09736 on Mar. 26, 2001, now Pat. No. 7,635,479, said application No. 11/415,271 is a continuation-in-part of application No. 11/223,945, filed on Sep. 13, 2005, now Pat. No. 7,820,180, which is a continuation-in-part of application No. 10/949,667, filed on Sep. 24, 2004, now Pat. No. 7,794,729, which is a continuation-in-part of application No. 10/441,851, filed on May 20, 2003, now Pat. No. 7,135,188, which is a continuation-in-part of application No. 09/535,212, filed on Mar. 27, 2000, now Pat. No. 6,565,852, which is a continuation-in-part of application No. 08/336,372, filed on Nov. 8, 1994, now Pat. No. 6,051,237.

(51) Int. Cl.
*A61K 39/02* (2006.01)

(52) U.S. Cl. ............... 424/200.1; 424/234.1; 424/277.1; 424/192.1; 424/184.4

(58) Field of Classification Search ......................... None
See application file for complete search history.

(56) References Cited

U.S. PATENT DOCUMENTS

| | | |
|---|---|---|
| 4,521,382 A | 6/1985 | Kessick |
| 4,567,041 A | 1/1986 | Likhite |
| 4,777,239 A | 10/1988 | Schoolnik et al. |
| 4,816,253 A | 3/1989 | Likhite et al. |
| 4,879,213 A | 11/1989 | Fox et al. |
| 5,262,177 A | 11/1993 | Brown et al. |
| 5,342,774 A | 8/1994 | Boon et al. |
| 5,369,008 A | 11/1994 | Arilnghause et al. |
| 5,643,599 A | 7/1997 | Lee et al. |
| 5,681,570 A | 10/1997 | Yang et al. |
| 5,728,399 A | 3/1998 | Wu et al. |
| 5,824,538 A | 10/1998 | Branstrom et al. |
| 5,830,702 A * | 11/1998 | Portnoy et al. ............... 435/69.3 |
| 5,858,682 A | 1/1999 | Gruenwald et al. |
| 5,876,735 A | 3/1999 | Reed |
| 5,877,159 A | 3/1999 | Powell et al. |
| 6,015,567 A | 1/2000 | Hudziak et al. |
| 6,051,237 A | 4/2000 | Paterson et al. |
| 6,306,404 B1 | 10/2001 | LaPosta et al. |
| 6,333,169 B1 | 12/2001 | Hudziak et al. |
| 6,479,258 B1 | 11/2002 | Short |
| 6,521,449 B1 | 2/2003 | Polack et al. |
| 6,565,852 B1 | 5/2003 | Paterson |
| 6,767,542 B2 | 7/2004 | Paterson et al. |
| 6,855,320 B2 | 2/2005 | Paterson |
| 7,135,188 B2 | 11/2006 | Paterson |
| 7,198,792 B2 * | 4/2007 | Regts et al. ............... 424/199.1 |
| 7,488,490 B2 | 2/2009 | Davis et al. |
| 2002/0025323 A1 * | 2/2002 | Paterson et al. ............ 424/192.1 |
| 2003/0028206 A1 | 2/2003 | Shiber |
| 2003/0202985 A1 | 10/2003 | Paterson |
| 2003/0220239 A1 | 11/2003 | Simard et al. |
| 2004/0013690 A1 * | 1/2004 | Portnoy et al. ............. 424/200.1 |
| 2004/0197343 A1 * | 10/2004 | Dubensky et al. ......... 424/184.1 |
| 2004/0228877 A1 | 11/2004 | Dubensky et al. |
| 2005/0118184 A1 | 6/2005 | Paterson et al. |
| 2005/0129715 A1 | 6/2005 | Paterson et al. |
| 2006/0051380 A1 | 3/2006 | Schulick et al. |
| 2006/0093582 A1 | 5/2006 | Paterson et al. |
| 2006/0104991 A1 | 5/2006 | Paterson et al. |
| 2006/0121053 A1 | 6/2006 | Sweeney et al. |

(Continued)

FOREIGN PATENT DOCUMENTS

EP 0 902 086 3/1999

(Continued)

OTHER PUBLICATIONS

Meneguzzi et al. (Virology, 1991, vol. 181, p. 62-69).* Gene Bank Accession No. AA 435505 (1999, p. 1-4).*
Adams et al. (1992) "Cre-*lox* recombination in *Escherichia coli* cells. Mechanistic differences from the in vitro reaction." *J. Mol. Biol.* 226:661-673.
Allison et al. (1997) "Cloning and characterization of a *Prevotella melaninogenica* hemolysin." *Infect Immun.* 65(7)2765-71.
An et al. (1996) "A recombinant minigene vaccine containing a nonameric cytoxic-T-Lymphocyte epitope confers limited protection against *Listeria monocytogenes* infection" *Infect. Immun* 64,(5):1685-1693.

(Continued)

*Primary Examiner* — Agnieszka Boesen
(74) *Attorney, Agent, or Firm* — Mark S. Cohen; Pearl Cohen Zedek Latzer, LLP

(57) ABSTRACT

The present invention provides methods of treating, protecting against, and inducing an immune response against cervical cancer, comprising the step of administering to a subject a recombinant *Listeria* strain, comprising a fusion peptide that comprises an LLO fragment and an E7 and/or E6 antigen. The present invention also provides methods for inducing an anti-E7 response in a human subject and treating HPV-mediated diseases, disorders, and symptoms comprising administration of the recombinant *Listeria* strain.

15 Claims, 33 Drawing Sheets

U.S. PATENT DOCUMENTS

| | | | |
|---|---|---|---|
| 2006/0205067 | A1 | 9/2006 | Paterson et al. |
| 2006/0210540 | A1 | 9/2006 | Paterson et al. |
| 2006/0233835 | A1 | 10/2006 | Paterson et al. |
| 2006/0269561 | A1 | 11/2006 | Paterson et al. |
| 2008/0124354 | A1 | 6/2008 | Paterson et al. |

FOREIGN PATENT DOCUMENTS

| | | |
|---|---|---|
| JP | 63-173594 | 7/1988 |
| WO | WO 90/12594 | 11/1990 |
| WO | WO 92/20356 | 11/1992 |
| WO | WO 93/15212 | 8/1993 |
| WO | WO 94/17192 | 8/1994 |
| WO | WO 96/14087 | 5/1996 |
| WO | WO 96/34631 | 11/1996 |
| WO | WO 98/48026 | 10/1998 |
| WO | WO 99/06544 | 2/1999 |
| WO | WO 99/07861 | 2/1999 |
| WO | WO 99/08544 | 2/1999 |
| WO | WO 99/10496 | 3/1999 |
| WO | WO 99/25376 | 5/1999 |
| WO | WO 01/27295 | 4/2001 |
| WO | WO 01/72329 | 10/2001 |
| WO | WO 03/015716 | 2/2003 |
| WO | WO 03/092600 | 11/2003 |
| WO | WO 2004/006837 | 1/2004 |
| WO | WO 2006/036550 | 4/2006 |
| WO | WO 2007/061848 | 5/2007 |
| WO | WO 2007/106476 | 9/2007 |
| WO | WO 2007/130455 | 11/2007 |

OTHER PUBLICATIONS

Anderson (1998) "Human gene therapy." *Nature*. Apr. 30;392(8679 Suppl):25-30

Angelakopoulos at al. (2002) "Safety and shedding of an attenuated strain of *Listeria monocytogenes* with a deletion of actA/plcB in adult volunteers: a dose escalation study of oral inoculation." *Infect Immun*. 70(7):3592-601.

Attwood et al. (2000) "The Babel of Bioinformatics" *Science* 290(5491):471-473.

Awwad (1989) "Cyclophosphamide-induced immunologically mediated regression of a cyclophosphamide-resistant murine tumor: a consequence of eliminating precursor L3T4+ suppressor T-cells." *Cancer Res*. 49(7): 1649-1654.

Barry et al. (1992) "Pathogenicity and immunogenicity of *Listeria monocytogenes* small-plaque mutants defective for intracellular growth and cell-to-cell spread." *Infection and Immunity* 60 (4): 1625-32.

Bast et al. (1975) "Antitumor activity of bacterial infection. II. effect of *Listeria monocytogenes* on growth of a guinea pig hepatoma." *J Natl. Cancer inst.*, 54(3): 757-761.

Bear (1986) "Tumor-specific suppressor T-cells which inhibit the in vitro generation of cytolytic T-cells from immune and early tumor-bearing host spleens." *Cancer Res*. Apr;46(4 Pt 1):1805-12.

Beatly, Dissertation Abstracts International, 2000, 61/10B:5224 Abstract Only.

Bernhard et al. (2002) "Vaccination against the HER-2/neu oncogenic protein." *Endocrine-Related Cancer*, 9:33-44.

Bielecki et al. (1990) "*Bacillus subtilis* expressing a haemolysin gene from *Listeria monocytogenes* can grow in mammalian cells" *Nature* 354:175-176.

Billington et al. (1997) "The Arcanobacterium (Actinomyces) pyogenes hemolysin, pyolysin, is a novel member of the thiol-activated cytolysin femay." *J Bacteriol*. Oct.:179(19):6100-6.

Bodmer et al. (1988) "Enhanced recognition of a modified peptide antigen by cytotoxic T cells specific for influenza nucleoprotein." *Cell* 52: 253-258.

Boon et al. (2006) "Human T cell responses against melanoma" *Annu Rev Immunol*. 24:175-208.

Bourquin et al. (2000) "Myelin oligodendrocyte glycoprotein—DNA vaccination induces antibody-mediated autoaggression in experimental autoimmune encephalomyelitis" *Eur J Immunol* 30:3663-3671.

Boyer et al. (2005) "DNA prime Listeria boost induces a cellular immune response to SIV antigens in the rhesus macaque model that is capable of limited suppression of SIV239 viral replication." *Virology*. Mar. 1;33311188-101.

Brasseur et al. (1992) "Human gene MAGE-1, which codes for a tumor-rejection antigen, is expressed by some breast tumors." *Int. J Cancer* 52(5):839-841.

Brockstedt et al. (2004) "Listeria-based cancer vaccines that segregate immunogenicity from toxicity." *Proc Natl Acad Sci USA*. 101(38)13832-7.

Bron et al. (2004) "Identification of *Lactobacillus plantarum* genes that are induced in the gastrointestinal tract of mice." *J Bacterial*. Sep.;186(17):5721-9.

Brown et al. (1988) "Site-specific integration in *Saccharopolyspora erythraea* and multisite integration in *Streptomyces lividans* of actinomycete plasmid pSE101." *J. Bacteriology* 170: 2287-2295.

Bruhn et al. (2005) "Characterization of anti-self CD8 T-cell responses stimulated by recombinant *Listeria monocytogenes* expressing the melanoma antigen TRP-2." *Vaccine*. Jul. 21;23(33):4263-72.

Brundage et al. (1993) "Expression and phosphorylation of the *Listeria monocytogenes* ActA protein in mammalian cells." *Proc. Natl. Acad. Sci. USA* 90: 11890-11894.

Bubert et al. (1997) "The *Listeria monocytogenes* iap gene as an indicator gene for the study of PrfA-dependent regulation" *Mol Gen Genet*. Sep.;256(1):54-62.

Burnham (2003) "Bad bugs: good for cancer therapy?" *Drug Discovery Today* 8(2):54-55.

Calendar et al. Poster presented at the ISOPOL Meeting 2001, http://64.233.169.104/search?q=cache:mA_uJpQsCrcJ:www.ma.uni-heidelberg.de/inst/imh/download/isopol.doc+Portnoy+Isopol+2001& hl=en&ct=clnk&cd=3&gl=us.

Camilli et al. (1993) "Dual roles of picA in *Listeria monocytogenes* pathogenesis" *Mol. Microbiol*. 8:143-157.

Carbone (1989) "Induction of ovalbumin-specific cytotoxic T cells by in vivo peptide immunization." *J Exp Med* 169:603-812.

Carbone (1990) "Class I-restricted processing and presentation of exogenous cell-associated antigen in vivo." *J Exp Med* 171:377-387.

Chamberlain et al. (2000) "Innovations and strategies for the development of anticancer vaccines." *Expert Opinion on Pharmacotherapy* 1(4):603-614.

Courvalin et al. (1995) "Gene transfer from bacteria to mammalian cells." *C R Acad Sci III*. Dec.;318(12):1207-12.

Cunto-Amesty et al. (2003) "Strategies in cancer vaccines development ." *Int J Parasitol*. 33(5-6):597-613.

Dakappagari et al. (2000) "Prevention of mammary tumors with a chimeric HER-2 B-cell epitope peptide vaccine" *Cancer Res*. Jul. 15:60(14):3782-9.

Darji et al. (2003) "Induction of immune responses by attenuated isogenic mutant strains of *Listeria monocytogenes*." *Vaccine* 1;21 Suppl 2:S102-9.

Darji et al. (1997) "Oral somatic transgene vaccination using attenuated *S. typhimurium*" *Cell* 91:765-775.

Darji et al. (1995) "Hyperexpression of listeriolysin in the nonpathogenic species *Listeria innocua* and high yield purification." *J Biotechnol*. Dec 15;43(3):205-12.

Darji et al. (1995) "Listeriolysin generates a route for the presentation of exogenous antigens by major histocompatibility complex class I." *Eur J Immunol*. Oct. 25(10)2967-71.

Darji et al. (1997) "TAP-dependent major histocompatibility complex class I presentation of soluble proteins using listeriotysin." *Eur J Immunol*. Jun. 27(6):1353-9.

Decatur et al. (2000) "A PEST-like sequence in Listeriolysin O essential for *Listeria monocytogenes* pathogenicity" *Science* 290(5493):992-995.

Dermime et al. (2004) "Vaccine and antibody-directed T cell tumour immunotherapy." *Biochim Biophys Acta*. 1704(1):11-35.

Deshpande et al. (1997) "Isolation of a contact-dependent haemolysin from *Mycobacterium tuberculosis*." *J Med Microbiol*. Mar.;46(3):233-8.

Dietrich et al. (1998) "Delivery of antigen-encoding plasmid DNA into the cytosol of macrophages by attenuated suicide *Listeria monocytogenes*" *Nature Biotechnology* 15:181-185.

Dietrich et al. (2001) "From evil to good: a cytolysin in vaccine development." *Trends Microbiol*. Jan.:9(1):23-8.

Dramsi et al. (1995) "Entry of *Listeria monocytogenes* into hepatocytes requires expression of inIB, a surface protein of the internal-in multigene family." *Mol Microbiol*. I 6(2):251-61.

Dunn et al. (1991) "Selective radition resistance of immunologically induced T cells as the basis for irradiation-induced T-cell-mediated regression of immunogenic tumor." *J Leukoc Biol*. 49(4): 388-396.

Ebert et al. (1990) "Selective immunosuppressive action of a factor produced by colon cancer cells." *Cancer Res*. 50(19): 6158-6161.

Ezzel (1995) "Cancer Vaccines: An Idea Whose Time Has Come?" *J. NIH Res*., 7:48-49.

Falk et al. (1991) "Identification of naturally processed viral nonapeptides allows their quantification in infected cells and suggests an allele-specific T cell epitope forecast." *J Exp Med*. 174(2). 425-434.

Finn et al. (2003) "Cancer vaccines: between the idea and the reality." *Nature Reviews Immunology* 3:630-641.

Frankel et al. (1995) "Induction of cell-mediated immune responses to human immunodeficiency virus type 1 Gag protein by using *Listeria monocytogenes* as a live vaccine vector." *J. Immunol*. 155:4775-4782.

Frey (1993) "Rat adenocarcinoma 13762 expresses tumor rejection antigens but tumor-bearing animals exhibit tumor-specific immunosuppression." *Clin lmmunol Immunopathol*. 69(2):223-233.

Friedman et al. (2000) "Induction of human immunodeficiency virus (HIV)-specific CD8 T-cell responses by *Listeria monocytogenes* and a hyperattenuated Listens strain engineered to express HIV antigens." *J. Virology* 74 9987-9993.

Fu et al. (1990) "Expansion of immunoregulatory macrophages by granulocyte-macrophage colony-stimulating factor derived from a murine mammary tumor." *Cancer Res*. 50(2):227-234.

Fujii (1987) "Significance of suppressor macrophages for immunosurveillance of tumor-bearing mice." *J Natl Cancer Inst*. 78(3):509-517.

Furukawa (1993) "Nude mouse metastatic models of human stomach cancer constructed using orthotopic implantation of histologically intact tissue." *Cancer Res*. 53(5):1204-1208.

Galen et al. (2001) "Can a 'flawless' live vector vaccine strain be engineered?" *Trends Microbiol*. 9(8):372-6.

Gentschev et al. (1995) "Salmonella strain secreting active Listeriolysin changes its intracellular localization" *Infect. Immun*. 63:4202-4205.

Gentschev et al. (1996) "Development of antigen-delivery systems, based on the *Escherichiata coil* hemolysin secreatiohn pathway." *Gene* 179:133-140.

Gilmore et al. (1989) "A *Bacillus cereus* cytolytic determinant, cereolysin AB, which comprises the phospholipase C and sphingomyelinase genes: nucleotide sequence and genetic linkage." *J Bacteriol*. Feb.;171(2)744-53.

Glomski et al. (2002) "The *Listeria monocytogenes* hemolysin has an acidic pH optimum to compartmentalize activity and prevent damage to infected host cells." *J Cell Biol*. Mar. 18;156(6)1029-38.

Goebel et al. (1993) "*Listeria monocytogenes*—a model system for studying the pathomechanisms of an intracellular microorganism." *Zbl. Bakt*. 278:334-347.

Goossens et al. (1992) "Induction of protective CD8+ T lymphocytes by an attenuated *Listeria monocytogenes* actA mutant." *Int Immunol*. Dec;4(12):1413-8.

Goossens et al. (1995) "Attenuated *Listeria monocytogenes* as a live vector for induction of CD8+T cells in vivo: a study with the nucleoprotein of the lymphocytic choriomeningitis virus." *Int Immunol*. May:7(5):797-805.

Gregory et al. (1997) "Intemalin B promotes the replication of *Listeria monocytogenes* in mouse hepatocytes". *Infect lmmun*. 65(12):5137-41.

Gunn (2001) "Two *Listeria monocytogenes* vaccine vectors that express different molecular forms of human papilloma virus-16 (HPV-16) E7 induce qualitatively different T cell immunity that correlates with their ability to induce regression of established tumors immortalized by HPV-16." *J Immunol*. 167(11) 6471-6479.

Gunn et al. (2002) "Recombinant Intra-cellular Bacteria as Carriers for Tumor Antigens ." In *Vaccine Delivery Strategies*, Chapter 14, Eds. Guido Dietrich and Werner Goebel, Horizon Scientific Press, UK.

Gunn, Dissertation Abstracts International, 2001, 62/5B:2244 Abstract Only.

Gunn et al. (2001) "Listeriolysin—a useful cytolysin." Trends MicrobioI.9(4):161-162.

Guzman et al. (1998) "Attenuated *Listeria monocytogenes* carrier strains can deliver an HIV-1 gp120 T helper epitope to MHC class II-restricted human CD4+ T cells" *European Journal of Immunology* 28:1807-1814.

Harty et al. (1996) "Primary and secondary immune responses to *Listeria monocytogenes*." *Curr Opin Immunol*. 8:525-530.

Hassan et al. (2004) "Mesothelia: a new target for immunotherapy." *Clin Cancer Res*. 10(12 Pt 1):3937-42.

Hauf et al. (1997) "*Listens monocytogenes* infection of P388D1 macrophages results in a biphasic NF-kappaB (ReIA/p50) activation induced by lipoteictioic acid and bacterial phospholipases and mediated by IkappaBalpha and IkappaBbeta degradation." *Proc Natl Acad Sci U S A*. Aug. 19;94(17):9394-9.

Hess et al. (1995) "*Listeria monocytogenes* p60 supports host cell invasion by and in vivo survival of attenuated *Salmonella typhimurium*." *Infect Immun*. May;63(5):2047-53.

Hess et al. (1996) "*Salmonella typhimurium* aroA—infection in gene-targeted immunodeficient mice: major role of CD4+ TCR-alpha beta cells and IFN-gamma in bacterial clearance independent of intracellular location." *J Immuno*. May 1;156(9):3321-6.

Hess et al. (1996) "Superior efficacy of secreted over somatic antigen display in recombinant *Salmonella* vaccine induced protection against listeriosis" *Proc. Nat. Acad. Sci*. 93:1458-1463.

Hess et al. (1997) "Protection against murine listeriosis by an attenuated recombinant *Salmonella typhimurium* vaccine strain that secretes the naturally somatic antigen superoxide dismutase." *Infect lmmun*. Apr.;65(4):1286-92.

Hess et al. (1998) "*Mycobacterium bovis* bacilli Calmette-Guerin strains secreting listeriolysin of *Listeria monocytogenes*" *Proc. Natl. Acad. Sci*. 95:5299-5304.

Higgins et al. (1998) "Bacterial delivery of DNA evolves." *Nat Biotechriol*. Feb.:16(2):138-9.

Hodgson (2000) "Generalized transduction of serotype 1/2 and serotype 4b strains of *Listeria monocytogenes*." *Mol Microbiol*. 35(2):312-23.

Hu et al. (2004) "*Escherichia coil* expressing recombinant antigen and listeriolysin O stimulate class I-restricted CD8+ T cells following uptake by human APC." *J. Immunology* 172:1595-1801.

Huang et al. (1994) "Role of bone marrow-derived cells in presenting MHC class I-restricted tumor antigens." *Science* 264961-965.

Hussain et al. (2004) "CD4+CD25+ regulatory T cells that secrete TGFbeta and IL-10 are preferentially induced by a vaccine vector." *J lmmunother*. Sep.-Oct.;27(5):339-46.

Ikonomidis et al. (1994) Abstract E-90, Abstracts, 94th General Meeting of the American Society for Microbiology, May 23-27.

Ikonomidis et al. (1994) "Delivery of a viral antigen to the class I processing and presentation oathway by *Listeria monocytogenes*" *Journal of Experimental Medicine* 180(6):2209-2218.

Jensen (1997) "Recombinant *Listeria monocytogenes* vaccination eliminates papillomavirus-induced tumors and prevents papilloma formation from viral DNA." *J virol*. 71(11):8467-8474.

Jensen et al. (1997) "Recombinant *Listeria monocytogenes* as a live vaccine vehicle and a probe for studying cell-mediated immunity" *Immunological Review* 158:147-157.

Jones et al. (1994) "Characterization of *Listeria monocytogenes* pathogenesis in a strain expressing perfringotysin O in place of listeriolysin O." *Infect. Immun*. 62:5608-5613.

Kaufman et al. (1999) "Impact of intracellular location of and antigen display by intracellular bacteria: implications for vaccine development" *J lmmunol. Lett*, 65(1-2):81-84.

Kerksiek (1999) "T cell responses to bacterial infection" *Curr Opin. Immunol*. 1(4):400-405.

Kocks et al. (1992) "*L. monocytogenes*-induced actin assembly requires the ActA gene product" *Cell* 68(3):521-531.

Kovacsovics-Bankowski et al. (1993) "Efficient major histocompatibility complex class I presentation of exogenous antigen upon phagocytosis by macrophages." *Proc. Natl. Acad. Sci. USA* 90:4942-4946.

Lamikanra et al. (2001) "Regression of established human papillomavirus type 16 (HPV-16) immortalized tumors in vivo by vaccinia viruses expressing different forms of HPV-16 E7 correlates with enhanced CD8(+) T-cell responses that home to the tumor site." *J. Virology* 75(20):9654-9664.

Lampson et al. (1993) "Exploiting the lacZ reporter gene for quantitative analysis of disseminated tumor growth within the brain: use of the lacZ gene product as a tumor antigen, for evaluation of antigenic modulation, and to facilitate image analysis of tumor growth in situ." *Cancer Research* 53:176-182.

Lara-Tejero et al. (2004) "T cell responses to *Listeria monocytogenes*." *Curr Opin Microbiol.* 7(1):45-50.

Lasa et al. (1997) "Identification of two regions in the N-terminal domain of ActA involved in the actin comet tail formation by *Listeria monocytogenes*" *Embo* 16(7):1531-40.

Lauer et al. (2002) "Construction, characterization, and use of two *Listeria monocytogenes* site-specific phage integration vectors." *J. Bacteriology* 184: 4177-4185.

Lauer et al. ASM Meeting, Abstract 1999.

Lebrun et al. (1996) "Internalin must be on the bacterial surface to mediate entry of *Listeria monocytogenes* into epithelial cells" *Molecular Microbiology* 21(3):579-592.

Leão et al. (1995) "A species-specific nucleotide sequence of *Mycobacterium tuberculosis* encodes a protein that exhibits hemolytic activity when expressed in *Escherichia coli*." *Infect Immun.* Nov.:63(11):4301-6.

Lee et al. (1991) "Construction of single-copy integration vectors for *Staphylococcus aureus*." *Gene* 103:101-5.

Lehner et al. (1996) "Processing and delivery of peptides presented by MHC class I molecules." *Curr Opin Immunol.* 8(1):59-67.

Lejeune (1994) "Nitric oxide involvement in tumor-induced immunosuppression." *J Immunol.* 152(10):5077-5083.

Liau et al. (2002) "Tumor immunity within the central nervous system stimulated by recombinant *Listeria monocytogenes* vaccination." *Cancer Res.* 62(8):2287-93.

Lin et al. (1986) "Treatment of established tumors with a novel vaccine that enhances Major Histocompatibility Class II presentation of tumor antigen" *Cancer Res*, 56:21-26.

Lin et al. (2002) "Oral vaccination with recombinant *Listeria monocytogenes* expressing human papillomavirus type 16 E7 can cause tumor growth in mice to regress." *Int J Cancer.* Dec. 20;102(6):629-37.

Lingnau et al. (1995) "Expression of the *Listeria monocytogenes* EGD inlA and inlB genes, whose products mediate bacterial entry into tissue culture cell lines, by PrfA-dependent and- independent mechanisms." *Infect Immun.* Oct.;63(10):3896-903.

Loeffler et al. (2006) "Comparison of different live vaccine strategies in vivo for delivery of protein antigen or antigen-encoding DNA and mRNA by virulence-attenuated *Listeria monocytogenes*." *Infect Immun.* Jul.;74(7):3946-57.

Loessner et al. (1995) "Heterogeneous endolysins in *Listeria monocytogenes* bacteriophages: a new class of enzymes and evidence for conserved holin genes within the siphoviral lysis cassettes." *Mol Microbiol.* Jun.;16(6):1231-41.

Loessner et al. (2000) "Complete nucleotide sequence, molecular analysis and genome structure of bacteriophage A118 of *Listeria monocytogenes*: implications for phage evolution." *Molecular Microbiology* 35(2):324-40.

Makela et al. (1987) Hand Book of Experimental Immunology, vol. 1, chapter 3. pp 3.1-3.13.

Mandal et al. (2002) "Listeriolysin O-liposome-mediated cytosolic delivery of macromolecule antigen in vivo: enhancement of antigen-specific cytotoxic T lymphocyte frequency, activity, and tumor protection." *BBA* 1563 7-17.

Manjili et al. (2003) "HSP110-HER2/neu chaperone complex vaccine induces protective immunity against spontaneous mammary tumors in HER-2/neu transgenic mice." *J Immunol.* Oct. 15;171(8):4054-61.

Marquis et al. (1997) "Proteolytic pathways of activation and degradation of a bacterial phospholipase C during intracellular infection by *Listeria monocytogenes*." *J. Cell Biol.* 137;1381-1392.

Martin et al. (1986) "Nucleotide sequence of the tetM tetracycline resistance determinant of the streptococcal conjugative shuffle transposon Tn1545." *Nucleic Acid Res.* 14:7047-7058.

Marx et al. (2002) "Broad-host-range cre-lox system for antibiotic marker recycling in gram-negative bacteria." *Biotechniques.* Nov.; 33(5):1062-7.

McLaughlan et al. (1998) "Molecular characterization of an autolytic amidase of Listens monocytogenes EGD." *Microbiology.* May:144(Pt 5):1359-67.

Mengaud et al. (1988) "Expression in *Escherichia coli* and sequence analysis of the Listeriolysin O determinant of *Listeria monocytogenes*" *Infection and Immunity* 56(4):766-772.

Mikayama et al. (1993) "Molecular cloning and functional expression of a CDNA encoding gycosylation-inhibiting factor" *Proc. Natl. Acad. Sci. USA* 90:10056-10060.

Mlynárova et al. (2002) "The promiscuity of heterospecific lox sites increases dramatically in the presence of palindromic DNA." *Gene.* Aug. 21;298(1-2):129-37.

Mollet et al. (1993) "Directed genomic integration, gene replacement, and integrative gene expression in *Streptococcus thermophilus*." *J. Bacteriology* 175:4315-4324.

Moriishi et al. (1998) "Sequence analysis of the actA gene of *Listeria monocytogenes* isolated from human" *Microbiol. Imrnunol.* 42(2):129-132.

Ngo et al. (1994) The Protein Folding Problem and Tertiary Structure Prediction 492-495.

Ochsenbein et al. (1999) "A comparison of T cell memory against the same antigen induced by virus versus intracellular bacteria." *Proc Nati Acad Sci U S A.* Aug. 3;96(16):9293-8.

Oscarsson et al. (1996) "Induction of haemolytic activity in *Escherichia coli* by the slyA gene producL" Mo, Microbiol. Apr.; 20(1):191-9.

Paglia et al. (1997) "The defined attenuated *Listens monocytogenes* delta mp12 mutant is an effective oral vaccine carrier to trigger a long-lasting immune response against a mouse fibrosarcoma" *Eur J Immunol* 27:1570-1575.

Palmeros et al. (2000) "A family of removable cassettes designed to obtain antibiotic-resistance-free genomic modifications of *Escherichia coil* and other bacteria." *Gene.* Apr. 18;247(1-2):255-64.

Pan (1999) "Regression of established B16F10 melanoma with a recombinant *Listeria monocytogenes* vaccine." *Cancer Res* 59(20):5264-5269.

Pan et al. (1995) "A recombinant *Listeria monocytogenes* vaccine expressing a model tumour antigen protects mice against lethal tumour cell challenge and causes regression of established turnouts." *Nature Med.* 1:471-477.

Pan et al. (1995) "Regression of established tumors in mice mediated by the oral administration of a recombinant *Listeria monocytogenes* vaccine" *Cancer Res* 55:4776-4779.

Parida et al. (1998) "Intemalin B is essential for adhesion and mediates the invasion of *Listeria monocytogenes* into human endothelial cells." *Mol Microbiol.* Apr.;28(1):81-93.

Paul et al. (1989) "Fundamental Immunology", Second Edition, Raven Press, 987-988.

Peng et al. (2004) "The ability of two *Listeria monocytogenes* vaccines targeting human papillomavirus-16 E7 to induce an antitumor response correlates with myeloid dendritic cell function." *J. Immunol.* 172:6030-6038.

Penichet et al. (2001) "Antibody-cytokine fusion proteins for the therapy of cancer." *J. Immunological Methods* 248:91-101.

Peters et al. (2003) "Tailoring host immune responses to Listeria by manipulation of virulence genes—the interface between innate and acquired immunity." *FEMS Immunol Med Microbiol.* Apr. 1:35(3):243-53.

Pfeifer et al. (1993) "Phagocytic processing of bacterial antigens for class 1 MHC presentation to T cells." *Nature.* Jan. 28;361(6410):359-62.

Pupa et al. (2001) "Prevention of spontaneous neu-expressing mammary tumor development in mice transgenic for rat proto-neu by DNA vaccination." *Gene Ther.* Jan.;8(1):75-9.

Quénéet al. (2005) "Combined sacB-based negative selection and cre-lox antibiotic marker recycling for efficient gene deletion in *Pseudomonas aeruginosa*." *Biotechniques.* Jan.;38(1):63-7.

Radford et al. (2002) "A recombinant *E. coli* vaccine to promote MHC class I-dependent antigen presentation: application to cancer immunotherapy." *Gene Therapy* 9:1455-1463.

Radford et al. (2003) "Recombinant *E. coli* efficiently delivers antigen and maturation signals to human dendritic cells; presentation of MART1 to CD8+ T cells." *Int. J. Cancer* 105:811-819.

Raveneau et al. (1992) "Reduced virulence of a *Listeria monocytogenes* phospholipase-deficient mutant obtained by transposon insertion into the zinc metalloprotease gene." *Infect. immun.* 60: 916-921.

Realini et al. (1994) "KEKE motifs. Proposed roles in protein-protein association and presentation of peptides by MHC class I receptors" *FEBS Letters* 348:109-113.

Rechsteiner at al. (1996) "PEST sequences and regulation by proteolysis" *TIBS* 21:267-271.

Reiter et al. (1989) "Transfer RNA genes frequently serve as integration sites for prokaryotic genetic elements." *Nucleic Acids Research* 17(5)1907-14.

Renard at al. (2003) "HER-2 DNA and protein vaccines containing potent Th cell epitopes induce distinct protective and therapeutic antitumor responses in HER-2 transgenic mice." *J Immunol .* 171(3):1588-95.

Repique (1992) "Immunosuppression derived from human B-lymphoblastoid and melanoma cell lines." *Cancer Invest.* 10(3):201-208.

Roden et al. (2004) "Vaccination to prevent and treat cervical cancer." *Hum Patriot* 35(8):971-82.

Rüssmann et al. (1998) "Delivery of epitopes by the Salmonella type III secretion system for vaccine development." *Science.* Jul. 24;281(5376):565-8.

Safley et al. (1991) "Role of Listeriolysin-o (LLO) in the T Lymphocyte response to infection with *Listeria monocytogenes*" *J immunol.* 146(10):3604-3616.

Schafer et al. (1992) "Induction of a cellular immune response to a foreign antigen by a recombinant *Listeria monocytogenes* vaccine." *J. Immunol.* 149(1):53-59.

Scheirlinck et al. (1989) "Integration and expression of alpha-amylase and endoglucanase genes in the *Lactobacillus plantarum* chromosome." *Appl Environ Microbiol* 55(9)2130-7.

Schmidt et al. (1995) "Molecular Analysis of the Plasmid-Encoded Hemolysin of *Escherichia coil* O157:H7 Strain EDL 933" *Infection and Immunity*, 63(3):1055-1061.

Scortti et al. (2007) "The PrfA virulence regulon." *Microbes infect.* Aug;9(10):1196-207.

Sewell et al. (2004) "Regression of HPV-positive tumors treated with a new *Listeria monocytogenes* vaccine." *Arch Otolaryngol Head Neck Surg* 130:92-97.

Sewell et al. (2004) "Recombinant *Listeria* vaccines containing Pest sequences are potent immune adjuvants for the tumor-associated antigen human Papillomavirus-16 E7." *Cancer Res.* Dec. 15;64(24):8821-5.

Shen et al. (1985) "Recombinant *Listeria monocytogenes* as a live vaccine vehicle for the induction of protective anti-viral cell-mediated immunity." *Proc Nat'l Acad Sci U S A.* 92(9):3987-91.

Shen et al. (1998) "*Listeria monocytogenes* as a probe to study cell-mediated immunity" *Curr. Opin. Immunol.* 10(4):450-458.

Shen et al. (1998) "Compartmentalization of bacterial antigens: differential effects on priming of CD8 T cells and protective immunity." *Cell.* Feb. 20;92(4):535-45.

Shetron-Rama et al. (2002) "Intracellular induction of *Listeria monocytogenes* actA expression." *Infect. lmmun.* 70:1087-1096.

Shimizu et al. (1994) "Effects of CD4+ and CD8+ T cells in tumor-bearing mice on antibody production." *Cancer Immunol Immunother.* 38(4):272-276.

Singh et al. (2005) "Fusion to Listeriolysin O and delivery by *Listeria monocytogenes* enhances the immunogenicity of HER-2/neu and reveals subdominant epitopes in the FVB/N mouse." *J Immunol.* Sep. 15:175(6):3663-73.

Sirard et al. (1997) "Intracytoplasmic delivery of Listeriolysin O by a vaccinel strain of *Bacillus anthracis* induces CD8-mediated protection against *Listeria monocytogenes*" *J Immun.* 159:4435-4443.

Skoble, J. et al. (2000). "Three regions within acta promote arp2/3 complex-mediated actin nucleation and *Listeria monocytogenes* motility" *The Journal of Cell Biology* 150(3);527-537.

Skolnick et al. (2000) "From genes to protein structure and function: novel applications of computational approached in the genomic era" *Trends in Biotech.* 18(1):34-39.

Slifka et al. (1996) "Antiviral cytotoxic T-cell memory by vaccination with recombinant *Listeria monocytogenes.*" *J. Viral.* 70(5):2902-10.

Smith et al. (1995) "The two distinct phospholipases C of *Listeria monocytogenes* have overtapping roles in escape from a vacuole and cell-to-cell spread." *Infect. Immun.* 63 4231-4237.

Smith et al. (1995) "Asymmetric Distribution of the *Listeria monocytogenes* ActA Protein is Required and Sufficient to Direct Actin-Based Motility" *Molecular Microbiology* 17:945-951.

Souders et al. (2006) "In vivo bactofection: listeria can function as a DNA-cancer vaccine." *DNA Cell Biol.* Mar.;25(3):142-51.

Stahl et al. (1984) "Replacement of the *Bacillus subtilis* subtilisin structural gene with an in vitro-derived deletion mutation." *J. Bacterial* 158:411-418.

Starks et al. (2004) "*Listeria monocytogenes* as a vaccine vector: virulence attenuation or existing antivector immunity does not diminish therapeutic efficacy." *J. Immunology* 173:420-427.

Stitz et al. (1990) "Characterization and immunological properties of influenza A virus nucleoprotein (NP): cell-associated NP isolated from infected cells or viral NP expressed by vaccinia recombinant virus do not confer protection." *J Gen Virol.* 71(Pt 5):1169-1179.

Strugnell et al. (1990) "Stable expression of foreign antigens from the chromosome of *Salmonella typhimurium* vaccine strains." *Gene* 88:57-63.

Stryer et al. (1998) Biochemistry, Third Edition, WH Freeman Company, New York, 31-33.

Sun et al. (1990) "Isolation of *Listeria monocytogenes* small-plaque mutants defective for intracellular growth and cell-to-cell spread." *Infect. Immun.* 58 3770-3778.

Tanabe et al. (1999) "Induction of Protective T Cells against *Listeria monocytogenes* in Mice by Immunization with a Listeriolysin O-Negative Avirulent Strain of Bacteria . And Liposome-Encapsulated Listeriolysin O" *Infect. Immun.* 67(2):568-575.

Tilney et al. (1989) "Actin filaments and the growth, movement, and spread of the intracellular bacterial parasite, *Listeria monocytogenes.*" *J Cell Biol.* Oct.:109(4 Pt 1):1597-608.

Vasil et al. (1982) "Cloning of a phosphate-regulated hemolysin gene (phospholipase C) from *Pseudomonas aeruginosa.*" *J Bacteriol.* Oct.;152(1):431-40.

Vazquez-Boland et al. (1992) "Nucleotide sequence of the lecithinase operon of *Listeria monocytogenes* and possible role of lecithinase in cell-to-cell spread." *Infect Immun.* 60:219-230.

Verch et al. (2004) "*Listeria monocytogenes*-based antibiotic resistance gene-free antigen delivery system applicable to other bacterial vectors and DNA vaccines." *Infect Immun.* Nov.;72(11):6418-25.

Verma et al. (1995) "Delivery of class I and class II MHC-restricted T-cell epitopes of listeriolysin of *Listeria monocytogenes* by attenuated salmonella". *Vaccine* 13(2):142-150.

Walker et al. (1994) "Tumor growth alters T cell and macrophage production of and responsiveness to granulocyte-macrophage colony-stimulating factor: partial dysregulation through interleukin-10." *Cell lmmunol.* 154(1):342-357.

Watson et al. (1991) "Splenic macrophages from tumor-bearing mice co-expressing MAC-1 and MAC-2 antigens exert immunoregulatory functions via two distinct mechanisms." *J Leukoc Biol.* 49(2): 126-138.

Wei et al. (2005) "*Listeria monocytogenes* phosphatidylinositol-specific phospholipase C has evolved for virulence by greatly reduced activity on GPI anchors." *Proc. Natl. Acad. Sci. USA* 102: 12927-12931.

Weidt et al. (1994) "CD8+ T lymphocyte-mediated antiviral immunity in mice as a result of injection of recombinant viral proteins." *J Immunol.* Sep. 15;153(6):2554-61.

Weiskirch et al. (1997) "*Listeria monocytogenes*: a potent vaccine vector for neoplastic and infectious disease." *Immunological Reviews* 158:159-169.

Welch et al. (1998) "Interaction of Human Arp2/3 Complex and the *Listeria monocytogenes* ActA Protein in Actin Filament Nucleation" *Science* 281:105-108.

Wirth et al. (1986) "Highly efficient protolast transformation system for *Streptococcus faecalis* and a new *Escherichia coli-S. faecalis* shuttle vector." *J Bacteriol.* 165(3):831-6.

Wu et al. (1995) "Engineering an intracellular pathway for major histocompatibility complex class II presentation of antigens" *Cancer Res.* 56:21-26.

Young et al. (1992) "Tumor-derived cytokines induce bone marrow suppressor cells that mediate immunosuppression through transforming growth factor beta." *Cancer Immunol Immunother.* 35(1): 14-18.

Young et al. (1995) "Holins: form and function in bacteriophage lysis." *FEMS Microbiol Rev.* Aug.;17(1-2):191-205.

Zhang et al. (1993) "Functional replacement of the hemolysin A transport signal by a different primary sequence" *Proc Natl Acad Sci USA.* May 1;90(9):4211-5.

Abachin et al., "Formation of D-alanyl-lipoteichoic acid is required for adhesion and virulence of *Listeria monocytogenes*", Molecular Microbiology, 2002, 43(1), 1-14.

Aggarwal et al., "Oral Salmonella: Malaria Circumsporozoite Recombinants Induce Specific CD8+ Cytotoxic T Cells", J. Exp. Med 1990, 172, 1083-1090.

Alexander et al., "Characterization of an aromatic amino acid-dependent *Listeria monocytogenes* mutant: attenuation, persistance, and ability to induce protective immunity in mice", infection and immunity, May 1993, p. 2245-2248.

Amici et al,, "DNA vaccination with full-length or truncated Neu induces protective immunity against the development of spontaneous mammary tumors in HER-2/neu transgenic mice", Gene Therapy, 2000, 7, 703-706.

Angelov et al., "Therapeutic vaccine for acute and chronic motor neuron diseases: Implications for amyotrophic lateral sclerosis", PNAS. Apr. 2003, vol. 100, No. 8, 4790-4795.

Anido et al., "Biosynthesis of tumorigenic HER2 C-terminal fragments by alternative initiation of translation", The EMBO Journal, 2006, 25, 3234-3244.

Bai et al., "Antigenic drift as a mechanism for tumor evasion of destruction by cytplytic T lymphocytes", J. Clin. Invest., 2003, 111, 1487-1496.

Bast et al., "Antitumor activity of bacterial infection, I. Effect of *Listeria monocyfogenes* on growth of a murine fibrosarcoma", J. Natl. Cancer Inst.; 54:749-756, 1975.

Baxeranis et al., Immunobiology of HER-2/neu oncoprotein and its potential application in cancer immunotherapy, Cancer Immunol. Immunother., 2004, 53, 166-175.

Beattie et al., "Cloning and characterization of T-cell-reactive protein antigens from *Listeria monocytogenes*", Infect Immun , Sep. 1990: 58(9):2792-803.

Beatty, "A dual role for IFN-gamma in resolving the balance between tumor progression and regression", Univerity of Pennsylvania, 2001, ii-xiii pp. 1-10, AAT 9989567, UMI number 9989567, Bell and Howell Information and Learning Company, Ann Arbor, Michigan.

Bergmann et al., "The neu oncogene encodes an epidermal growth factor receptor-related protein", Nature, vol. 319, Jan. 1986, 226-230.

Biragyn et al., "Models for Lymphoma", Current Protocols in Immunology, 2001, 20.6.1-20.6.30.

Boon et al., "Tumor Antigens Recognized by T Lymphocytes", Annu, Rev. Immunol. 1994,12, 337-365.

Bouwer et al., "Acquired immunity to an intracellular pathogen: immunologic recognition of *L. monocytogenes*-infected cells", Aug. 1997;158:137-46.

Bouwer et al , "Cytotoxic-T-lymphocyte responses to epitopes of listeriolysin O and p60 following infection with *Listeria monocytogenes*", Infect. Immun., Jul. 1996; 64(7):2515-22.

Bowie et al., "Deciphering the message in protein sequences: tolerance to amino acid substitutions", Science 247:1306-1310, 1990.

Bron et al., "Use of the alr gene as a food-grade selection marker in lactic acid bacteria", Applied and Environmental Microbiology, Nov. 2002, vol. 68, No. 11, p. 5663-5670.

Bruder et al., "Efficient induction of cytotoxic CD8+ T cells against exogenous proteins: establishment and charcterization of a T cell line specific for the membrane protein ActA of *Listeria monocytogenes*", Eur. J. Immunol., Sep. 1998, 28(9):2630-9.

Brunner et al., "Quantitative assay of the lytic action of immune lymphoid cells on cr-labelled allogeneic target cells in vitro; inhibition by isoantibody and by drugs", Immunology, 1968, 14, 181-196.

Camilli et al., "*Listeria monocytogenes* mutants lacking phosphatidylinositol-specific phospholipase C are avirulent", J. Exp. Med., vol. 173, 751-754, Mar. 1991.

Catic et al., "Introduction of protein or DNA delivered via recombinant *Salmonella typhimurium* into the major histocompatibility complex class I pesentation pathway of macrophages", Microbes Infect., Feb. 1999, 1(2):113-21.

Chazin et al., "Transformation mediated by the human HER-2 gene independent of the epidermal growth factor receptor", Oncogene, 1992, 7, 1859-1866.

Cheever et al., "T-Cell Immunity to Oncogeneic Proteins Including Mutated RAS and Chimeric BCR-ABL", Ann. N.Y. Acad. Sci. 1993, 690:101-112.

Chen et al., "DNA Vaccines Encoding Full-Length or Truncated Neu Induce Protective Immunity against Neu-expressing Mammary Tumors", Cancer Research 58, 1965-1971, May 1, 1998.

Cho et al., "Structure of the extracellular region ot HER2 alone and in complex with the herceptin Fab", Nature, vol. 421. Feb. 2003, 756-760.

Ciurea et al., "Viral persistence in vivo through selection of neutralizing antibody-escape variants", PNAS, Mar. 2000, vol. 97, No. 6, 2749-2754.

Cohen, J. "Cancer vaccines get a shot in the arm", Science 262:841-843.

Concetti et al., "Autoantibody to P1 $85^{erbB2/neu}$ oncoprotein by vaccination with xenogenic DNA", Cancer Immunol. Immunother., 1996, 43, 307-315.

Coussens et al., "Tyrosine kinase receptor with extensive homology to EGF receptor shares chromosomal location with neu oncogene", Sceince, vol. 230, 1132-1139, Dec. 1985.

Darji et al., "Antigen-specific T cell receptor antagonism by antigen-presenting cells treated with the hemolysin of *Lestria monocytogenes*: a novel type of immune escape", Eur. J. Immunol., Jul. 1997; 27(7):1696-703.

Darji et al., "T-cell anergy induced by antigen presenting cells treated with the hemolysin of *Listeria monocytogenes*", Immunol. Lett., Jun. 1997; 57(1-3):33-7.

Darji et al., "The role of the bacterial membrane protein ActA in immunity and pro ection against *Listeria monocytogenes*", J. Immunol., Sep. 1, 1998; 161(5):2414-20.

Di Carlo et al., "Inhibition of Mammary Carcinogenesis by systemic interleukin 12 or P185$^{neu}$ DNA vaccination in HER-2/neu transgenic BALB/c mice", Clinical Cancer Research, Mar. 2001, vol. 7, 830s-837s.

Disis et al., "Effect of dose on immune response in patients vaccinated with an her-2/neu intracellular domain protein-based vaccine", Journal of Clinical Oncology, vol. 22, No. 10, May 2004, 1916-1925.

Disis et al., "Generation of T-cell Immunity to the HER-2/neu Protein After Active Immunization with HER-2/neu Peptide-Based Vaccines", J. Clin. Oncol. 20:2624-2632, 2002.

Disis et al., "HER-2/neu protein: A target for antigen-specific immunotherapy of Human Cancer", Adv Cancer Res 71:343-371,1997.

Disis et al., "Immunity to the HER-2/neu oncogenic protein", Ciba Found. Symp. 1994 187:198-211.

Disis et al , "Peptide-Based, but not whole protein, vaccines elicit immunity to HER-2/neu, an oncogenic self-protein", The Journal of Immunology, 1996, 156:3151-3158.

Doling et al., "Cytotoxic T-Iymphocyte epitopes fused to anthrax toxin induce protective antiviral immunity", Infect. Immun., Jul. 1999, 67(7):3290-6.

Dumitrescu et al., "Understanding breast cancer risk—where do we stand in 2005?", J. Cell Mol. Med., vol. 9, No. 1, 2005, pp. 208-221.

Dunn et al., "A critical function for type I interferons in cancer immunoediting", vol, 6, No. 7, Jul. 2005, Nature Immunology, 722-729.

Dunn et al., "Cancer immunoediting from immunosurveillance to tumor escape", Nature Immunology, vol. 3, No. 11, Nov. 2002, 991-998.
Dunn et al., "Interferon-γ and cancer Immunoediting", Immunologic Research, 2005, 32/1-3: 231-245.
Dunn, "The Immunobiology of cancer Immunosurveillance and Immunoediting", Immunity, Aug. 2004, vol. 21, 137-148.
Ercolini et al., "Recruitment of latent pools of high-avidity CD8+ T cells to the antitumor immune response", Jem, vol, 201, No. 10, May 2005, 1591-1602.
Esserman et al., "Vaccination with the extracellular domain of P185$^{neu}$ prevents mammary tumor development in neu transgenic mice", Cancer Immunol. Immunother., 1999, 47, 337-342.
Fields, "Preparation of antipeptide antibodies—Introduction to peptide synthesis", Current Protocols in Molecular Biology, 2002, 11.15.1-11.15.9.
Finn et al., "MUC-1 Epithelial Tumor Mucin-Baseci Immunity and Cancer Vaccines", Immuno, Rev. 1995, 145:61-89.
Foy et al., "Vaccination with HER-2/neu DNA or protein subunits protects against growth of HER-2/neu—expressing murine tumor", Vaccine, 19, 2001, 2598-2606.
Freshney, "Culture of animal cells—a manual of basic technique". Chapter 1, Second Edition, 1983, 1-6.
Gallo et al., "Xenogeneic immunization in mice using HER2 DNA delivered by an adenoviral vector", Int. J Cancer. 113, 67-77, 2005.
Gansbacher et al., "Interleukin 2 Gene Transfer into Tumor Cells Abrogates Tumorigeni ity and Induces Protective Immunity", J. Exp. Med. 1990, 172, 1217-1224.
Garay-Malpar-Fida et al., "Caspredictor: a new computer-based tool for caspase substrate prediction", Bioinformatics, vol. 21, l. suppl. 1, 2005, p. 169-176.
Garcia-Lora et al., "MHC class I-deficient metastatic tumor variants immunoselectect by T lymphocytes originate from the corrdinated downregulation of Apm components", Int, J. Cancer, 106, 521-527, 2003.
Gillespie et al., "The potential of melanoma antigen expression in cancer therapy", Cancer Treat. Rev. 1999, 25(4):219-27.
Glenting et al., "A plasmid selection system in *Lactococcus lactis* and its use for gene expression in *L lactis* and human kidney fibroblasts", Applied and Environmental Microbiology, Oct. 2002, vol. 68, No, 10, p. 5051-5056.
Golsteyn et al., "Structural and functional similarities between the human cytoskeletal protein zyxin and the ActA protein of *Listeria monocytogenes*", J. Cell Sci. 110:1893-1906, 1997.
Golumbek et al., "Treatment of Established Renal Cancer by Tumor Cells Engineered to Secrete Interleukin-4", Science 1991, 254, 713-716.
Gregory et al., 1997, "Internalin B promotes the replication of *Listeria monocytngenes* in mouse hepatocytes", Infect. Immun. 65(12):5137-41.
Gritzapis et al., "Vaccination with Human HER-2/neu (435-443) CTL peptide induces effective antitumor immunity against HER-2/neu—expressing tumor cells in vivo", Cancer Res., 66, May 10, 2006, 5452-5460.
Gunn, "Recombinant *Listeria monocytogenes* as a tumor therapeutic", Univ. of Pennsylvania—*Electronic Dissertations*. Paper AAI3015316, UMI Microform 3015316, 2001, pp. v-vi, Bell and Howell Information and Learning Company, Ann Arbor, Michigan, abstract.
Guy et al., "Expression of the neu proto oncogene in the mammary epithelium of transgenic mice induces metastatic disease", Proc. Natl. Acad Sci. USA, Nov. 1992, vol. 89, pp. 10578-10582.
Harris et al., "Molecular Basis for Hetreogeneity of the Human p53 protein", Molecular and Cellular Biology, Dec. 1986. vol. 6. No. 12, p. 4650-4656.
Harty et al., "CD8 T lymphocytes specific for the secreted p60 antigen protect against *Listeria monocytogenes* infection", J. Immunol., May 1, 1995; 154(9):4642-50.
Hess et al., "Live antigen carriers as tools for improved anti-tuberculosis vaccines", FEMS Immunol. Med. Microbiol., Feb. 1999, 23(2), 165-73.

Higgins et al., "Delivery of protein to the cytosol of macrophages using *Escherichia coli* K-12", Mol. Microbiol., Mar. 1999, 31(6):1631-41.
Hiltbold et al., "Mechanisms of processing and presentation of the antigens of *Listeria monocytogenes*", Infect. Agents Dis., Oct. 1993; 2(5):314-23.
Hiltbold et al., "The presentation of class I and class II epitopes of listeriolysin O is regulated by intracellular localization and by intracellular localization and by intercellular spread of *Listeria monocytogenes*", J. lmmunol., Aug. 1996; 157(3):1163-75.
Hoogenboom et al., "By passing Immunisation—human antibodies from synthetic repertoires of germline $V_H$ gene segments rearranged in vitro", J. Mol. Biol., 1992, 227, 381-388.
Hueman et al., "Phase I clinical trial of a HER-2/neu peptide (E75) vaccine for the prevention of prostate—specific antigen recurrence in high-risk prostate cancer patients", Clin. Cancer Res., 11(20), Oct. 2005, 7470-7479.
Ikonomidis et al., "Influenza-specific immunity induced by recombinant *Listeria monocytogenes* vaccines", Vaccine, vol. 15, No. 4, pp. 433-440, 1997.
Ikonomidis et al., "Recombinant *Listeria monocytogenes* Cancer Vaccines", Vaccine 95, 1995, 95:317-326.
Ikonomidis et al., ASM Las Vegas, The 94$^{th}$ General Meeting of The American Society for Microbiology, May 23-27, 1994, Las Vegas Convention Center, Las Vactes, Nevada, p. 29, 159, 662, 664.
International Search Report of Application No. PCT/US01/09736 dated Jul. 27, 2001.
International Search Report of Application No, PCT/US05/32682 dated Jun. 1, 2006.
International Search Report of Application No. PCT/US07/06292 dated Jun. 17, 2008.
International Search Report of Application No. PCT/US07/10635 dated Sep. 11, 2008.
International Search Report at Application No. PCT/US08/03067 dated Aug. 29, 2008.
International Search Report of Application No. PCT/US08/06048 dated Nov. 20, 2008.
International Search Report of Application No. PCT/US95/14741 dated Feb. 15, 1996.
Jenson et al., "Recombinant *Listeria monocytogenes* as a live vaccine vehicle and a probe for studying cell-mediated Immunity", Immunological Review, vol. 158, 147-157.
Kawashima et al., "The Ivlulti-epitope Approach for Immunotherapy for Cancer: Identification of Several CTL Epitopes from Various Tumor-Associated Antiaens Expressed on Solid Epithelial Tumors", Hum. Immunol. 1998 59:1-14.
Khong et al., "Identification of multiple antigens recognized by tumor-infiltrating lymphocytes from a single patient: Tumor escape by antigen loss and loss of MHC expression", J. Immunother., 2004, 27, 184-190.
King et al., "Amplification of a Novel v-erbB-related gene in a human mammary carcinoma", Science, Sep. 1985, vol. 229, 974-976.
Kohler et al., "Expression of the iap gene coding for protein p50 of *Listeria monocytogenes* is controlled on the posttranscriptional level", Journal of Bacteriology, Aug. 1991, vol. 173, No. 15, p. 4668-4674.
Kruisbeek, "In vivo depletion of CD4- and CD8-specific T cells" Current Protocols in Immunology, John Wiley & Sons, Inc., eds., 1991, V.1, 4.1,1-4,1,2.
Kumar et al., "Amino acid variations at a single residue in an autoimmune peptide profoundly affect its properties: T-cell activation, major histocompatibility complex binding, and ability to block experimental allergic encephalomyelitis", PNAS, 87:1337-1341, 1990.
Kuntson et al., "Neu antigen negative variants can be generated after neu-specific antibody therapy in neu transgenic mice", Cancer Research 64, Feb. 2004, 1146-1151.
Kuntson et al , "Immunization with a HER-2/neu helper peptide vaccine generates HER-2/neu CD8 T-cell immunity in cancer patients", The Journal of Clinical Investigation, 107:477-484,2001.
Kyte et al., "A simple method for displaying the hydropathic character of a protein", J. Mol. Biol., 1982, 157, 105-132.

Lacey et al., "Phase IIa safety and immunogenicity of a therapeutic vaccine, TA-GW, in persons with genital warts", The Journal of Infectious Diseases, 1999, 179:612-8.

Lauer et al., "Systematic mutational analysis of the amino-terminal domain of the Listeria monocytogenes ActA protein reveals novel functions in actin-based motility", Molecular Microbiology 42(5):1163-1177, 2001.

Lee et al., "Delivery of macromolecules into cytosol using liposomes containing hemolysin from Listeria monocytogenes", J. Biol. Chem., Mar. 29, 1996; 271(13):7249-52.

Lee et al., "The murine MHC class I genes, H-2D and H-2L, and two genes reported to encode tumor-specific antigens", J. Exp, Med., Nov. 1988, vol. 168, 1719-1739.

Leitner et al., "DNA and RNA-based vaccines: prinicples, progress and prospects", Vaccine, Dec. 1999, 18(9-10):765-777.

Lipford et al., "Vaccination with immunodorninant peptides encapsulated in Quil A-containing liposomes induces peptide-specific primary CD8+ cytotoxic T cells", Vaccine, Jan. 1994; 12(1):73-80.

Liu, "Vaccine developments", Nature Medicine Vaccine Supplement, May 1998, vol, 4, No. 5, 515-519.

Marks et al., "By-Passing immunization human antibodies from V-gene libraries displayed on phage", J. Mol. Biol. 1991, 222, 581-597.

Mata et al., "Evalution of a recombinant Listeria monocytogenes expressing an HIV protein that protects mice against viral challenge", Vaccine, 19, 2001, 1435-1445.

Mazzaccaro et al., "Major histocompatibility Class I presentation of soluble antigen facilitated by Mycobacterium tuberculosis infection", Proc, Natl, Acad. Sci. USA; Oct. 15, 1996; 93(21)11786-91.

McCarty et al., "Targeting p53 for Adoptive T-Cell Immunotherapy", Cancer Research 1998, 15:582601-5.

McKaig et al., "Human Papillomavirus and Head and Neck Cancer Epidemiology and Molecule Biology", Head Neck 1998, 20 (3):250-65.

Mengaud et al., "Expression in Escherichia coli and sequence analysis of the Listeriolysin O determinant of Listeria monocytogenes", Infect. Immun., vol. 56, No. 4, 766-772, 1988.

Miller et al., "Targeted vectors for gene therapy", The FASEB Journal, Feb. 1995, vol. 9, p. 190-199.

Muller, "Expression of activated oncogenes in the murine mammary gland: transgenic models for human breast cancer", Cancer and Metastasis Reviews, 10:217-227, 1991.

Murali et al., "Structural analysis of P185$^{C-neu}$ and epidermal growth factor receptor tyrosine kinases: oligomerization of kinase domains", Proc. Natl. Acad. Sci. USA, vol. 93, pp. 6252-6257, Jun. 1996, Biochemistry.

Naz et al., "Novel human prostate-specific cDNA: molecular cloning, expression, and immunobiology of the recombinant protein", Biochemical and Biophysical Research Communictions 297, 2002, 1075-1084.

Neeson et al., "A DNA prime-oral listeria boost vaccine in rhesus macaques induces a SIV—specific CD8 T cell mucosal response characterized by high levels of α4β7 integrin and an effector memory phenotype", Virology, Oct. 2006, 354(2), 299-315.

Neeson et al., "Listeriolysin O is an improved protein carrier for lymphoma immunoglobulin idiotype and provides systemic protection against 38c/3 lymphoma", Cancer Immunol. Immunother., 2007, 13 pages.

Nielsen et al., "Peptide nucleic acids as therapeutic agents", Nucleic acids, p. 353-357, Curr Opinion Struc Biol 9(3): 353-7, Jun. 1997.

Pagano, J.S., "Epstein-Barr Virus: The First Human Tumor Virus and its Role in Cancer", Proc. Assoc. Am. Physicians 1999 111(6):573-80.

Pardoll, "Cancer Vaccines", Nature Medicine Vaccine Supplement, May 1998, vol. 4, No. 5, 525-531.

Paterson et al., "Recombinant Listeria monocytogenes cancer vaccines", Curr Opin Immunol. 1996 Oct.8(5) 664-669.

Paterson et al., Proceeding of the American Association for Cancer Research, Mar. 2000, 41:890, abstract #S25.

Paterson, "Rational approaches to immune regulation", Immunogenic Research, 27(2-3).451-462, Jun. 2003.

Piechocki et al., "Complementary Antitumor Immunity Induced by Plasmid DNA Encoding Secreted and Cytoplasmic Human ErbB-2", The Journal of Immunology, 2001, 167:3367-3374.

Pilgrim et al., "Bactofection of mammalian cells by Listeria monocytogenes: improvement and mechanism of DNA delivery", Gene Therapy, 2003, 10, 2036-2045.

Pilon et al , "Vaccination with Crytoplasmic ErbB-2 DNA Protects Mice from Mammary Tumor Growth Without Anti-ErbB-2 Antibody", The Journal of Immunology, 2001, 167:3201-3206.

Pricher et al., "Viral escape by selection of cytotoxic T cell-resistant virus variants in vivo", Nature, vol. 346, Aug. 1990, 629-633.

Pucci et al., "Straphylococcus hameolyticus contains two D-glutamic acid biosynthetic activities, a glutamate racemase and a D-amino acid transaminase", Journal of Bacteriology, Jan. 1995, vol. 177, No. 2, p. 336-342.

Punwaney et al., "Human Papillomavirus May be Common within Nasopharyngeal Carcinoma of Caucasian Americans: investigation of Epstein-Barr virus and human papillomavirus in Eastern and Western Nasopharyngeal Carcinoma using Ligation-Dependent polymerase chain reaction", Head Neck, 1999, 21(1):21-9.

Raffaghello et al., "Multiple defects of the antigen-processing machinery components in human neuroblastoma: immunotherapeutic implications", Oncogene, 2005, 24, 4634-4644.

Reilly et al., "HER-2/neu is a tumor rejection target in tolerized HER-2/neu transgenic mice", Cancer Research 60, 3569-3576, Jul. 2000.

Restifo et al., "Identification of Human Cancers Deficient in Antigen Processing", J. Exp. Med. 1993, 177, 265-272.

Restifo et al., "The promise of nucleic acid vaccines", Gene Ther., Jan. 2000, 7(2):89-92.

Rogers et al., "Amino acid sequences common to rapidly degraded proteins: the PEST hypothesis", Science, Reports, Oct. 1986, vol. 234, 364-368.

Romero et al., "Coordinated downregulation of the anti gen presentation machinery and HLA class I/β2-microglobulin complex is responsible for HLA-ABC loss in bladder cancer", Int. J. Cancer, 2005, 113, 605-610.

Rovero et al., "DNA Vacciniation Against Rat Her-2/Neu p185 More Effectively Inhibits Carcinogenesis Than Transplantable Carcinomas in Transgenic BALB/c Mice", The Journal of Immunology, 2000, 165:5133-5142.

Scardino et al., "HER-2/neu and hTERT cryptic epitopes as Novel targets for broad spectrum tumor Immunotherapy", The Journal of Immunology, 2002, 168:5900-5906.

Schlom et al., "Cancer Vaccines:Mov ng Beyond Current Paradigms", Clin. Cancer Res. 2007; 13(13), Jul. 1, 2007.

Schmidt et al., "Molecular Analysis of the Plasrnid-Encoded Hemolysin of Escherichia coli O157:H7 Strain EDL 933", Infection and Immunity, 63(3):1055-1061, 1995.

Schneider et al., "Induction of pulmonary allergen-specific IgA responses or airway hyperresponsiveness in the absence of alergic lung disease folowing sensitzaton with limting doses of ovalburnin-alum", Cellular Immunology, 212, 101-109, 2001.

Schnupf et al., "Phosphorylation, ubiquitination and degradation of listeriolysin O in mammalian cells: role of the PEST-like sequence", Cellular Microbiology 8(2):353-364, 2006.

Schwartz, "T cell energy", Annu. Rev. Immunol., 2003, 21, 305-34.

Scortti et al., "The PrfA virulence regulon", Microbes Infect. Aug. 2007;9(10):1196-207. Epub May 7, 2007.

Seffernick et al., "Melamine deaminase and atrazine chlorohydrolase: 98 percent identical but functionally different", J. Bacteriol. 183(8):2405-10, Apr. 2001.

Serth et al., "Increased Levels of Human Papillomavirus Type 16 DNA in a Subset of Prostate Cancers", Cancer Res. 1999 15:59(4):823-5.

Sewell et al., "Regression of HPV-positive tumors treated with a new Listeria monocytogenes vaccine", Arch Otolaryngol Head Neck Surg, Jan. 2004, vol. 130, 92-97.

Shen et al., "Recombinant Listeria monocytogenes as a Live Vaccine Vehicle for the Induction of Protective Anti-Viral Cell-Mediated Immunity", Proc. Natl. Acad. Sci., USA, 92;3987-3991, Apr. 25, 1995.

Shrikant et al., "CTLA-4 blockade reverses CD8+ T cell tolerance to tumor by a CD4+ T cell—and IL-2-dependent mechanism", Immunity, Oct. 1999, vol. 11, 483-493.

Silverman et al., "Expression of c-myc, c-raf-1, and c-Ki-ras in azaserine-induced pancreatic carcinomas and growing pancreas in rats" Mol. Carcinog 3(6)379-86, 1990.

Singh et al., "Structure-Based design of a potent, selective arid irreversible inhibitor of the catalytic domain of the erbb receptor subfamily of protein tyrosine kinases", J. Med. Chem., 1997, 40, 1130-1135.

Singh et al., "Vaccination strategy determines the emergence and dominance of CD8+ T-cell epitopes in a FVB/N Rat HER-2/neu mouse model of breast cancer", Cancer Res., 66, Aug. 15, 2006, 7748-7757.

Stover et al.. "New Use of BCG for Recombinant Vaccines", Nature 1991, 351, 456-460.

Strych et al., "Mutant analysis shows that alanine racemases from *Pseudomonas aeruginosa* and *Escherichia coli* are dimeric", Journal of Bacteriology, Aug. 2002, p. 4321-4325.

Szalay et al., "Presentation of *Listeria monocytogenes* antigens by major histocompatibility complex class I molecules to CD8 cytotoxic T lymphocytes independent of listeriolysin secretion and virulence", Eur. J. Immunol., Jul. 1994; 24(7):1471-7.

Teitelbaum et al., "Mycobacterial infection of macrophages results in membrane-permeable phagosomes", Proc. Natl. Acad. Sci. USA, Dec. 1999; 96(26):15190-5.

Thompson et al., "Pathogenicity and lmmunogenicity of a listeria monocytogenes strain that requires D-alanine for growth", Infection and Immunity, Aug. 1998, vol. 66, No. 8, p. 3552-3561.

Thull et al., "Recognition and management of hereditary breast cancer syndromes", The Oncologist, 2004; 9:13-24.

Townsend et al., "Tumor Rejection after Direct Costimulation of CD8+ T Cells by B7—Transfected Melanoma Cells", Science 1993, 259, 368-370.

Travis, "A Stimulating New Approach to Cancer Treatment", Science 1993, 259, 310-311.

Ulmanen et al., "Transcription and Translation of Foreign genes in *Bacillus subtilis* by the aid of a secretion vector", Journal of Bacteriology, Apr. 1985, vol. 162, No. 1, p. 176-182.

Uyttenhove et al., "Escape of mouse mastocytoma P815 after Nearly complete rejection is due to antigen-loss variants rather than immunosuppression", J. Exp. Med., vol. 157, Mar. 1983, 1040-1052.

Vazquez et al., "Differerential regulation of Ia expression and antigen presentation by listeriolysin-producing versus non-producing strains of *Listerian monocytogenes*", J. Leukoc Biol., May 1996; 59(5):683-90.

Villanueva et al., "Listeriolysin is processed efficiently into an MHC class I-associated epitope in *Listens monocytogenes*-infected cells", J. Immunol., Dec. 1, 1995: 155(11):5227-33.

Vines et al., "Identification and charcterization of nucleotide sequence difference in there virulence-associate genes of *Listeria monocytogenes* strains representing clinically important serotypes", Current Microbiology, May 1998, vol. 36, No. 5, pp. 309-318.

Vitiello et al., "Development of a Lipopeptide-based Therapeutic Vaccine to treat chronic HBV infection", J. Olin Invest., vol. 95, Jan. 1995, 341-349.

Watson et al., "Imrnunosuryeillance is active in colorectal cancer as downregulation but not complee loss of MHC class I expession corelaes wth a poor pognosis", Int. J. Cancer 2006, 118, 6-10.

Wei et al., "Protection against mammary tumor growth by vaccination with full-length, modified human ErbB-2 DNA", Int. J. Cancer, 81, 748-754, 1999.

Wilson et al., "Transient expression of bacterial gene fragments in eukaryotic cells: implications for CD8(+) T cell epitope analysis", J. Immunol. Methods, Feb. 2000, 234(1-2):137-47.

Wingens et al., "Structural analysis of an epidermal growth factor / transforming growth factor-$\alpha$ chimera with uniqe ErbB binding specificity", The Journal of Biological Chemistry, vol. 278, No. 40, Issue of Oct. 3, pp. 39114-39123, 2003.

Witkowski et al., "Conversion of a beta-ketoacyl synthase to a malonyl decarboxylase by replacement of the active-site cysteine with glutamine", Biochemistry 38(36):11643-50, Sep. 7, 1999.

Wu et al., "Engineering an intracellular pathway for major histocompatibility complex class II presentation of antigens", Proc. Natl. Acad. Sci. USA, 1995, 92:11671-5.

Wunderlich et al., "Assays for T cell function: induction and measurement of cytotoxic T lymphocyte activity", Current Protocols in Immunology, 1997, vol. 3, p. 3.11.1-3.11.20.

Yaghmai et al., "Optimized regulation of gene expression using artificial transcription factors", Molecular Therapy, Jun. 2002, vol. 5, No. 6, 685-694.

Young et al., "Cloning and Expression of Influenza Virus Genes", The Origin of Pandemic Influenza Viruses, W.G. Laver, eds., Elsevier Science Publishing Co., Inc., NY, 1983, p. 129.

Zhang et al., "Selection of Tumor Antigens as Targets for Immune Attack Using Immunohistochemistry: Protein Antigens", Clin. Cancer Res. 1998 4:2669-2676.

Zubair et al., "Live recombinant vaccine vectors for HPV antigens associated with infection and malignancy", In: Vaccines for Human Papillomavirus Infection and Anogential Disease (ed. Robert W. Tindle), 1999, pp. 173-192.

Zwickey et al., "Peptide epitopes from noncytosolic *Listeria monocytogenes* can be presented by major histocompatibiity complex class I molecules", Infect. Immun., May 1996; 64(5):1870-2.

zwickey et al.,"Antigen secreted from noncytosolic *Listeria monocytogenes* is processed by the classical MHC class I processing pathway", J. Immunol., Jun. 1999, 162(11):6341-50.

Borysiewicz et al. "A recombinant vaccinia virus encoding Human Papillomavirus Types 16 and 18, E6 and E7 proteins as immunotherapy for Cervical Cancer" Lancet, 0099-5355, Jun. 1, 1996, vol. 347, Issue 9014.

Einstein et al. "Heat shock fusion protein-based immunotherapy for treatment of cervical intraepithelial neoplasia III" Gynecologic Oncology 106 (2007) 453-460.

Hausen et al. "Papillomaviruses causing cancer: evasion from host-cell control in early events in carcinogenesis." J Natl Cancer Inst. May 3, 2000;92(9):690-8.

Jager et al. "Identification of NY-ESO-1 epitopes presented by human histocompatibility antigen (HLA)-DRB4*0101-0103 and recognized by CD4(+) T lymphocytes of patients with NY-ESO-1-expressing melanoma" J Exp Med. Feb. 21, 2000;191(4):625-30.

Mandavi et al. "Vaccines against Human Papillomavirus and Cervical Cancer: Promises and Challenges" The Oncologist 2005; 10:528-538.

Peng et al. "Adjuvant properties of listeriolysin O protein in a DNA vaccination strategy" Cancer Immunol Immunother. Jun. 2000;56(6):797-806.

* cited by examiner

1: Liver
2: Spleen
3: Thyroid
4: Thymus

5. Cathepsin S
6. E7
7. Actin
8. Negative Control

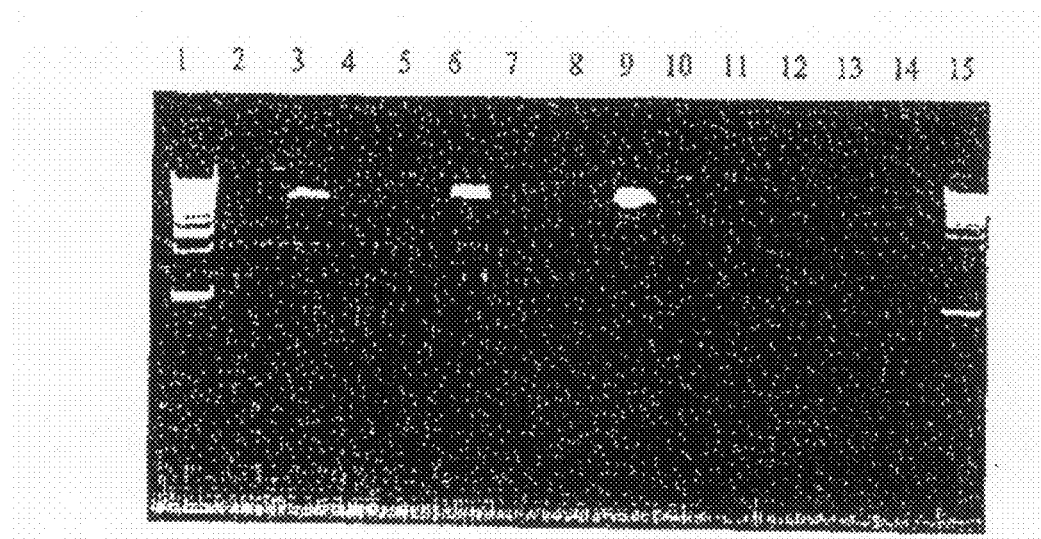

| Lane | Sample | Lane | Sample |
|---|---|---|---|
| 1 | 1Kb ladder | 9 | LB B, generation 5 |
| 2 | 100ng reference pGG55 | 10 | LB A, generation 9 |
| 3 | LB A, generation 5 | 11 | LB B, generation 14 |
| 4 | LB A, generation 9 | 12 | LB B, generation 19* |
| 5 | LB A, generation 14 | 13 | LB B, generation 24* |
| 6 | LB A, generation 19 | 14 | LB B, generation 29* |
| 7 | LB A, generation 24 | 15 | 1Kb ladder |
| 8 | LB A, generation 29 | | |

* Residual ethanol remaining in sample, therefore the majority of the sample did not load into the well, resulting in a less intense plasmid band

Figure 16A

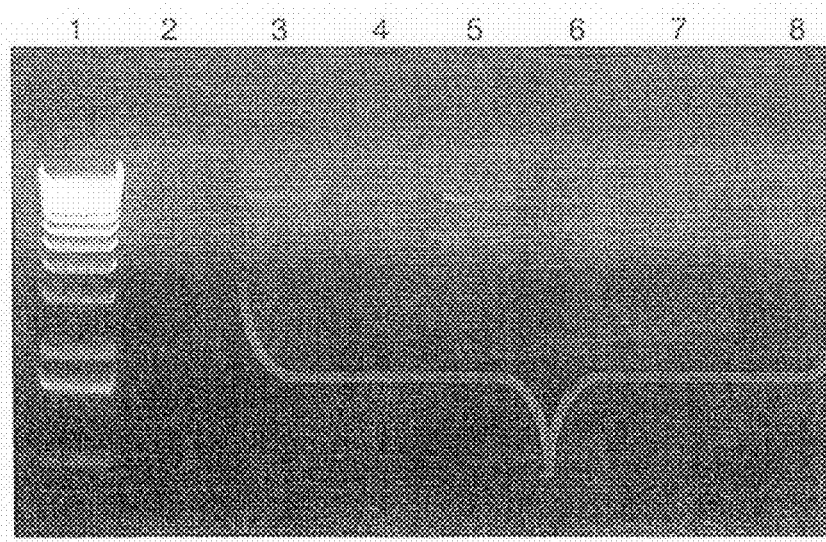

| Lane | Sample | Lane | Sample |
|---|---|---|---|
| 1 | 1Kb ladder | 5 | TB, generation 21 |
| 2 | 100ng reference pGG55 | 6 | TB, generation 28 |
| 3 | TB, generation 7 | 7 | TB, generation 35 |
| 4 | TB, generation 14 | 8 | TB, generation 42 |

SEQUENCE LISTING

<160> NUMBER OF SEQ ID NOS: 35

<210> SEQ ID NO 1
<211> LENGTH: 32
<212> TYPE: PRT
<213> ORGANISM: Listeria monocytogenes

<400> SEQUENCE: 1

Lys Glu Asn Ser Ile Ser Ser Met Ala Pro Pro Ala Ser Pro Pro Ala
1               5                   10                  15

Ser Pro Lys Thr Pro Ile Glu Lys Lys His Ala Asp Glu Ile Asp Lys
            20                  25                  30

<210> SEQ ID NO 2
<211> LENGTH: 14
<212> TYPE: PRT
<213> ORGANISM: Listeria monocytogenes

<400> SEQUENCE: 2

Lys Thr Glu Glu Gln Pro Ser Glu Val Asn Thr Gly Pro Arg
1               5                   10

<210> SEQ ID NO 3
<211> LENGTH: 28
<212> TYPE: PRT
<213> ORGANISM: Listeria monocytogenes -continued

<400> SEQUENCE: 3

Lys Ala Ser Val Thr Asp Thr Ser Glu Gly Asp Leu Asp Ser Ser Met
1               5                   10                  15

Gln Ser Ala Asp Glu Ser Thr Pro Gln Pro Leu Lys
            20                  25

<210> SEQ ID NO 4
<211> LENGTH: 20
<212> TYPE: PRT
<213> ORGANISM: Listeria monocytogenes

<400> SEQUENCE: 4

Lys Asn Glu Glu Val Asn Ala Ser Asp Phe Pro Pro Pro Pro Thr Asp
1               5                   10                  15

Glu Glu Leu Arg
            20

<210> SEQ ID NO 5
<211> LENGTH: 33
<212> TYPE: PRT
<213> ORGANISM: Listeria monocytogenes

<400> SEQUENCE: 5

Arg Gly Gly Ile Pro Thr Ser Glu Glu Phe Ser Ser Leu Asn Ser Gly
1               5                   10                  15

Asp Phe Thr Asp Asp Glu Asn Ser Glu Thr Thr Glu Glu Glu Ile Asp
            20                  25                  30

Arg

<210> SEQ ID NO 6
<211> LENGTH: 17
<212> TYPE: PRT
<213> ORGANISM: Streptococcus sp.

<400> SEQUENCE: 6

Lys Gln Asn Thr Ala Ser Thr Glu Thr Thr Thr Thr Asn Glu Gln Pro
1               5                   10                  15

Lys

<210> SEQ ID NO 7
<211> LENGTH: 17
<212> TYPE: PRT
<213> ORGANISM: Streptococcus equisimilis

<400> SEQUENCE: 7

Lys Gln Asn Thr Ala Asn Thr Glu Thr Thr Thr Thr Asn Glu Gln Pro
1               5                   10                  15

Lys

<210> SEQ ID NO 8
<211> LENGTH: 22
<212> TYPE: DNA
<213> ORGANISM: Artificial
<220> FEATURE:
<223> OTHER INFORMATION: primer

<400> SEQUENCE: 8
ggctcgagca tggagataca cc                                    22

<210> SEQ ID NO 9
<211> LENGTH: 28

<212> TYPE: DNA
<213> ORGANISM: Artificial
<220> FEATURE:
<223> OTHER INFORMATION: primer

<400> SEQUENCE: 9
ggggactagt ttatggtttc tgagaaca                                          28

<210> SEQ ID NO 10
<211> LENGTH: 31
<212> TYPE: DNA
<213> ORGANISM: Artificial
<220> FEATURE:
<223> OTHER INFORMATION: primer

<400> SEQUENCE: 10
gggggctagc cctcctttga ttagtatatt c                                      31

<210> SEQ ID NO 11
<211> LENGTH: 28
<212> TYPE: DNA
<213> ORGANISM: Artificial
<220> FEATURE:
<223> OTHER INFORMATION: primer

<400> SEQUENCE: 11
ctccctcgag atcataattt acttcatc                                          28

<210> SEQ ID NO 12
<211> LENGTH: 55
<212> TYPE: DNA
<213> ORGANISM: Artificial
<220> FEATURE:
<223> OTHER INFORMATION: primer

<400> SEQUENCE: 12
gactacaagg acgatgaccg acaagtgata acccgggatc taaataaatc cgttt           55

<210> SEQ ID NO 13
<211> LENGTH: 27
<212> TYPE: DNA
<213> ORGANISM: Artificial
<220> FEATURE:
<223> OTHER INFORMATION: primer

<400> SEQUENCE: 13
cccgtcgacc agctcttctt ggtgaag                                           27

<210> SEQ ID NO 14
<211> LENGTH: 31
<212> TYPE: DNA
<213> ORGANISM: Artificial
<220> FEATURE:
<223> OTHER INFORMATION: primer

<400> SEQUENCE: 14
ggggtctaga cctcctttga ttagtatatt c                                      31

<210> SEQ ID NO 15
<211> LENGTH: 45
<212> TYPE: DNA
<213> ORGANISM: Artificial
<220> FEATURE:
<223> OTHER INFORMATION: primer

<400> SEQUENCE: 15
atcttcgcta tctgtcgccg cggcgcgtgc ttcagtttgt tgcgc                       45

<210> SEQ ID NO 16
<211> LENGTH: 45
<212> TYPE: DNA
<213> ORGANISM: Artificial
<220> FEATURE:
<223> OTHER INFORMATION: primer

<400> SEQUENCE: 16
gcgcaacaaa ctgaagcagc ggccgcggcg acagatagcg aagat        45

<210> SEQ ID NO 17
<211> LENGTH: 42
<212> TYPE: DNA
<213> ORGANISM: Artificial
<220> FEATURE:
<223> OTHER INFORMATION: primer

<400> SEQUENCE: 17
tgtaggtgta tctccatgct cgagagctag gcgatcaatt tc           42

<210> SEQ ID NO 18
<211> LENGTH: 42
<212> TYPE: DNA
<213> ORGANISM: Artificial
<220> FEATURE:
<223> OTHER INFORMATION: primer

<400> SEQUENCE: 18
ggaattgatc gcctagctct cgagcatgga gatacaccta ca           42

<210> SEQ ID NO 19
<211> LENGTH: 42
<212> TYPE: DNA
<213> ORGANISM: Artificial
<220> FEATURE:
<223> OTHER INFORMATION: primer

<400> SEQUENCE: 19
aaacggattt atttagatcc cgggttatgg tttctgagaa ca           42

<210> SEQ ID NO 20
<211> LENGTH: 42
<212> TYPE: DNA
<213> ORGANISM: Artificial
<220> FEATURE:
<223> OTHER INFORMATION: primer

<400> SEQUENCE: 20
tgttctcaga aaccataacc cgggatctaa ataaatccgt tt           42

<210> SEQ ID NO 21
<211> LENGTH: 28
<212> TYPE: DNA
<213> ORGANISM: Artificial
<220> FEATURE:
<223> OTHER INFORMATION: primer

<400> SEQUENCE: 21
gggggtcgac cagctcttct tggtgaag                           28

<210> SEQ ID NO 22
<211> LENGTH: 9
<212> TYPE: PRT
<213> ORGANISM: Human papillomavirus type 16

<400> SEQUENCE: 22

```
Arg Ala His Tyr Asn Ile Val Thr Phe
1               5

<210> SEQ ID NO 23
<211> LENGTH: 390
<212> TYPE: PRT
<213> ORGANISM: Listeria monocytogenes

<400> SEQUENCE: 23

Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
            20                  25                  30

Asn Thr Asp Glu Trp Glu Glu Lys Thr Glu Glu Gln Pro Ser Glu
        35                  40                  45

Val Asn Thr Gly Pro Arg Tyr Glu Thr Ala Arg Glu Val Ser Ser Arg
    50                  55                  60

Asp Ile Lys Glu Leu Glu Lys Ser Asn Lys Val Arg Asn Thr Asn Lys
65                  70                  75                  80

Ala Asp Leu Ile Ala Met Leu Lys Glu Lys Ala Glu Lys Gly Pro Asn
                85                  90                  95

Ile Asn Asn Asn Ser Glu Gln Thr Glu Asn Ala Ala Ile Asn Glu
            100                 105                 110

Glu Ala Ser Gly Ala Asp Arg Pro Ala Ile Gln Val Glu Arg Arg His
        115                 120                 125

Pro Gly Leu Pro Ser Asp Ser Ala Ala Glu Ile Lys Lys Arg Lys
    130                 135                 140

Ala Ile Ala Ser Ser Asp Ser Glu Leu Glu Ser Leu Thr Tyr Pro Asp
145                 150                 155                 160

Lys Pro Thr Lys Val Asn Lys Lys Val Ala Lys Glu Ser Val Ala
                165                 170                 175

Asp Ala Ser Glu Ser Asp Leu Asp Ser Ser Met Gln Ser Ala Asp Glu
            180                 185                 190

Ser Ser Pro Gln Pro Leu Lys Ala Asn Gln Gln Pro Phe Phe Pro Lys
        195                 200                 205

Val Phe Lys Lys Ile Lys Asp Ala Gly Lys Trp Val Arg Asp Lys Ile
    210                 215                 220

Asp Glu Asn Pro Glu Val Lys Lys Ala Ile Val Asp Lys Ser Ala Gly
225                 230                 235                 240

Leu Ile Asp Gln Leu Leu Thr Lys Lys Lys Ser Glu Glu Val Asn Ala
                245                 250                 255

Ser Asp Phe Pro Pro Pro Thr Asp Glu Glu Leu Arg Leu Ala Leu
            260                 265                 270

Pro Glu Thr Pro Met Leu Leu Gly Phe Asn Ala Pro Ala Thr Ser Glu
        275                 280                 285

Pro Ser Ser Phe Glu Phe Pro Pro Pro Thr Asp Glu Glu Leu Arg
    290                 295                 300

Leu Ala Leu Pro Glu Thr Pro Met Leu Leu Gly Phe Asn Ala Pro Ala
305                 310                 315                 320

Thr Ser Glu Pro Ser Ser Phe Glu Phe Pro Pro Pro Thr Glu Asp
                325                 330                 335

Glu Leu Glu Ile Ile Arg Glu Thr Ala Ser Ser Leu Asp Ser Ser Phe
            340                 345                 350

Thr Arg Gly Asp Leu Ala Ser Leu Arg Asn Ala Ile Asn Arg His Ser
        355                 360                 365
```

Gln Asn Phe Ser Asp Phe Pro Pro Ile Pro Thr Glu Glu Leu Asn
            370                 375                 380

Gly Arg Gly Gly Arg Pro
385                 390

<210> SEQ ID NO 24
<211> LENGTH: 1170
<212> TYPE: DNA
<213> ORGANISM: Listeria monocytogenes

<400> SEQUENCE: 24

```
atgcgtgcga tgatggtggt tttcattact gccaattgca ttacgattaa ccccgacata      60
atatttgcag cgacagatag cgaagattct agtctaaaca cagatgaatg ggaagaagaa     120
aaaacagaag agcaaccaag cgaggtaaat acgggaccaa gatacgaaac tgcacgtgaa     180
gtaagttcac gtgatattaa agaactagaa aaatcgaata agtgagaaa tacgaacaaa      240 gcagacctaa tagcaatgtt gaaagaaaaa gcagaaaaag tccaaatat caataataac      300 aacagtgaac aaactgagaa tgcggctata aatgaagagg cttcaggagc cgaccgacca     360
gctatacaag tggagcgtcg tcatccagga ttgccatcgg atagcgcagc ggaaattaaa     420
aaaagaagga aagccatagc atcatcggat agtgagcttg aaagccttac ttatccggat     480
aaaccaacaa aagtaaataa gaaaaaagtg gcgaaagagt cagttgcgga tgcttctgaa     540
agtgacttag attctagcat gcagtcagca gatgagtctt caccacaacc tttaaaagca     600
aaccaacaac catttttccc taaagtattt aaaaaaataa aagatgcggg gaatgggta     660 cgtgataaaa tcgacgaaaa tcctgaagta agaaagcga ttgttgataa aagtgcaggg     720
ttaattgacc aattattaac caaaaagaaa agtgaagagg taaatgcttc ggacttcccg     780
ccaccaccta cggatgaaga gttaagactt gctttgccag agacaccaat gcttcttggt     840
tttaatgctc ctgctacatc agaaccgagc tcattcgaat tccaccacc acctacggat     900 gaagagttaa gacttgcttt gccagagacg ccaatgcttc ttggttttaa tgctcctgct     960
acatcggaac cgagctcgtt cgaatttcca ccgcctccaa cagaagatga actagaaatc    1020
atccgggaaa cagcatcctc gctagattct agttttacaa gaggggattt agctagtttg    1080
agaaatgcta ttaatcgcca tagtcaaaat ttctctgatt tcccaccaat cccaacagaa    1140
gaagagttga acgggagagg cggtagacca                                     1170
```

<210> SEQ ID NO 25
<211> LENGTH: 441
<212> TYPE: PRT
<213> ORGANISM: Listeria monocytogenes

<400> SEQUENCE: 25

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
                100                 105                 110

Ala Asp Ile Gln Val Val Asn Ala Ile Ser Ser Leu Thr Tyr Pro Gly
            115                 120                 125

Ala Leu Val Lys Ala Asn Ser Glu Leu Val Glu Asn Gln Pro Asp Val
130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
                260                 265                 270

Ala Val Thr Lys Glu Gln Leu Gln Ala Leu Gly Val Asn Ala Glu Asn
            275                 280                 285

Pro Pro Ala Tyr Ile Ser Ser Val Ala Tyr Gly Arg Gln Val Tyr Leu
        290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp
        435                 440

<210> SEQ ID NO 26
<211> LENGTH: 416
<212> TYPE: PRT
<213> ORGANISM: Listeria monocytogenes

<400> SEQUENCE: 26

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Ala Ser
            35                  40                  45

Pro Lys Thr Pro Ile Glu Lys Lys His Ala Asp Glu Ile Asp Lys Tyr
 50                  55                  60

Ile Gln Gly Leu Asp Tyr Asn Lys Asn Asn Val Leu Val Tyr His Gly
 65                  70                  75                  80

Asp Ala Val Thr Asn Val Pro Pro Arg Lys Gly Tyr Lys Asp Gly Asn
                 85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
            115                 120                 125

Ala Leu Val Lys Ala Asn Ser Glu Leu Val Glu Asn Gln Pro Asp Val
            130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
            195                 200                 205

Glu Met Ala Tyr Ser Glu Ser Gln Leu Ile Ala Lys Phe Gly Thr Ala
210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
            275                 280                 285

Pro Pro Ala Tyr Ile Ser Ser Val Ala Tyr Gly Arg Gln Val Tyr Leu
            290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
            355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

<210> SEQ ID NO 27
<211> LENGTH: 529
<212> TYPE: PRT
<213> ORGANISM: Listeria monocytogenes

<400> SEQUENCE: 27

```
Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Ala Ser Pro Pro Ala Ser
        35                  40                  45

Pro Lys Thr Pro Ile Glu Lys Lys His Ala Asp Glu Ile Asp Lys Tyr
        50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
                100                 105                 110

Ala Asp Ile Gln Val Val Asn Ala Ile Ser Ser Leu Thr Tyr Pro Gly
            115                 120                 125

Ala Leu Val Lys Ala Asn Ser Glu Leu Val Glu Asn Gln Pro Asp Val
            130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
                180                 185                 190

Tyr Ala Gln Ala Tyr Pro Asn Val Ser Ala Lys Ile Asp Tyr Asp Asp
            195                 200                 205

Glu Met Ala Tyr Ser Glu Ser Gln Leu Ile Ala Lys Phe Gly Thr Ala
            210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
                260                 265                 270

Ala Val Thr Lys Glu Gln Leu Gln Ala Leu Gly Val Asn Ala Glu Asn
            275                 280                 285

Pro Pro Ala Tyr Ile Ser Ser Val Ala Tyr Gly Arg Gln Val Tyr Leu
            290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
                340                 345                 350

Lys Asp Glu Val Gln Ile Ile Asp Gly Asn Leu Gly Asp Leu Arg Asp
            355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Ser Lys Ala Tyr Thr Asp
                405                 410                 415

Gly Lys Ile Asn Ile Asp His Ser Gly Gly Tyr Val Ala Gln Phe Asn
```

```
                        420                 425                 430
Ile Ser Trp Asp Glu Val Asn Tyr Asp Pro Glu Gly Asn Glu Ile Val
            435                 440                 445

Gln His Lys Asn Trp Ser Glu Asn Asn Lys Ser Lys Leu Ala His Phe
        450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
            485                 490                 495

Asp Asp Arg Asn Leu Pro Leu Val Lys Asn Arg Asn Ile Ser Ile Trp
        500                 505                 510

Gly Thr Thr Leu Tyr Pro Lys Tyr Ser Asn Lys Val Asp Asn Pro Ile
        515                 520                 525

Glu

<210> SEQ ID NO 28
<211> LENGTH: 25
<212> TYPE: DNA
<213> ORGANISM: Artificial
<220> FEATURE:
<223> OTHER INFORMATION: primer

<400> SEQUENCE: 28
gcggatccca tggagataca cctac                                          25

<210> SEQ ID NO 29
<211> LENGTH: 22
<212> TYPE: DNA
<213> ORGANISM: Artificial
<220> FEATURE:
<223> OTHER INFORMATION: primer

<400> SEQUENCE: 29
gctctagatt atggtttctg ag                                             22

<210> SEQ ID NO 30
<211> LENGTH: 98
<212> TYPE: PRT
<213> ORGANISM: Human papillomavirus type 16

<400> SEQUENCE: 30

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
            85                  90                  95

Lys Pro

<210> SEQ ID NO 31
<211> LENGTH: 105
<212> TYPE: PRT
<213> ORGANISM: Human papillomavirus type 16
```

-continued

```
<400> SEQUENCE: 31

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
                20                  25                  30

Asp Ser Glu Glu Glu Asn Asp Glu Ile Asp Gly Val Asn His Gln His
            35                  40                  45

Leu Pro Ala Arg Arg Ala Glu Pro Gln Arg His Thr Met Leu Cys Met
    50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln
                100                 105

<210> SEQ ID NO 32
<211> LENGTH: 158
<212> TYPE: PRT
<213> ORGANISM: Human papillomavirus type 16

<400> SEQUENCE: 32

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
                20                  25                  30

Ile Ile Leu Glu Cys Val Tyr Cys Lys Gln Gln Leu Leu Arg Arg Glu
            35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
                100                 105                 110

Cys Gln Lys Pro Leu Cys Pro Glu Glu Lys Gln Arg His Leu Asp Lys
            115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155

<210> SEQ ID NO 33
<211> LENGTH: 158
<212> TYPE: PRT
<213> ORGANISM: Human papillomavirus type 16

<400> SEQUENCE: 33

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
                20                  25                  30

Val Tyr Cys Lys Thr Val Leu Glu Leu Thr Glu Val Phe Glu Phe Ala
            35                  40                  45

Phe Lys Asp Leu Phe Val Val Tyr Arg Asp Ser Ile Pro His Ala Ala
    50                  55                  60
```

```
Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
        130             135             140

Ala Arg Gln Glu Arg Leu Gln Arg Arg Glu Thr Gln Val
145             150                 155

<210> SEQ ID NO 34
<211> LENGTH: 9
<212> TYPE: PRT
<213> ORGANISM: Human immunodeficiency virus

<400> SEQUENCE: 34

Ala Met Gln Met Leu Lys Glu Thr Ile
1               5

<210> SEQ ID NO 35
<211> LENGTH: 9
<212> TYPE: PRT
<213> ORGANISM: Listeria monocytogenes

<400> SEQUENCE: 35

Gly Tyr Lys Asp Gly Asn Glu Tyr Ile
1               5
```

COMPOSITIONS AND METHODS FOR TREATMENT OF CERVICAL CANCER

CROSS REFERENCE TO RELATED APPLICATIONS

This application is a Continuation-in-Part of co-pending U.S. application Ser. No. 11/415,271, filed May 2, 2006, which is (1) a Continuation-in-Part of U.S. application Ser. No. 11/373,528, filed Mar. 13, 2006, now U.S. Pat. No. 7,662, 396 which is a Continuation-in-Part of U.S. application Ser. No. 10/835,662, filed Apr. 30, 2004, now U.S. Pat. No. 7,588, 930 which is a Continuation-in-Part of U.S. application Ser. No. 10/239,703, filed Aug. 7, 2003, now U.S. Pat. No. 7,635, 479 which is a National Phase Application of PCT International Application No. PCT/US01/09736, International Filing Date Mar. 26, 2001, now expired, which corresponds to (a) U.S. application Ser. No. 09/735,450, filed Dec. 13, 2000, now U.S. Pat. No. 6,767,542; and (b) U.S. application Ser. No. 09/537,642, filed Mar. 29, 2000, now U.S. Pat. No. 6,855, 320; and is (2) a Continuation-in-Part of U.S. application Ser. No. 11/223,945, filed Sep. 13, 2005, now U.S Pat. No. 7,820, 180 which is a Continuation-in-Part of U.S. application Ser. No. 10/949,667, filed Sep. 24, 2004, now U.S. Pat. No. 7,794, 729 which is a Continuation-in-Part of U.S. application Ser. No. 10/441,851, filed May 20, 2003, now U.S. Pat. No. 7,135, 188 which is a Continuation-in-Part of U.S. application Ser. No. 09/535,212, filed Mar. 27, 2000, now U.S. Pat. No. 6,565, 852, which is a Continuation-in-Part of U.S. application Ser. No. 08/336,372, filed Nov. 8, 1994, now U.S. Pat. No. 6,051, 237. These applications are hereby incorporated in their entirety by reference herein.

FIELD OF INVENTION

The present invention provides methods of treating, protecting against, and inducing an immune response against cervical cancer, comprising the step of administering to a subject a recombinant *Listeria* strain, comprising a fusion peptide that comprises an LLO fragment and an E7 and/or E6 antigen. The present invention also provides methods for inducing an anti-E7 CTL response in a human subject and treating HPV-mediated diseases, disorders, and symptoms, comprising administration of the recombinant *Listeria* strain.

BACKGROUND OF THE INVENTION

Worldwide, approximately 500,000 cases of cervical cancer are diagnosed each year. Cancer of the cervix (cervical cancer) begins in the lining of the cervix. Normal cervical cells gradually develop pre-cancerous changes that turn into cancer. Several terms are used to describe these pre-cancerous changes, including cervical intraepithelial neoplasia (CIN), squamous intraepithelial lesion (SIL), and neoplasia in situ, dysplasia.

There are 2 major types of cervical cancers: squamous cell carcinoma and adenocarcinoma. Cervical cancers and cervical precancers are classified by microscopic appearance. About 80%-90% of cervical cancers are squamous cell carcinomas, which are composed of cells that resemble the flat, thin cells called squamous cells that cover the surface of the endocervix. Squamous cell carcinomas most often begin where the ectocervix joins the endocervix.

The remaining 10%-20% of cervical cancers are adenocarcinomas. Adenocarcinomas are becoming more common in women born in the last 20 to 30 years. Cervical adenocarcinoma develops from the mucus-producing gland cells of the endocervix. Less commonly, cervical cancers have features of both squamous cell carcinomas and adenocarcinomas. These are called "adenosquamous carcinomas" or "mixed carcinomas."

Improved therapies for cervical cancers are urgently needed in the art.

SUMMARY OF THE INVENTION

The present invention provides methods of treating, protecting against, and inducing an immune response against cervical cancer, comprising the step of administering to a subject a recombinant *Listeria* strain, comprising a fusion peptide that comprises an LLO fragment and an E7 and/or E6 antigen. The present invention also provides methods for inducing an anti-E7 CTL response in a human subject and treating HPV-mediated diseases, disorders, and symptoms, comprising administration of the recombinant *Listeria* strain.

In one embodiment, the present invention provides a method of treating a cervical cancer in a human subject, comprising the step of administering to the subject a recombinant *Listeria* strain, the recombinant *Listeria* strain comprising a recombinant polypeptide comprising an N-terminal fragment of an LLO protein fused to an Human Papilloma Virus (HPV) E7 antigen, whereby the recombinant *Listeria* strain induces an immune response against the E7 antigen, thereby treating a cervical cancer in a human subject.

In another embodiment, the present invention provides a method of protecting a human subject against a cervical cancer, comprising the step of administering to the subject a recombinant *Listeria* strain, the recombinant *Listeria* strain comprising a recombinant polypeptide comprising an N-terminal fragment of an LLO protein fused to an HPV E7 antigen, whereby the recombinant *Listeria* strain induces an immune response against the E7 antigen, thereby protecting a human subject against a cervical cancer. In another embodiment, the recombinant *Listeria* strain comprises a plasmid that encodes the recombinant polypeptide. In another embodiment, the method further comprises the step of boosting the human subject with a recombinant *Listeria* strain of the present invention. In another embodiment, the method further comprises the step of boosting the human subject with an immunogenic composition comprising an E7 antigen. In another embodiment, the method further comprises the step of boosting the human subject with an immunogenic composition that directs a cell of the subject to express an E7 antigen. Each possibility represents a separate embodiment of the present invention.

In another embodiment, the present invention provides a method for inducing an immune response against a cervical cancer in a human subject, comprising the step of administering to the subject a recombinant *Listeria* strain, the recombinant *Listeria* strain comprising a recombinant polypeptide comprising an N-terminal fragment of an LLO protein fused to an HPV E7 antigen, whereby the recombinant *Listeria* strain induces an immune response against the E7 antigen, thereby inducing an immune response against a cervical cancer in a human subject. In another embodiment, the recombinant *Listeria* strain comprises a plasmid that encodes the recombinant polypeptide. In another embodiment, the method further comprises the step of boosting the human subject with a recombinant *Listeria* strain of the present invention. In another embodiment, the method further comprises the step of boosting the human subject with an immunogenic composition comprising an E7 antigen. In another embodiment, the method further comprises the step of boosting the human subject with an immunogenic composition that directs a cell of the subject to express an E7 antigen. Each possibility represents a separate embodiment of the present invention.

In another embodiment, the present invention provides a method for inducing an anti-E7 cytotoxic T cell response in a human subject, comprising the step of administering to the subject a recombinant *Listeria* strain, the recombinant *Listeria* strain comprising a recombinant polypeptide comprising an N-terminal fragment of an LLO protein fused to an HPV E7 antigen, whereby the recombinant *Listeria* strain induces an immune response against the E7 antigen, thereby inducing an anti-E7 cytotoxic T cell response in a human subject. In another embodiment, the recombinant *Listeria* strain comprises a plasmid that encodes the recombinant polypeptide. In another embodiment, the method further comprises the step of boosting the human subject with a recombinant *Listeria* strain of the present invention. In another embodiment, the method further comprises the step of boosting the human subject with an immunogenic composition comprising an E7 antigen. In another embodiment, the method further comprises the step of boosting the human subject with an immunogenic composition that directs a cell of the subject to express an E7 antigen. Each possibility represents a separate embodiment of the present invention.

DETAILED DESCRIPTION OF THE INVENTION

Figure 1:
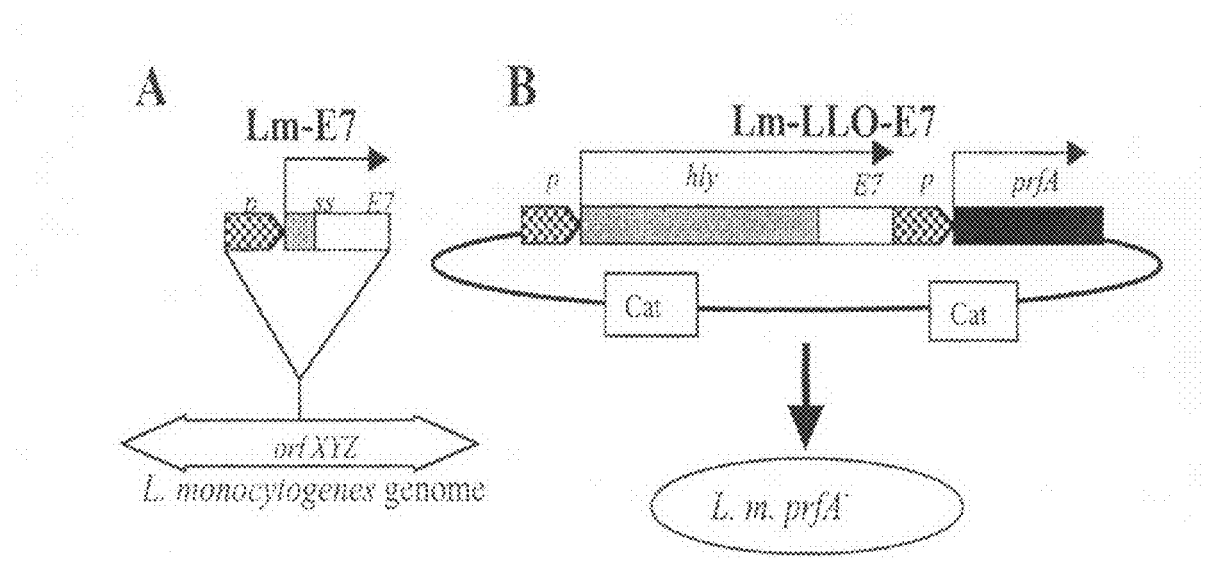
FIG. 1. Lm-E7 and Lm-LLO-E7 use different expression systems to express and secrete E7. Lm-E7 was generated by introducing a gene cassette into the orfZ domain of the *L. monocytogenes* genome (A). The hly promoter drives expression of the hly signal sequence and the first five amino acids (AA) of LLO followed by HPV-16 E7. B), Lm-LLO-E7 was generated by transforming the prfA-strain XFL-7 with the plasmid pGG-55. pGG-55 has the hly promoter driving expression of a nonhemolytic fusion of LLO-E7. pGG-55 also contains the prfA gene to select for retention of the plasmid by XFL-7 in vivo.

The present invention provides methods of treating, protecting against, and inducing an immune response against cervical cancer, comprising the step of administering to a subject a recombinant *Listeria* strain, comprising a fusion peptide that comprising a listeriolysin O (LLO) fragment and an E7 antigen. The present invention also provides methods for inducing an anti-E7 CTL response in a human subject and treating HPV-mediated diseases, disorders, and symptoms, comprising administration of the recombinant *Listeria* strain.

In one embodiment, the present invention provides a method of treating a cervical cancer in a human subject, comprising the step of administering to the subject a recombinant *Listeria* strain, the recombinant *Listeria* strain comprising a recombinant polypeptide comprising an N-terminal fragment of an LLO protein and an Human Papilloma Virus (HPV) E7 antigen, whereby the recombinant *Listeria* strain induces an immune response against the E7 antigen, thereby treating a cervical cancer in a human subject. In another embodiment, the recombinant *Listeria* strain expresses the recombinant polypeptide. In another embodiment, the recombinant *Listeria* strain comprises a plasmid that encodes the recombinant polypeptide. In another embodiment, the method further comprises the step of boosting the human subject with a recombinant *Listeria* strain of the present invention. In another embodiment, the method further comprises the step of boosting the human subject with an immunogenic composition comprising an E7 antigen. In another embodiment, the method further comprises the step of boosting the human subject with an immunogenic composition that directs a cell of the subject to express an E7 antigen. Each possibility represents a separate embodiment of the present invention.

The N-terminal LLO protein fragment and HPV E7 antigen are, in another embodiment, fused directly to one another. In another embodiment, the genes encoding the N-terminal LLO protein fragment and HPV E7 antigen are fused directly to one another. In another embodiment, the N-terminal LLO protein fragment and HPV E7 antigen are attached via a linker peptide. In another embodiment, the N-terminal LLO protein fragment and HPV E7 antigen are attached via a heterologous peptide. In another embodiment, the N-terminal LLO protein fragment is N-terminal to the HPV E7 antigen. In another embodiment, the N-terminal LLO protein fragment is the N-terminal-most portion of the fusion protein. Each possibility represents a separate embodiment of the present invention.

In another embodiment, the present invention provides a method of protecting a human subject against a cervical cancer, comprising the step of administering to the subject a recombinant *Listeria* strain, the recombinant *Listeria* strain comprising a recombinant polypeptide comprising an N-terminal fragment of an LLO protein and an HPV E7 antigen, whereby the recombinant *Listeria* strain induces an immune response against the E7 antigen, thereby protecting a human subject against a cervical cancer. In another embodiment, the recombinant *Listeria* strain expresses the recombinant polypeptide. In another embodiment, the recombinant *Listeria* strain comprises a plasmid that encodes the recombinant polypeptide. In another embodiment, the method further comprises the step of boosting the human subject with a recombinant *Listeria* strain of the present invention. In another embodiment, the method further comprises the step of boosting the human subject with an immunogenic composition comprising an E7 antigen. In another embodiment, the method further comprises the step of boosting the human subject with an immunogenic composition that directs a cell of the subject to express an E7 antigen. Each possibility represents a separate embodiment of the present invention.

In another embodiment, the present invention provides a method for inducing an immune response against a cervical cancer in a human subject, comprising the step of administering to the subject a recombinant *Listeria* strain, the recombinant *Listeria* strain comprising a recombinant polypeptide comprising an N-terminal fragment of an LLO protein and an HPV E7 antigen, thereby inducing an immune response against a cervical cancer in a human subject. In another embodiment, the recombinant *Listeria* strain expresses the recombinant polypeptide. In another embodiment, the recombinant *Listeria* strain comprises a plasmid that encodes the recombinant polypeptide. In another embodiment, the method further comprises the step of boosting the human subject with a recombinant *Listeria* strain of the present invention. In another embodiment, the method further comprises the step of boosting the human subject with an immunogenic composition comprising an E7 antigen. In another embodiment, the method further comprises the step of boosting the human subject with an immunogenic composition that directs a cell of the subject to express an E7 antigen. Each possibility represents a separate embodiment of the present invention.

As provided herein, recombinant *Listeria* strains expressing LLO-antigen fusions induce anti-tumor immunity (Example 1), elicit antigen-specific T cell proliferation (Example 2), generate antigen-specific, tumor-infiltrating T cells (Example 4), and abrogate central and peripheral tolerance to antigens such as E6 and E7 (Examples 5-9). Thus, vaccines of the present invention are efficacious at inducing immune responses against E7 and E6. Further, the recombinant *Listeria* strains are safe and improve disease indicators in human subjects (Example 10).

In another embodiment, the present invention provides a method of treating a cervical cancer in a human subject, comprising the step of administering to the subject a recombinant *Listeria* strain, the recombinant *Listeria* strain comprising a recombinant polypeptide comprising an N-terminal fragment of an ActA protein and an HPV E7 antigen, whereby the recombinant *Listeria* strain induces an immune response against the E7 antigen, thereby treating a cervical cancer in a human subject. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

In another embodiment, the present invention provides a method of protecting a human subject against a cervical cancer, comprising the step of administering to the subject a recombinant *Listeria* strain, the recombinant *Listeria* strain comprising a recombinant polypeptide comprising an N-terminal fragment of an ActA protein and an HPV E7 antigen, whereby the recombinant *Listeria* strain induces an immune response against the E7 antigen, thereby protecting a human subject against a cervical cancer. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

In another embodiment, the present invention provides a method for inducing an immune response against a cervical cancer in a human subject, comprising the step of administering to the subject a recombinant *Listeria* strain, the recombinant *Listeria* strain comprising a recombinant polypeptide comprising an N-terminal fragment of an ActA protein and an HPV E7 antigen, thereby inducing an immune response against a cervical cancer in a human subject. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

As provided herein, recombinant *Listeria* strains expressing ActA-antigen fusions induce anti-tumor immunity (Example 3), generate antigen-specific, tumor-infiltrating T cells (Example 4), and abrogate central and peripheral tolerance to antigens such as E6 and E7 (Examples 5-9). Further, recombinant *Listeria* strains of the present invention are safe and improve disease indicators in human subjects (Example 10).

The N-terminal ActA protein fragment and HPV E7 antigen are, in another embodiment, fused directly to one another. In another embodiment, the genes encoding the N-terminal ActA protein fragment and HPV E7 antigen are fused directly to one another. In another embodiment, the N-terminal ActA protein fragment and HPV E7 antigen are attached via a linker peptide. In another embodiment, the N-terminal ActA protein fragment and HPV E7 antigen are attached via a heterologous peptide. In another embodiment, the N-terminal ActA protein fragment is N-terminal to the HPV E7 antigen. In another embodiment, the N-terminal ActA protein fragment is the N-terminal-most portion of the fusion protein. Each possibility represents a separate embodiment of the present invention.

In another embodiment, the present invention provides a method of treating a cervical cancer in a human subject, comprising the step of administering to the subject a recombinant *Listeria* strain, the recombinant *Listeria* strain comprising a recombinant polypeptide comprising a PEST-like sequence-containing peptide and an HPV E7 antigen, whereby the recombinant *Listeria* strain induces an immune response against the E7 antigen, thereby treating a cervical cancer in a human subject. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

In another embodiment, the present invention provides a method of protecting a human subject against a cervical cancer, comprising the step of administering to the subject a recombinant *Listeria* strain, the recombinant *Listeria* strain comprising a recombinant polypeptide comprising a PEST-like sequence-containing peptide and an HPV E7 antigen, whereby the recombinant *Listeria* strain induces an immune response against the E7 antigen, thereby protecting a human subject against a cervical cancer. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

In another embodiment, the present invention provides a method for inducing an immune response against a cervical cancer in a human subject, comprising the step of administering to the subject a recombinant *Listeria* strain, the recombinant *Listeria* strain comprising a recombinant polypeptide comprising a PEST-like sequence-containing peptide and an HPV E7 antigen, thereby inducing an immune response against a cervical cancer in a human subject. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

The PEST-like sequence-containing peptide and HPV E7 antigen are, in another embodiment, fused directly to one another. In another embodiment, the genes encoding the PEST-like sequence-containing peptide and HPV E7 antigen are fused directly to one another. In another embodiment, the PEST-like sequence-containing peptide and HPV E7 antigen are attached via a linker peptide. In another embodiment, the PEST-like sequence-containing peptide and HPV E7 antigen are attached via a heterologous peptide. In another embodiment, the PEST-like sequence-containing peptide is N-terminal to the HPV E7 antigen. In another embodiment, the PEST-like sequence-containing peptide is the N-terminal-most portion of the fusion protein. Each possibility represents a separate embodiment of the present invention.

As provided herein, recombinant *Listeria* strains expressing PEST-like sequence-antigen fusions induce anti-tumor immunity (Example 3) and generate antigen-specific, tumor-infiltrating T cells (Example 4). Further, recombinant *Listeria* strains of the present invention are safe and improve disease indicators in human subjects (Example 10).

In another embodiment, the present invention provides a method for vaccinating a human subject against an HPV, comprising the step of administering to the subject a recombinant *Listeria* strain, the recombinant *Listeria* strain comprising a recombinant polypeptide comprising an N-terminal fragment of an LLO protein and an HPV E7 antigen, thereby vaccinating a human subject against an HPV. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

In another embodiment, the present invention provides a method for vaccinating a human subject against an HPV, comprising the step of administering to the subject a recombinant *Listeria* strain, the recombinant *Listeria* strain comprising a recombinant polypeptide comprising a PEST-like sequence-containing peptide and an HPV E7 antigen, thereby vaccinating a human subject against an HPV. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

In another embodiment, the present invention provides a method for vaccinating a human subject against an HPV, comprising the step of administering to the subject a recombinant *Listeria* strain, the recombinant *Listeria* strain comprising a recombinant polypeptide comprising an N-terminal fragment of an LLO protein and an HPV E7 antigen, thereby vaccinating a human subject against an HPV. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

As provided herein, recombinant *Listeria* strains expressing fusions of an antigen to LLO, ActA, or a PEST-like sequence-containing peptide induce anti-E6 and E7 immunity (Example 3), and abrogate central and peripheral tolerance to antigens such as E6 and E7 (Examples 5-9). Further, recombinant *Listeria* strains of the present invention are safe and improve disease indicators in human subjects (Example 10). Thus, *Listeria* strains of the present invention can be used to vaccinate a subject against an HPV, thereby preventing or inhibiting HPV-mediated carcinogenesis.

In another embodiment, the subject is at risk for developing an HPV-mediated carcinogenesis (e.g. a cervical cancer). In another embodiment, the subject is HPV-positive. In another embodiment, the subject's husband is HPV-positive. In another embodiment, the subject exhibits cervical intraepithelial neoplasia. In another embodiment, the subject exhibits a squamous intraepithelial lesion. In another embodiment, the subject exhibits a dysplasia in the cervix. Each possibility represents a separate embodiment of the present invention.

The HPV that is the target of methods of the present invention is, in another embodiment, an HPV 16. In another embodiment, the HPV is an HPV-18. In another embodiment, the HPV is selected from HPV-16 and HPV-18. In another embodiment, the HPV is an HPV-31. In another embodiment, the HPV is an HPV-35. In another embodiment, the HPV is an HPV-39. In another embodiment, the HPV is an HPV-45. In another embodiment, the HPV is an HPV-51. In another embodiment, the HPV is an HPV-52. In another embodiment, the HPV is an HPV-58. In another embodiment, the HPV is a high-risk HPV type. In another embodiment, the HPV is a mucosal HPV type. Each possibility represents a separate embodiment of the present invention.

In another embodiment, the present invention provides a method for inducing a regression of a cervical cancer in a human subject, comprising the step of administering to the subject a recombinant *Listeria* strain, the recombinant *Listeria* strain comprising a recombinant polypeptide comprising an N-terminal fragment of an LLO protein and an HPV E7 antigen, thereby inducing a regression of a cervical cancer in a human subject. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

In another embodiment, the present invention provides a method for reducing an incidence of relapse of a cervical cancer in a human subject, comprising the step of administering to the subject a recombinant *Listeria* strain, the recombinant *Listeria* strain comprising a recombinant polypeptide comprising an N-terminal fragment of an LLO protein and an HPV E7 antigen, thereby reducing an incidence of relapse of a cervical cancer in a human subject. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

In another embodiment, the present invention provides a method for suppressing a formation of a cervical tumor in a human subject, comprising the step of administering to the subject a recombinant *Listeria* strain, the recombinant *Listeria* strain comprising a recombinant polypeptide comprising an N-terminal fragment of an LLO protein and an HPV E7 antigen, thereby suppressing a formation of a cervical tumor in a human subject. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

In another embodiment, the present invention provides a method for inducing a remission of a cervical cancer in a human subject, comprising the step of administering to the subject a recombinant *Listeria* strain, the recombinant *Listeria* strain comprising a recombinant polypeptide comprising an N-terminal fragment of an LLO protein and an HPV E7 antigen, thereby inducing a remission of a cervical cancer in a human subject. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

In another embodiment, the present invention provides a method for impeding a growth of a cervical tumor in a human subject, comprising the step of administering to the subject a recombinant *Listeria* strain, the recombinant *Listeria* strain comprising a recombinant polypeptide comprising an N-terminal fragment of an LLO protein and an HPV E7 antigen, thereby impeding a growth of a cervical tumor in a human subject. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

In another embodiment, the present invention provides a method for reducing a size of a cervical tumor in a human subject, comprising the step of administering to the subject a recombinant *Listeria* strain, the recombinant *Listeria* strain comprising a recombinant polypeptide comprising an N-terminal fragment of an LLO protein and an HPV E7 antigen, thereby reducing a size of a cervical tumor in a human subject. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

The cervical tumor targeted by methods of the present invention is, in another embodiment, a squamous cell carcinoma. In another embodiment, the cervical tumor is an adenocarcinoma. In another embodiment, the cervical tumor is an adenosquamous carcinoma. In another embodiment, the cervical tumor is a small cell carcinoma. In another embodiment, the cervical tumor is any other type of cervical tumor known in the art. Each possibility represents a separate embodiment of the present invention.

In another embodiment, an HPV E6 antigen is utilized instead of or in addition to an E7 antigen in a method of the present invention for treating, protecting against, or inducing an immune response against a cervical cancer.

In another embodiment, an ActA protein fragment is utilized instead of or in addition to an LLO fragment in a method of the present invention for treating, protecting against, or inducing an immune response against a cervical cancer.

In another embodiment, a PEST-like sequence-containing protein fragment is utilized instead of or in addition to an LLO fragment in a method of the present invention for treating, protecting against, or inducing an immune response against a cervical cancer.

In another embodiment, the present invention provides a method for inducing an anti-E7 cytotoxic T cell (CTL) response in a human subject, comprising the step of administering to the subject a recombinant *Listeria* strain, the recombinant *Listeria* strain comprising a recombinant polypeptide comprising an N-terminal fragment of an LLO protein and an HPV E7 antigen, thereby inducing an anti-E7 CTL response in a human subject. In another embodiment, the recombinant *Listeria* strain comprises a plasmid that encodes the recombinant polypeptide. In another embodiment, the method further comprises the step of boosting the subject with a recombinant *Listeria* strain of the present invention. In another embodiment, the method further comprises the step of boosting the subject with an immunogenic composition comprising an E7 antigen. In another embodiment, the method further comprises the step of boosting the subject with an immunogenic composition that directs a cell of the subject to express an E7 antigen. In another embodiment, the CTL response is capable of therapeutic efficacy against an HPV-mediated disease, disorder, or symptom. In another embodiment, the CTL response is capable of prophylactic efficacy against an HPV-mediated disease, disorder, or symptom. Each possibility represents a separate embodiment of the present invention.

In another embodiment, the present invention provides a method of treating or ameliorating an HPV-mediated disease, disorder, or symptom in a subject, comprising the step of administering to the subject a recombinant *Listeria* strain, the recombinant *Listeria* strain comprising a recombinant polypeptide comprising an N-terminal fragment of an LLO protein and an HPV E7 antigen, whereby the recombinant *Listeria* strain induces an immune response against the E7 antigen, thereby treating or ameliorating an HPV-mediated disease, disorder, or symptom in a subject. In another embodiment, the subject is a human subject. In another embodiment, the subject is any other type of subject known in the art. Each possibility represents a separate embodiment of the present invention.

The HPV causing the disease, disorder, or symptom is, in another embodiment, an HPV 16. In another embodiment, the HPV is an HPV-18. In another embodiment, the HPV is an HPV-31. In another embodiment, the HPV is an HPV-35. In another embodiment, the HPV is an HPV-39. In another embodiment, the HPV is an HPV-45. In another embodiment, the HPV is an HPV-51. In another embodiment, the HPV is an HPV-52. In another embodiment, the HPV is an HPV-58. In another embodiment, the HPV is a high-risk HPV type. In another embodiment, the HPV is a mucosal HPV type. Each possibility represents a separate embodiment of the present invention.

In another embodiment, the HPV-mediated disease, disorder, or symptom is genital warts. In another embodiment, the HPV-mediated disease, disorder, or symptom is non-genital warts. In another embodiment, the HPV-mediated disease, disorder, or symptom is a respiratory papilloma. In another embodiment, the HPV-mediated disease, disorder, or symptom is any other HPV-mediated disease, disorder, or symptom known in the art. Each possibility represents a separate embodiment of the present invention.

In another embodiment, an HPV E6 antigen is utilized instead of or in addition to an E7 antigen in a method of the present invention for treating or ameliorating an HPV-mediated disease, disorder, or symptom.

In another embodiment, an ActA protein fragment is utilized instead of or in addition to an LLO fragment in a method of the present invention for treating or ameliorating an HPV-mediated disease, disorder, or symptom.

In another embodiment, a PEST-like sequence-containing protein fragment is utilized instead of or in addition to an LLO fragment in a method of the present invention for treating or ameliorating an HPV-mediated disease, disorder, or symptom.

In another embodiment, an HPV E6 antigen is utilized instead of or in addition to an E7 antigen in a method of the present invention for treating or ameliorating an HPV-mediated disease, disorder, or symptom.

The antigen of methods and compositions of the present invention is, in another embodiment, an HPV E7 protein. In another embodiment, the antigen is an HPV E6 protein. In another embodiment, the antigen is any other HPV protein known in the art. Each possibility represents a separate embodiment of the present invention.

"E7 antigen" refers, in another embodiment, to an E7 protein. In another embodiment, the term refers to an E7 fragment. In another embodiment, the term refers to an E7 peptide. In another embodiment, the term refers to any other type of E7 antigen known in the art. Each possibility represents a separate embodiment of the present invention.

The E7 protein of methods and compositions of the present invention is, in another embodiment, an HPV 16 E7 protein. In another embodiment, the E7 protein is an HPV-18 E7 protein. In another embodiment, the E7 protein is an HPV-31 E7 protein. In another embodiment, the E7 protein is an HPV-35 E7 protein. In another embodiment, the E7 protein is an HPV-39 E7 protein. In another embodiment, the E7 protein is an HPV-45 E7 protein. In another embodiment, the E7 protein is an HPV-51 E7 protein. In another embodiment, the E7 protein is an HPV-52 E7 protein. In another embodiment, the E7 protein is an HPV-58 E7 protein. In another embodiment, the E7 protein is an E7 protein of a high-risk HPV type. In another embodiment, the E7 protein is an E7 protein of a mucosal HPV type. Each possibility represents a separate embodiment of the present invention.

"E6 antigen" refers, in another embodiment, to an E6 protein. In another embodiment, the term refers to an E6 fragment. In another embodiment, the term refers to an E6 peptide. In another embodiment, the term refers to any other type of E6 antigen known in the art. Each possibility represents a separate embodiment of the present invention.

The E6 protein of methods and compositions of the present invention is, in another embodiment, an HPV 16 E6 protein. In another embodiment, the E6 protein is an HPV-18 E6 protein. In another embodiment, the E6 protein is an HPV-31 E6 protein. In another embodiment, the E6 protein is an HPV-35 E6 protein. In another embodiment, the E6 protein is an HPV-39 E6 protein. In another embodiment, the E6 protein is an HPV-45 E6 protein. In another embodiment, the E6 protein is an HPV-51 E6 protein. In another embodiment, the E6 protein is an HPV-52 E6 protein. In another embodiment, the E6 protein is an HPV-58 E6 protein. In another embodiment, the E6 protein is an E6 protein of a high-risk HPV type. In another embodiment, the E6 protein is an E6 protein of a mucosal HPV type. Each possibility represents a separate embodiment of the present invention.

In another embodiment, the present invention provides a method of vaccinating a human subject against an antigen of interest, the method comprising the step of administering intravenously to the human subject a recombinant *Listeria* strain comprising or expressing the antigen of interest, wherein the first peptide is selected from (a) an N-terminal fragment of an LLO protein; (b) an ActA protein or N-terminal fragment thereof; and (c) a PEST-like sequence-containing peptide, thereby vaccinating a human subject against an antigen of interest.

In another embodiment, the present invention provides a method of vaccinating a human subject against an antigen of interest, the method comprising the step of administering intravenously to the human subject an immunogenic composition, comprising a fusion of a first peptide to the antigen of interest, wherein the first peptide is selected from (a) an N-terminal fragment of an LLO protein; (b) an ActA protein or N-terminal fragment thereof; and (c) a PEST-like sequence-containing peptide, thereby vaccinating a human subject against an antigen of interest.

In another embodiment, the present invention provides a method of vaccinating a human subject against an antigen of interest, the method comprising the step of administering intravenously to the human subject a recombinant *Listeria* strain comprising a recombinant polypeptide, the recombinant polypeptide comprising a first peptide fused to the antigen of interest, wherein the first peptide is selected from (a) an N-terminal fragment of an LLO protein; (b) an ActA protein or N-terminal fragment thereof; and (c) a PEST-like sequence-containing peptide, thereby vaccinating a human subject against an antigen of interest.

In another embodiment, the present invention provides a method of inducing a CTL response in a human subject against an antigen of interest, the method comprising the step of administering to the human subject a recombinant *Listeria* strain comprising or expressing the antigen of interest, thereby inducing a CTL response in a human subject against an antigen of interest. In another embodiment, the step of administering is intravenous administration. Each possibility represents a separate embodiment of the present invention.

As provided herein, recombinant *Listeria* strains expressing LLO-antigen fusions induce anti-tumor immunity (Example 1), elicit antigen-specific T cell proliferation (Example 2), generate antigen-specific, tumor-infiltrating T cells (Example 4), and abrogate peripheral tolerance to antigens such as E6 and E7 (Examples 5-9). Thus, vaccines of the present invention are efficacious at inducing immune responses against E7 and E6. Further, the recombinant *Listeria* strains are safe and improve disease indicators in human subjects (Example 10).

In another embodiment, the antigen of interest is HPV-E7. In another embodiment, the antigen is HPV-E6. In another embodiment, the antigen is Her-2. In another embodiment, the antigen is NY-ESO-1. In another embodiment, the antigen is telomerase. In another embodiment, the antigen is SCCE. In another embodiment, the antigen is HMW-MAA. In another embodiment, the antigen is WT-1. In another embodiment, the antigen is HIV-1 Gag. In another embodiment, the antigen is Proteinase 3. In another embodiment, the antigen is Tyrosinase related protein 2. In another embodiment, the antigen is PSA (prostate-specific antigen). In another embodiment, the antigen is selected from E7, E6, Her-2, NY-ESO-1, telomerase, SCCE, HMW-MAA, WT-1, HIV-1 Gag, Proteinase 3, Tyrosinase related protein 2, PSA (prostate-specific antigen). In another embodiment, the antigen is a tumor-associated antigen. In another embodiment, the antigen is an infectious disease antigen.

In other embodiments, the antigen is derived from a fungal pathogen, bacteria, parasite, helminth, or viruses. In other embodiments, the antigen is selected from tetanus toxoid, hemagglutinin molecules from influenza virus, diphtheria toxoid, HIV gp120, HIV gag protein, IgA protease, insulin peptide B, *Spongospora subterranea* antigen, vibriose antigens, *Salmonella* antigens, pneumococcus antigens, respiratory syncytial virus antigens, *Haemophilus influenza* outer membrane proteins, *Helicobacter pylori* urease, *Neisseria meningitidis* pilins, *N. gonorrhoeae* pilins, the melanoma-associated antigens (TRP-2, MAGE-1, MAGE-3, gp-100, tyrosinase, MART-1, HSP-70, beta-HCG), human papilloma virus antigens E1 and E2 from type HPV-16, -18, -31, -33, -35 or -45 human papilloma viruses, the tumor antigens CEA, the ras protein, mutated or otherwise, the p53 protein, mutated or otherwise, Muc1, or pSA.

In other embodiments, the antigen is associated with one of the following diseases; cholera, diphtheria, *Haemophilus*, hepatitis A, hepatitis B, influenza, measles, meningitis, mumps, pertussis, small pox, pneumococcal pneumonia, polio, rabies, rubella, tetanus, tuberculosis, typhoid, Varicella-zoster, whooping cough3 yellow fever, the immunogens and antigens from Addison's disease, allergies, anaphylaxis, Bruton's syndrome, cancer, including solid and blood borne tumors, eczema, Hashimoto's thyroiditis, polymyositis, dermatomyositis, type 1 diabetes mellitus, acquired immune deficiency syndrome, transplant rejection, such as kidney, heart, pancreas, lung, bone, and liver transplants, Graves' disease, polyendocrine autoimmune disease, hepatitis, microscopic polyarteritis, polyarteritis nodosa, pemphigus, primary biliary cirrhosis, pernicious anemia, coeliac disease, antibody-mediated nephritis, glomerulonephritis, rheumatic diseases, systemic lupus erthematosus, rheumatoid arthritis, seronegative spondylarthritides, rhinitis, sjogren's syndrome, systemic sclerosis, sclerosing cholangitis, Wegener's granulomatosis, dermatitis herpetiformis, psoriasis, vitiligo, multiple sclerosis, encephalomyelitis, Guillain-Barre syndrome, myasthenia gravis, Lambert-Eaton syndrome, sclera, episclera, uveitis, chronic mucocutaneous candidiasis, urticaria, transient hypogammaglobulinemia of infancy, myeloma, X-linked hyper IgM syndrome, Wiskott-Aldrich syndrome, ataxia telangiectasia, autoimmune hemolytic anemia, autoimmune thrombocytopenia, autoimmune neutropenia, Waldenstrom's macroglobulinemia, amyloidosis, chronic lymphocytic leukemia, non-Hodgkin's lymphoma, malarial circumsporozoite protein, microbial antigens, viral antigens, autoantigens, and listeriosis.

In other embodiments, the antigen is 1 of the following tumor antigens: a MAGE (Melanoma-Associated Antigen E) protein, e.g. MAGE 1, MAGE 2, MAGE 3, MAGE 4, a tyrosinase; a mutant ras protein; a mutant p53 protein; p97 melanoma antigen, a ras peptide or p53 peptide associated with advanced cancers; the HPV 16/18 antigens associated with cervical cancers, KLH antigen associated with breast carcinoma, CEA (carcinoembryonic antigen) associated with colorectal cancer, gp100, a MARTI antigen associated with melanoma, or the PSA antigen associated with prostate cancer.

Each antigen represents a separate embodiment of the present invention.

The immune response induced by methods and compositions of the present invention is, in another embodiment, a T cell response. In another embodiment, the immune response comprises a T cell response. In another embodiment, the response is a CD8+ T cell response. In another embodiment, the response comprises a CD8+ T cell response. Each possibility represents a separate embodiment of the present invention.

The N-terminal LLO protein fragment of methods and compositions of the present invention comprises, in another embodiment, SEQ ID No: 1. In another embodiment, the fragment comprises an LLO signal peptide. In another embodiment, the fragment comprises SEQ ID No: 25. In another embodiment, the fragment consists approximately of SEQ ID No: 25. In another embodiment, the fragment consists essentially of SEQ ID No: 25. In another embodiment, the fragment corresponds to SEQ ID No: 25. In another embodiment, the fragment is homologous to SEQ ID No: 25. In another embodiment, the fragment is homologous to a fragment of SEQ ID No: 25. The ΔLLO used in some of the Examples was 416 AA long (exclusive of the signal sequence), as 88 residues from the amino terminus which is inclusive of the activation domain containing cysteine 484 were truncated. It will be clear to those skilled in the art that any ΔLLO without the activation domain, and in particular without cysteine 484, are suitable for methods and compositions of the present invention. In another embodiment, fusion of an E7 or E6 antigen to any ΔLLO, including the PEST-like AA sequence, SEQ ID NO: 1, enhances cell mediated and anti-tumor immunity of the antigen. Each possibility represents a separate embodiment of the present invention.

The LLO protein utilized to construct vaccines of the present invention has, in another embodiment, the sequence:

```
MKKIMLVFITLILVSLPIAQQTEAKDASAFNKENSISSMAPPASPPASPKT
PIEKKHADEIDKYIQGLDYNKNNVLVYHGDAVTNVPPRKGYKDGNEYIVVE
KKKKSINQNNADIQVVNAISSLTYPGALVKANSELVENQPDVLPVKRDSLT
LSIDLPGMTNQDNKIVVKNATKSNVNNAVNTLVERWNEKYAQAYPNVSAKI
DYDDEMAYSESQLIAKFGTAFKAVNNSLNVNFGAISEGKMQEEVISFKQIY
YNVNVNEPTRPSRFFGKAVTKEQLQALGVNAENPPAYISSVAYGRQVYLKL
STNSHSTKVKAAFDAAVSGKSVSGDVELTNIIKNSSFKAVIYGGSAKDEVQ
IIDGNLGDLRDILKKGATFNRETPGVPIAYTTNFLKDNELAVIKANNSEYI
ETTKAYTDGKINIDHSGGYVAQFNISWDEVNYDPEGNEIVQHKNWSENNKS
KLAHFTSSIYLPGNARNINVYAKECTGLAWEWWRTVIDDRNLPLVKNRNIS
IWGTTLPKYSNKVDNPIE
```

(GenBank Accession No. P13128; SEQ ID NO: 27; nucleic acid sequence is set forth in GenBank Accession No. X15127). The first 25 AA of the proprotein corresponding to this sequence are the signal sequence and are cleaved from LLO when it is secreted by the bacterium. Thus, in this embodiment, the full length active LLO protein is 504 residues long. In another embodiment, the above LLO fragment is used as the source of the LLO fragment incorporated in a vaccine of the present invention. Each possibility represents a separate embodiment of the present invention.

In another embodiment, the N-terminal fragment of an LLO protein utilized in compositions and methods of the present invention has the sequence:

```
                                      (SEQ ID NO: 25)
MKKIMLVFITLILVSLPIAQQTEAKDASAFNKENSISSVAPPASPPASPKT
PIEKKHADEIDKYIQGLDYNKNNVLVYHGDAVTNVPPRKGYKDGNEYIVVE
KKKKSINQNNADIQVVNAISSLTYPGALVKANSELVENQPDVLPVKRDSLT
LSIDLPGMTNQDNKIVVKNATKSNVNNAVNTLVERWNEKYAQAYSNVSAKI
DYDDEMAYSESQLIAKFGTAFKAVNNSLNVNFGAISEGKMQEEVISFKQIY
YNVNVNEPTRPSRFFGKAVTKEQLQALGVNAENPPAYISSVAYGRQVYLKL
TSTNSHSKVKAAFDAAVSGKSVSGDVELTNIIKNSSFKAVIYGGSAKDEVQ
DIIDGNLGLRDILKKGATFNRETPGVPIAYTTNFLKDNELAVIKNNSEYIE
TTSKAYTDGKINIDHSGGYVAQFNISWDEVNYD.
```

In another embodiment, the LLO fragment corresponds to about AA 20-442 of an LLO protein utilized herein.

In another embodiment, the LLO fragment has the sequence:

(SEQ ID NO: 26)
MKKIMLVFITLILVSLPIAQQTEAKDASAFNKENSISSVAPPASPPASPKT

PIEKKHADEIDKYIQGLDYNKNNVLVYHGDAVTNVPPRKGYKDGNEYIVVE

KKKKSINQNNADIQVVNAISSLTYPGALVKANSELVENQPDVLPVKRDSLT

LSIDLPGMTNQDNKIVVKNATKSNVNNAVNTLVERWNEKYAQAYSNVSAKI

DYDDEMAYSESQLIAKFGTAFKAVNNSLNVNFGAISEGKMQEEVISFKQIY

YNVNVNEPTRPSRFFGKAVTKEQLQALGVNAENPPAYISSVAYGRQVYLKL

STNSHSTKVKAAFDAAVSGKSVSGDVELTNIIKNSSFKAVIYGGSAKDEVQ

IIDGNLGDLRDILKKGATFNRETPGVPIAYTTNFKDNELAVIKNNSEYIET

TSKAYTD.

In another embodiment, "truncated LLO" or "ΔLLO" refers to a fragment of LLO that comprises the PEST-like domain. In another embodiment, the terms refer to an LLO fragment that comprises a PEST sequence.

In another embodiment, the terms refer to an LLO fragment that does not contain the activation domain at the amino terminus and does not include cysteine 484. In another embodiment, the terms refer to an LLO fragment that is not hemolytic. In another embodiment, the LLO fragment is rendered non-hemolytic by deletion or mutation of the activation domain. In another embodiment, the LLO fragment is rendered non-hemolytic by deletion or mutation of cysteine 484. In another embodiment, the LLO fragment is rendered non-hemolytic by deletion or mutation at another location. Each possibility represents a separate embodiment of the present invention.

In another embodiment, the LLO fragment consists of about the first 441 AA of the LLO protein. In another embodiment, the LLO fragment consists of about the first 420 AA of LLO. In another embodiment, the LLO fragment is a non-hemolytic form of the LLO protein.

In another embodiment, the LLO fragment contains residues of a homologous LLO protein that correspond to one of the above AA ranges. The residue numbers need not, in another embodiment, correspond exactly with the residue numbers enumerated above; e.g. if the homologous LLO protein has an insertion or deletion, relative to an LLO protein utilized herein, then the residue numbers can be adjusted accordingly.

In another embodiment, the LLO fragment is any other LLO fragment known in the art. Each possibility represents a separate embodiment of the present invention.

In another embodiment, the recombinant Listeria strain is administered to the human subject at a dose of $1 \times 10^9$–$3.31 \times 10^{10}$ CFU. In another embodiment, the dose is $5$-$500 \times 10^8$ CFU. In another embodiment, the dose is $7$-$500 \times 10^8$ CFU. In another embodiment, the dose is $10$-$500 \times 10^8$ CFU. In another embodiment, the dose is $20$-$500 \times 10^8$ CFU. In another embodiment, the dose is $30$-$500 \times 10^8$ CFU. In another embodiment, the dose is $50$-$500 \times 10^8$ CFU. In another embodiment, the dose is $70$-$500 \times 10^8$ CFU. In another embodiment, the dose is $100$-$500 \times 10^8$ CFR. In another embodiment, the dose is $150$-$500 \times 10^8$ CFU. In another embodiment, the dose is $5$-$300 \times 10^8$ CFU. In another embodiment, the dose is $5$-$200 \times 10^8$ CFU. In another embodiment, the dose is $5$-$150 \times 10^8$ CFU. In another embodiment, the dose is $5$-$100 \times 10^8$ CFU. In another embodiment, the dose is $5$-$70 \times 10^8$ CFU. In another embodiment, the dose is $5$-$50 \times 10^8$ CFU. In another embodiment, the dose is $5$-$30 \times 10^8$ CFU. In another embodiment, the dose is $5$-$20 \times 10^8$ CFU. In another embodiment, the dose is $1$-$30 \times 10^9$ CFU. In another embodiment, the dose is $1$-$20 \times 10^9$ CFU. In another embodiment, the dose is $2$-$30 \times 10^9$ CFU. In another embodiment, the dose is $1$-$10 \times 10^9$ CFU. In another embodiment, the dose is $2$-$10 \times 10^9$ CFU. In another embodiment, the dose is $3$-$10 \times 10^9$ CFU. In another embodiment, the dose is $2$-$7 \times 10^9$ CFU. In another embodiment, the dose is $2$-$5 \times 10^9$ CFU. In another embodiment, the dose is $3$-$5 \times 10^9$ CFU.

In another embodiment, the dose is $1 \times 10^9$ organisms. In another embodiment, the dose is $1.5 \times 10^9$ organisms. In another embodiment, the dose is $2 \times 10^9$ organisms. In another embodiment, the dose is $3 \times 10^9$ organisms. In another embodiment, the dose is $4 \times 10^9$ organisms. In another embodiment, the dose is $5 \times 10^9$ organisms. In another embodiment, the dose is $6 \times 10^9$ organisms. In another embodiment, the dose is $7 \times 10^9$ organisms. In another embodiment, the dose is $8 \times 10^9$ organisms. In another embodiment, the dose is $10 \times 10^9$ organisms. In another embodiment, the dose is $1.5 \times 10^{10}$ organisms. In another embodiment, the dose is $2 \times 10^{10}$ organisms. In another embodiment, the dose is $2.5 \times 10^{10}$ organisms. In another embodiment, the dose is $3 \times 10^{10}$ organisms. In another embodiment, the dose is $3.3 \times 10^{10}$ organisms. In another embodiment, the dose is $4 \times 10^{10}$ organisms. In another embodiment, the dose is $5 \times 10^{10}$ organisms.

Each dose and range of doses represents a separate embodiment of the present invention.

In another embodiment, the recombinant polypeptide of methods of the present invention is expressed by the recombinant Listeria strain. In another embodiment, the expression is mediated by a nucleotide molecule carried by the recombinant Listeria strain. Each possibility represents a separate embodiment of the present invention.

In another embodiment, the recombinant Listeria strain expresses the recombinant polypeptide by means of a plasmid that encodes the recombinant polypeptide. In another embodiment, the plasmid comprises a gene encoding a bacterial transcription factor. In another embodiment, the plasmid encodes a Listeria transcription factor. In another embodiment, the transcription factor is prfA. In another embodiment, the transcription factor is any other transcription factor known in the art. Each possibility represents a separate embodiment of the present invention.

In another embodiment, the plasmid comprises a gene encoding a metabolic enzyme. In another embodiment, the metabolic enzyme is a bacterial metabolic enzyme. In another embodiment, the metabolic enzyme is a Listerial metabolic enzyme. In another embodiment, the metabolic enzyme is an amino acid metabolism enzyme. In another embodiment, the amino acid metabolism gene is involved in a cell wall synthesis pathway. In another embodiment, the metabolic enzyme is the product of a D-amino acid aminotransferase gene (dat). In another embodiment, the metabolic enzyme is the product of an alanine racemase gene (dal). In another embodiment, the metabolic enzyme is any other metabolic enzyme known in the art. Each possibility represents a separate embodiment of the present invention.

In another embodiment, a method of present invention further comprises the step of boosting the human subject with a recombinant Listeria strain of the present invention. In another embodiment, the recombinant Listeria strain used in the booster inoculation is the same as the strain used in the initial "priming" inoculation. In another embodiment, the booster strain is different from the priming strain. In another embodiment, the same doses are used in the priming and boosting inoculations. In another embodiment, a larger dose is used in the booster. In another embodiment, a smaller dose is used in the booster. Each possibility represents a separate embodiment of the present invention.

In another embodiment, a method of present invention further comprises the step of inoculating the human subject with an immunogenic composition comprising the E7 antigen. In another embodiment, the immunogenic composition comprises a recombinant E7 protein or fragment thereof. In another embodiment, the immunogenic composition comprises a nucleotide molecule expressing a recombinant E7 protein or fragment thereof. In another embodiment, the non-Listerial inoculation is administered after the Listerial inoculation. In another embodiment, the non-Listerial inoculation is administered before the Listerial inoculation. Each possibility represents a separate embodiment of the present invention.

"Boosting" refers, in another embodiment, to administration of an additional vaccine dose to a subject. In another embodiment of methods of the present invention, 2 boosts (or a total of 3 inoculations) are administered. In another embodiment, 3 boosts are administered. In another embodiment, 4 boosts are administered. In another embodiment, 5 boosts are administered. In another embodiment, 6 boosts are administered. In another embodiment, more than 6 boosts are administered. Each possibility represents a separate embodiment of the present invention.

The recombinant *Listeria* strain of methods and compositions of the present invention is, in another embodiment, a recombinant *Listeria monocytogenes* strain. In another embodiment, the *Listeria* strain is a recombinant *Listeria seeligeri* strain. In another embodiment, the *Listeria* strain is a recombinant *Listeria grayi* strain. In another embodiment, the *Listeria* strain is a recombinant *Listeria ivanovii* strain. In another embodiment, the *Listeria* strain is a recombinant *Listeria murrayi* strain. In another embodiment, the *Listeria* strain is a recombinant *Listeria welshimeri* strain. In another embodiment, the *Listeria* strain is a recombinant strain of any other *Listeria* species known in the art. Each possibility represents a separate embodiment of the present invention.

In another embodiment, a recombinant *Listeria* strain of the present invention has been passaged through an animal host. In another embodiment, the passaging maximizes efficacy of the strain as a vaccine vector. In another embodiment, the passaging stabilizes the immunogenicity of the *Listeria* strain. In another embodiment, the passaging stabilizes the virulence of the *Listeria* strain. In another embodiment, the passaging increases the immunogenicity of the *Listeria* strain. In another embodiment, the passaging increases the virulence of the *Listeria* strain. In another embodiment, the passaging removes unstable sub-strains of the *Listeria* strain. In another embodiment, the passaging reduces the prevalence of unstable sub-strains of the *Listeria* strain. In another embodiment, the *Listeria* strain contains a genomic insertion of the gene encoding the antigen-containing recombinant peptide. In another embodiment, the *Listeria* strain carries a plasmid comprising the gene encoding the antigen-containing recombinant peptide. In another embodiment, the passaging is performed as described herein (e.g. in Example 12). In another embodiment, the passaging is performed by any other method known in the art. Each possibility represents a separate embodiment of the present invention.

In another embodiment, the recombinant *Listeria* strain utilized in methods of the present invention has been stored in a frozen cell bank. In another embodiment, the recombinant *Listeria* strain has been stored in a lyophilized cell bank. Each possibility represents a separate embodiment of the present invention.

In another embodiment, the cell bank of methods and compositions of the present invention is a master cell bank. In another embodiment, the cell bank is a working cell bank. In another embodiment, the cell bank is Good Manufacturing Practice (GMP) cell bank. In another embodiment, the cell bank is intended for production of clinical-grade material. In another embodiment, the cell bank conforms to regulatory practices for human use. In another embodiment, the cell bank is any other type of cell bank known in the art. Each possibility represents a separate embodiment of the present invention.

"Good Manufacturing Practices" are defined, in another embodiment, by (21 CFR 210-211) of the United States Code of Federal Regulations. In another embodiment, "Good Manufacturing Practices" are defined by other standards for production of clinical-grade material or for human consumption; e.g. standards of a country other than the United States. Each possibility represents a separate embodiment of the present invention.

In another embodiment, a recombinant *Listeria* strain utilized in methods of the present invention is from a batch of vaccine doses.

In another embodiment, a recombinant *Listeria* strain utilized in methods of the present invention is from a frozen stock produced by a method disclosed herein.

In another embodiment, a recombinant *Listeria* strain utilized in methods of the present invention is from a lyophilized stock produced by a method disclosed herein.

In another embodiment, a cell bank, frozen stock, or batch of vaccine doses of the present invention exhibits viability upon thawing of greater than 90%. In another embodiment, the thawing follows storage for cryopreservation or frozen storage for 24 hours. In another embodiment, the storage is for 2 days. In another embodiment, the storage is for 3 days. In another embodiment, the storage is for 4 days. In another embodiment, the storage is for 1 week.

In another embodiment, the storage is for 2 weeks. In another embodiment, the storage is for 3 weeks. In another embodiment, the storage is for 1 month. In another embodiment, the storage is for 2 months. In another embodiment, the storage is for 3 months. In another embodiment, the storage is for 5 months. In another embodiment, the storage is for 6 months. In another embodiment, the storage is for 9 months. In another embodiment, the storage is for 1 year. Each possibility represents a separate embodiment of the present invention.

In another embodiment, a cell bank, frozen stock, or batch of vaccine doses of the present invention is cryopreserved by a method that comprises growing a culture of the *Listeria* strain in a nutrient media, freezing the culture in a solution comprising glycerol, and storing the *Listeria* strain at below −20 degrees Celsius. In another embodiment, the temperature is about −70 degrees Celsius. In another embodiment, the temperature is about −70-−80 degrees Celsius.

In another embodiment, a cell bank, frozen stock, or batch of vaccine doses of the present invention is cryopreserved by a method that comprises growing a culture of the *Listeria* strain in a defined media of the present invention (as described below), freezing the culture in a solution comprising glycerol, and storing the *Listeria* strain at below −20 degrees Celsius. In another embodiment, the temperature is about −70 degrees Celsius. In another embodiment, the temperature is about −70-−80 degrees Celsius. In another embodiment, any defined microbiological media of the present invention may be used in this method. Each defined microbiological media represents a separate embodiment of the present invention.

In another embodiment of methods and compositions of the present invention, the culture (e.g. the culture of a *Listeria* vaccine strain that is used to produce a batch of *Listeria* vaccine doses) is inoculated from a cell bank. In another embodiment, the culture is inoculated from a frozen stock. In another embodiment, the culture is inoculated from a starter culture. In another embodiment, the culture is inoculated from a colony. In another embodiment, the culture is inoculated at mid-log growth phase. In another embodiment, the culture is inoculated at approximately mid-log growth phase. In another embodiment, the culture is inoculated at another growth phase. Each possibility represents a separate embodiment of the present invention.

In another embodiment of methods and compositions of the present invention, the solution used for freezing contains glycerol in an amount of 2-20%. In another embodiment, the amount is 2%. In another embodiment, the amount is 20%. In another embodiment, the amount is 1%. In another embodiment, the amount is 1.5%. In another embodiment, the amount is 3%. In another embodiment, the amount is 4%. In another embodiment, the amount is 5%. In another embodiment, the amount is 2%. In another embodiment, the amount is 2%. In another embodiment, the amount is 7%. In another embodiment, the amount is 9%. In another embodiment, the amount is 10%. In another embodiment, the amount is 12%. In another embodiment, the amount is 14%. In another embodiment, the amount is 16%. In another embodiment, the amount is 18%. In another embodiment, the amount is 222%. In another embodiment, the amount is 25%. In another embodiment, the amount is 30%. In another embodiment, the amount is 35%. In another embodiment, the amount is 40%. Each possibility represents a separate embodiment of the present invention.

In another embodiment, the solution used for freezing contains another colligative additive or additive with anti-freeze properties, in place of glycerol. In another embodiment, the solution used for freezing contains another colligative additive or additive with anti-freeze properties, in addition to glycerol. In another embodiment, the additive is mannitol. In another embodiment, the additive is DMSO. In another embodiment, the additive is sucrose. In another embodiment, the additive is any other colligative additive or additive with anti-freeze properties that is known in the art. Each possibility represents a separate embodiment of the present invention.

In another embodiment, the nutrient media utilized for growing a culture of a *Listeria* strain is LB. In another embodiment, the nutrient media is TB. In another embodiment, the nutrient media is a defined media. In another embodiment, the nutrient media is a defined media of the present invention. In another embodiment, the nutrient media is any other type of nutrient media known in the art. Each possibility represents a separate embodiment of the present invention.

In another embodiment of methods and compositions of the present invention, the step of growing is performed with a shake flask. In another embodiment, the flask is a baffled shake flask. In another embodiment, the growing is performed with a batch fermenter. In another embodiment, the growing is performed with a stirred tank or flask. In another embodiment, the growing is performed with an airflit fermenter. In another embodiment, the growing is performed with a fed batch. In another embodiment, the growing is performed with a continuous cell reactor. In another embodiment, the growing is performed with an immobilized cell reactor. In another embodiment, the growing is performed with any other means of growing bacteria that is known in the art. Each possibility represents a separate embodiment of the present invention.

In another embodiment, a constant pH is maintained during growth of the culture (e.g. in a batch fermenter). In another embodiment, the pH is maintained at about 7.0. In another embodiment, the pH is about 6. In another embodiment, the pH is about 6.5. In another embodiment, the pH is about 7.5. In another embodiment, the pH is about 8. In another embodiment, the pH is 6.5-7.5. In another embodiment, the pH is 6-8. In another embodiment, the pH is 6-7. In another embodiment, the pH is 7-8. Each possibility represents a separate embodiment of the present invention.

In another embodiment, a constant temperature is maintained during growth of the culture. In another embodiment, the temperature is maintained at about 37° C. In another embodiment, the temperature is 37° C. In another embodiment, the temperature is 25° C. In another embodiment, the temperature is 27° C. In another embodiment, the temperature is 28° C. In another embodiment, the temperature is 30° C. In another embodiment, the temperature is 32° C. In another embodiment, the temperature is 34° C. In another embodiment, the temperature is 35° C. In another embodiment, the temperature is 36° C. In another embodiment, the temperature is 38° C. In another embodiment, the temperature is 39° C. Each possibility represents a separate embodiment of the present invention.

In another embodiment, a constant dissolved oxygen concentration is maintained during growth of the culture. In another embodiment, the dissolved oxygen concentration is maintained at 20% of saturation. In another embodiment, the concentration is 15% of saturation. In another embodiment, the concentration is 16% of saturation. In another embodiment, the concentration is 18% of saturation. In another embodiment, the concentration is 22% of saturation. In another embodiment, the concentration is 25% of saturation. In another embodiment, the concentration is 30% of saturation. In another embodiment, the concentration is 35% of saturation. In another embodiment, the concentration is 40% of saturation. In another embodiment, the concentration is 45% of saturation. In another embodiment, the concentration is 50% of saturation. In another embodiment, the concentration is 55% of saturation. In another embodiment, the concentration is 60% of saturation. In another embodiment, the concentration is 65% of saturation. In another embodiment, the concentration is 70% of saturation. In another embodiment, the concentration is 75% of saturation. In another embodiment, the concentration is 80% of saturation. In another embodiment, the concentration is 85% of saturation. In another embodiment, the concentration is 90% of saturation. In another embodiment, the concentration is 95% of saturation. In another embodiment, the concentration is 100% of saturation. In another embodiment, the concentration is near 100% of saturation. Each possibility represents a separate embodiment of the present invention.

In another embodiment of methods and compositions of the present invention, the culture is grown in media having a maximum volume of 2 liters (L) per vessel. In another embodiment, the media has a maximum volume of 200 ml per vessel. In another embodiment, the media has a maximum volume of 300 ml per vessel. In another embodiment, the media has a maximum volume of 500 ml per vessel. In another embodiment, the media has a maximum volume of 750 ml per vessel. In another embodiment, the media has a maximum volume of 1 L per vessel. In another embodiment, the media has a maximum volume of 1.5 L per vessel. In another embodiment, the media has a maximum volume of 2.5 L per vessel. In another embodiment, the media has a maximum volume of 3 L per vessel.

In another embodiment, the media has a minimum volume of 2 L per vessel. In another embodiment, the media has a minimum volume of 500 ml per vessel. In another embodiment, the media has a minimum volume of 750 ml per vessel. In another embodiment, the media has a minimum volume of 1 L per vessel. In another embodiment, the media has a minimum volume of 1.5 L per vessel. In another embodiment, the media has a minimum volume of 2.5 L per vessel. In another embodiment, the media has a minimum volume of 3 L per vessel. In another embodiment, the media has a minimum volume of 4 L per vessel. In another embodiment, the media has a minimum volume of 5 L per vessel. In another embodiment, the media has a minimum volume of 6 L per vessel. In another embodiment, the media has a minimum volume of 8 L per vessel. In another embodiment, the media has a minimum volume of 10 L per vessel.

Each volume represents a separate embodiment of the present invention.

In another embodiment of methods and compositions of the present invention, the step of freezing or lyophilization is performed when the culture has an $OD_{600}$ of 0.7 units. In another embodiment, the culture has an $OD_{600}$ of 0.8 units. In another embodiment, the $OD_{600}$ is about 0.7 units. In another embodiment, the $OD_{600}$ is about 0.8 units. In another embodiment, the $OD_{600}$ is 0.6 units. In another embodiment, the $OD_{600}$ is 0.65 units. In another embodiment, the $OD_{600}$ is 0.75 units. In another embodiment, the $OD_{600}$ is 0.85 units. In another embodiment, the $OD_{600}$ is 0.9 units. In another embodiment, the $OD_{600}$ is 1 unit. In another embodiment, the $OD_{600}$ is 0.6-0.9 units. In another embodiment, the $OD_{600}$ is 0.65-0.9 units. In another embodiment, the $OD_{600}$ is 0.7-0.9 units. In another embodiment, the $OD_{600}$ is 0.75-0.9 units. In another embodiment, the $OD_{600}$ is 0.8-0.9 units. In another embodiment, the $OD_{600}$ is 0.75-1 units. In another embodiment, the $OD_{600}$ is 0.9-1 units. In another embodiment, the $OD_{600}$ is greater than 1 unit.

In another embodiment, the $OD_{600}$ is significantly greater than 1 unit (e.g. when the culture is produced in a batch fermenter). In another embodiment, the $OD_{600}$ is 7.5-8.5 units. In another embodiment, the $OD_{600}$ is 1.2 units. In another embodiment, the $OD_{600}$ is 1.5 units. In another embodiment, the $OD_{600}$ is 2 units. In another embodiment, the $OD_{600}$ is 2.5 units. In another embodiment, the $OD_{600}$ is 3 units. In another embodiment, the $OD_{600}$ is 3.5 units. In another embodiment, the $OD_{600}$ is 4 units. In another embodiment, the $OD_{600}$ is 4.5 units. In another embodiment, the $OD_{600}$ is 5 units. In another embodiment, the $OD_{600}$ is 5.5 units. In another embodiment, the $OD_{600}$ is 6 units. In another embodiment, the $OD_{600}$ is 6.5 units. In another embodiment, the $OD_{600}$ is 7 units. In another embodiment, the $OD_{600}$ is 7.5 units. In another embodiment, the $OD_{600}$ is 8 units. In another embodiment, the $OD_{600}$ is 8.5 units. In another embodiment, the $OD_{600}$ is 9 units. In another embodiment, the $OD_{600}$ is 9.5 units. In another embodiment, the $OD_{600}$ is 10 units. In another embodiment, the $OD_{600}$ is more than 10 units.

In another embodiment, the $OD_{600}$ is 1-2 units. In another embodiment, the $OD_{600}$ is 1.5-2.5 units. In another embodiment, the $OD_{600}$ is 2-3 units. In another embodiment, the $OD_{600}$ is 2.5-3.5 units. In another embodiment, the $OD_{600}$ is 3-4 units. In another embodiment, the $OD_{600}$ is 3.5-4.5 units. In another embodiment, the $OD_{600}$ is 4-5 units. In another embodiment, the $OD_{600}$ is 4.5-5.5 units. In another embodiment, the $OD_{600}$ is 5-6 units. In another embodiment, the $OD_{600}$ is 5.5-6.5 units. In another embodiment, the $OD_{600}$ is 1-3 units. In another embodiment, the $OD_{600}$ is 1.5-3.5 units.

In another embodiment, the $OD_{600}$ is 2-4 units. In another embodiment, the $OD_{600}$ is 2.5-4.5 units. In another embodiment, the $OD_{600}$ is 3-5 units. In another embodiment, the $OD_{600}$ is 4-6 units. In another embodiment, the $OD_{600}$ is 5-7 units. In another embodiment, the $OD_{600}$ is 2-5 units. In another embodiment, the $OD_{600}$ is 3-6 units. In another embodiment, the $OD_{600}$ is 4-7 units. In another embodiment, the $OD_{600}$ is 5-8 units. In another embodiment, the $OD_{600}$ is 1.2-7.5 units. In another embodiment, the $OD_{600}$ is 1.5-7.5 units. In another embodiment, the $OD_{600}$ is 2-7.5 units. In another embodiment, the $OD_{600}$ is 2.5-7.5 units. In another embodiment, the $OD_{600}$ is 3-7.5 units. In another embodiment, the $OD_{600}$ is 3.5-7.5 units. In another embodiment, the $OD_{600}$ is 4-7.5 units. In another embodiment, the $OD_{600}$ is 4.5-7.5 units. In another embodiment, the $OD_{600}$ is 5-7.5 units. In another embodiment, the $OD_{600}$ is 5.5-7.5 units. In another embodiment, the $OD_{600}$ is 6-7.5 units. In another embodiment, the $OD_{600}$ is 6.5-7.5 units. In another embodiment, the $OD_{600}$ is 7-7.5 units. In another embodiment, the $OD_{600}$ is more than 10 units. In another embodiment, the $OD_{600}$ is 1.2-8.5 units. In another embodiment, the $OD_{600}$ is 1.5-8.5 units. In another embodiment, the $OD_{600}$ is 2-8.5 units. In another embodiment, the $OD_{600}$ is 2.5-8.5 units. In another embodiment, the $OD_{600}$ is 3-8.5 units. In another embodiment, the $OD_{600}$ is 3.5-8.5 units. In another embodiment, the $OD_{600}$ is 4-8.5 units. In another embodiment, the $OD_{600}$ is 4.5-8.5 units. In another embodiment, the $OD_{600}$ is 5-8.5 units. In another embodiment, the $OD_{600}$ is 5.5-8.5 units. In another embodiment, the $OD_{600}$ is 6-8.5 units. In another embodiment, the $OD_{600}$ is 6.5-8.5 units. In another embodiment, the $OD_{600}$ is 7-8.5 units. In another embodiment, the $OD_{600}$ is 7.5-8.5 units. In another embodiment, the $OD_{600}$ is 8-8.5 units. In another embodiment, the $OD_{600}$ is 9.5-8.5 units. In another embodiment, the $OD_{600}$ is 10 units.

In another embodiment, the step of freezing or lyophilization is performed when the culture has a biomass of $1 \times 10^9$ colony-forming units (CFU)/ml. In another embodiment, the biomass is $1.5 \times 10^9$ CFR/ml. In another embodiment, the biomass is $1.5 \times 10^9$ CFR/ml. In another embodiment, the biomass is $2 \times 10^9$ CFR/ml. In another embodiment, the biomass is $3 \times 10^9$ CFR/ml. In another embodiment, the biomass is $4 \times 10^9$ CFR/ml. In another embodiment, the biomass is $5 \times 10^9$ CFR/ml. In another embodiment, the biomass is $7 \times 10^9$ CFR/ml. In another embodiment, the biomass is $9 \times 10^9$ CFR/ml. In another embodiment, the biomass is $10 \times 10^9$ CFR/ml. In another embodiment, the biomass is $12 \times 10^9$ CFR/ml. In another embodiment, the biomass is $15 \times 10^9$ CFR/ml. In another embodiment, the biomass is $20 \times 10^9$ CFR/ml. In another embodiment, the biomass is $25 \times 10^9$ CFR/ml. In another embodiment, the biomass is $30 \times 10^9$ CFR/ml. In another embodiment, the biomass is $33 \times 10^9$ CFR/ml. In another embodiment, the biomass is $40 \times 10^9$ CFR/ml. In another embodiment, the biomass is $50 \times 10^9$ CFR/ml. In another embodiment, the biomass is more than $50 \times 10^9$ CFR/ml.

Each number and range of $OD_{600}$ readings and culture biomass measurements represents a separate embodiment of the present invention.

In another embodiment of methods and compositions of the present invention, the *Listeria* culture is flash-frozen in liquid nitrogen, followed by storage at the final freezing temperature. In another embodiment, the culture is frozen in a more gradual manner; e.g. by placing in a vial of the culture in the final storage temperature. In another embodiment, the culture is frozen by any other method known in the art for freezing a bacterial culture. Each possibility represents a separate embodiment of the present invention.

In another embodiment of methods and compositions of the present invention, the storage temperature of the culture is between −20 and −80 degrees Celsius (° C.). In another embodiment, the temperature is significantly below −20° C. In another embodiment, the temperature is not warmer than −70° C. In another embodiment, the temperature is −70° C. In another embodiment, the temperature is about −70° C. In another embodiment, the temperature is −20° C. In another embodiment, the temperature is about −20° C. In another embodiment, the temperature is −30° C. In another embodiment, the temperature is −40° C. In another embodiment, the temperature is −50° C. In another embodiment, the temperature is −60° C. In another embodiment, the temperature is −80° C. In another embodiment, the temperature is −30-−70° C. In another embodiment, the temperature is −40-−70° C. In another embodiment, the temperature is −50-−70° C. In another embodiment, the temperature is −60-−70° C. In another embodiment, the temperature is −30-−80° C. In another embodiment, the temperature is −40-−80° C. In another embodiment, the temperature is −50-−80° C. In another embodiment, the temperature is −60-−80° C. In another embodiment, the temperature is −70-−80° C. In another embodiment, the temperature is colder than −70° C. In another embodiment, the temperature is colder than −80° C. Each possibility represents a separate embodiment of the present invention.

In another embodiment of methods and compositions of the present invention, the cryopreservation, frozen storage, or lyophilization is for a maximum of 24 hours. In another embodiment, the cryopreservation, frozen storage, or lyophilization is for maximum of 2 days. In another embodiment, the cryopreservation, frozen storage, or lyophilization is for maximum of 3 days. In another embodiment, the cryopreservation, frozen storage, or lyophilization is for maximum of 4 days. In another embodiment, the cryopreservation, frozen storage, or lyophilization is for maximum of 1 week. In another embodiment, the cryopreservation, frozen storage, or lyophilization is for maximum of 2 weeks. In another embodiment, the cryopreservation, frozen storage, or lyophilization is for maximum of 3 weeks. In another embodiment, the cryopreservation, frozen storage, or lyophilization is for maximum of 1 month. In another embodiment, the cryopreservation, frozen storage, or lyophilization is for maximum of 2 months. In another embodiment, the cryopreservation, frozen storage, or lyophilization is for maximum of 3 months. In another embodiment, the cryopreservation, frozen storage, or lyophilization is for maximum of 5 months. In another embodiment, the cryopreservation, frozen storage, or lyophilization is for maximum of 6 months. In another embodiment, the cryopreservation, frozen storage, or lyophilization is for maximum of 9 months. In another embodiment, the cryopreservation, frozen storage, or lyophilization is for maximum of 1 year.

In another embodiment, the cryopreservation, frozen storage, or lyophilization is for a minimum of 1 week. In another embodiment, the cryopreservation, frozen storage, or lyophilization is for minimum of 2 weeks. In another embodiment, the cryopreservation, frozen storage, or lyophilization is for minimum of 3 weeks. In another embodiment, the cryopreservation, frozen storage, or lyophilization is for minimum of 1 month. In another embodiment, the cryopreservation, frozen storage, or lyophilization is for minimum of 2 months. In another embodiment, the cryopreservation, frozen storage, or lyophilization is for minimum of 3 months. In another embodiment, the cryopreservation, frozen storage, or lyophilization is for minimum of 5 months. In another embodiment, the cryopreservation, frozen storage, or lyophilization is for minimum of 6 months. In another embodiment, the cryopreservation, frozen storage, or lyophilization is for minimum of 9 months. In another embodiment, the cryopreservation, frozen storage, or lyophilization is for minimum of 1 year. In another embodiment, the cryopreservation, frozen storage, or lyophilization is for minimum of 1.5 years. In another embodiment, the cryopreservation, frozen storage, or lyophilization is for minimum of 2 years. In another embodiment, the cryopreservation, frozen storage, or lyophilization is for minimum of 3 years. In another embodiment, the cryopreservation, frozen storage, or lyophilization is for minimum of 5 years. In another embodiment, the cryopreservation, frozen storage, or lyophilization is for minimum of 7 years. In another embodiment, the cryopreservation, frozen storage, or lyophilization is for minimum of 10 years. In another embodiment, the cryopreservation, frozen storage, or lyophilization is for longer than 10 years.

Each length of cryopreservation, frozen storage, or lyophilization represents a separate embodiment of the present invention.

In another embodiment of methods and compositions of the present invention, the *Listeria* bacteria exhibit exponential growth essentially immediately after thawing following an extended period of cryopreservation or frozen storage (Example 14). In another embodiment, the *Listeria* bacteria exhibit exponential growth essentially immediately after reconstitution following an extended period of lyophilization. In another embodiment, "essentially immediately" refers to within about 1 hour after inoculating fresh media with cells from the cell bank or starter culture. In another embodiment, the bacteria exhibit exponential growth shortly after (e.g. in various embodiments, after 10 minutes (min), 20 min, 30 min, 40 min, 50 min, 1 hour, 75 min, 90 min, 105 min, or 2 hours) thawing following the period of cryopreservation or storage. Each possibility represents a separate embodiment of the present invention.

The "extended period" of cryopreservation, frozen storage, or lyophilization is, in another embodiment, 1 month. In another embodiment, the period is 2 months. In another embodiment, the period is 3 months. In another embodiment, the period is 5 months. In another embodiment, the period is 6 months. In another embodiment, the period is 9 months. In another embodiment, the period is 1 year. In another embodiment, the period is 1.5 years. In another embodiment, the period is 2 years. Each possibility represents a separate embodiment of the present invention.

In another embodiment, "exponential growth" refers to a doubling time that is close to the maximum observed for the conditions (e.g. media type, temperature, etc.) in which the culture is growing. In another embodiment, "exponential growth" refers to a doubling time that is reasonable constant several hours (e.g. 1 hour, 1.5 hours, 2 hours, or 2.5 hours) after dilution of the culture; optionally following a brief recovery period. Each possibility represents a separate embodiment of the present invention.

In another embodiment, a *Listeria* vaccine strain of methods and compositions of the present invention retains a viability of over 90% after thawing following 14 days of cryopreservation (Example 14). In another embodiment, the viability upon thawing is close to 100% following the period of cryopreservation. In another embodiment, the viability upon thawing is about 90%. In another embodiment, the viability upon thawing is close to 90%. In another embodiment, the viability upon thawing is at least 90%. In another embodiment, the viability upon thawing is over 80%. Each possibility represents a separate embodiment of the present invention.

In another embodiment, a *Listeria* vaccine strain of methods and compositions of the present invention retains a viability of over 90% after reconstitution following lyophilization. In another embodiment, the viability upon thawing is close to 100% following the period of lyophilization. In another embodiment, the viability upon thawing is about 90%. In another embodiment, the viability upon thawing is close to 90%. In another embodiment, the viability upon thawing is at least 90%. In another embodiment, the viability upon thawing is over 80%. Each possibility represents a separate embodiment of the present invention.

In another embodiment, a cell bank, frozen stock, or batch of vaccine doses of the present invention is grown in a defined microbiological media, comprising: (1) between about 0.3 and about 0.6 g/L of methionine; and (2) effective amounts of: (a) cysteine; (b) a pH buffer; (c) a carbohydrate; (d) a divalent cation; (e) ferric or ferrous ions; (f) glutamine or another nitrogen source; (g) riboflavin; (h) thioctic acid (also known as lipoic acid); (i) another or more components selected from leucine, isoleucine, valine, arginine, histidine, tryptophan, and phenylalanine; (j) one or more components selected from adenine, biotin, thiamine, pyridoxal, para-aminobenzoic acid, pantothenate, and nicotinamide; and (k) one or more components selected from cobalt, copper, boron, manganese, molybdenum, zinc, calcium, and citrate.

In another embodiment, the cell bank, frozen stock, or batch of vaccine doses is grown in a defined microbiological media, comprising: (1) between about 0.3 and about 0.6 g/L of cysteine; and (2) effective amounts of: (a) methionine; (b) a pH buffer; (c) a carbohydrate; (d) a divalent cation; (e) ferric or ferrous ions; (f) glutamine or another nitrogen source; (g) riboflavin; (h) thioctic acid; (i) one or more components selected from leucine, isoleucine, valine, arginine, histidine, tryptophan, and phenylalanine; (j) one or more components selected from adenine, biotin, thiamine, pyridoxal, para-aminobenzoic acid, pantothenate, and nicotinamide; and (k) one or more components selected from cobalt, copper, boron, manganese, molybdenum, zinc, calcium, and citrate.

In another embodiment, the cell bank, frozen stock, or batch of vaccine doses is grown in a defined microbiological media, comprising: (1) between about 0.00123-0.00246 moles of ferric or ferrous ions per liter; and (2) effective amounts of: (a) a pH buffer; (b) a carbohydrate; (c) a divalent cation; (d) methionine; (e) cysteine; (f) glutamine or another nitrogen source; (g) riboflavin; (h) thioctic acid; (i) one or more components selected from leucine, isoleucine, valine, arginine, histidine, tryptophan, and phenylalanine; (j) one or more components selected from adenine, biotin, thiamine, pyridoxal, para-aminobenzoic acid, pantothenate, and nicotinamide; and (k) one or more components selected from cobalt, copper, boron, manganese, molybdenum, zinc, calcium, and citrate.

In another embodiment, the cell bank, frozen stock, or batch of vaccine doses is grown in a defined microbiological media, comprising: (1) between about 1.8-3.6 g/L of glutamine or another nitrogen source; and (2) effective amounts of: (a) a pH buffer; (b) a carbohydrate: (c) a divalent cation; (d) methionine (e) cysteine; (f) ferric or ferrous ions (g) riboflavin (h); thioctic acid; (i) one or more components selected from leucine, isoleucine, valine, arginine, histidine, tryptophan, and phenylalanine; (j) one or more components selected from adenine, biotin, thiamine, pyridoxal, para-aminobenzoic acid, pantothenate, and nicotinamide; and (k) one or more components selected from cobalt, copper, boron, manganese, molybdenum, zinc, calcium, and citrate.

In another embodiment, the cell bank, frozen stock, or batch of vaccine doses is grown in a defined microbiological media, comprising: (1) between about 15 and about 30 mg/L of riboflavin; and (2) effective amounts of: (a) a pH buffer; (b) a carbohydrate; (c) a divalent cation; (d) methionine; (e) cysteine; (f) ferric or ferrous ions; (g) glutamine or another nitrogen source; (h) thioctic acid; (i) one or more components selected from leucine, isoleucine, valine, arginine, histidine, tryptophan, and phenylalanine; (j) one or more components selected from adenine, biotin, thiamine, pyridoxal, para-aminobenzoic acid, pantothenate, and nicotinamide; and (k) one or more components selected from cobalt, copper, boron, manganese, molybdenum, zinc, calcium, and citrate.

In another embodiment, the cell bank, frozen stock, or batch of vaccine doses is grown in a defined microbiological media, comprising (1) between about 0.3 and about 0.6 g/L of thioctic acid; and (2) effective amounts of: (a) a pH buffer; (b) a carbohydrate (c) a divalent cation; (d) methionine (e) cysteine; (f) ferric or ferrous ions; (g) glutamine or another nitrogen source; (h) riboflavin; (i) one or more components selected from leucine, isoleucine, valine, arginine, histidine, tryptophan, and phenylalanine; (j) one or more components selected from adenine, biotin, thiamine, pyridoxal, para-aminobenzoic acid, pantothenate, and nicotinamide; and (k) one or more components selected from cobalt, copper, boron, manganese, molybdenum, zinc, calcium, and citrate.

In another embodiment, the cell bank, frozen stock, or batch of vaccine doses is grown in a defined microbiological media, comprising: (1) between about 0.3 and about 0.6 g/L each of methionine and cysteine; (2) between about 0.00123 and 0.00246 moles of ferric or ferrous ions per liter; (3) between about 1.8 and about 3.6 g/L of glutamine or another nitrogen source; (4) between about 0.3 and about 0.6 g/L of thioctic acid; (5) between about 15 and about 30 mg/L of riboflavin; and (6) effective amounts of: (a) a pH buffer; (b) a carbohydrate; (c) a divalent cation; (d) one or more components selected from leucine, isoleucine, valine, arginine, histidine, tryptophan, and phenylalanine; (e) one or more components selected from adenine, biotin, thiamine, pyridoxal, para-aminobenzoic acid, pantothenate, and nicotinamide; and (f) one or more components selected from cobalt, copper, boron, manganese, molybdenum, zinc, calcium, and citrate.

In another embodiment, the cell bank, frozen stock, or batch of vaccine doses is grown in a defined microbiological media, comprising: (1) between about 0.3 and about 0.6 g/L each of methionine and cysteine; (2) between about 0.00123 and 0.00246 moles of ferric or ferrous ions per liter; (3) between about 1.8 and about 3.6 g/L of glutamine or another nitrogen source; (4) between about 0.3 and about 0.6 g/L of thioctic acid; (5) between about 15 and about 30 mg/L of riboflavin; and (6) effective amounts of: (a) a pH buffer; (b) a carbohydrate; (c) a divalent cation; (d) leucine; (e) isoleucine; (f) valine; (g) arginine; (h) histidine; (i) tryptophan; (j) phenylalanine; (k) one or more components selected from adenine, biotin, thiamine, pyridoxal, para-aminobenzoic acid, pantothenate, and nicotinamide; and (l) one or more components selected from cobalt, copper, boron, manganese, molybdenum, zinc, calcium, and citrate.

In another embodiment, the cell bank, frozen stock, or batch of vaccine doses is grown in a defined microbiological media, comprising (1) between about 0.3 and about 0.6 g/L each of one or more components selected from leucine, isoleucine, valine, arginine, histidine, tryptophan, and phenylalanine; and (2) effective amounts of: (a) a pH buffer; (b) a carbohydrate; (c) a divalent cation; (d) methionine; (e) cysteine; (f) ferric or ferrous ions; (g) glutamine or another nitrogen source; (h) riboflavin; (i) thioctic acid; (j) one or more components selected from adenine, biotin, thiamine, pyridoxal, para-aminobenzoic acid, pantothenate, and nicotinamide; and (k) one or more components selected from cobalt, copper, boron, manganese, molybdenum, zinc, calcium, and citrate.

In another embodiment, the cell bank, frozen stock, or batch of vaccine doses is grown in a defined microbiological media, comprising (1) between about 0.3 and about 0.6 g/L each of leucine, isoleucine, valine, arginine, histidine, tryptophan, and phenylalanine; and (2) effective amounts of: (a) a pH buffer; (b) a carbohydrate; (c) a divalent cation; (d) methionine; (e) cysteine; (f) ferric or ferrous ions; (g) glutamine or another nitrogen source; (h) riboflavin; (i) thioctic acid; (j) one or more components selected from adenine, biotin, thiamine, pyridoxal, para-aminobenzoic acid, pantothenate, and nicotinamide; and (k) one or more components selected from cobalt, copper, boron, manganese, molybdenum, zinc, calcium, and citrate.

In another embodiment, the cell bank, frozen stock, or batch of vaccine doses is grown in a defined microbiological media, comprising (1) between about 0.2 and about 0.75 of one or more components selected from biotin and adenine; and (2) effective amounts of: (a) a pH buffer; (b) a carbohydrate; (c) a divalent cation; (d) methionine; (e) cysteine; (f) ferric or ferrous ions; (g) glutamine or another nitrogen source; (h) riboflavin; (i) thioctic acid; (j) one or more components selected from leucine, isoleucine, valine, arginine, histidine, tryptophan, and phenylalanine; (k) one or more components selected from thiamine, pyridoxal, para-aminobenzoic acid, pantothenate, and nicotinamide; and (l) one or more components selected from cobalt, copper, boron, manganese, molybdenum, zinc, calcium, and citrate.

In another embodiment, the cell bank, frozen stock, or batch of vaccine doses is grown in a defined microbiological media, comprising (1) between about 3 and about 6 mg/L each of one or more components selected from thiamine, pyridoxal, para-aminobenzoic acid, pantothenate, and nicotinamide; and (2) effective amounts of: (a) a pH buffer; (b) a carbohydrate; (c) a divalent cation; (d) methionine; (e) cysteine; (f) ferric or ferrous ions; (g) glutamine or another nitrogen source; (h) riboflavin; (i) thioctic acid; (j) one or more components selected from leucine, isoleucine, valine, arginine, histidine, tryptophan, and phenylalanine; (k) biotin; (1) adenine; and (1) one or more components selected from cobalt, copper, boron, manganese, molybdenum, zinc, calcium, and citrate.

In another embodiment, the cell bank, frozen stock, or batch of vaccine doses is grown in a defined microbiological media, comprising: (1) between about 0.2 and about 0.75 mg/L each of one or more components selected from biotin and adenine; (2) between about 3 and about 6 mg/L each of one or more components selected from thiamine, pyridoxal, para-aminobenzoic acid, pantothenate, and nicotinamide; and (3) effective amounts of: (a) a pH buffer; (b) a carbohydrate; (c) a divalent cation; (d) methionine; (e) cysteine; (f) ferric or ferrous ions; (g) glutamine or another nitrogen source; (h) riboflavin; (i) thioctic acid; (j) one or more components selected from leucine, isoleucine, valine, arginine, histidine, tryptophan, and phenylalanine; and (k) one or more components selected from cobalt, copper, boron, manganese, molybdenum, zinc, calcium, and citrate.

In another embodiment, the cell bank, frozen stock, or batch of vaccine doses is grown in a defined microbiological media, comprising: (1) between about 0.005 and about 0.02 g/L each of one or more components selected from cobalt, copper, boron, manganese, molybdenum, zinc, and calcium; and (2) effective amounts of: (a) a pH buffer; (b) a carbohydrate; (c) a divalent cation; (d) methionine; (e) cysteine; (f) ferric or ferrous ions; (g) glutamine or another nitrogen source; (h) riboflavin; (i) thioctic acid; (j) one or more components selected from leucine, isoleucine, valine, arginine, histidine, tryptophan, and phenylalanine; and (k) one or more components selected from adenine, biotin, thiamine, pyridoxal, para-aminobenzoic acid, pantothenate, and nicotinamide.

In another embodiment, the cell bank, frozen stock, or batch of vaccine doses is grown in a defined microbiological media, comprising: (1) between about 0.4 and about 1 g/L of citrate; and (2) effective amounts of: (a) a pH buffer; (b) a carbohydrate; (c) a divalent cation; (d) methionine; (e) cysteine; (f) ferric or ferrous ions; (g) glutamine or another nitrogen source; (h) riboflavin; (i) thioctic acid; (j) one or more components selected from leucine, isoleucine, valine, arginine, histidine, tryptophan, and phenylalanine; (k) one or more components selected from cobalt, copper, boron, manganese, molybdenum, zinc, and calcium; and (l) one or more components selected from adenine, biotin, thiamine, pyridoxal, para-aminobenzoic acid, pantothenate, and nicotinamide.

In another embodiment, the cell bank, frozen stock, or batch of vaccine doses is grown in a defined microbiological media, comprising: (1) between about 0.3 and about 0.6 g/L each of methionine and cysteine; (2) between about 0.00123 and 0.00246 moles of ferric or ferrous ions per liter; (3) between about 1.8 and about 3.6 g/L of glutamine or another nitrogen source; (4) between about 0.3 and about 0.6 g/L of thioctic acid; (5) between about 15 and about 30 mg/L of riboflavin; (6) between about 0.3 and about 0.6 g/L each of one or more components selected from leucine, isoleucine, valine, arginine, histidine, tryptophan, and phenylalanine; (7) between about 0.2 and about 0.75 mg/L each of one or more components selected from biotin and adenine; (8) between about 3 and about 6 mg/L each of one or more components selected from thiamine, pyridoxal, para-aminobenzoic acid, pantothenate, and nicotinamide; (9) between about 0.005 and about 0.02 g/L each of one or more components selected from cobalt, copper, boron, manganese, molybdenum, zinc, and calcium; (10) between about 0.4 and about 1 g/L of citrate; and (11) effective amounts of: (a) a pH buffer; (b) a carbohydrate; and (c) a divalent cation.

In another embodiment, the cell bank, frozen stock, or batch of vaccine doses is grown in a defined microbiological media, comprising: (1) between about 0.3 and about 0.6 g/L each of methionine and cysteine; (2) between about 0.00123 and 0.00246 moles of ferric or ferrous ions per liter; (3) between about 1.8 and about 3.6 g/L of glutamine or another nitrogen source; (4) between about 0.3 and about 0.6 g/L of thioctic acid; (5) between about 15 and about 30 mg/L of riboflavin; (6) between about 0.3 and about 0.6 g/L each of leucine, isoleucine, valine, arginine, histidine, tryptophan, and phenylalanine; (7) between about 0.2 and about 0.75 mg/L each of one or more components selected from biotin and adenine; (8) between about 3 and about 6 mg/L each of one or more components selected from thiamine, pyridoxal, para-aminobenzoic acid, pantothenate, and nicotinamide; (9) between about 0.005 and about 0.02 g/L each of one or more components selected from cobalt, copper, boron, manganese, molybdenum, zinc, and calcium; (10) between about 0.4 and about 1 g/L of citrate; and (11) effective amounts of: (a) a pH buffer; (b) a carbohydrate; and (c) a divalent cation.

In another embodiment, the cell bank, frozen stock, or batch of vaccine doses is grown in a defined microbiological media, comprising: (1) between about 0.3 and about 0.6 g/L each of methionine and cysteine; (2) between about 0.00123 and 0.00246 moles of ferric or ferrous ions per liter; (3) between about 1.8 and about 3.6 g/L of glutamine or another nitrogen source; (4) between about 0.3 and about 0.6 g/L of thioctic acid; (5) between about 15 and about 30 mg/L of riboflavin; (6) between about 0.3 and about 0.6 g/L each of leucine, isoleucine, valine, arginine, histidine, tryptophan, and phenylalanine; (7) between about 0.2 and about 0.75 mg/L each of biotin and adenine; (8) between about 3 and about 6 mg/L each of thiamine, pyridoxal, para-aminobenzoic acid, pantothenate, and nicotinamide; (9) between about 0.005 and about 0.02 g/L each of one or more components selected from cobalt, copper, boron, manganese, molybdenum, zinc, and calcium; (10) between about 0.4 and about 1 g/L of citrate; and (11) and effective amounts of: (a) a pH buffer; (b) a carbohydrate; and (c) a divalent cation.

In another embodiment, a defined microbiological media of the present invention further comprises an aqueous solvent. In another embodiment, the aqueous solvent is water. In another embodiment, the aqueous solvent is any other aqueous solvent known in the art. Each possibility represents a separate embodiment of the present invention.

The carbohydrate utilized in methods and compositions of the present invention is, in another embodiment, glucose. In another embodiment, the carbohydrate is lactose. In another embodiment, the carbohydrate is fructose. In another embodiment, the carbohydrate is mannose. In another embodiment, the carbohydrate is cellobiose. In another embodiment, the carbohydrate is trehalose. In another embodiment, the carbohydrate is maltose. In another embodiment, the carbohydrate is glycerol. In another embodiment, the carbohydrate is glucosamine. In another embodiment, the carbohydrate is N-acetylglucosamine. In another embodiment, the carbohydrate is N-acetylmuramic acid. In another embodiment, the carbohydrate is any other carbohydrate that can be utilized by *Listeria*. Each possibility represents a separate embodiment of the present invention.

In another embodiment, the amount of a carbohydrate present in a defined microbiological media of methods and compositions of the present invention is between about 12-18 grams/liter (g/L). In another embodiment, the amount is 15 g/L. In another embodiment, the amount is 10 g/L. In another embodiment, the amount is 9 g/L. In another embodiment, the amount is 11 g/L. In another embodiment, the amount is 12 g/L. In another embodiment, the amount is 13 g/L. In another embodiment, the amount is 14 g/L. In another embodiment, the amount is 16 g/L. In another embodiment, the amount is 17 g/L. In another embodiment, the amount is 18 g/L. In another embodiment, the amount is 19 g/L. In another embodiment, the amount is 20 g/L. In another embodiment, the amount is more than 20 g/L.

In another embodiment, the amount is 9-15 g/L. In another embodiment, the amount is 10-15 g/L. In another embodiment, the amount is 11-15 g/L. In another embodiment, the amount is 12-16 g/L. In another embodiment, the amount is 13-17 g/L. In another embodiment, the amount is 14-18 g/L. In another embodiment, the amount is 16-19 g/L. In another embodiment, the amount is 17-20 g/L. In another embodiment, the amount is 10-20 g/L. In another embodiment, the amount is 12-20 g/L. In another embodiment, the amount is 15-20 g/L.

In another embodiment, the total amount of carbohydrate in the media is one of the above amounts. In another embodiment, the amount of one of the carbohydrates in the media is one of the above amounts. In another embodiment, the amount of each of the carbohydrates in the media is one of the above amounts.

Each of the above amounts of carbohydrates represents a separate embodiment of the present invention.

The cobalt present in defined microbiological media of methods and compositions of the present invention is, in another embodiment, present as a cobalt ion. In another embodiment, the cobalt is present as a cobalt salt. In another embodiment, the salt is cobalt chloride. In another embodiment, the salt is any other cobalt salt known in the art. In another embodiment, the cobalt is present as any other form of cobalt known in the art.

In another embodiment, the cobalt salt is a hydrate (e.g. cobalt chloride hexahydrate). In another embodiment, the cobalt salt is anhydrous. In another embodiment, the cobalt salt is any other form of a cobalt salt known in the art. Each of the above forms of cobalt represents a separate embodiment of the present invention.

A hydrate of a component of a defined media of methods and compositions of the present invention is, in another embodiment, a monohydrate. In another embodiment, the hydrate is a dihydrate. In another embodiment, the hydrate is a trihydrate. In another embodiment, the hydrate is a tetrahydrate. In another embodiment, the hydrate is a pentahydrate. In another embodiment, the hydrate is a hexahydrate. In another embodiment, the hydrate is a heptahydrate. In another embodiment, the hydrate is any other hydrate known in the art. Each possibility represents a separate embodiment of the present invention.

The copper present in defined microbiological media of methods and compositions of the present invention is, in another embodiment, present as a copper ion. In another embodiment, the copper ion is a copper (I) ion. In another embodiment, the copper ion is a copper (II) ion. In another embodiment, the copper ion is a copper (III) ion.

In another embodiment, the copper is present as a copper salt. In another embodiment, the salt is copper chloride. In another embodiment, the salt is any other copper salt known in the art. In another embodiment, the copper is present as any other form of copper known in the art.

In another embodiment, the copper salt is a hydrate (e.g. copper chloride dihydrate). In another embodiment, the copper salt is anhydrous. In another embodiment, the copper salt is any other form of a copper salt known in the art. Each of the above forms of copper represents a separate embodiment of the present invention.

The boron present in defined microbiological media of methods and compositions of the present invention is, in another embodiment, present as a borate ion. In another embodiment, the boron is present as a borate acid (e.g. boric acid, $H_3BO_3$). In another embodiment, the boron is present as any other form of boron known in the art.

In another embodiment, the borate salt or borate acid is a hydrate. In another embodiment, the borate salt or borate acid is anhydrous. In another embodiment, the borate salt or borate acid is any other form of a borate salt or borate acid known in the art. Each of the above forms of boron represents a separate embodiment of the present invention.

The manganese present in defined microbiological media of methods and compositions of the present invention is, in another embodiment, present as a manganese ion. In another embodiment, the manganese is present as a manganese salt. In another embodiment, the salt is manganese sulfate. In another embodiment, the salt is any other manganese salt known in the art. In another embodiment, the manganese is present as any other form of manganese known in the art.

In another embodiment, the manganese salt is a hydrate (e.g. manganese sulfate monohydrate). In another embodiment, the manganese salt is anhydrous. In another embodiment, the manganese salt is any other form of a manganese salt known in the art. Each of the above forms of manganese represents a separate embodiment of the present invention.

The molybdenum present in defined microbiological media of methods and compositions of the present invention is, in another embodiment, present as a molybdate ion. In another embodiment, the molybdenum is present as a molybdate salt. In another embodiment, the salt is sodium molybdate. In another embodiment, the salt is any other molybdate salt known in the art. In another embodiment, the molybdenum is present as any other form of molybdenum known in the art.

In another embodiment, the molybdate salt is a hydrate (e.g. sodium molybdate dihydrate). In another embodiment, the molybdate salt is anhydrous. In another embodiment, the molybdate salt is any other form of a molybdate salt known in the art. Each of the above forms of molybdenum represents a separate embodiment of the present invention.

The zinc present in defined microbiological media of methods and compositions of the present invention is, in another embodiment, present as a zinc ion. In another embodiment, the zinc is present as a zinc salt. In another embodiment, the salt is zinc chloride. In another embodiment, the salt is any other zinc salt known in the art. In another embodiment, the zinc is present as any other form of zinc known in the art.

In another embodiment, the zinc salt is a hydrate (e.g. zinc chloride heptahydrate). In another embodiment, the zinc salt is anhydrous. In another embodiment, the zinc salt is any other form of a zinc salt known in the art. Each of the above forms of zinc represents a separate embodiment of the present invention.

The iron present in defined microbiological media of methods and compositions of the present invention is, in another embodiment, present as a ferric ion. In another embodiment, the iron is present as a ferrous ion. In another embodiment, the iron is present as a ferric salt. In another embodiment, the iron is present as a ferrous salt. In another embodiment, the salt is ferric sulfate. In another embodiment, the salt is ferric citrate. In another embodiment, the salt is any other ferric salt known in the art. In another embodiment, the salt is any other ferrous salt known in the art. In another embodiment, the iron is present as any other form of iron known in the art.

In another embodiment, the ferric or ferrous salt is a hydrate (e.g. ferric sulfate monohydrate). In another embodiment, the ferric or ferrous salt is anhydrous. In another embodiment, the ferric or ferrous salt is any other form of a ferric or ferrous salt known in the art. Each of the above forms of iron represents a separate embodiment of the present invention.

The calcium present in defined microbiological media of methods and compositions of the present invention is, in another embodiment, present as a calcium ion. In another embodiment, the calcium is present as a calcium salt. In another embodiment, the salt is calcium chloride. In another embodiment, the salt is any other calcium salt known in the art. In another embodiment, the calcium is present as any other form of calcium known in the art.

In another embodiment, the calcium salt is a hydrate (e.g. calcium chloride dihydrate). In another embodiment, the calcium salt is anhydrous. In another embodiment, the calcium salt is any other form of a calcium salt known in the art. Each of the above forms of calcium represents a separate embodiment of the present invention.

The citrate present in defined microbiological media of methods and compositions of the present invention is, in another embodiment, present as a citrate ion. In another embodiment, the citrate is present as a citrate salt. In another embodiment, the citrate is present as a citrate acid (e.g. citric acid). In another embodiment, the citrate is present as both ferric citrate and citric acid (Examples 15-16). In another embodiment, the citrate is present as any other form of citrate known in the art.

In another embodiment, the citrate salt or citrate acid is a hydrate. In another embodiment, the citrate salt or citrate acid is anhydrous. In another embodiment, the citrate salt or citrate acid is any other form of a citrate salt or citrate acid known in the art. Each of the above forms of citrate represents a separate embodiment of the present invention.

The cobalt present in defined microbiological media of methods and compositions of the present invention is, in another embodiment, present in an amount of 0.02 g/L (Examples 15-16). In another embodiment, the amount is about 0.02 g/L. In another embodiment, the amount is 0.003 g/L. In another embodiment, the amount is 0.005 g/L. In another embodiment, the amount is 0.007 g/L. In another embodiment, the amount is 0.01 g/L. In another embodiment, the amount is 0.015 g/L. In another embodiment, the amount is 0.025 g/L. In another embodiment, the amount is 0.03 g/L. In another embodiment, the amount is 0.003-0.006 g/L. In another embodiment, the amount is 0.005-0.01 g/L. In another embodiment, the amount is 0.01-0.02 g/L. In another embodiment, the amount is 0.02-0.04 g/L. In another embodiment, the amount is 0.03-0.06 g/L.

In another embodiment, the cobalt is present in an amount that is the molar equivalent of 0.02 g/L of cobalt chloride hexahydrate. In another embodiment, the amount of cobalt present is the molar equivalent of about 0.02 g/L of cobalt chloride hexahydrate. In another embodiment, the amount of cobalt present is the molar equivalent of another of the above amounts or ranges of cobalt chloride hexahydrate. Each of the above amounts or ranges of cobalt represents a separate embodiment of the present invention.

The copper present in defined microbiological media of methods and compositions of the present invention is, in another embodiment, present in an amount of 0.019 g/L (Examples 15-16). In another embodiment, the amount is about 0.019 g/L. In other embodiments, the amount is any of the amounts or ranges listed above for cobalt.

In another embodiment, the copper is present in an amount that is the molar equivalent of 0.019 g/L of copper chloride dihydrate. In another embodiment, the amount of copper present is the molar equivalent of about 0.019 g/L of copper chloride dihydrate. In another embodiment, the amount of copper present is the molar equivalent of copper chloride dihydrate in any of the amounts or ranges listed above for cobalt. Each of the above amounts or ranges of copper represents a separate embodiment of the present invention.

The borate present in defined microbiological media of methods and compositions of the present invention is, in another embodiment, present in an amount of 0.016 g/L (Examples 15-16). In another embodiment, the amount is about 0.016 g/L. In other embodiments, the amount is any of the amounts or ranges listed above for cobalt.

In another embodiment, the borate is present in an amount that is the molar equivalent of 0.016 g/L of boric acid. In another embodiment, the amount of borate present is the molar equivalent of about 0.016 g/L of boric acid. In another embodiment, the amount of borate present is the molar equivalent of boric acid in any of the amounts or ranges listed above for cobalt. Each of the above amounts or ranges of borate represents a separate embodiment of the present invention.

The manganese present in defined microbiological media of methods and compositions of the present invention is, in another embodiment, present in an amount of 0.016 g/L (Examples 15-16). In another embodiment, the amount is about 0.016 g/L. In other embodiments, the amount is any of the amounts or ranges listed above for cobalt.

In another embodiment, the manganese is present in an amount that is the molar equivalent of 0.016 g/L of manganese sulfate monohydrate. In another embodiment, the amount of manganese present is the molar equivalent of about 0.016 g/L of manganese sulfate monohydrate. In another embodiment, the amount of manganese present is the molar equivalent of manganese sulfate monohydrate in any of the amounts or ranges listed above for cobalt. Each of the above amounts or ranges of manganese represents a separate embodiment of the present invention.

The molybdenum present in defined microbiological media of methods and compositions of the present invention is, in another embodiment, present in an amount of 0.02 g/L (Examples 15-16). In another embodiment, the amount is about 0.02 g/L. In other embodiments, the amount is any of the amounts or ranges listed above for cobalt.

In another embodiment, the molybdenum is present in an amount that is the molar equivalent of 0.2 g/L of sodium molybdate dihydrate. In another embodiment, the amount of molybdenum present is the molar equivalent of about 0.02 g/L of sodium molybdate dihydrate. In another embodiment, the amount of molybdenum present is the molar equivalent of sodium molybdate dihydrate in any of the amounts or ranges listed above for cobalt. Each of the above amounts or ranges of molybdenum represents a separate embodiment of the present invention.

The zinc present in defined microbiological media of methods and compositions of the present invention is, in another embodiment, present in an amount of 0.02 g/L (Examples 15-16). In another embodiment, the amount is about 0.02 g/L. In other embodiments, the amount is any of the amounts or ranges listed above for cobalt.

In another embodiment, the zinc is present in an amount that is the molar equivalent of 0.02 g/L of zinc chloride heptahydrate. In another embodiment, the amount of zinc present is the molar equivalent of about 0.02 g/L of zinc chloride heptahydrate. In another embodiment, the amount of zinc present is the molar equivalent of zinc chloride heptahydrate in any of the amounts or ranges listed above for cobalt. Each of the above amounts or ranges of zinc represents a separate embodiment of the present invention.

In another embodiment, ferric sulfate or a related compound is present in defined microbiological media of methods and compositions of the present invention. In another embodiment, the ferric sulfate or related compound is present in an amount of 0.01 g/L (Examples 15-16). In another embodiment, the amount is about 0.01 g/L. In other embodiments, the amount is any of the amounts or ranges listed above for cobalt.

In another embodiment, the iron is present in an amount that is the molar equivalent of 0.01 g/L of ferric sulfate. In another embodiment, the amount of iron present is the molar equivalent of about 0.01 g/L of ferric sulfate. In another embodiment, the amount of iron present is the molar equivalent of ferric sulfate in any of the amounts or ranges listed above for cobalt. Each of the above amounts or ranges of iron represents a separate embodiment of the present invention.

The calcium present in defined microbiological media of methods and compositions of the present invention is, in another embodiment, present in an amount of 0.01 g/L (Examples 15-16). In another embodiment, the amount is about 0.01 g/L. In other embodiments, the amount is any of the amounts or ranges listed above for cobalt.

In another embodiment, the calcium is present in an amount that is the molar equivalent of 0.01 g/L of calcium chloride dihydrate. In another embodiment, the amount of calcium present is the molar equivalent of about 0.01 g/L of calcium chloride dihydrate. In another embodiment, the amount of calcium present is the molar equivalent of calcium chloride dihydrate in any of the amounts or ranges listed above for cobalt. Each of the above amounts or ranges of calcium represents a separate embodiment of the present invention.

The citrate present in defined microbiological media of methods and compositions of the present invention is, in another embodiment, present in an amount of 0.9 g/L (Examples 15-16). In another embodiment, the amount is 0.6 g/L in the form of citric acid (Examples 15-16). In another embodiment, the amount is 0.4 g/L in the form of ferric citrate (Examples 15-16). In another embodiment, the amount is 0.6 g/L in the form of citric acid and 0.4 g/L in the form of ferric citrate (Examples 15-16). In another embodiment, the amount is about 0.6 g/L. In another embodiment, the amount is 0.1 g/L. In another embodiment, the amount is 0.2 g/L. In another embodiment, the amount is 0.3 g/L. In another embodiment, the amount is 0.4 g/L. In another embodiment, the amount is 0.5 g/L. In another embodiment, the amount is 0.7 g/L. In another embodiment, the amount is 0.8 g/L. In another embodiment, the amount is 1 g/L. In another embodiment, the amount is more than 1 g/L.

In another embodiment, the citrate is present in an amount that is the molar equivalent of 0.6 g/L of citric acid. In another embodiment, the amount of citrate present is the molar equivalent of about 0.6 g/L of citric acid. In another embodiment, the amount of citrate present is the molar equivalent of about 0.4 g/L of ferric citrate. In another embodiment, the amount of citrate present is the molar equivalent of 0.4 g/L of ferric citrate. In another embodiment, the amount of citrate present is the molar equivalent of 0.6 g/L of citric acid and 0.4 g/L of ferric citrate. In another embodiment, the amount of citrate present is the about molar equivalent of 0.6 g/L of citric acid and 0.4 g/L of ferric citrate. In another embodiment, the amount of citrate present is the molar equivalent of citric acid in any of the amounts or ranges listed above for citrate. Each of the above amounts or ranges of citrate represents a separate embodiment of the present invention.

One or more of the adenine, biotin, thiamine, pyridoxal, para-aminobenzoic acid, pantothenate, and nicotinamide present in defined microbiological media of methods and compositions of the present invention are, in another embodiment, present as the free compound. In another embodiment, one of the above compounds is present as a salt thereof. In another embodiment, one of the above compounds is present as a derivative thereof. In another embodiment, one of the above compounds is present as a hydrate thereof. In other embodiments, the salt, derivative, or hydrate can be any salt, derivative, or hydrate known in the art. Each of the above forms of adenine, biotin, thiamine, pyridoxal, para-aminobenzoic acid, pantothenate, and nicotinamide represents a separate embodiment of the present invention.

The thiamine (vitamin B1) present in defined microbiological media of methods and compositions of the present invention is, in another embodiment, present in the form of thiamine HCl. In another embodiment, the thiamine is present as any other salt, derivative, or hydrate of thiamine known in the art. In another embodiment, another form of vitamin B1 is substituted for thiamine. Each possibility represents a separate embodiment of the present invention.

In another embodiment, the thiamine is present in an amount of 4 mg/L (Examples 15-16). In another embodiment, the amount is about 0.5 mg/L. In another embodiment, the amount is 0.7 mg/L. In another embodiment, the amount is 1 mg/L. In another embodiment, the amount is 1.5 mg/L. In another embodiment, the amount is 2 mg/L. In another embodiment, the amount is 3 mg/L. In another embodiment, the amount is 5 mg/L. In another embodiment, the amount is 6 mg/L. In another embodiment, the amount is 8 mg/L. In another embodiment, the amount is more than 8 mg/L. In another embodiment, the thiamine is present in an amount that is the molar equivalent of 4 mg/L of thiamine HCl. In another embodiment, the thiamine is present in an amount that is the molar equivalent of thiamine HCl in one of the above amounts. Each possibility represents a separate embodiment of the present invention.

The pyridoxal (vitamin B6) present in defined microbiological media of methods and compositions of the present invention is, in another embodiment, present in the form of pyridoxal HCl. In another embodiment, the pyridoxal is present as any other salt, derivative, or hydrate of pyridoxal known in the art. In another embodiment, another form of vitamin B6 is substituted for pyridoxal. Each possibility represents a separate embodiment of the present invention.

In another embodiment, the pyridoxal is present in an amount of 4 mg/L (Examples 15-16). In another embodiment, the amount is any of the amounts or ranges listed above for thiamine. In another embodiment, the amount of pyridoxal present is the molar equivalent of about 4 mg/L of pyridoxal HCl. In another embodiment, the amount of pyridoxal present is the molar equivalent of pyridoxal HCl in any of the amounts or ranges listed above for thiamine. Each possibility represents a separate embodiment of the present invention.

The adenine (vitamin B4) present in defined microbiological media of methods and compositions of the present invention is, in another embodiment, present in the form of free adenine. In another embodiment, the adenine is present as any other salt, derivative, or hydrate of adenine known in the art. In another embodiment, another form of vitamin B4 is substituted for adenine. Each possibility represents a separate embodiment of the present invention.

In another embodiment, the adenine is present in an amount of 0.25 mg/L (Examples 15-16). In another embodiment, the amount is any of the amounts or ranges listed above for cobalt. In another embodiment, the amount of adenine present is the molar equivalent of about 0.25 mg/L of free adenine. In another embodiment, the amount of adenine present is the molar equivalent of free adenine in any of the amounts or ranges listed above for cobalt. Each possibility represents a separate embodiment of the present invention.

The biotin (vitamin B7) present in defined microbiological media of methods and compositions of the present invention is, in another embodiment, present in the form of free biotin. In another embodiment, the biotin is present as any other salt, derivative, or hydrate of biotin known in the art. In another embodiment, another form of vitamin B7 is substituted for biotin. Each possibility represents a separate embodiment of the present invention.

In another embodiment, the biotin is present in an amount of 2 mg/L (Examples 15-16). In another embodiment, the amount is any of the amounts or ranges listed above for thiamine. In another embodiment, the amount of biotin present is the molar equivalent of about 2 mg/L of free biotin. In another embodiment, the amount of biotin present is the molar equivalent of free biotin in any of the amounts or ranges listed above for thiamine. Each possibility represents a separate embodiment of the present invention.

The para-aminobenzoic acid (vitamin B-x) present in defined microbiological media of methods and compositions of the present invention is, in another embodiment, present in the form of free para-aminobenzoic acid. In another embodiment, the para-aminobenzoic acid is present as any other salt, derivative, or hydrate of para-aminobenzoic acid known in the art. In another embodiment, another form of vitamin B-x is substituted for para-aminobenzoic acid. Each possibility represents a separate embodiment of the present invention.

In another embodiment, the para-aminobenzoic acid is present in an amount of 4 mg/L (Examples 15-16). In another embodiment, the amount is any of the amounts or ranges listed above for thiamine. In another embodiment, the amount of para-aminobenzoic acid present is the molar equivalent of about 4 mg/L of free para-aminobenzoic acid. In another embodiment, the amount of para-aminobenzoic acid present is the molar equivalent of free para-aminobenzoic acid in any of the amounts or ranges listed above for thiamine. Each possibility represents a separate embodiment of the present invention.

The pantothenate (vitamin B5) present in defined microbiological media of methods and compositions of the present invention is, in another embodiment, present in the form of calcium pantothenate. In another embodiment, the pantothenate is present as any other salt, derivative, or hydrate of pantothenate known in the art. In another embodiment, another form of vitamin B5 is substituted for pantothenate. Each possibility represents a separate embodiment of the present invention.

In another embodiment, the pantothenate is present in an amount of 4 mg/L (Examples 15-16). In another embodiment, the amount is any of the amounts or ranges listed above for thiamine. In another embodiment, the amount of pantothenate present is the molar equivalent of about 4 mg/L of calcium pantothenate. In another embodiment, the amount of pantothenate present is the molar equivalent of calcium pantothenate in any of the amounts or ranges listed above for thiamine. Each possibility represents a separate embodiment of the present invention.

The nicotinamide (vitamin B3) present in defined microbiological media of methods and compositions of the present invention is, in another embodiment, present in the form of free nicotinamide. In another embodiment, the nicotinamide is present as any other salt, derivative, or hydrate of nicotinamide known in the art. In another embodiment, another form of vitamin B3 is substituted for nicotinamide. Each possibility represents a separate embodiment of the present invention.

In another embodiment, the nicotinamide is present in an amount of 4 mg/L (Examples 15-16). In another embodiment, the amount is any of the amounts or ranges listed above for thiamine. In another embodiment, the amount of nicotinamide present is the molar equivalent of about 4 mg/L of free nicotinamide. In another embodiment, the amount of nicotinamide present is the molar equivalent of free nicotinamide in any of the amounts or ranges listed above for thiamine. Each possibility represents a separate embodiment of the present invention.

One or more of the leucine, isoleucine, valine, arginine, histidine, tryptophan, and phenylalanine present in defined microbiological media of methods and compositions of the present invention are, in another embodiment, present as free amino acids. In another embodiment, one of the above compounds is present as a salt thereof. In another embodiment, one of the above compounds is present as a derivative thereof. In another embodiment, one of the above compounds is present as a hydrate thereof. In other embodiments, the salt, derivative, or hydrate can be any salt, derivative, or hydrate known in the art. Each of the above forms of adenine, biotin, thiamine, pyridoxal, para-aminobenzoic acid, pantothenate, and nicotinamide represents a separate embodiment of the present invention.

In another embodiment, one or more of the leucine, isoleucine, valine, arginine, histidine, tryptophan, and phenylalanine is present in an amount of 0.4 g/L (Examples 15-16). In another embodiment, the amount is about 0.05 g/L. In another embodiment, the amount is 0.07 g/L. In another embodiment, the amount is 0.1 g/L. In another embodiment, the amount is 0.15 g/L. In another embodiment, the amount is 0.2 g/L. In another embodiment, the amount is 0.3 g/L. In another embodiment, the amount is 0.5 g/L. In another embodiment, the amount is 0.6 g/L. In another embodiment, the amount is 0.8 g/L. In another embodiment, the amount is more than 0.8 g/L. In another embodiment, one or more of these AA is present in an amount that is the molar equivalent of 0.4 g/L of the free AA. In another embodiment, the amount is the molar equivalent of thiamine the free AA in one of the above amounts. Each possibility represents a separate embodiment of the present invention.

In another embodiment, a defined media of methods and compositions of the present invention contains two of the amino acids (AA) listed in the second section of Table 3B, e.g. leucine, isoleucine, valine, arginine, histidine, tryptophan, and phenylalanine. In another embodiment, the defined media contains 3 of these AA. In another embodiment, the media contains 4 of these AA. In another embodiment, the media contains 3 of these AA. In another embodiment, the media contains 5 of these AA. In another embodiment, the media contains 6 of these AA. In another embodiment, the media contains all of these AA. In another embodiment, the media contains at least 2 of these AA. In another embodiment, the media contains at least 3 of these AA. In another embodiment, the media contains at least 4 of these AA. In another embodiment, the media contains at least 5 of these AA. In another embodiment, the media contains at least 6 of these AA. Each possibility represents a separate embodiment of the present invention.

In another embodiment, a defined media of methods and compositions of the present invention contains 2 of the vitamins listed in the third section of Table 3B, e.g. adenine, biotin, thiamine pyridoxal, para-aminobenzoic acid, pantothenate, and nicotinamide. In another embodiment, the defined media contains 3 of these vitamins. In another embodiment, the media contains 4 of these vitamins. In another embodiment, the media contains 3 of these vitamins. In another embodiment, the media contains 5 of these vitamins. In another embodiment, the media contains 6 of these vitamins. In another embodiment, the media contains all of these vitamins. In another embodiment, the media contains at least 2 of these vitamins. In another embodiment, the media contains at least 3 of these vitamins. In another embodiment, the media contains at least 4 of these vitamins. In another embodiment, the media contains at least 5 of these vitamins. In another embodiment, the media contains at least 6 of these vitamins. Each possibility represents a separate embodiment of the present invention.

In another embodiment, a defined media of methods and compositions of the present invention contains 2 of the trace elements listed in the fourth section of Table 3B, e.g. cobalt, copper, boron, manganese, molybdenum, zinc, iron, calcium, and citrate. In another embodiment, the defined media contains 3 of these trace elements. In another embodiment, the media contains 4 of these trace elements. In another embodiment, the media contains 3 of these trace elements. In another embodiment, the media contains 5 of these trace elements. In another embodiment, the media contains 6 of these trace elements. In another embodiment, the media contains 7 of these trace elements. In another embodiment, the media contains 7 of these trace elements. In another embodiment, the media contains all of these trace elements. In another embodiment, the media contains at least 2 of these trace elements. In another embodiment, the media contains at least 3 of these trace elements. In another embodiment, the media contains at least 4 of these trace elements. In another embodiment, the media contains at least 5 of these trace elements. In another embodiment, the media contains at least 6 of these trace elements. In another embodiment, the media contains at least 7 of these trace elements. In another embodiment, the media contains at least 8 of these trace elements. Each possibility represents a separate embodiment of the present invention.

In another embodiment, a defined media of methods and compositions of the present invention contains more than 1 component from 2 of the above classes of components; e.g more than one of the AA listed in the second section of Table 3B, and more than one of the vitamins listed in the third section. In another embodiment, the media contains more than 2 components from 2 of the above classes of components; e.g more than 2 of the AA listed in the second section of Table 3B, and more than 2 of the trace elements listed in the fourth section. In another embodiment, the media contains more than 3 components from 2 of the above classes. In another embodiment, the media contains more than 4 components from 2 of the above classes. In another embodiment, the media contains more than 5 components from 2 of the above classes. In another embodiment, the media contains more than 6 components from 2 of the above classes. In another embodiment, the media contains all of the components from 2 of the above classes.

In another embodiment, a defined media of methods and compositions of the present invention contains more than 1 component from all of the above classes of components (e.g. more than 1 component each from AA, vitamins and trace elements). In another embodiment, the media contains more than 2 components from all of the above classes of components. In another embodiment, the media contains more than 3 components from all of the above classes.

In another embodiment, the media contains more than 4 components from all of the above classes. In another embodiment, the media contains more than all components from 2 of the above classes. In another embodiment, the media contains more than 6 components from all of the above classes. In another embodiment, the media contains all of the components from all of the above classes.

In another embodiment, the media contains any other combination of numbers of components from each of the above classes; e.g. 2 AA, 2 vitamins, and 3 trace elements; 3 AA, 3 vitamins, and 2 trace elements; 2 AA, 3 vitamins, and all of the trace elements, etc.

Each of the above combinations of numbers of components from each of the above classes represents a separate embodiment of the present invention.

In another embodiment, a defined media of methods and compositions of the present invention consists of one of the above recipes, mixtures of components, lists of components in specified amounts, or combinations of numbers of components from each of the above classes. Each possibility represents a separate embodiment of the present invention.

The divalent cation present in defined microbiological media of methods and compositions of the present invention is, in another embodiment, Mg. In another embodiment, the divalent cation is Ca. In another embodiment, the divalent cation is any other divalent cation known in the art. Mg can, in other embodiments, be present in any form of Mg known in the art, e.g. $MgSO_4$ (Examples 15-16). In another embodiment, the divalent cation is present in an amount that is the molar equivalent of about 0.41 g/mL. In other embodiments, the divalent cation is present in another effective amount, as known to those skilled in the art.

In another embodiment, a nitrogen source other than glutamine is utilized in defined media of the present invention. In another embodiment, the nitrogen source is another AA. In another embodiment, the nitrogen source is another source of peptides or proteins (e.g. casitone or casamino acids). In another embodiment, the nitrogen source is ammonium chloride. In another embodiment, the nitrogen source is ammonium nitrate. In another embodiment, the nitrogen source is ammonium sulfate. In another embodiment, the nitrogen source is another ammonium salt. In another embodiment, the nitrogen source is any other nitrogen source known in the art. Each possibility represents a separate embodiment of the present invention.

In another embodiment, a defined microbiological media of methods and compositions of the present invention does not contain a component derived from an animal source. In another embodiment, the defined microbiological media does not contain an animal-derived component of incompletely defined composition (e.g. yeast extract, bacto-tryptone, etc.). Each possibility represents a separate embodiment of the present invention.

In another embodiment, "defined microbiological media" refers to a media whose components are known. In another embodiment, the term refers to a media that does not contain a component derived from an animal source. In another embodiment, the term refers to a media whose components have been chemically characterized. Each possibility represents a separate embodiment of the present invention.

In another embodiment, a defined media of methods and compositions of the present invention supports growth of the *Listeria* strain to about $1.1 \times 10^{10}$ CFU/mL (e.g. when grown in flasks; Examples 13-16). In another embodiment, the defined media supports growth to about $1.1 \times 10^{10}$ CFU/mL (e.g. when grown in fermenters; Examples 13-16). In another embodiment, the defined media supports growth to about $5 \times 10^9$ CFU/mL (e.g. when grown in fermenters; Examples 13-16). In another embodiment, the defined media supports growth of viable bacteria (e.g. bacteria that can be cryopreserved without significant loss of viability) to about $3 \times 10^{10}$ CFU/mL (e.g. when grown in fermenters; Examples 13-16). In another embodiment, the defined media supports growth to an $OD_{600}$ of about 4.5 (Examples 13-16). In other embodiments, the defined media supports growth to another $OD_{600}$ value enumerated herein. In other embodiments, the defined media supports growth to another CFU/mL value enumerated herein. In another embodiment, the defined media supports growth to a density approximately equivalent to that obtained with TB. In another embodiment, the defined media supports growth to a density approximately equivalent to that obtained with LB. Each possibility represents a separate embodiment of the present invention.

In another embodiment, a defined media of methods and compositions of the present invention supports a growth rate of the *Listeria* strain of about $0.25\ h^{-1}$ (Examples). In another embodiment, the growth rate is about $0.15\ h^{-1}$. In another embodiment, the growth rate is about $0.2\ h^{-1}$. In another embodiment, the growth rate is about $0.3\ h^{-1}$. In another embodiment, the growth rate is about $0.4\ h^{-1}$. In another embodiment, the growth rate is about $0.5\ h^{-1}$. In another embodiment, the growth rate is about $0.6\ h^{-1}$. In another embodiment, the defined media supports a growth rate approximately equivalent to that obtained with TB. In another embodiment, the defined media supports a growth rate approximately equivalent to that obtained with LB. Each possibility represents a separate embodiment of the present invention.

As provided herein, vaccines of the present invention were completely well tolerated in 5/6 patients, even though the patients were very sick with metastatic cancer. It should be noted that halting of therapy in the case of the other patient, Patient 5, was done purely as a precaution. At no point was the patient's life considered to be even remotely in danger. The safety results in such patients, at least some of which were likely to be immunosuppressed, shows that the *Listeria* vaccines can be safely administered to a wide variety of patients.

In another embodiment, a peptide of the present invention is a fusion peptide. In another embodiment, "fusion peptide" refers to a peptide or polypeptide comprising 2 or more proteins linked together by peptide bonds or other chemical bonds. In another embodiment, the proteins are linked together directly by a peptide or other chemical bond. In another embodiment, the proteins are linked together with 1 or more AA (e.g. a "spacer") between the 2 or more proteins. Each possibility represents a separate embodiment of the present invention.

In another embodiment, a vaccine of the present invention further comprises an adjuvant. The adjuvant utilized in methods and compositions of the present invention is, in another embodiment, a granulocyte/macrophage colony-stimulating factor (GM-CSF) protein. In another embodiment, the adjuvant comprises a GM-CSF protein. In another embodiment, the adjuvant is a nucleotide molecule encoding GM-CSF. In another embodiment, the adjuvant comprises a nucleotide molecule encoding GM-CSF. In another embodiment, the adjuvant is saponin QS21. In another embodiment, the adjuvant comprises saponin QS21. In another embodiment, the adjuvant is monophosphoryl lipid A. In another embodiment, the adjuvant comprises monophosphoryl lipid A. In another embodiment, the adjuvant is SBAS2. In another embodiment, the adjuvant comprises SBAS2. In another embodiment, the adjuvant is an unmethylated CpG-containing oligonucleotide. In another embodiment, the adjuvant comprises an unmethylated CpG-containing oligonucleotide. In another embodiment, the adjuvant is an immune-stimulating cytokine. In another embodiment, the adjuvant comprises an immune-stimulating cytokine. In another embodiment, the adjuvant is a nucleotide molecule encoding an immune-stimulating cytokine. In another embodiment, the adjuvant comprises a nucleotide molecule encoding an immune-stimulating cytokine. In another embodiment, the adjuvant is or comprises a quill glycoside. In another embodiment, the adjuvant is or comprises a bacterial mitogen. In another embodiment, the adjuvant is or comprises a bacterial toxin. In another embodiment, the adjuvant is or comprises any other adjuvant known in the art. Each possibility represents a separate embodiment of the present invention.

In another embodiment, a nucleotide of the present invention is operably linked to a promoter/regulatory sequence that drives expression of the encoded peptide in the *Listeria* strain. Promoter/regulatory sequences useful for driving constitutive expression of a gene are well known in the art and include, but are not limited to, for example, the $P_{hlyA}$, $P_{ActA}$, and p60 promoters of *Listeria*, the *Streptococcus* bac promoter, the

*Streptomyces griseus* sgiA promoter, and the *B. thuringiensis* phaZ promoter. In another embodiment, inducible and tissue specific expression of the nucleic acid encoding a peptide of the present invention is accomplished by placing the nucleic acid encoding the peptide under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In another embodiment, a promoter that is induced in response to inducing agents such as metals, glucocorticoids, and the like, is utilized. Thus, it will be appreciated that the invention includes the use of any promoter/regulatory sequence, which is either known or unknown, and which is capable of driving expression of the desired protein operably linked thereto.

An N-terminal fragment of an ActA protein utilized in methods and compositions of the present invention has, in another embodiment, the sequence set forth in SEQ ID NO: 23:

MRAMMVVFITANCITINPLNIFAATDSEDSSLNTDEWEEEKTEEQPSEVNT

GPRYETAREVSSRDIKELEKSNKVRNTNKADLIAMLKEKAEKGPNINNNNS

EQTENAMNEEASGADRPAIQVERRHPGLPSDSAAEIKKRRKAIASSDSELE

SLTYPDKPTKVNKKKVAKESVADASESDLDSSMQSADESSPQPLICANQQP

ITPKVFKKIKDAGKWVRDKIDENPEVKKAIVDKSAGLIDQLLTKKKSEEVN

ASDFPPPPTDEELRLALPETPMLLGFNAPATSEPSSFEFPPPPTDEELRLA

LPETPMLLGFNAPATSEPSSFEFPPPPTEDELEHRETASSLDSSFTRGDLA

SLRNAINRHSQNFSDFPPIPTEEELNGRGGRP.

In another embodiment, the ActA fragment comprises the sequence set forth in SEQ ID NO: 23. In another embodiment, the ActA fragment is any other ActA fragment known in the art. Each possibility represents a separate embodiment of the present invention.

In another embodiment, the recombinant nucleotide encoding a fragment of an ActA protein comprises the sequence set forth in SEQ ID NO: 24:

Atgcgtgcgatgatggtggttttcattactgccaattgcattacgattaac cccgacataatatttgcagcgacagatagcgaagattctagtctaaacaca gatgaatgggaagaagaaaaaacagaagagcaaccaagcgaggtaaatacg ggaccaagatacgaaactgcacgtgaagtaagttcacgtgatattaaagaa ctagaaaaatcgaataaagtgagaaatacgaacaaagcagacctaatagca atgttgaaagaaaaagcagaaaaaggtccaaatatcaataataacaacagt gaacaaactgagaatgcggctataaatgaagaggcttcaggagccgaccga ccagctatacaagtggagcgtcgtcatccaggattgccatcggatagcgca gcggaaattaaaaaaagaaggaaagccatagcatcatcggatagtgagctt gaaagccttacttatccggataaaccaacaaaagtaaataagaaaaaagtg gcgaaagagtcagttgcggatgcttctgaaagtgacttagattctagcatg cagtcagcagatgagtcttcaccacaacctttaaaagcaaaccaacaacca tttttccctaaagtatttaaaaaaataaaagatgcggggaaatgggtacgt gataaaatcgacgaaaatcctgaagtaaagaaagcgattgttgataaaagt gcagggttaattgaccaattattaaccaaaaagaaaagtgaagaggtaaat gatcggacaccgccaccacctacggatgaagagttaagacttgctugcca gagacaccaatgcttcttggttttaatgctcctgctacatcagaaccgagc tcattcgaatttccaccaccacctacggatgaagagttaagacttgctttg ccagagacgccaatgcttcttggttttaatgctcctgctacatcggaaccg agctcgttcgaatttccaccgcctccaacagaagatgaactagaaatcatc cgggaaacagcatcctcgctagattctagttttacaagagggatttagct agtttgagaaatgctattaatcgccatagtcaaaatttctctgatttccca ccaatcccaacagaagaagagttgaacgggagaggcggtagacca.

In another embodiment, the recombinant nucleotide has the sequence set forth in SEQ ID NO: 24. In another embodiment, the recombinant nucleotide comprises any other sequence that encodes a fragment of an ActA protein. Each possibility represents a separate embodiment of the present invention.

In another embodiment of methods and compositions of the present invention, a PEST-like AA sequence is fused to the E7 or E6 antigen. As provided herein, recombinant *Listeria* strains expressing PEST-like sequence-antigen fusions induce anti-tumor immunity (Example 3) and generate antigen-specific, tumor-infiltrating T cells (Example 4). Further, enhanced cell mediated immunity was demonstrated for fusion proteins comprising an antigen and LLO containing the PEST-like AA sequence KENSISSMAPPASPPASPKT-PIEKKHADEIDK (SEQ ID NO: 1).

Thus, fusion of an antigen to other LM PEST-like sequences and PEST-like sequences derived from other prokaryotic organisms will also enhance immunogenicity of the antigen. The PEST-like AA sequence has, in another embodiment, a sequence selected from SEQ ID NO: 2-7. In another embodiment, the PEST-like sequence is a PEST-like sequence from the LM ActA protein. In another embodiment, the PEST-like sequence is KTEEQPSEVNTGPR (SEQ ID NO: 2), KASVTDTSEGDLDSSMQSADESTPQPLK (SEQ ID NO: 3), KNEEVNASDFPPPPTDEELR (SEQ ID NO: 4), or RGGIPTSEEFSSLNSGDFTDDENSETTEEEIDR (SEQ ID NO: 5). In another embodiment, the PEST-like sequence is from Streptolysin 0 protein of *Streptococcus* sp. In another embodiment, the PEST-like sequence is from *Streptococcus pyogenes* Streptolysin 0, e.g. KQNTASTETTTTNEQPK (SEQ ID NO: 6) at AA 35-51. In another embodiment, the PEST-like sequence is from *Streptococcus equisimilis* Streptolysin O, e.g. KQNTANTETTTTNEQPK (SEQ ID NO: 7) at AA 38-54. In another embodiment, the PEST-like sequence is another PEST-like AA sequence derived from a prokaryotic organism. In another embodiment, the PEST-like sequence is any other PEST-like sequence known in the art. Each possibility represents a separate embodiment of the present invention.

PEST-like sequences of other prokaryotic organism can be identified in accordance with methods such as described by, for example Rechsteiner and Rogers (1996, Trends Biochem. Sci. 21:267-271) for LM. Alternatively, PEST-like AA sequences from other prokaryotic organisms can also be identified based by this method. Other prokaryotic organisms wherein PEST-like AA sequences would be expected to include, but are not limited to, other *Listeria* species. In another embodiment, the PEST-like sequence is embedded within the antigenic protein. Thus, in another embodiment, "fusion" refers to an antigenic protein comprising both the antigen and the PEST-like amino acid sequence either linked at one end of the antigen or embedded within the antigen.

In another embodiment, the PEST-like sequence is identified using any other method or algorithm known in the art, e.g the CaSPredictor (Garay-Malpartida H M, Occhiucci J M, Alves J, Belizario J E. Bioinformatics. 2005 June; 21 Suppl 1:i169-76). In another embodiment, the following method is used:

A PEST index is calculated for each 30-35 AA stretch by assigning a value of 1 to the amino acids Ser, Thr, Pro, Glu, Asp, Asn, or Gln. The coefficient value (CV) for each of the PEST residue is 1 and for each of the other AA (non-PEST) is 0.

Each method for identifying a PEST-like sequence represents a separate embodiment of the present invention.

In another embodiment, the LLO protein, ActA protein, or fragment thereof of the present invention need not be that which is set forth exactly in the sequences set forth herein, but rather other alterations, modifications, or changes can be made that retain the functional characteristics of an LLO or ActA protein fused to an antigen as set forth elsewhere herein. In another embodiment, the present invention utilizes an analog of an LLO protein, ActA protein, or fragment thereof. Analogs differ, in another embodiment, from naturally occurring proteins or peptides by conservative AA sequence differences or by modifications which do not affect sequence, or by both.

In another embodiment, either a whole E7 protein or a fragment thereof is fused to a LLO protein, ActA protein, or PEST-like sequence-containing peptide to generate a recombinant peptide of methods of the present invention. The E7 protein that is utilized (either whole or as the source of the fragments) has, in another embodiment, the sequence
MHGDTPTLHEYMLDLQPETTDLY-CYEQLNDSSEEEDEIDGPAGQAEPDRAHYNI VTFC-CKCDSTLRLCVQSTHVDIRTLEDLL-MGTLGIVCPICSQKP (SEQ ID No: 30). In another embodiment, the E7 protein is a homologue of SEQ ID No: 30. In another embodiment, the E7 protein is a variant of SEQ ID No: 30. In another embodiment, the E7 protein is an isomer of SEQ ID No: 30. In another embodiment, the E7 protein is a fragment of SEQ ID No: 30. In another embodiment, the E7 protein is a fragment of a homologue of SEQ ID No: 30. In another embodiment, the E7 protein is a fragment of a variant of SEQ ID No: 30. In another embodiment, the E7 protein is a fragment of an isomer of SEQ ID No: 30. Each possibility represents a separate embodiment of the present invention.

In another embodiment, the sequence of the E7 protein is:
MHGPKATLQDIVLHLEPQ-NEIPVDLLCHEQLSDSEEENDEIDGVNHQHLPARRAE PQRHTMLCMCCKCEARIELVVESSADDL-RAFQQLFLNTLSFVCPWCASQQ (SEQ ID No: 31). In another embodiment, the E6 protein is a homologue of SEQ ID No: 31. In another embodiment, the E6 protein is a variant of SEQ ID No: 31. In another embodiment, the E6 protein is an isomer of SEQ ID No: 31. In another embodiment, the E6 protein is a fragment of SEQ ID No: 31. In another embodiment, the E6 protein is a fragment of a homologue of SEQ ID No: 31. In another embodiment, the E6 protein is a fragment of a variant of SEQ ID No: 31. In another embodiment, the E6 protein is a fragment of an isomer of SEQ ID No: 31. Each possibility represents a separate embodiment of the present invention.

In another embodiment, the E7 protein has a sequence set forth in one of the following GenBank entries: M24215, NC_004500, V01116, X62843, or M14119. In another embodiment, the E7 protein is a homologue of a sequence from one of the above GenBank entries. In another embodiment, the E7 protein is a variant of a sequence from one of the above GenBank entries. In another embodiment, the E7 protein is an isomer of a sequence from one of the above GenBank entries. In another embodiment, the E7 protein is a fragment of a sequence from one of the above GenBank entries. In another embodiment, the E7 protein is a fragment of a homologue of a sequence from one of the above GenBank entries. In another embodiment, the E7 protein is a fragment of a variant of a sequence from one of the above GenBank entries. In another embodiment, the E7 protein is a fragment of an isomer of a sequence from one of the above GenBank entries. Each possibility represents a separate embodiment of the present invention.

In another embodiment, either a whole E6 protein or a fragment thereof is fused to a LLO protein, ActA protein, or PEST-like sequence-containing peptide to generate a recombinant peptide of methods of the present invention. The E6 protein that is utilized (either whole or as the source of the fragments) has, in another embodiment, the sequence
MHQKRTAMFQDPQERPRKLPQLCTELQT-TIHDIILECVYCKQQLLRREVYDFAFR DLCIVYRDGNPYAVCDKCLKFYSKISEY-RHYCYSLYGTTLEQQYNKPLCDLLIRCINCQ KPLCPEEKQRHLDKKQRFHNIRGRWT-GRCMSCCRSSRTRRETQL (SEQ ID No: 32). In another embodiment, the E6 protein is a homologue of SEQ ID No: 32. In another embodiment, the E6 protein is a variant of SEQ ID No: 32. In another embodiment, the E6 protein is an isomer of SEQ ID No: 32. In another embodiment, the E6 protein is a fragment of SEQ ID No: 32. In another embodiment, the E6 protein is a fragment of a homologue of SEQ ID No: 32. In another embodiment, the E6 protein is a fragment of a variant of SEQ ID No: 32. In another embodiment, the E6 protein is a fragment of an isomer of SEQ ID No: 32. Each possibility represents a separate embodiment of the present invention.

In another embodiment, the sequence of the E6 protein is:
MARFEDPTRRPYKLP-DLCTELNTSLQDIEITCVYCKTV-LELTEVFEFAFKDLFVVYRDSIPHAACHKCIDFYSRIR ELRHYSDSVYGDTLEKLTNTGLYNLLIRCLRCQKP LNPAEKLRHLNEKRRFHNIAGHYRGQCHSCCNRA RQERLQRRRETQV (SEQ ID No: 33). In another embodiment, In another embodiment, the E6 protein is a homologue of SEQ ID No: 33. In another embodiment, the E6 protein is a variant of SEQ ID No: 33. In another embodiment, the E6 protein is an isomer of SEQ ID No: 33. In another embodiment, the E6 protein is a fragment of SEQ ID No: 33. In another embodiment, the E6 protein is a fragment of a homologue of SEQ ID No: 33. In another embodiment, the E6 protein is a fragment of a variant of SEQ ID No: 33. In another embodiment, the E6 protein is a fragment of an isomer of SEQ ID No: 33. Each possibility represents a separate embodiment of the present invention.

In another embodiment, the E6 protein has a sequence set forth in one of the following GenBank entries: M24215, M14119, NC_004500, V01116, X62843, or M14119. In another embodiment, the E6 protein is a homologue of a sequence from one of the above GenBank entries. In another embodiment, the E6 protein is a variant of a sequence from one of the above GenBank entries. In another embodiment, the E6 protein is an isomer of a sequence from one of the above GenBank entries. In another embodiment, the E6 protein is a fragment of a sequence from one of the above GenBank entries. In another embodiment, the E6 protein is a fragment of a homologue of a sequence from one of the above GenBank entries. In another embodiment, the E6 protein is a fragment of a variant of a sequence from one of the above GenBank entries. In another embodiment, the E6 protein is a fragment of an isomer of a sequence from one of the above GenBank entries. Each possibility represents a separate embodiment of the present invention.

In another embodiment, "homology" refers to identity to an LLO sequence (e.g. to one of SEQ ID No: 25-27) of greater than 70%. In another embodiment, "homology" refers to identity to one of SEQ ID No: 25-27 of greater than 72%. In another embodiment, "homology" refers to identity to one of SEQ ID No: 25-27 of greater than 75%. In another embodiment, "homology" refers to identity to one of SEQ ID No: 25-27 of greater than 78%. In another embodiment, "homology" refers to identity to one of SEQ ID No: 25-27 of greater than 80%. In another embodiment, "homology" refers to identity to one of SEQ ID No: 25-27 of greater than 82%. In another embodiment, "homology" refers to identity to one of SEQ ID No: 25-27 of greater than 83%. In another embodiment, "homology" refers to identity to one of SEQ ID No: 25-27 of greater than 85%. In another embodiment, "homology" refers to identity to one of SEQ ID No: 25-27 of greater than 87%. In another embodiment, "homology" refers to identity to one of SEQ ID No: 25-27 of greater than 88%. In another embodiment, "homology" refers to identity to one of SEQ ID No: 25-27 of greater than 90%. In another embodiment, "homology" refers to identity to one of SEQ ID No: 25-27 of greater than 92%. In another embodiment, "homology" refers to identity to one of SEQ ID No: 25-27 of greater than 93%. In another embodiment, "homology" refers to identity to one of SEQ ID No: 25-27 of greater than 95%. In another embodiment, "homology" refers to identity to one of SEQ ID No: 25-27 of greater than 96%. In another embodiment, "homology" refers to identity to one of SEQ ID No: 25-27 of greater than 97%. In another embodiment, "homology" refers to identity to one of SEQ ID No: 25-27 of greater than 98%. In another embodiment, "homology" refers to identity to one of SEQ ID No: 25-27 of greater than 99%. In another embodiment, "homology" refers to identity to one of SEQ ID No: 25-27 of 100%. Each possibility represents a separate embodiment of the present invention.

In another embodiment, "homology" refers to identity to an E7 sequence (e.g. to one of SEQ ID No: 30-31) of greater than 70%. In another embodiment, "homology" refers to identity to one of SEQ ID No: 30-31 of greater than 72%. In another embodiment, "homology" refers to identity to one of SEQ ID No: 30-31 of greater than 75%. In another embodiment, "homology" refers to identity to one of SEQ ID No: 30-31 of greater than 78%. In another embodiment, "homology" refers to identity to one of SEQ ID No: 30-31 of greater than 80%. In another embodiment, "homology" refers to identity to one of SEQ ID No: 30-31 of greater than 82%. In another embodiment, "homology" refers to identity to one of SEQ ID No: 30-31 of greater than 83%. In another embodiment, "homology" refers to identity to one of SEQ ID No: 30-31 of greater than 85%. In another embodiment, "homology" refers to identity to one of SEQ ID No: 30-31 of greater than 87%. In another embodiment, "homology" refers to identity to one of SEQ ID No: 30-31 of greater than 88%. In another embodiment, "homology" refers to identity to one of SEQ ID No: 30-31 of greater than 90%. In another embodiment, "homology" refers to identity to one of SEQ ID No: 30-31 of greater than 92%. In another embodiment, "homology" refers to identity to one of SEQ ID No: 30-31 of greater than 93%. In another embodiment, "homology" refers to identity to one of SEQ ID No: 30-31 of greater than 95%. In another embodiment, "homology" refers to identity to one of SEQ ID No: 30-31 of greater than 96%. In another embodiment, "homology" refers to identity to one of SEQ ID No: 30-31 of greater than 97%. In another embodiment, "homology" refers to identity to one of SEQ ID No: 30-31 of greater than 98%. In another embodiment, "homology" refers to identity to one of SEQ ID No: 30-31 of greater than 99%. In another embodiment, "homology" refers to identity to one of SEQ ID No: 30-31 of 100%. Each possibility represents a separate embodiment of the present invention.

In another embodiment, "homology" refers to identity to an E6 sequence (e.g. to one of SEQ ID No: 32-33) of greater than 70%. In another embodiment, "homology" refers to identity to one of SEQ ID No: 32-33 of greater than 72%. In another embodiment, "homology" refers to identity to one of SEQ ID No: 32-33 of greater than 75%. In another embodiment, "homology" refers to identity to one of SEQ ID No: 32-33 of greater than 78%. In another embodiment, "homology" refers to identity to one of SEQ ID No: 32-33 of greater than 80%. In another embodiment, "homology" refers to identity to one of SEQ ID No: 32-33 of greater than 82%. In another embodiment, "homology" refers to identity to one of SEQ ID No: 32-33 of greater than 83%. In another embodiment, "homology" refers to identity to one of SEQ ID No: 32-33 of greater than 85%. In another embodiment, "homology" refers to identity to one of SEQ ID No: 32-33 of greater than 87%. In another embodiment, "homology" refers to identity to one of SEQ ID No: 32-33 of greater than 88%. In another embodiment, "homology" refers to identity to one of SEQ ID No: 32-33 of greater than 90%. In another embodiment, "homology" refers to identity to one of SEQ ID No: 32-33 of greater than 92%. In another embodiment, "homology" refers to identity to one of SEQ ID No: 32-33 of greater than 93%. In another embodiment, "homology" refers to identity to one of SEQ ID No: 32-33 of greater than 95%. In another embodiment, "homology" refers to identity to one of SEQ ID No: 32-33 of greater than 96%. In another embodiment, "homology" refers to identity to one of SEQ ID No: 32-33 of greater than 97%. In another embodiment, "homology" refers to identity to one of SEQ ID No: 32-33 of greater than 98%. In another embodiment, "homology" refers to identity to one of SEQ ID No: 32-33 of greater than 99%. In another embodiment, "homology" refers to identity to one of SEQ ID No: 32-33 of 100%. Each possibility represents a separate embodiment of the present invention.

In another embodiment, "homology" refers to identity to a PEST-like sequence (e.g. to one of SEQ ID No: 1-7) or to an ActA sequence (e.g. to one of SEQ ID No: 23-24) of greater than 70%. In another embodiment, "homology" refers to identity to one of SEQ ID No: 1-7 or SEQ ID No: 23-24 of greater than 72%. In another embodiment, "homology" refers to identity to one of SEQ ID No: 1-7 or SEQ ID No: 23-24 of greater than 75%. In another embodiment, "homology" refers to identity to one of SEQ ID No: 1-7 or SEQ ID No: 23-24 of greater than 78%. In another embodiment, "homology" refers to identity to one of SEQ ID No: 1-7 or SEQ ID No: 23-24 of greater than 80%. In another embodiment, "homology" refers to identity to one of SEQ ID No: 1-7 or SEQ ID No: 23-24 of greater than 82%. In another embodiment, "homology" refers to identity to one of SEQ ID No: 1-7 or SEQ ID No: 23-24 of greater than 83%. In another embodiment, "homology" refers to identity to one of SEQ ID No: 1-7 or SEQ ID No: 23-24 of greater than 85%. In another embodiment, "homology" refers to identity to one of SEQ ID No: 1-7 or SEQ ID No: 23-24 of greater than 87%. In another embodiment, "homology" refers to identity to one of SEQ ID No: 1-7 or SEQ ID No: 23-24 of greater than 88%. In another embodiment, "homology" refers to identity to one of SEQ ID No: 1-7 or SEQ ID No: 23-24 of greater than 90%. In another embodiment, "homology" refers to identity to one of SEQ ID No: 1-7 or SEQ ID No: 23-24 of greater than 92%. In another embodiment, "homology" refers to identity to one of SEQ ID No: 1-7 or SEQ ID No: 23-24 of greater than 93%. In another embodiment, "homology" refers to identity to one of SEQ ID No: 1-7 or SEQ ID No: 23-24 of greater than 95%. In another embodiment, "homology" refers to identity to one of SEQ ID No: 1-7 or SEQ ID No: 23-24 of greater than 96%. In another embodiment, "homology" refers to identity to one of SEQ ID No: 1-7 or SEQ ID No: 23-24 of greater than 97%. In another embodiment, "homology" refers to identity to one of SEQ ID No: 1-7 or SEQ ID No: 23-24 of greater than 98%. In another embodiment, "homology" refers to identity to one of SEQ ID No: 1-7 or SEQ ID No: 23-24 of greater than 99%. In another embodiment, "homology" refers to identity to one of SEQ ID No: 1-7 or SEQ ID No: 23-24 of 100%. Each possibility represents a separate embodiment of the present invention.

Protein and/or peptide homology for any AA sequence listed herein is determined, in one embodiment, by methods well described in the art, including immunoblot analysis, or via computer algorithm analysis of AA sequences, utilizing any of a number of software packages available, via established methods. Some of these packages include the FASTA, BLAST, MPsrch or Scanps packages, and employ, in other embodiments, the use of the Smith and Waterman algorithms, and/or global/local or BLOCKS alignments for analysis, for example. Each method of determining homology represents a separate embodiment of the present invention.

In another embodiment, the LLO protein, ActA protein, or fragment thereof is attached to the E7 or E6 antigen by chemical conjugation. In another embodiment, glutaraldehyde is used for the conjugation. In another embodiment, the conjugation is performed using any suitable method known in the art. Each possibility represents another embodiment of the present invention.

In another embodiment, fusion proteins of the present invention are prepared by any suitable method, including, for example, cloning and restriction of appropriate sequences or direct chemical synthesis by methods discussed below. In another embodiment, subsequences are cloned and the appropriate subsequences cleaved using appropriate restriction enzymes. The fragments are then ligated, in another embodiment, to produce the desired DNA sequence. In another embodiment, DNA encoding the fusion protein is produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The insert is then ligated into a plasmid.

In another embodiment, the LLO protein, ActA protein, or fragment thereof and the E7, E6, or fragment thereof are conjugated by a means known to those of skill in the art. In another embodiment, the E7, E6, or fragment thereof is conjugated, either directly or through a linker (spacer), to the ActA protein or LLO protein. In another embodiment, the chimeric molecule is recombinantly expressed as a single-chain fusion protein.

In another embodiment, a fusion peptide of the present invention is synthesized using standard chemical peptide synthesis techniques. In another embodiment, the chimeric molecule is synthesized as a single contiguous polypeptide. In another embodiment, the LLO protein, ActA protein, or fragment thereof; and the E7, E6, or fragment thereof are synthesized separately, then fused by condensation of the amino terminus of one molecule with the carboxyl terminus of the other molecule, thereby forming a peptide bond. In another embodiment, the ActA protein or LLO protein and antigen are each condensed with one end of a peptide spacer molecule, thereby forming a contiguous fusion protein.

In another embodiment, the peptides and proteins of the present invention are prepared by solid-phase peptide synthesis (SPPS) as described by Stewart et al. in Solid Phase Peptide Synthesis, 2nd Edition, 1984, Pierce Chemical Company, Rockford, Ill.; or as described by Bodanszky and Bodanszky (The Practice of Peptide Synthesis, 1984, Springer-Verlag, New York). In another embodiment, a suitably protected AA residue is attached through its carboxyl group to a derivatized, insoluble polymeric support, such as cross-linked polystyrene or polyamide resin. "Suitably protected" refers to the presence of protecting groups on both the alpha-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial AA, and couple thereto of the carboxyl end of the next AA in the sequence of the desired peptide. This AA is also suitably protected. The carboxyl of the incoming AA can be activated to react with the N-terminus of the support-bound AA by formation into a reactive group such as formation into a carbodiimide, a symmetric acid anhydride or an "active ester" group such as hydroxybenzotriazole or pentafluorophenyl esters.

In another embodiment, the present invention provides a kit comprising vaccine of the present invention, an applicator, and instructional material that describes use of the methods of the invention. Although model kits are described below, the contents of other useful kits will be apparent to the skilled artisan in light of the present disclosure. Each of these kits represents a separate embodiment of the present invention.

EXPERIMENTAL DETAILS SECTION

Example 1

LLO-Antigen Fusions Induce Anti-Tumor Immunity

Materials and Experimental Methods (Examples 1-2)

Cell Lines

The C57BL/6 syngeneic TC-1 tumor was immortalized with HPV-16 E6 and E7 and transformed with the c-Ha-ras oncogene. TC-1, provided by T. C. Wu (Johns Hopkins University School of Medicine, Baltimore, Md.) is a highly tumorigenic lung epithelial cell expressing low levels of with HPV-16 E6 and E7 and transformed with the c-Ha-ras oncogene. TC-1 was grown in RPMI 1640, 10% FCS, 2 mM L-glutamine, 100 U/ml penicillin, 100 µg/ml streptomycin, 100 µM nonessential amino acids, 1 mM sodium pyruvate, 50 micromolar (mcM) 2-ME, 400 microgram (mcg)/ml G418, and 10% National Collection Type Culture-109 medium at 37° with 10% $CO_2$. C3 is a mouse embryo cell from C57BL/6 mice immortalized with the complete genome of HPV 16 and transformed with pEJ-ras. EL-4/E7 is the thymoma EL-4 retrovirally transduced with E7.

L. monocytogenes Strains and Propagation

Figure 2:
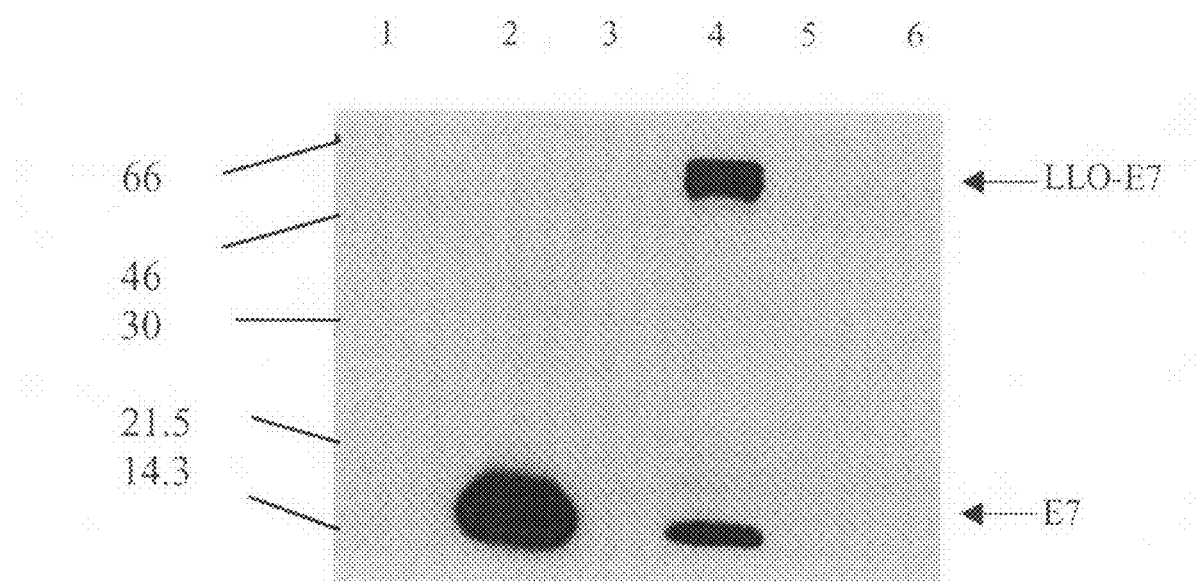
FIG. 2. Lm-E7 and Lm-LLO-E7 secrete E7. Lm-Gag (lane 1), Lm-E7 (lane 2), Lm-LLO-NP (lane 3), Lm-LLO-E7 (lane 4), XFL-7 (lane 5), and 10403S (lane 6) were grown overnight at 37° C. in Luria-Bertoni broth. Equivalent numbers of bacteria, as determined by OD at 600 nm absorbance, were pelleted and 18 ml of each supernatant was TCA precipitated. E7 expression was analyzed by Western blot. The blot was probed with an anti-E7 mAb, followed by HRP-conjugated anti-mouse (Amersham), then developed using ECL detection reagents.

Listeria strains used were Lm-LLO-E7 (hly-E7 fusion gene in an episomal expression system; FIG. 1A), Lm-E7 (single-copy E7 gene cassette integrated into Listeria genome), Lm-LLO-NP ("DP-L2028"; hly-NP fusion gene in an episomal expression system), and Lm-Gag ("ZY-18"; single-copy HIV-1 Gag gene cassette integrated into the chromosome). E7 was amplified by PCR using the primers 5'-GG CTCGAGCATGGAGATACACC-3' (SEQ ID No: 8; XhoI site is underlined) and 5'-GGGG ACTAGTTTATGGTTTCTGAGAACA-3' (SEQ ID No: 9; SpeI site is underlined) and ligated into pCR2.1 (Invitrogen, San Diego, Calif.). E7 was excised from pCR2.1 by XhoI/SpeI digestion and ligated into pGG-55. The hly-E7 fusion gene and the pluripotential transcription factor prfA were cloned into pAM401, a multicopy shuttle plasmid (Wirth R et al, J Bacteriol, 165: 831, 1986), generating pGG-55. The hly promoter drives the expression of the first 441 AA of the hly gene product, (lacking the hemolytic C-terminus, referred to below as "ΔLLO," and having the sequence set forth in SEQ ID No: 25), which is joined by the XhoI site to the E7 gene, yielding a hly-E7 fusion gene that is transcribed and secreted as LLO-E7. Transformation of a prfA negative strain of Listeria, XFL-7 (provided by Dr. Hao Shen, University of Pennsylvania), with pGG-55 selected for the retention of the plasmid in vivo (FIGS. 1A-B). The hly promoter and gene fragment were generated using primers 5'-GGGG GCTAGCCCTCCTTTGATTAGTATATTC-3' (SEQ ID No: 10; NheI site is underlined) and 5'-CTCC CTCGAGATCATAATTTACTTCATC-3' (SEQ ID No: 11; XhoI site is underlined). The prfA gene was PCR amplified using primers 5'-GACTACAAGGACGATGACCGA-CAAGTGATAACCCGGGATCTAAATAAATCCGTTT-3' (SEQ ID No: 12; XbaI site is underlined) and 5'-CCC GTCGACCAGCTCTTCTTGGTGAAG-3' (SEQ ID No: 13; SalI site is underlined). Lm-E7 was generated by introducing an expression cassette containing the hly promoter and signal sequence driving the expression and secretion of E7 into the orfZ domain of the LM genome. E7 was amplified by PCR using the primers 5'-GC GGATCCCATGGAGATACACCTAC-3' (SEQ ID No: 28; BamHI site is underlined) and 5'-GC TCTAGATTATGGTTTCTGAG-3' (SEQ ID No: 29; XbaI site is underlined). E7 was then ligated into the pZY-21 shuttle vector. LM strain 10403S was transformed with the resulting plasmid, pZY-21-E7, which includes an expression cassette inserted in the middle of a 1.6-kb sequence that corresponds to the orfX, Y, Z domain of the LM genome. The homology domain allows for insertion of the E7 gene cassette into the orfZ domain by homologous recombination. Clones were screened for integration of the E7 gene cassette into the orfZ domain. Bacteria were grown in brain heart infusion medium with (Lm-LLO-E7 and Lm-LLO-NP) or without (Lm-E7 and ZY-18) chloramphenicol (20 μg/ml). Bacteria were frozen in aliquots at −80° C. Expression was verified by Western blotting (FIG. 2).

Western Blotting

Listeria strains were grown in Luria-Bertoni medium at 37° C. and were harvested at the same optical density measured at 600 nm. The supernatants were TCA precipitated and resuspended in 1× sample buffer supplemented with 0.1 N NaOH. Identical amounts of each cell pellet or each TCA-precipitated supernatant were loaded on 4-20% Tris-glycine SDS-PAGE gels (NOVEX, San Diego, Calif.). The gels were transferred to polyvinylidene difluoride and probed with an anti-E7 monoclonal antibody (mAb) (Zymed Laboratories, South San Francisco, Calif.), then incubated with HRP-conjugated anti-mouse secondary Ab (Amersham Pharmacia Biotech, Little Chalfont, U.K.), developed with Amersham ECL detection reagents, and exposed to Hyperfilm (Amersham Pharmacia Biotech).

Measurement of Tumor Growth

Tumors were measured every other day with calipers spanning the shortest and longest surface diameters. The mean of these two measurements was plotted as the mean tumor diameter in millimeters against various time points. Mice were sacrificed when the tumor diameter reached 20 mm. Tumor measurements for each time point are shown only for surviving mice.

Effects of Listeria Recombinants on Established Tumor Growth

Six- to 8-wk-old C57BL/6 mice (Charles River) received $2 \times 10^5$ TC-1 cells s.c. on the left flank. One week following tumor inoculation, the tumors had reached a palpable size of 4-5 mm in diameter. Groups of eight mice were then treated with $0.1 LD_{50}$ i.p. Lm-LLO-E7 ($10^7$ CFU), Lm-E7 ($10^6$ CFU), Lm-LLO-NP ($10^7$ CFU), or Lm-Gag ($5 \times 10^5$ CFU) on days 7 and 14.

$^{51}$Cr Release Assay

C57BL/6 mice, 6-8 wk old, were immunized i.p. with 0.1 $LD_{50}$ Lm-LLO-E7, Lm-E7, Lm-LLO-NP, or Lm-Gag. Ten days post-immunization, spleens were harvested. Splenocytes were established in culture with irradiated TC-1 cells (100:1, splenocytes:TC-1) as feeder cells; stimulated in vitro for 5 days, then used in a standard $^{51}$Cr release assay, using the following targets: EL-4, EL-4/E7, or EL-4 pulsed with E7H-2b peptide (RAHYNIVTF). E:T cell ratios, performed in triplicate, were 80:1, 40:1, 20:1, 10:1, 5:1, and 2.5:1. Following a 4-h incubation at 37° C., cells were pelleted, and 50 μl supernatant was removed from each well. Samples were assayed with a Wallac 1450 scintillation counter (Gaithersburg, Md.). The percent specific lysis was determined as [(experimental counts per minute (cpm)−spontaneous cpm)/(total cpm−spontaneous cpm)]×100.

TC-1-Specific Proliferation

C57BL/6 mice were immunized with 0.1 $LD_{50}$ and boosted by i.p. injection 20 days later with 1 $LD_{50}$ Lm-LLO-E7, Lm-E7, Lm-LLO-NP, or Lm-Gag. Six days after boosting, spleens were harvested from immunized and naive mice. Splenocytes were established in culture at $5 \times 10^5$/well in flat-bottom 96-well plates with $2.5 \times 10^4$, $1.25 \times 10^4$, $6 \times 10^3$ or $3 \times 10^3$ irradiated TC-1 cells/well as a source of E7 Ag, or without TC-1 cells or with 10 μg/ml Con A. Cells were pulsed 45 h later with 0.5 μCi [$^3$H]thymidine/well. Plates were harvested 18 h later using a Tomtec harvester 96 (Orange, Conn.), and proliferation was assessed with a Wallac 1450 scintillation counter. The change in cpm was calculated as experimental cpm−no Ag cpm.

Flow Cytometric Analysis

C57BL/6 mice were immunized intravenously (i.v.) with 0.1 $LD_{50}$ Lm-LLO-E7 or Lm-E7 and boosted 30 days later. Three-color flow cytometry for CD8 (53-6.7, PE conjugated), CD62 ligand (CD62L; MEL-14, APC conjugated), and E7H-2 Db tetramer was performed using a FACSCalibur® flow cytometer with CellQuest® software (Becton Dickinson, Mountain View, Calif.). Splenocytes harvested 5 days after the boost were stained at room temperature (rt) with H-2 Db tetramers loaded with the E7 peptide (RAHYNIVTF) or a control (HIV-Gag) peptide. Tetramers were used at a 1/200 dilution and were provided by Dr. Larry R. Pease (Mayo Clinic, Rochester, Minn.) and by the NIAID Tetramer Core Facility and the NIH AIDS Research and Reference Reagent Program. Tetramer$^+$, CD8$^+$, CD62L$^{low}$ cells were analyzed.

B16F0-Ova Experiment

24 C57BL/6 mice were inoculated with $5 \times 10^5$ B16F0-Ova cells. On days 3, 10 and 17, groups of 8 mice were immunized with 0.1 LD$_{50}$ Lm-OVA ($10^6$ cfu), Lm-LLO-OVA ($10^8$ cfu) and eight animals were left untreated.

Statistics

For comparisons of tumor diameters, mean and SD of tumor size for each group were determined, and statistical significance was determined by Student's t test. $p \leq 0.05$ was considered significant.

Results

Figure 3:
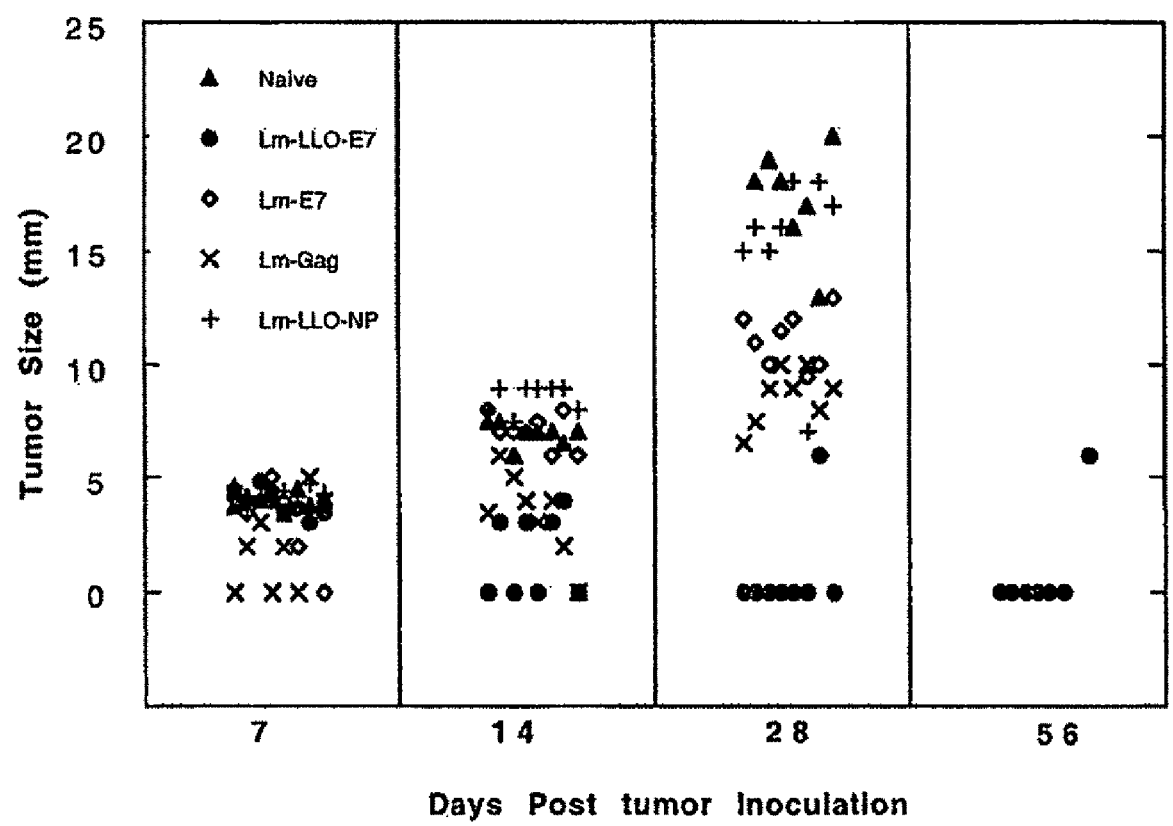
FIG. 3. Tumor immunotherapeutic efficacy of LLO-E7 fusions. Tumor size in millimeters in mice is shown at 7, 14, 21, 28 and 56 days post tumor-inoculation. Naive mice: open-circles; Lm-LLO-E7: filled circles; Lm-E7: squares; Lm-Gag: open diamonds; and Lm-LLO-NP: filled triangles.

Lm-E7 and Lm-LLO-E7 were compared for their abilities to impact on TC-1 growth. Subcutaneous tumors were established on the left flank of C57BL/6 mice. Seven days later tumors had reached a palpable size (4-5 mm). Mice were vaccinated on days 7 and 14 with 0.1 LD$_{50}$ Lm-E7, Lm-LLO-E7, or, as controls, Lm-Gag and Lm-LLO-NP. Lm-LLO-E7 induced complete regression of 75% of established TC-1 tumors, while tumor growth was controlled in the other 2 mice in the group (FIG. 3). By contrast, immunization with Lm-E7 and Lm-Gag did not induce tumor regression. This experiment was repeated multiple times, always with very similar results. In addition, similar results were achieved for Lm-LLO-E7 under different immunization protocols. In another experiment, a single immunization was able to cure mice of established 5 mm TC-1 tumors.

In other experiments, similar results were obtained with 2 other E7-expressing tumor cell lines: C3 and EL-4/E7. To confirm the efficacy of vaccination with Lm-LLO-E7, animals that had eliminated their tumors were re-challenged with TC-1 or EL-4/E7 tumor cells on day 60 or day 40, respectively. Animals immunized with Lm-LLO-E7 remained tumor free until termination of the experiment (day 124 in the case of TC-1 and day 54 for EL-4/E7).

Thus, expression of an antigen as a fusion protein with ΔLLO enhances the immunogenicity of the antigen.

Example 2

LM-LLO-E7 Treatment Elicits TC-1 Specific Splenocyte Proliferation

Figure 4:
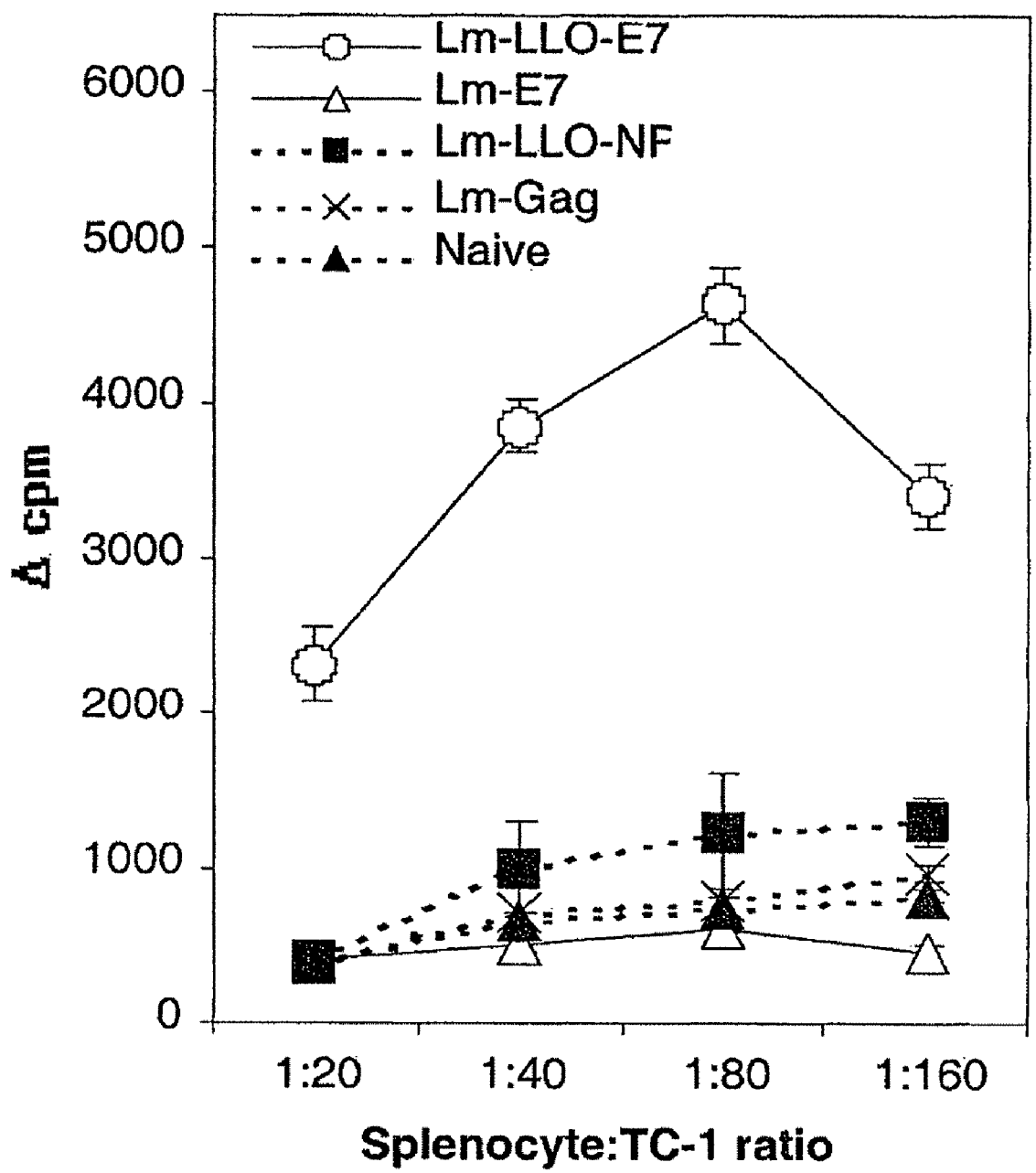
FIG. 4. Splenocytes from Lm-LLO-E7-immunized mice proliferate when exposed to TC-1 cells. C57BL/6 mice were immunized and boosted with Lm-LLO-E7, Lm-E7, or control rLm strains. Splenocytes were harvested 6 days after the boost and plated with irradiated TC-1 cells at the ratios shown. The cells were pulsed with $^3$H thymidine and harvested. Cpm is defined as (experimental cpm)−(no-TC-1 control).

To measure induction of T cells by Lm-E7 with Lm-LLO-E7, TC-1-specific proliferative responses, a measure of antigen-specific immunocompetence, were measured in immunized mice. Splenocytes from Lm-LLO-E7-immunized mice proliferated when exposed to irradiated TC-1 cells as a source of E7, at splenocyte: TC-1 ratios of 20:1, 40:1, 80:1, and 160:1 (FIG. 4). Conversely, splenocytes from Lm-E7 and rLm control-immunized mice exhibited only background levels of proliferation.

Example 3

ActA-E7 and PEST-E7 Fusions Confer Anti-Tumor Immunity

Materials and Experimental Methods

Construction of Lm-ActA-E7

Lm-ActA-E7 is a recombinant strain of LM, comprising a plasmid that expresses the E7 protein fused to a truncated version of the actA protein. Lm-actA-E7 was generated by introducing a plasmid vector pDD-1, constructed by modifying pDP-2028, into *Listeria*. pDD-1 comprises an expression cassette expressing a copy of the 310 bp hly promoter and the hly signal sequence (ss), which drives the expression and secretion of ActA-E7; 1170 bp of the actA gene that comprises four PEST sequences (SEQ ID NO: 24) (the truncated ActA polypeptide consists of the first 390 AA of the molecule, SEQ ID NO: 23); the 300 bp HPV E7 gene; the 1019 bp prfA gene (controls expression of the virulence genes); and the CAT gene (chloramphenicol resistance gene) for selection of transformed bacteria clones (Sewell et al. (2004), Arch. Otolaryngol. Head Neck Surg., 130: 92-97).

The hly promoter (pHly) and gene fragment were PCR amplified from pGG55 (Example 1) using primer 5'-GGGG TCTAGACCTCCTTTGATTAGTATATTC-3' (Xba I site is underlined; SEQ ID NO: 14) and primer 5'-ATCTTCGC-TATCTGTCGC CGCGGCGCGTGCTTCAGTTTGTTGCGC-'3 (Not I site is underlined. The first 18 nucleotides are the ActA gene overlap; SEQ ID NO: 15). The actA gene was PCR amplified from the LM 10403s wildtype genome using primer 5'-GCG-CAACAAACTGAAGCAGC GGCCGCGGCGACAGATAGCGAAGAT-3' (NotI site is underlined; SEQ ID NO: 16) and primer 5'-TGTAGGTG-TATCTCCATGCTCGAGAGCTAGGCGATCAATTTC-3' (XhoI site is underlined; SEQ ID NO: 17). The E7 gene was PCR amplified from pGG55 (pLLO-E7) using primer 5'-GGAATTGATCGCCTAGCT CTCGAGCATGGAGATACACCTACA-3' (XhoI site is underlined; SEQ ID NO: 18) and primer 5'-AAACGGATT-TATTTAGATCCCGGGTTATGGTTTCTGAGAACA-3' (XmaI site is underlined; SEQ ID NO: 19). The prfA gene was PCR amplified from the LM 10403s wild-type genome using primer 5'-TGTTCTCAGAAACCATAA CCCGGGATCTAAATAAATCCGTTT-3' (XmaI site is underlined; SEQ ID NO: 20) and primer 5'-GGGGG TCGACCAGCTCTTCTTGGTGAAG-3' (SalI site is underlined; SEQ ID NO: 21). The hly promoter-actA gene fusion (pHly-actA) was PCR generated and amplified from purified pHly DNA and purified actA DNA using the upstream pHly primer (SEQ ID NO: 14) and downstream actA primer (SEQ ID NO: 17).

The E7 gene fused to the prfA gene (E7-prfA) was PCR generated and amplified from purified E7 DNA and purified prfA DNA using the upstream E7 primer (SEQ ID NO: 18) and downstream prfA gene primer (SEQ ID NO: 21).

The pHly-actA fusion product fused to the E7-prfA fusion product was PCR generated and amplified from purified fused pHly-actA DNA product and purified fused E7-prfA DNA product using the upstream pHly primer (SEQ ID NO: 14) and downstream prfA gene primer (SEQ ID NO: 21) and ligated into pCRII (Invitrogen, La Jolla, Calif.). Competent *E. coli* (TOP10'F, Invitrogen, La Jolla, Calif.) were transformed with pCRII-ActAE7. After lysis and isolation, the plasmid was screened by restriction analysis using BamHI (expected fragment sizes 770 bp and 6400 bp (or when the insert was reversed into the vector: 2500 bp and 4100 bp)) and BstXI (expected fragment sizes 2800 bp and 3900 bp) and also screened with PCR analysis using the upstream pHly primer (SEQ ID NO: 14) and the downstream prfA gene primer (SEQ ID NO: 21).

The pHly-actA-E7-prfA DNA insert was excised from pCRII by double digestion with Xba I and Sal I and ligated into pDP-2028 also digested with Xba I and Sal I. After transforming TOP10'F competent *E. coli* (Invitrogen, La Jolla, Calif.) with expression system pActAE7, chloramphenicol resistant clones were screened by PCR analysis using the upstream pHly primer (SEQ ID NO: 14) and the downstream PrfA gene primer (SEQ ID NO: 21). A clone comprising pActAE7 was grown in brain heart infusion medium (with chloramphenicol (20 mcg (microgram)/ml (milliliter), Difco, Detroit, Mich.) and pActAE7 was isolated from the bacteria cell using a midiprep DNA purification system kit (Promega, Madison, Wis.). A prfA-negative strain of penicillin-treated *Listeria* (strain XFL-7) was transformed with expression system pActAE7, as described in Ikonomidis et al. (1994, J. Exp. Med. 180: 2209-2218) and clones were selected for the retention of the plasmid in vivo. Clones were grown in brain heart infusion with chloramphenicol (20 mcg/ml) at 37° C. Bacteria were frozen in aliquots at −80° C.

Immunoblot Verification of Antigen Expression

Figure 5A:
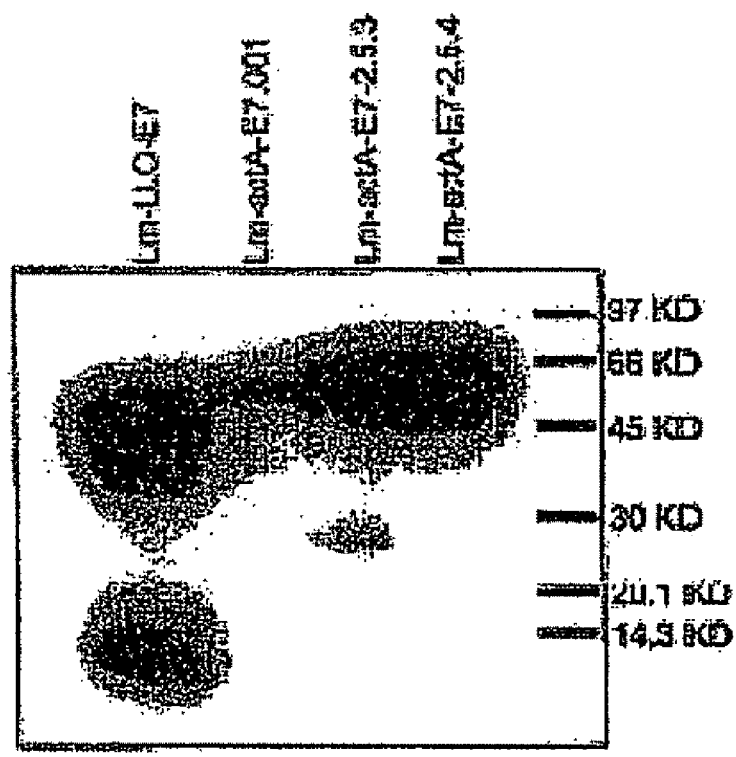
FIG. 5. A. Western blot demonstrating that Lm-ActA-E7 secretes E7. Lane 1: Lm-LLO-E7; lane 2: Lm-ActA-E7.001; lane 3; Lm-ActA-E7-2.5.3; lane 4: Lm-ActA-E7-2.5.4. B. Tumor size in mice administered Lm-ActA-E7 (rectangles), Lm-E7 (ovals), Lm-LLO-E7 (X), and naive mice (non-vaccinated; solid triangles).

To verify that Lm-ActA-E7 secretes ActA-E7, (about 64 kD), *Listeria* strains were grown in Luria-Bertoni (LB) medium at 37° C. Protein was precipitated from the culture supernatant with trichloroacetic acid (TCA) and resuspended in 1× sample buffer with 0.1N sodium hydroxide. Identical amounts of each TCA precipitated supernatant were loaded on 4% to 20% Tris-glycine sodium dodecyl sulfate-polyacrylamide gels (NOVEX, San Diego, Calif.). Gels were transferred to polyvinylidene difluoride membranes and probed with 1:2500 anti-E7 monoclonal antibody (Zymed Laboratories, South San Francisco, Calif.), then with 1:5000 horseradish peroxidase-conjugated anti-mouse IgG (Amersham Pharmacia Biotech, Little Chalfont, England). Blots were developed with Amersham enhanced chemiluminescence detection reagents and exposed to autoradiography film (Amersham) (FIG. 5A).

Figure 6A:
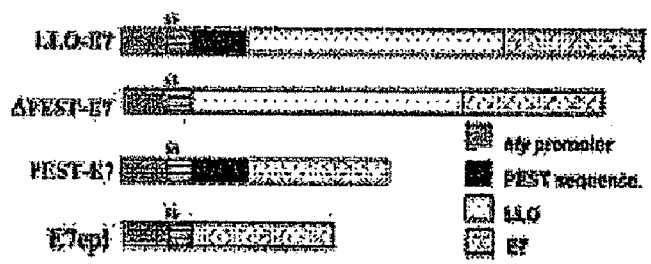
FIG. 6. A. schematic representation of the plasmid inserts used to create 4 LM vaccines. Lm-LLO-E7 insert contains all of the *Listeria* genes used. It contains the hly promoter, the first 1.3 kb of the hly gene (which encodes the protein LLO), and the HPV-16 E7 gene. The first 1.3 kb of hly includes the signal sequence (ss) and the PEST region. Lm-PEST-E7 includes the hly promoter, the signal sequence, and PEST and E7 sequences but excludes the remainder of the truncated LLO gene. Lm-ΔPEST-E7 excludes the PEST region, but contains the hly promoter, the signal sequence, E7, and the remainder of the truncated LLO. Lm-E7epi has only the hly promoter, the signal sequence, and E7. B. Top panel: *Listeria* constructs containing PEST regions induce tumor regression. Bottom panel: Average tumor sizes at day 28 post-tumor challenge in 2 separate experiments. C. *Listeria* constructs containing PEST regions induce a higher percentage of E7-specific lymphocytes in the spleen. Average and SE of data from 3 experiments are depicted.

Construction of Lm-PEST-E7, Lm-ΔPEST-E7, and Lm-E7epi (FIG. 6A)

Lm-PEST-E7 is identical to Lm-LLO-E7, except that it contains only the promoter and PEST sequence of the hly gene, specifically the first 50 AA of LLO. To construct Lm-PEST-E7, the hly promoter and PEST regions were fused to the full-length E7 gene using the SOE (gene splicing by overlap extension) PCR technique. The E7 gene and the hly-PEST gene fragment were amplified from the plasmid pGG-55, which contains the first 441 AA of LLO, and spliced together by conventional PCR techniques. To create a final plasmid, pVS16.5, the hly-PEST-E7 fragment and the prfA gene were subcloned into the plasmid pAM401, which includes a chloramphenicol resistance gene for selection in vitro, and the resultant plasmid was used to transform XFL-7.

Lm-ΔPEST-E7 is a recombinant *Listeria* strain that is identical to Lm-LLO-E7 except that it lacks the PEST sequence. It was made essentially as described for Lm-PEST-E7, except that the episomal expression system was constructed using primers designed to remove the PEST-containing region (bp 333-387) from the hly-E7 fusion gene. Lm-E7epi is a recombinant strain that secretes E7 without the PEST region or LLO. The plasmid used to transform this strain contains a gene fragment of the hly promoter and signal sequence fused to the E7 gene. This construct differs from the original Lm-E7, which expressed a single copy of the E7 gene integrated into the chromosome. Lm-E7epi is completely isogenic to Lm-LLO-E7, Lm-PEST-E7, and Lm-ΔPEST-E7 except for the form of the E7 antigen expressed.

Results

Figure 5B:
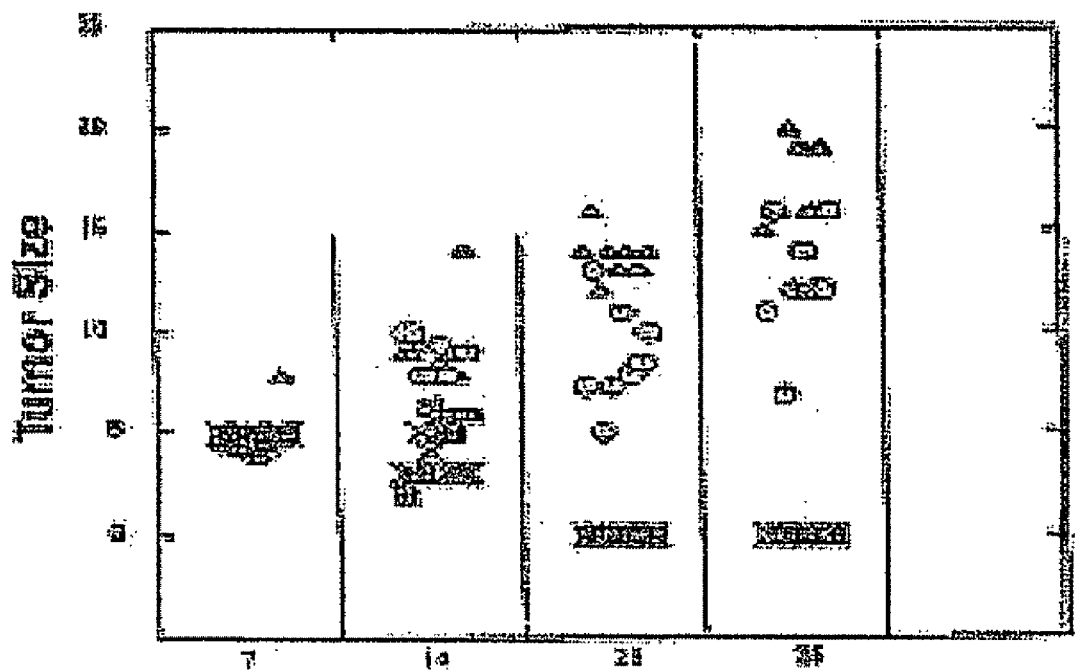

To compare the anti-tumor immunity induced by Lm-ActA-E7 versus Lm-LLO-E7, $2 \times 10^5$ TC-1 tumor cells were implanted subcutaneously in mice and allowed to grow to a palpable size (approximately 5 millimeters [mm]). Mice were immunized i.p. with one $LD_{50}$ of either Lm-ActA-E7 ($5 \times 10^8$ CFU), (crosses) Lm-LLO-E7 ($10^8$ CFU) (squares) or Lm-E7 ($10^6$ CFU) (circles) on days 7 and 14. By day 26, all of the animals in the Lm-LLO-E7 and Lm-ActA-E7 were tumor free and remained so, whereas all of the naive animals (triangles) and the animals immunized with Lm-E7 grew large tumors (FIG. 5B). Thus, vaccination with ActA-E7 fusions causes tumor regression.

Figure 6B:
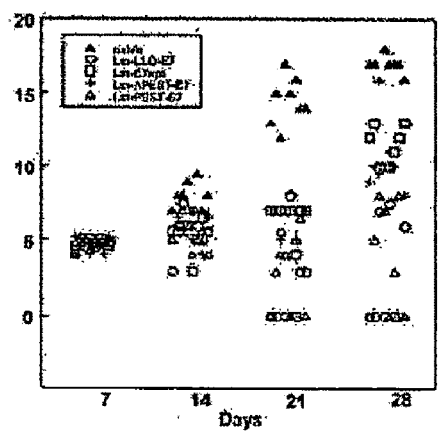
Figure 6C:
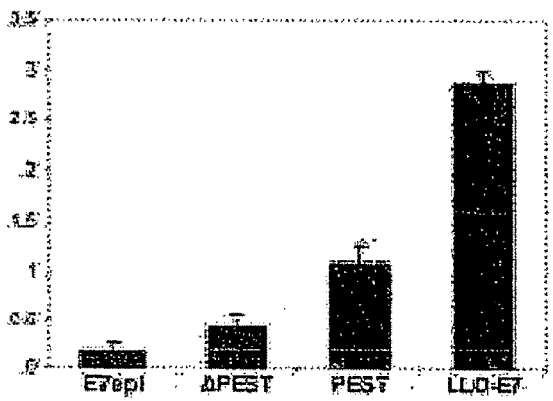

In addition, Lm-LLO-E7, Lm-PEST-E7, Lm-ΔPEST-E7, and Lm-E7epi were compared for their ability to cause regression of E7-expressing tumors. S.c. TC-1 tumors were established on the left flank of 40 C57BL/6 mice. After tumors had reached 4-5 mm, mice were divided into 5 groups of 8 mice. Each groups was treated with 1 of 4 recombinant LM vaccines, and 1 group was left untreated. Lm-LLO-E7 and Lm-PEST-E7 induced regression of established tumors in ⅝ and ⅜ cases, respectively. There was no statistical difference between the average tumor size of mice treated with Lm-PEST-E7 or Lm-LLO-E7 at any time point. However, the vaccines that expressed E7 without the PEST sequences, Lm-ΔPEST-E7 and Lm-E7epi, failed to cause tumor regression in all mice except one (FIG. 6B, top panel). This was representative of 2 experiments, wherein a statistically significant difference in mean tumor sizes at day 28 was observed between tumors treated with Lm-LLO-E7 or Lm-PEST-E7 and those treated with Lm-E7epi or Lm-ΔPEST-E7; $P<0.001$, Student's t test; FIG. 6B, bottom panel). In addition, increased percentages of tetramer-positive splenocytes were seen reproducibly over 3 experiments in the spleens of mice vaccinated with PEST-containing vaccines (FIG. 6C). Thus, vaccination with PEST-E7 fusions causes tumor regression.

Example 4

Fusion of E7 to LLO, ActA, or a PEST-Like Sequence Enhances E7-Specific Immunity and Generates Tumor-Infiltrating E7-Specific CD8+ Cells Materials and Experimental Methods 500 mcl (microliter) of MATRIGEL®, comprising 100 mcl of $2 \times 10^5$ TC-1 tumor cells in phosphate buffered saline (PBS) plus 400 mcl of MATRIGEL® (BD Biosciences, Franklin Lakes, N.J.) were implanted subcutaneously on the left flank of 12 C57BL/6 mice (n=3). Mice were immunized intraperitoneally on day 7, 14 and 21, and spleens and tumors were harvested on day 28. Tumor MATRIGELs were removed from the mice and incubated at 4° C. overnight in tubes containing 2 milliliters (ml) of RP 10 medium on ice. Tumors were minced with forceps, cut into 2 mm blocks, and incubated at 37° C. for 1 hour with 3 ml of enzyme mixture (0.2 mg/ml collagenase-P, 1 mg/ml DNAse-1 in PBS). The tissue suspension was filtered through nylon mesh and washed with 5% fetal bovine serum+0.05% of $NaN_3$ in PBS for tetramer and IFN-gamma staining.

Splenocytes and tumor cells were incubated with 1 micromole (mcm) E7 peptide for 5 hours in the presence of brefeldin A at $10^7$ cells/ml. Cells were washed twice and incubated in 50 mcl of anti-mouse Fc receptor supernatant (2.4 G2) for 1 hour or overnight at 4° C. Cells were stained for surface molecules CD8 and CD62L, permeabilized, fixed using the permeabilization kit Golgi-stop® or Golgi-Plug® (Pharmingen, San Diego, Calif.), and stained for IFN-gamma. 500,000 events were acquired using two-laser flow cytometer FACS-Calibur and analyzed using Cellquest Software (Becton Dickinson, Franklin Lakes, N.J.). Percentages of IFN-gamma secreting cells within the activated ($CD62L^{low}$) CD8+ T cells were calculated.

For tetramer staining, H-2D$^b$ tetramer was loaded with phycoerythrin (PE)-conjugated E7 peptide (RAHYNIVTF, SEQ ID NO: 22), stained at rt for 1 hour, and stained with anti-allophycocyanin (APC) conjugated MEL-14 (CD62L) and FITC-conjugated CD8β at 4° C. for 30 min. Cells were analyzed comparing tetramer$^+$CD8$^+$ CD62L$^{low}$ cells in the spleen and in the tumor.

Results

Figure 7A:
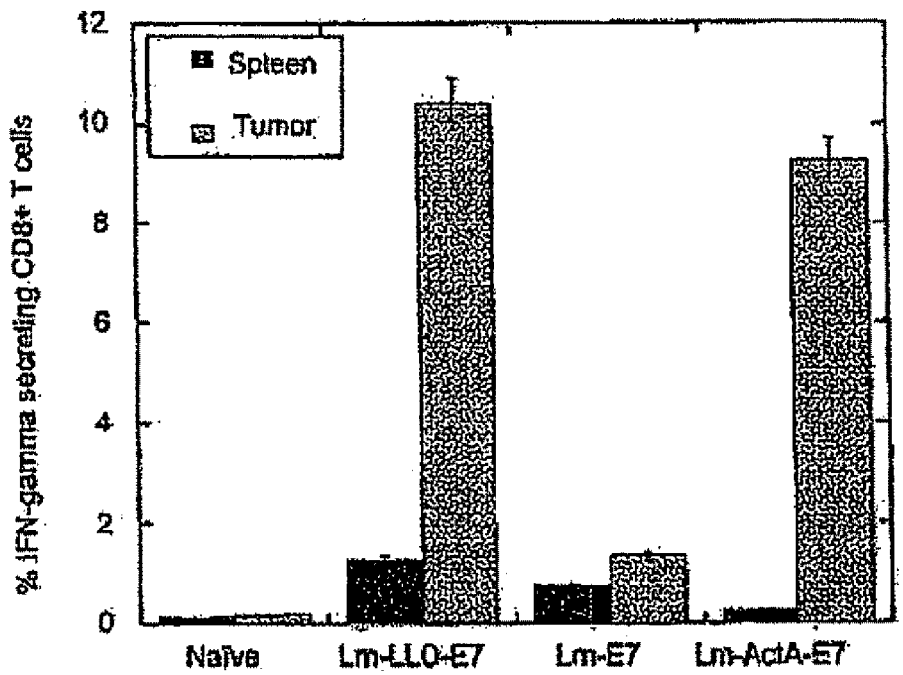
FIG. 7. A. Induction of E7-specific IFN-gamma-secreting CD8$^+$ T cells in the spleens and the numbers penetrating the tumors, in mice administered TC-1 tumor cells and subsequently administered Lm-E7, Lm-LLO-E7, Lm-ActA-E7, or no vaccine (naive). B. Induction and penetration of E7 specific CD8$^+$ cells in the spleens and tumors of the mice described for (A).
Figure 7B:
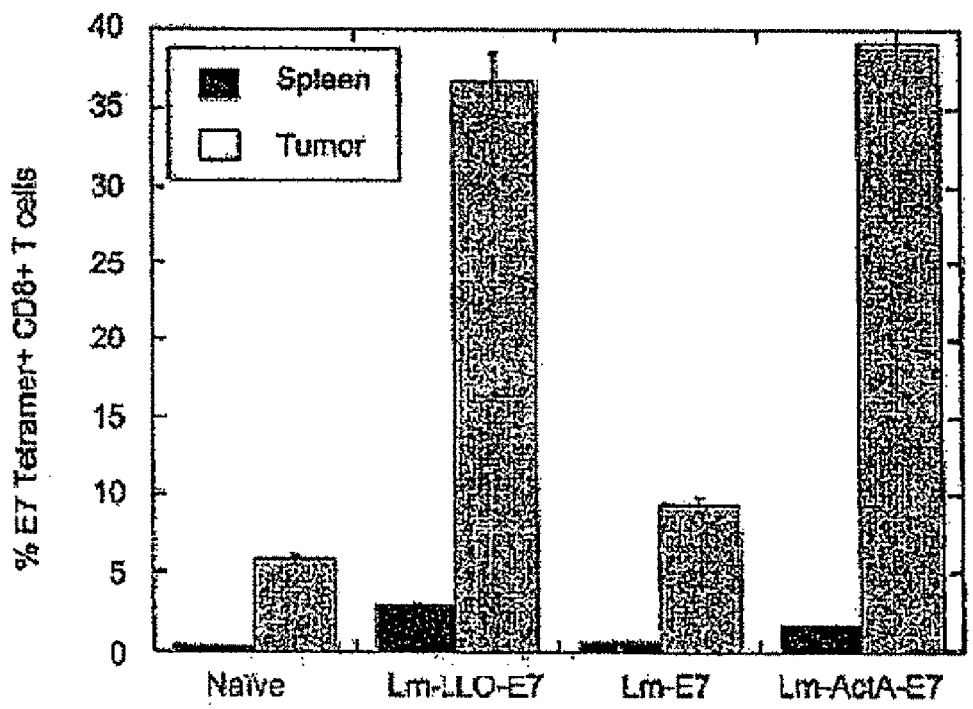

To analyze the ability of Lm-ActA-E7 to enhance antigen specific immunity, mice were implanted with TC-1 tumor cells and immunized with either Lm-LLO-E7 (1×10$^7$ CFU), Lm-E7 (1×10$^6$ CFU), or Lm-ActA-E7 (2×10$^8$ CFU), or were untreated (naïve). Tumors of mice from the Lm-LLO-E7 and Lm-ActA-E7 groups contained a higher percentage of IFN-gamma-secreting CD8$^+$ T cells (FIG. 7A) and tetramer-specific CD8$^+$ cells (FIG. 7B) than in Lm-E7 or naive mice.

Figure 8:
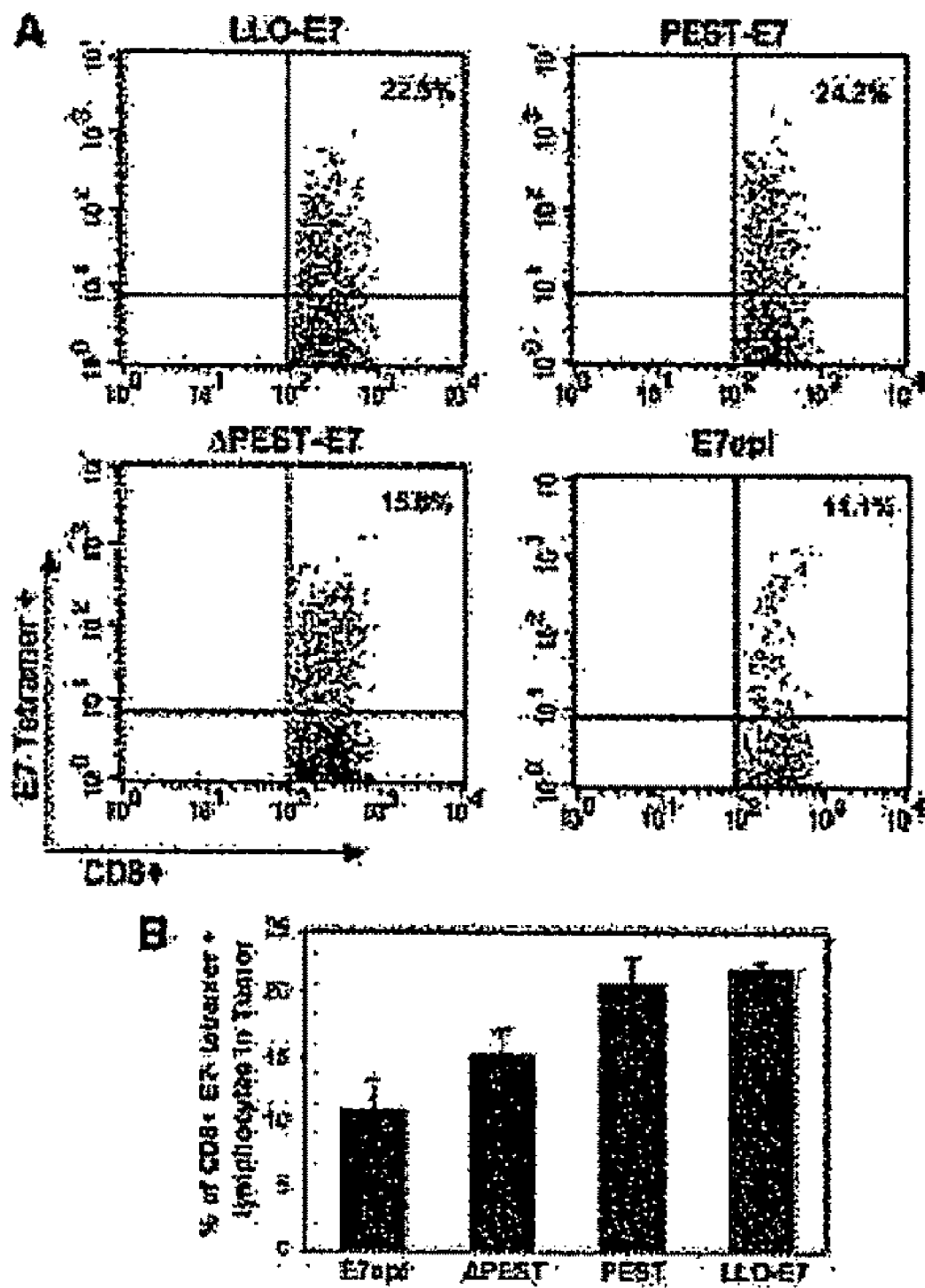
FIG. 8. *Listeria* constructs containing PEST regions induce a higher percentage of E7-specific lymphocytes within the tumor. A. representative data from 1 experiment. B. average and SE of data from all 3 experiments.

In another experiment, tumor-bearing mice were administered Lm-LLO-E7, Lm-PEST-E7, Lm-ΔPEST-E7, or Lm-E7epi, and levels of E7-specific lymphocytes within the tumor were measured. Mice were treated on days 7 and 14 with 0.1 LD$_{50}$ of the 4 vaccines. Tumors were harvested on day 21 and stained with antibodies to CD62L, CD8, and with the E7/Db tetramer. An increased percentage of tetramer-positive lymphocytes within the tumor were seen in mice vaccinated with Lm-LLO-E7 and Lm-PEST-E7 (FIG. 8A). This result was reproducible over three experiments (FIG. 8B).

Thus, Lm-LLO-E7, Lm-ActA-E7, and Lm-PEST-E7 are each efficacious at induction of tumor-infiltrating CD8$^+$ T cells and tumor regression.

Example 5

E6/E7 Transgenic Mouse Phenotype: a Model for Spontaneous Tumor Growth and Tolerance to a Tumor Antigen Materials and Experimental Methods Several C57BL/6 mouse zygotes were injected with plasmids containing the HPV-16 E6/E7 gene under the control of the thyroglobulin promoter (provided by M Parmentier, Brussels). Tail clippings of several litters were screened via PCR for the E6/E7 gene. The E7 gene and the thyroglobulin promoter were integrated into the majority of the progeny. Positive mosaic E7 transgenic mice were then selected for F0×wild type breeding. Subsequent F1 generations were screened, via PCR, for the presence of the E7 gene. E7 positive pups generated from F0×wt breeding pairs were selected for F1×F1 breeding. The zygosity of F1 breeding pair derived generations was determined by Taqman real-time PCR and the ΔΔCt method (Charles River, 2001). Homozygous E7 transgenic mice were selected for F2×F2 breeding. The subsequent F3 generation was screened via Taqman real-time PCR and backcrossing to confirm fidelity of homozygosity. The levels of gene copy number and transgene expression of the E7 gene was assessed for every homozygous line using Taqman real-time PCR. After 6 back-crossings, these lines were used as the parents of the colony. Transgene expression was further confirmed by appearance of thyroid hyperplasia, as described in the Results section.

Results

Figure 9:
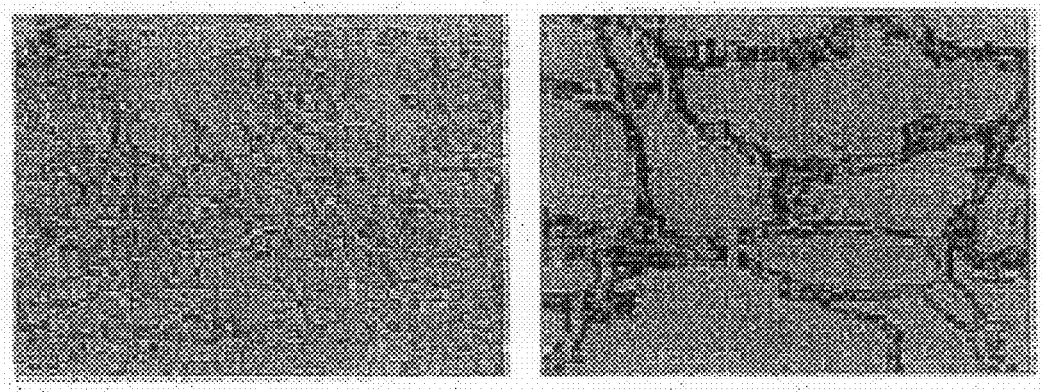
FIG. 9. E6/E7 transgenic mice develop tumors in their thyroid, where the E7 gene is expressed. Mice were sacrificed at 3 months and had their thyroids removed, sectioned, and stained by hematoxylin and eosin. A. Left panel: normal thyroid at 20× magnification. Follicles are of normal size and lined with cuboidal cells with abundant pink cytoplasm (arrow). Right panel: E6/E7 transgenic mouse thyroid. Note the greatly enlarged follicles because of the increased production of colloid. The cuboidal cells lining the follicles are smaller with very little cytoplasm.

E6/E7 transgenic mice were generated, and their phenotype assessed. The mice began to develop thyroid hyperplasia at 8 weeks and palpable goiters at 6 months. By 6 to 8 months, most mice exhibited thyroid cancer. Transgenic mice sacrificed at 3 months of age exhibited de-differentiation of the normal thyroid architecture, indicative of an early stage of cancer. The enlarged, de-differentiated cells were filled with colloid, where thyroid hormones accumulate (FIG. 9).

Example 6

E7 is Expressed in Medullary Thymic Epithelial Cells of E6/E7 Transgenic Mice

Figure 10:
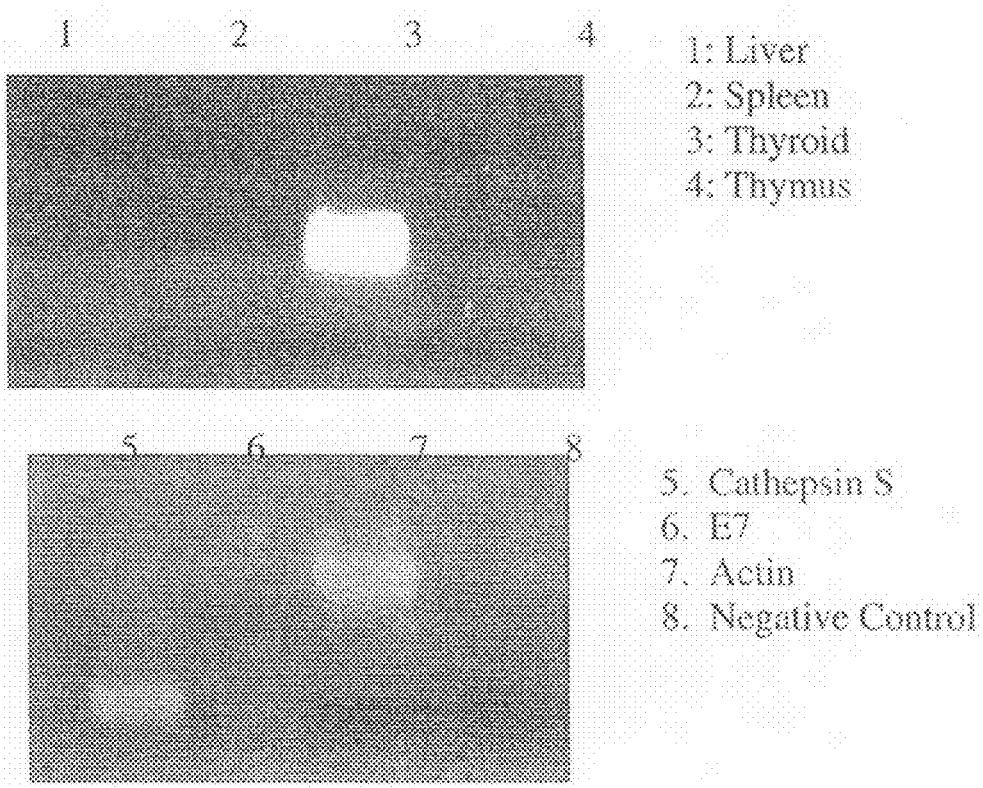
FIG. 10. E7 message is expressed in the thyroid and medullary thymic epithelial cells of the E6/E7 transgenic mouse. A. Tissue-specific expression of the E7 transgene is detected in the thyroid only but not the liver, spleen, or whole thymus. Lane 1: Liver; Lane 2: Spleen; Lane 3: Thyroid; Lane 4: Whole Thymus. B. Medullary thymic epithelial cells (mTECs) express E7. RT-PCR results are as shown for equivalent amounts of cDNA loaded for 40 cycles. Lane 5: Cathepsin S; Lane 6: E7; Lane 7: Actin; Lane 8: Negative Control.

To determine whether or not E7 was expressed in the thymus, liver, spleen, thymus and thyroid were examined for the expression of the transgene in 6 to 8 week old mice. Abundant E7 message was found in the thyroid but not in other tissues (FIG. 10A). The absence of E7 message in whole thymus preparations was not indicative of lack of expression in the thymus, since the level of message of a peripherally expressed, organ-specific antigen, including thyroglobulin, has been shown to be too low to detect in whole thymocyte preparations (Derbinski, J., A. Schulte, B. Kyewski, and L. Klein. 2001. Promiscuous gene expression in medullary thymic epithelial cells mirrors the peripheral self. Nat Immunol 2:1032).

Tolerance to peripheral antigens in the thymus, including thyroglobulin, is mediated by the transient expression of these genes by the autoimmune regulator (AIRE) in thymic medullary epithelial cells (mTECs), with peak expression occurring prior to birth. AIRE is a transcription factor that maintains tolerance to self. To determine whether E7 expression in the transgenic mice followed the same pattern, mTECs from E6/E7 thymi of young mice (3-5 weeks) were examined for E7 expression.

The mTECs expressed E7 message, and also expressed Cathepsin S, which is known to be expressed in mTECs (FIG. 10B). Thus, E7 is expressed in the thymus of the transgenic mice, showing that these mice exhibit tolerance to the E7 antigen.

Example 7

Figure 11:
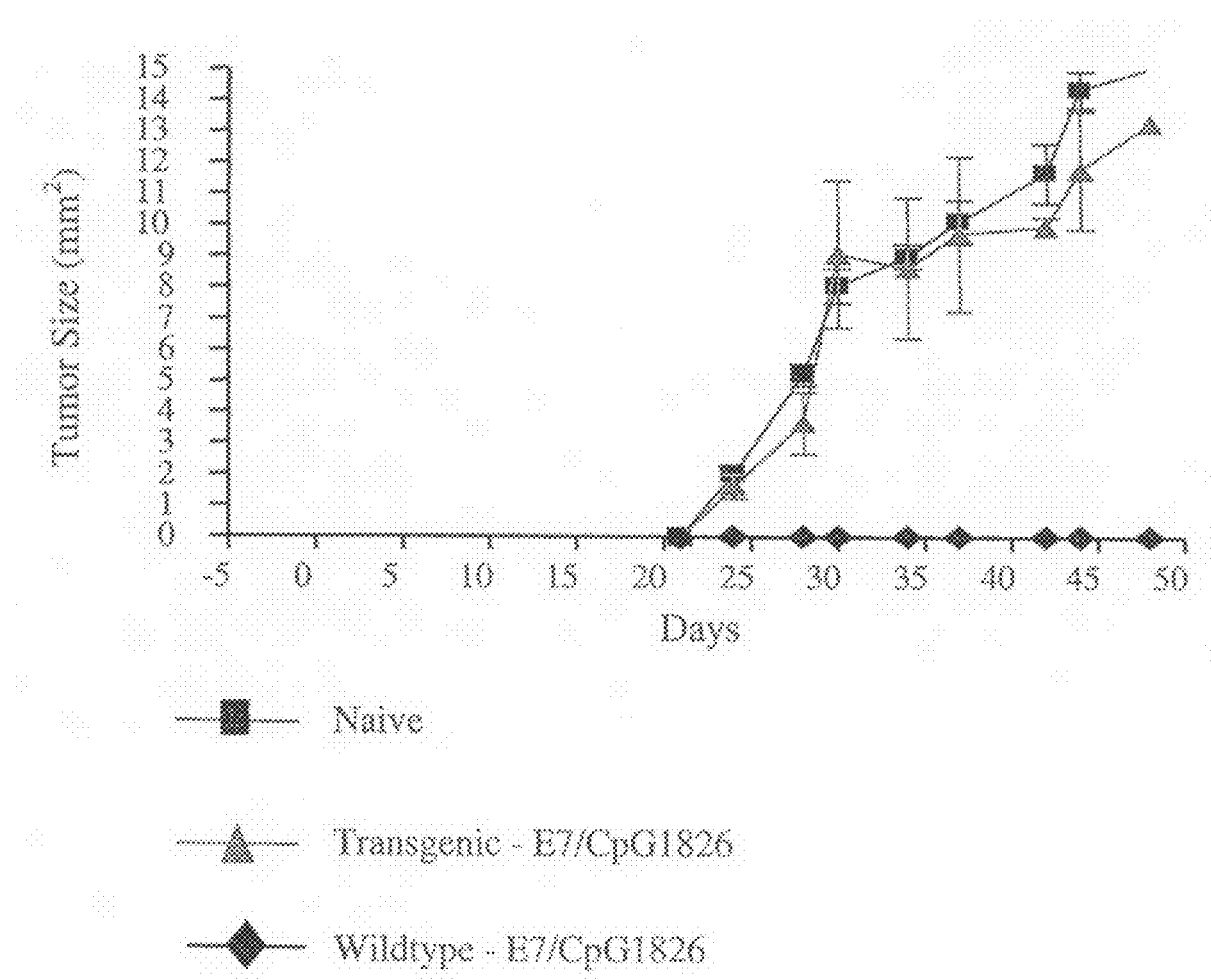
FIG. 11. RAHYNIVTF peptide plus CpG adjuvant does not protect against TC-1 challenge in E6/E7 transgenic mice. Two groups of transgenic mice received either E7 peptide plus adjuvant or PBS. A third group of wild type C57Bl/6 control mice received E7 peptide plus adjuvant. The mice were vaccinated twice intraperitoneally (i.p.), 7 days apart and challenged with 5×10$^4$ TC-1 cells 7 days later. Tumors were measured every 5 days until unimmunized mice needed to be sacrificed. Error bars: standard deviations from the mean value.

Peptide-Based Vaccines do not Protect Against Tumor Challenge in E6/E7 Transgenic Mice As a measure of the impact of the self-expression of E7 on vaccine efficacy, E6/E7 transgenic mice were tested in a tumor protection experiment using an E7 peptide (RAHYNIVTF)-based vaccine, along with the immunostimulatory CpG sequence 1826 (Krieg A M, Yi A K, Matson S, Waldschmidt T J, Bishop G A, Teasdale R, Koretzky G A, Klinman D M. Nature 374:546). While the peptide-based vaccine protected all the wild type mice from tumor challenge, it had no impact on tumor challenge in the transgenic mouse (FIG. 11). Thus, the E6/E7 mice exhibit reduced ability to reject tumor challenge, providing further evidence that they are tolerant to E7.

Example 8

Figure 12A:
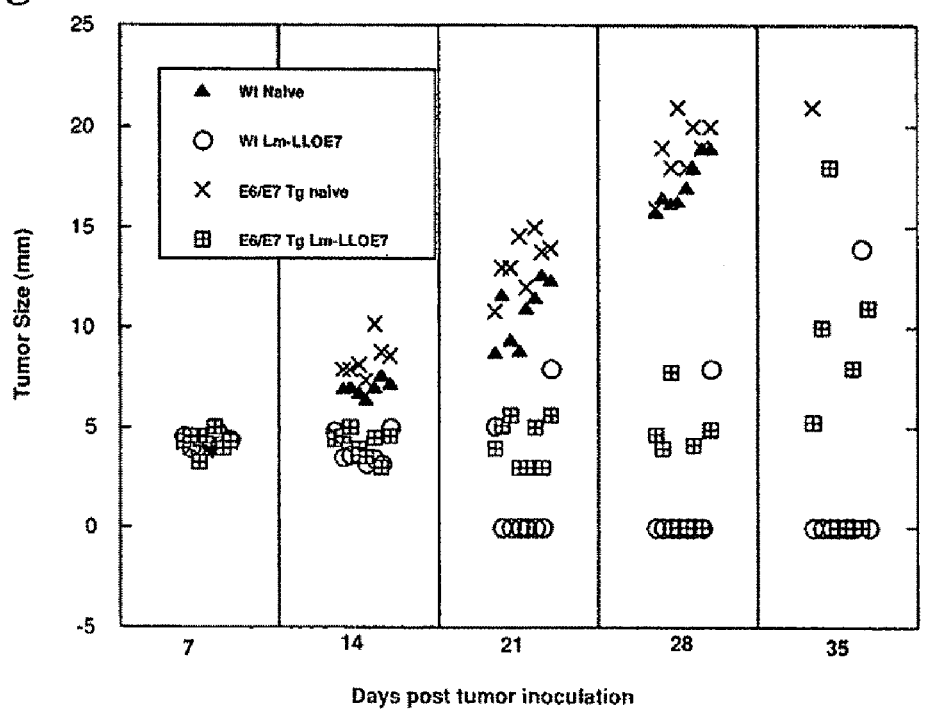
FIG. 12. Vaccines of the present invention induce regression of solid tumors in the E6/E7 transgenic mice in wild-type mice and transgenic mice immunized with LM-LLO-E7 (A), or LM-ActA-E7 (B), left naïve, or treated with LM-NP (control).
Figure 12B:
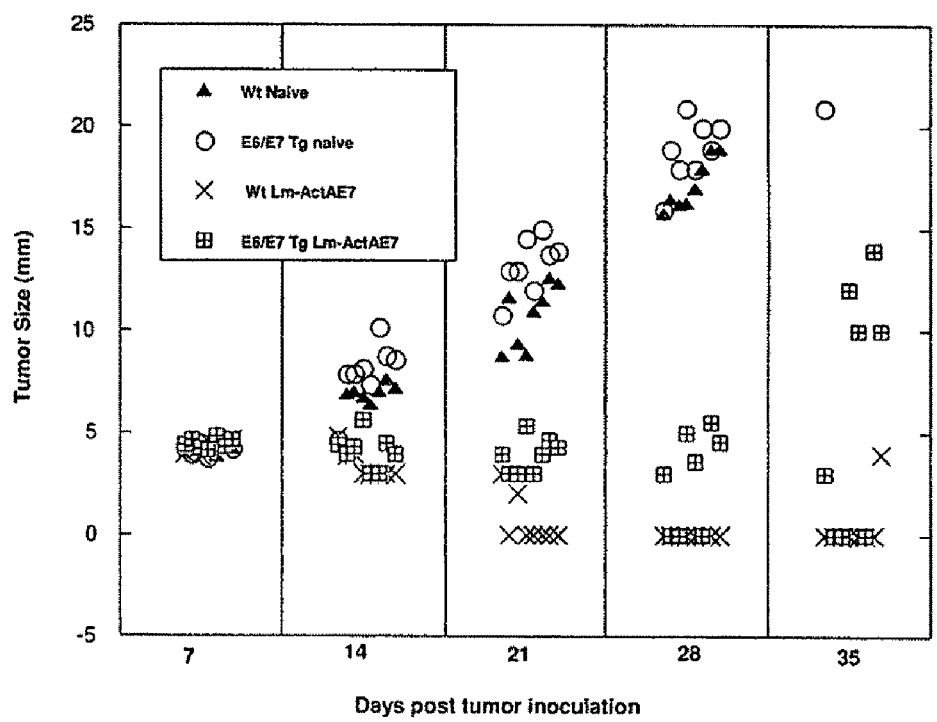

LLO and ActA Fusions Overcome Immune Tolerance of E6/E7 Transgenic Mice to E7-Expressing Tumors To test the ability of vaccines of the present invention to overcome the immune tolerance of E6/E7 transgenic mice to E7-expressing tumors, 10$^5$ TC-1 cells were implanted subcutaneously (s.c.) and allowed to form solid tumors in 6-8 week old wild-type and transgenic mice 7 and 14 days later, mice were left unimmunized or were immunized i.p. with LM-NP (control), $1 \times 10^8$ cfu LM-LLO-E7 (FIG. 12A) or $2.5 \times 10^8$ cfu LM-ActA-E7 (FIG. 12B). The naïve mice had a large tumor burden, as anticipated, and were sacrificed by day 28 or 35 due to tumors of over 2 cm. By contrast, by day 35, administration of either LM-LLO-E7 or LM-ActA-E7 resulted in complete tumor regression in 7/8 or 6/8, respectively, of the wild-type mice and 3/8 of the transgenic mice. In the transgenic mice that did not exhibit complete tumor regression, a marked slowing of tumor growth was observed in the LM-LLO-E7-vaccinated and LM-ActA-E7-vaccinated mice.

The effectiveness of vaccines of the present invention in inducing complete tumor regression and/or slowing of tumor growth in transgenic mice was in marked contrast to the inefficacy of the peptide-based vaccine. Thus, vaccines of the present invention were able to overcome immune tolerance of E6/E7 transgenic mice to E7-expressing tumors.

Example 9

LLO and ActA Fusions Reduce Autochthonous (Spontaneous) Tumors in E6/E7 Transgenic Mice To determine the impact of the Lm-LLO-E7 and Lm-ActA-E7 vaccines on autochthonous tumors in the E6/E7 transgenic mouse, 6 to 8 week old mice were immunized with $1 \times 10^8$ Lm-LLO-E7 or $2.5 \times 10^8$ Lm-ActA-E7 once per month for 8 months. Mice were sacrificed 20 days after the last immunization and their thyroids removed and weighed. This experiment was performed twice (Table 1).

TABLE 1

Thyroid weight (mg) in unvaccinated and vaccinated transgenic mice at 8 months of age (mg)*.

| Un-treated | ±S.D. | Lm-LLO-NP | ±S.D. | Lm-LLO-E7 | ±S.D. | Lm-ActA-E7 | ±S.D. |
|---|---|---|---|---|---|---|---|
| Expt. 1 408 | 123 | 385 | 130 | 225 | 54 | 305 | 92 |
| Expt. 2 588 | 94 | 503 | 86 | 239 | 68 | 275 | 84 |

*Statistical analyses performed using Student's t test showed that the difference in thyroid weight between Lm-LLO-NP treated mice and untreated mice was not significant but that the difference between Lm-LLO-E7 and Lm-ActA-E7 treated mice was highly significant (p < 0.001)

The difference in thyroid weight between Lm-LLO-E7 treated mice and untreated mice and between Lm-LLO-ActA treated mice and untreated mice was significant (p<0.001 and p<0.05, respectively) for both experiments, while the difference between Lm-LLO-NP treated mice (irrelevant antigen control) and untreated mice was not significant (Student's t test), showing that Lm-LLO-E7 and Lm-ActA-E7 controlled spontaneous tumor growth. Thus, vaccines of the present invention prevent formation of new E7-expressing tumors.

To summarize the findings in the above Examples, LLO-antigen and ActA-antigen fusions (a) induce tumor-specific immune response that include tumor-infiltrating antigen-specific T cells; and are capable of inducing tumor regression and controlling tumor growth of both normal and particularly aggressive tumors; (b) overcome tolerance to self antigens; and (c) prevent spontaneous tumor growth. These findings are generalizable to a large number of antigens, PEST-like sequences, and tumor types, as evidenced by their successful implementation with a variety of different antigens, PEST-like sequences, and tumor types.

Example 10

LM-LLO-E7 Vaccines are Safe and Improve Clinical Indicators in Cervical Cancer Patients Materials and Experimental Methods Inclusion criteria. All patients in the trial were diagnosed with "advanced, progressive or recurrent cervical cancer," and an assessment at the time of entry indicated that all were staged as having IVB disease. All patients manifested a positive immune response to an anergy panel containing 3 memory antigens selected from candidin, mumps, tetanus, or Tuberculin Purified Protein Derivative (PPD); were not pregnant or HIV positive, had taken no investigational drugs within 4 weeks, and were not receiving steroids.

Protocol: Patients were administered 2 vaccinations at a 3-week interval as a 30-minute intravenous (IV) infusion in 250 ml of normal saline to inpatients. After 5 days, patients received a single course of IV ampicillin and were released with an additional 10 days of oral ampicillin. Karnofsky Performance Index, which is a measurement of overall vitality and quality of life such as appetite, ability to complete daily tasks, restful sleep, etc, was used to determine overall well-being. In addition, the following indicators of safety and general well being were determined: alkaline phosphatase; bilirubin, both direct and total; gamma glutamyl transpeptidase (ggt); cholesterol; systole, diastole, and heart rate; Eastern Collaborative Oncology Group's (ECOG)'s criteria for assessing disease progression—a Karnofsky like-quality of life indicator; hematocrit; hemoglobin; platelet levels; lymphocytes levels; AST (aspartate aminotransferase); ALT (alanine aminotransferase); and LDH (lactate dehydrogenase). Patients were followed at 3 weeks and 3 months subsequent to the second dosing, at which time Response Evaluation Criteria in Solid Tumors (RECIST) scores of the patients were determined, scans were performed to determine tumor size, and blood samples were collected for immunological analysis at the end of the trial, which includes the evaluation of IFN-γ, IL-4, $CD4^+$ and $CD8^+$ cell populations.

*Listeria* strains: The creation of LM-LLO-E7 is described in Example 1. Bacteria were passaged twice through mice prior to preparation of the working cell bank, as described in Example 12. The cell bank exhibited viability upon thawing of greater than 90%.

Results

Prior to the clinical trial, a preclinical experiment was performed to determine the anti-tumor efficacy of intravenous (i.v.) vs. i.p. administration of LM-LLO-E7. A tumor containing $1 \times 10^4$ TC-1 cells was established sub-cutaneously. On days 7 and 14, mice were immunized with either $10^8$ LM-LLO-E7 i.p. or LM-LLO-E7 i.v. at doses of $10^8$, $10^7$, $10^6$, or $10^5$. At day 35, 5/8 of the mice that received $10^8$ LM-LLO-E7 by either route or $10^7$ LM-LLO-E7 i.v. and 4/8 of the mice that received $10^6$ LM-LLO-E7 i.v, were cured. By contrast, doses of less than $10^7$ or in some cases even $10^8$ LM-LLO-E7 administered i.p. were ineffective at controlling tumor growth. Thus, i.v. administration of LM-LLO-E7 is more effective than i.p. administration.

Clinical Trial

A phase I/II clinical trial was conducted to assess safety and efficacy of LM-LLO-E7 vaccines in patients with advanced, progressive, or recurrent cervical cancer. 5 patients each were assigned to cohorts 1-2, which received $1\times10^9$ or $3.3\times10^9$ CFU, respectfully. An additional 5 patients each will be assigned to cohorts 3-4, which will receive $1\times10^{10}$ or $3.31\times10^{10}$ CFU, respectfully.

Safety Data

First Cohort

All patients in the first cohort reported onset of mild-to-moderate fever and chills within 1-2 hours after onset of the infusion. Some patients exhibited vomiting, with or without nausea. With 1 exception (described below), a single dose of a non-steroidal agent such as paracetamol was sufficient to resolve these symptoms. Modest, transient cardiovascular effects were observed, consistent with, and sharing the time course of, the fever. No other adverse effects were reported.

At this late stage of cervical cancer, 1 year survival is typically 10-15% of patients and no tumor therapy has ever been effective. Indeed, Patient 2 was a young patient with very aggressive disease who passed away shortly after completing the trial.

Quantitative blood cultures were assessed on days 2, 3, and 5 post-administration. Of the 5 evaluable patients in this cohort, 4 exhibited no serum *Listeria* at any time and 1 had a very small amount (35 cfu) of circulating *Listeria* on day 2, with no detectable *Listeria* on day 3 or 5.

Patient 5 responded to initial vaccination with mild fever over the 48 hours subsequent to administration, and was treated with anti-inflammatory agents. On 1 occasion, the fever rose to moderate severity (at no time above 38.4° C.), after which she was given a course of ampicillin, which resolved the fever. During the antibiotic administration she experienced mild urticaria, which ended after antibiotic administration. Blood cultures were all sterile, cardiovascular data were within the range observed for other patients, and serum chemistry values were normal, showing that this patient had no listerial disease. Further, the anergy panel indicated a robust response to ⅓ memory antigens, indicating the presence of functional immunity (similar to the other patients). Patient 5 subsequently evidenced a response similar to all other patients upon receiving the boost.

Second Cohort and Overall Safety Observations

In both cohorts, minor and transient changes in liver function tests were observed following infusion. These changes were determined by the attending physician monitoring the trial to have no clinical significance, and were expected for a short-lived infection of bacteria that are rapidly removed from the systemic circulation to the liver and spleen. In general, all the safety indicators described in the Methods section above displayed little or no net change, indicative of an excellent safety profile. The side effect profile in this cohort was virtually identical to that seen in the in the initial cohort and appeared to be a dose independent series of symptoms related to the consequences of cytokines and similar agents that occur consequent to the induction of an iatrogenic infection. No serum *Listeria* was observed at any time and no dose limiting toxicity was observed in either cohort.

Efficacy-First Cohort

The following indications of efficacy were observed in the 3 patients in the first cohort that finished the trial: (Table 2).

Patient 1 entered the trial with 2 tumors of 20 mm each, which shrunk to 18 and 14 mm over the course of the trial, indicating therapeutic efficacy of the vaccine. In addition, patient 1 entered the trial with a Karnofsky Performance Index of 70, which rose to 90 after dosing. In the Safety Review Panel meeting, Siniša Radulovic, the chairman of the Department of Oncology, Institute for Oncology and Radiology, Belgrade, Serbia presented the results to a representative of the entity conducting the trials; Michael Kurman, an independent oncologist who works as a consultant for the entity; Kevin Ault, an academic gynecologic oncologist at Emory University who conducted the phase III Gardasil trials for Merck and the Cervarix trials for Glaxo SmithKline; and Tate Thigpen, a founder of the Gynecologic Oncology Group at NCI and professor of gynecologic oncology at the University of Mississippi. In the opinion of Dr. Radulovic, patient 1 exhibited a clinical benefit from treatment with the vaccine.

Before passing away, Patient 2 exhibited a mixed response, with ½ tumors shrinking.

Patient 3 enrolled with paraneoplastic disease, (an epiphenomenon of cancer wherein the overall debilitated state of the patient has other sequelae that are secondary to the cancer), including an elevation of platelet count to $936\times10^9$/ml. The count decreased to $465\times10^9$/ml, approximately a normal level, following the first dose.

Patient 4 entered the trial with 2 tumors of 20 mm each, which shrunk to 18 and 14 mm over the course of the trial, indicating therapeutic efficacy of the vaccine. Patient 4 exhibited a weight gain of 1.6 Kg and an increased hemoglobin count of approximately 10% between the first and second doses.

Efficacy—Second Cohort and General Observations

In the lowest dose cohort, 2 patients demonstrated the shrinkage of tumors. The timing of this effect was consistent with that observed in immunological responses, in that it followed chronologically development of the immune response. One of the 2 patients in the second cohort evaluated so far for tumor burden exhibited a dramatic tumor load reduction at a post-vaccination time point. At the start of the trial, this patient had 3 tumors of 13, 13, and 14 mm. After the 2 doses of the vaccine, 2 of the tumor had shrunk to 9.4 and 12 mm, and the third was no longer detectable.

Figure 13A:
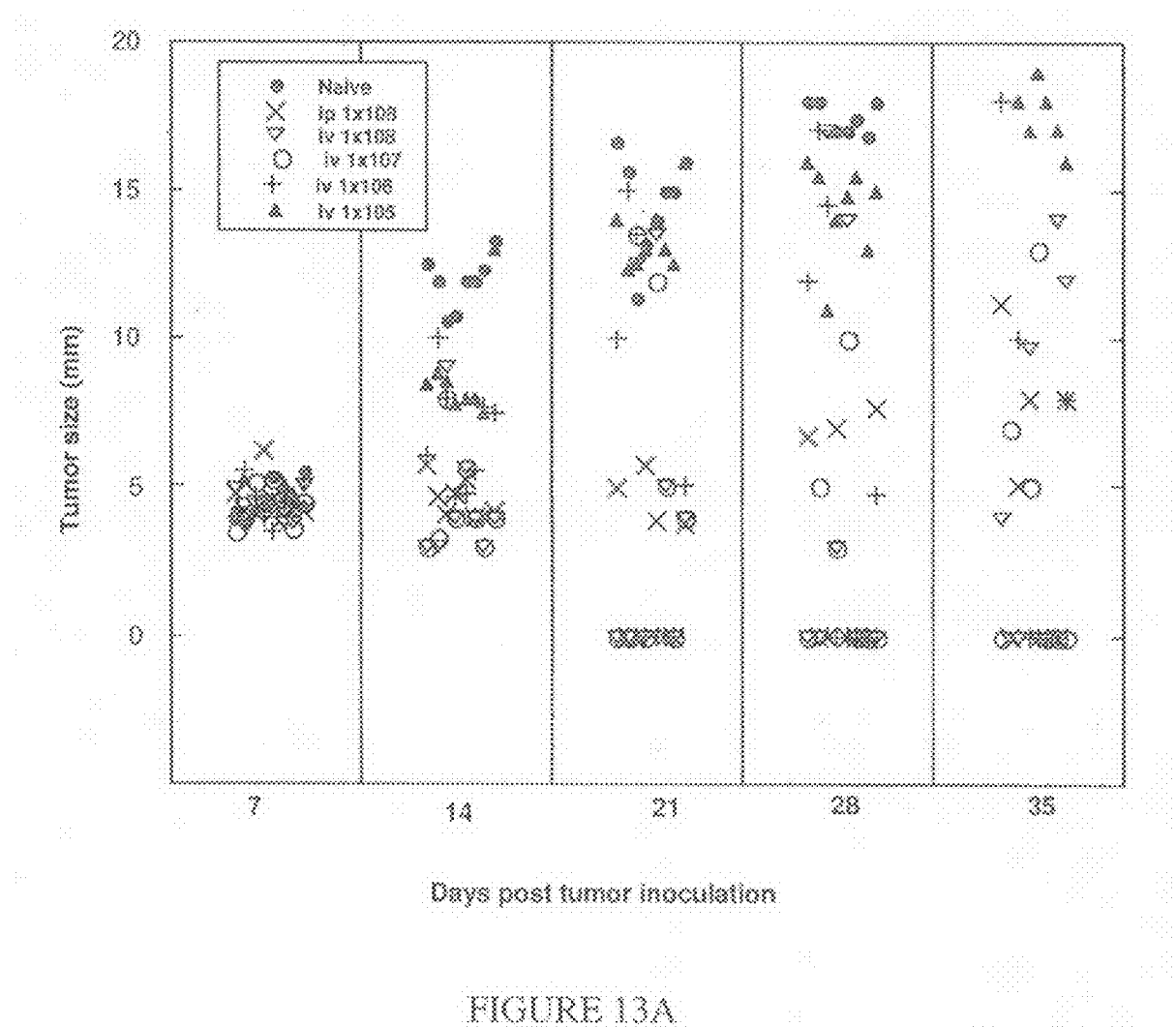
FIG. 13. A. IV immunization of LM-LLO-E7 is effective at inducing the regression of established tumors at doses as low as $1 \times 10^6$ CFU per mouse. B. Tumors loads for the 2 cohorts in the LM-LLO-E7 clinical trial.
Figure 13B:
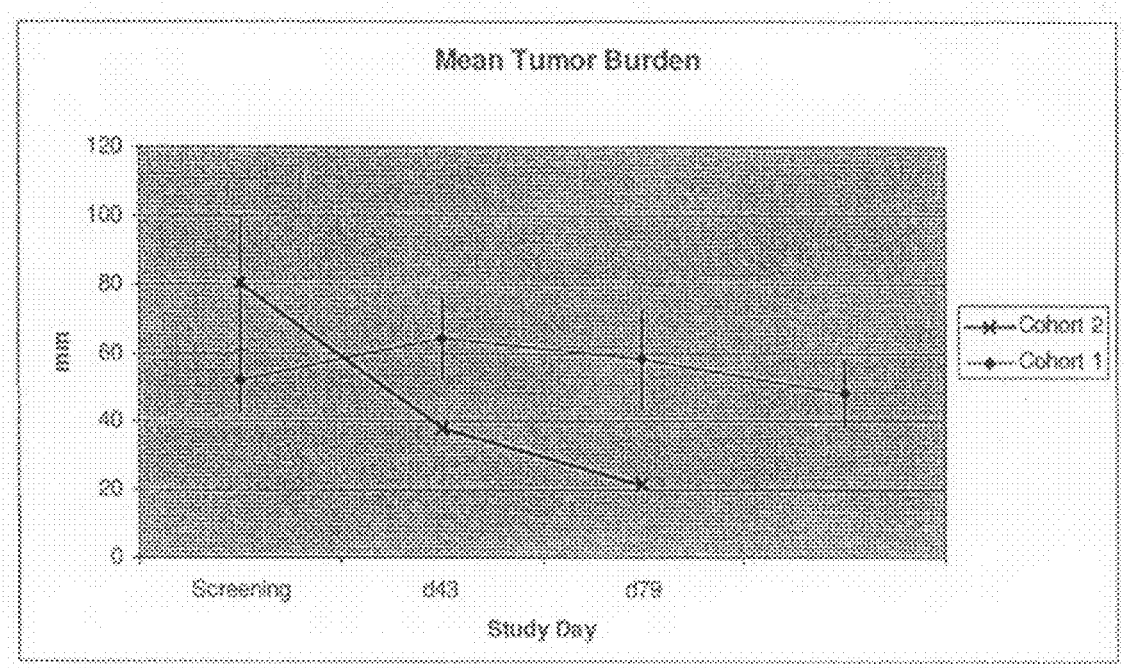

Tumors loads for the 2 cohorts are depicted in FIG. 13B. In summary, even relatively low doses of LM-LLO-E7, administered in a therapeutic regimen containing a priming injection and a single boost, achieved 3 objective responses out of 6 patients for whom data has been collected.

Discussion

At this late stage of cervical cancer, 1 year survival is typically 10-15% of patients and no tumor therapy has ever been effective. No treatment has shown to be effective in reversing stage IVB cervical cancer. Despite the difficulty of treating cervical cancer at this stage, an anti-tumor effect was observed in 2/6 patients. In addition, other indications of efficacy were observed in patients that finished the trial, as described hereinabove.

Thus, LM-LLO-E7 is safe in human subjects and improves clinical indicators of cervical cancer patients, even when administered at relatively low doses. Additional positive results are likely to be observed when the dose and number of booster vaccinations is increased; and/or when antibiotics are administered in smaller doses or at a later time point after infusion. Pre-clinical studies have shown that a dose increase of a single order of magnitude can cause dramatic changes in response rate (e.g. a change from 0% response rate to 50-100% complete remission rate. Additional booster doses are also very likely to further enhance the immune responses obtained. Moreover, the positive effects of the therapeutic immune response observed are likely to continue with the passage of additional time, as the immune system continues to attack the cancer.

Example 11

Safety and Efficacy of LM-LLO-E7 for the Treatment of Cervical Intraepithelial Neoplasia Stages II and III Materials and Experimental Methods Inclusion Criteria
- Age 18 or older and capable of providing informed consent according to federal, state and institutional guidelines.
- Patients must have either Stage II or Stage III Cervical Intraepithelial Neoplasia for which surgical intervention is indicated, and for whom the disease is sufficiently indolent to allow for a 6-month treatment and observation period to occur prior to surgery.
- HPV-16 E7 positive.
- Cytological evidence consistent with a diagnosis of CIN II/III.
- All patients eligible for this study must be discussed with the principal investigators and be approved by the principal investigators before study entry.
- Patients must respond positively to at least 1 of the test agents used in the anergy panel described for the previous Example. A positive reaction defined by the formation of a local tissue response of at least 5 mm in sum of the orthogonal measures in reaction to the administration of a delayed hypersensitivity stimulus is required.

Exclusion Criteria
- Patients who have had chemotherapy, radiotherapy, or steroids within 4 weeks prior to the initial study dose or those who have not recovered from adverse events due to agents administered more than 4 weeks earlier.
- Patients who have received any other investigational agents for 28 days prior to dosing.
- A history of Listeriosis.
- A history of prior cancer or concomitant cancer.
- Patients who are immunocompromised as demonstrated by a negative result from an anergy panel screening.
- Uncontrolled intercurrent illness including, but not limited to ongoing or active infection, symptomatic congestive heart failure, unstable angina pectoris, cardiac arrhythmia, or psychiatric illness/social situations that would limit compliance with study requirements.
- Hepatitis, cirrhosis, or any other impaired hepatic function as determined by serum enzymes.
- Pregnant women and women actively trying to become pregnant.
- Known HIV-positive patients.
- Penicillin allergy.

Primary Safety Endpoints:
- Incidence and severity of observations of the administration site including swelling, irritation, immune reaction or other abnormalities.
- Incidence and severity of adverse events assessed throughout the duration of the study.
- Changes in clinical hematology and serum chemistry test results at each time point from dosing through week 16.
- Rate of clearance of LM-LLO-E7 from the blood, as determined by quantitative blood cultures during the inpatient portion of the study following the initial administration.

Primary Efficacy Endpoints:
- Regression of CIN to normal upon colposcopic examination
- Regression of CIN toward normal sufficient to cancel or delay surgery
- Improved cytology subsequent to surgery Primary Immunogenicity Endpoints:
- HLA typing of patients for Class I and II,
- Quantification of a serum cytokine profile subsequent to dosing that corresponds with observed side effects,
- Quantification of macrophage activation parameters that assess macrophage activation subsequent to dosing,
- Identification of tumor-associated antigen (TAA)-specific activated T cells and quantification of T cell responses subsequent to dosing,
- Quantification of T cell subsets migrating to TAA DTH.

Immunogenicity Criteria:

Serum Cytokines
- IFN-γ, TNF-α, IL-2 & IL-12 are assessed in serum of patients, collected at the following times:
  - Screening, Day 1.
  - Day 1, pre-dose, Day 1, 3 h post-dose, Day 1, 12 h post-dose, Day 2, 24 h post-dose, and Day 5.
  - Day 22 pre-dose, Day 22, 3 h post-dose, Day 22, 12 h post-dose, Day 23, 24 h post-dose, and Day 26
  - Day 43 pre-dose, Day 43, 3 h post-dose, Day 43, 12 h post-dose, Day 44, 24 h post-dose, and Day 47

T Cell Responses
- The following cytokine release profiles are assessed HPV-16 E7 stimulated T cells of patients: IFN-γ, TNF-α, IL-2 & IL-4
- Assays are performed on cells sampled from patients at the following times: Screening, Day 1 pre-dosing, day 22 pre-dosing, day 43 pre-dosing, day 126, and day 180

Delayed Type Hypersensitivity Testing
- DTH testing is conducted on the following study days: Screening, Day 5, Day 26, Day 47, Day 126 and Day 180.

Macrophage Activation
- Samples for the assessment of macrophage activation are collected on the following study days and times:
  - Day 1 pre-dose, Day 1, 3 h post-dose, Day 1, 12 h post-dose, Day 2, 24 h post-dose, and Day 5.
  - Day 22 pre-dose, Day 22, 3 h post-dose, Day 22, 12 h post-dose, Day 23, 24 h post-dose, and Day 26.
  - Day 43 pre-dose, Day 43, 3 h post-dose, Day 43, 12 h post-dose, Day 44, 24 h post-dose, and Day 47.

Vaccine Administration
- LM-LLO-E7 is administered as a 30 min. i.v. infusion with each dose freshly thawed and diluted in 250 ml normal saline.

Safety Review
- Adverse Events are graded based on the National Cancer Institute (NCI) Common Toxicity Criteria. Dose limiting toxicity is defined as any of the following:

Non-Hematologic Toxicity:
1. Presumptive bacterial meningitis as determined by symptoms.
2. Persistent listeremia at day 5 and 15 after a 10-day course of antibiotics.
3. Clinical sepsis requiring ICU admission.
4. A drop in blood pressure sufficient to warrant therapeutic intervention,
5. Hepatitis as evidenced by grade 3-4 elevation in transaminases for a minimum of 7 days.
6. Gastrointestinal toxicity of grade 3-4 despite adequate medical intervention.
7. Any Grade 3 injection site reaction.
8. Any Grade 3 or higher adverse event that cannot be attributed to cervical cancer or other concurrent illnesses.

Hematologic Toxicity:
1. Absolute neutrophil count (ANC) grade 4 for a minimum of 7 days or neutropenic fever defined as Grade 4 neutropenia with temperature of ≧38.5° C.
2. Platelet count grade 4 or bleeding with Grade 3 platelet count.

Dose escalation to the next cohort proceeds in each case, provided that there are no Grade 3 or higher adverse events related to the therapeutic vaccine.

Results

Women are enrolled that have stage II or stage III Cervical Intraepithelial Neoplasia (CIN II/III) who have disease that is sufficiently indolent to allow for a 6 month period of treatment and evaluation to occur prior to surgery. Patients receive 3 doses of LM-LLO-E7 at 3 week intervals as inpatients and return for follow up visits to assess their response to the vaccine, collect samples for analysis, and assess their disease. Samples for immunologic analysis are collected throughout the trial and assayed upon the completion of the study.

Safety is assessed through standard physical, hematologic and serum chemistry measures, and by blood cultures to assess serum *Listeria*. Immunologic activity is assessed in the areas of serum cytokine release, activated T cell responses to tumor antigen, macrophage activation, and delayed hypersensitivity responses (DTH) to tumor antigen.

Clinically, patients are grouped by primary endpoints. Namely, whether patients exhibit sufficient remission of their disease to make surgery unnecessary. Patients that do require surgery, are grouped regarding whether they exhibit lesser disease than the control group. LM-LLO-E7 reduces the fraction of women that subsequently require surgery and/or the degree of disease among those that require surgery.

Example 12

Passaging of *Listeria* Vaccine Vectors Through Mice Elicits Increased Immune Responses to Heterologous and Endogenous Antigens Materials and Experimental Methods Bacterial Strains

*L. monocytogenes* strain 10403S, serotype 1 (ATCC, Manassas, Va.) was the wild type organism used in these studies and the parental strain of the constructs described below. Strain 10403S has an $LD_{50}$ of approximately $5 \times 10^4$ CFU when injected intraperitoneally into BALB/c mice. "Lm-Gag" is a recombinant LM strain containing a copy of the HIV-1 strain HXB (subtype B laboratory strain with a syncytia-forming phenotype) gag gene stably integrated into the listerial chromosome using a modified shuttle vector pKSV7. Gag protein was expressed and secreted by the strain, as determined by Western blot. All strains were grown in brain-heart infusion (BHI) broth or agar plates (Difco Labs, Detroit, Mich.).

Bacterial Culture

Bacteria from a single clone expressing the passenger antigen and/or fusion protein were selected and cultured in BHI broth overnight. Aliquots of this culture were frozen at −70° C. with no additives. From this stock, cultures were grown to 0.1-0.2 O.D. at 600 nm, and aliquots were again frozen at −70° C. with no additives. To prepare cloned bacterial pools, the above procedure was used, but after each passage a number of bacterial clones were selected and checked for expression of the target antigen, as described herein. Clones in which expression of the foreign antigen was confirmed were used for the next passage.

Passage of Bacteria in Mice 6-8 week old female BALB/c (H-2d) mice were purchased from Jackson Laboratories (Bar Harbor, Me.) and were maintained in a pathogen-free microisolator environment. The titer of viable bacteria in an aliquot of stock culture, stored frozen at −70° C., was determined by plating on BHI agar plates on thawing and prior to use. In all, $5 \times 10^5$ bacteria were injected intravenously into BALB/c mice. After 3 days, spleens were harvested, homogenized, and serial dilutions of the spleen homogenate were incubated in BHI broth overnight and plated on BHI agar plates. For further passage, aliquots were again grown to 0.1-0.2 O.D., frozen at −70° C., and bacterial titer was again determined by serial dilution. After the initial passage (passage 0), this sequence was repeated for a total of 4 times.

Intracellular Cytokine Stain for IFN-Gamma

Lymphocytes were cultured for 5 hours in complete RPMI-10 medium supplemented with 50 U/ml human recombinant IL-2 and 1 microliter/ml Brefeldin A (Golgistop™; PharMingen, San Diego, Calif.) in the presence or absence of either the cytotoxic T-cell (CTL) epitope for HIV-GAG (AMQMLKETI; SEQ ID No: 34), *Listeria* LLO (GYKDGNEYI; SEQ ID No: 35) or the HPV virus gene E7 (RAHYNIVTF (SEQ ID No: 22), at a concentration of 1 micromole. Cells were first surface-stained, then washed and subjected to intracellular cytokine stain using the Cytofix/Cytoperm kit in accordance with the manufacturer's recommendations (PharMingen, San Diego, Calif.). For intracellular IFN-gamma stain, FITC-conjugated rat anti-mouse IFN-gamma monoclonal antibody (clone XMG 1.2) and its isotype control Ab (rat IgG1; both from PharMingen) was used. In all, $10^6$ cells were stained in PBS containing 1% Bovine Serum Albumin and 0.02% sodium azide (FACS Buffer) for 30 minutes at 4° C. followed by 3 washes in FACS buffer. Sample data were acquired on either a FACScan™ flowcytometer or FACSCalibur™ instrument (Becton Dickinson, San Jose, Calif.). Three-color flow cytometry for CD8 (PERCP conjugated, rat anti-mouse, clone 53-6.7 Pharmingen, San Diego, Calif.), CD62L (APC conjugated, rat anti-mouse, clone MEL-14), and intracellular IFN-gamma was performed using a FACSCalibur™ flow cytometer, and data were further analyzed with CELLQuest software (Becton Dickinson, Mountain View, Calif.). Cells were gated on CD8 high and $CD62L^{low}$ before they were analyzed for $CD8^+$ and intracellular IFN-gamma staining.

Results

Passaging in Mice Increases the Virulence of Recombinant *Listeria* Monocytogenes Three different constructs were used to determine the impact of passaging on recombinant *Listeria* vaccine vectors. Two of these constructs carry a genomic insertion of the passenger antigen: the first comprises the HIV gag gene (Lm-Gag), and the second comprises the HPV E7 gene (Lm-E7). The third (Lm-LLO-E7) comprises a plasmid with the fusion gene for the passenger antigen (HPV E7) fused with a truncated version of LLO and a gene encoding prfA, the positive regulatory factor that controls *Listeria* virulence factors. This plasmid was used to complement a prfA negative mutant so that in a live host, selection pressures would favor conservation of the plasmid, because without it the bacterium is avirulent. All 3 constructs had been propagated extensively in vitro for many bacterial generations.

Figure 14A:
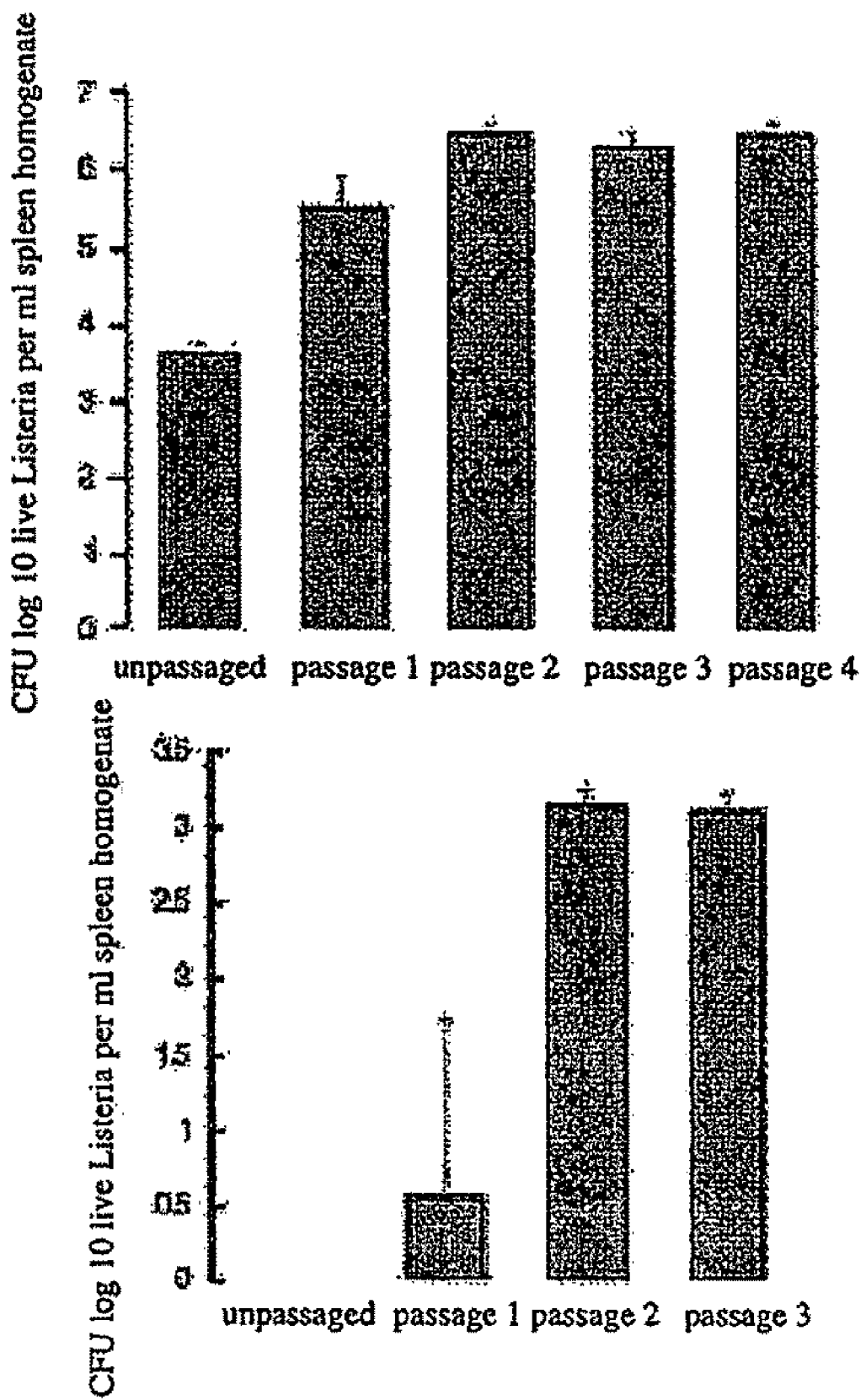
FIG. 14. A. Effect of passaging on bacterial load (virulence) of recombinant *Listeria* vaccine vectors. Top panel. Lm-Gag. Bottom panel. Lm-LLO-E7. B. Effect of passaging on bacterial load of recombinant Lm-E7 in the spleen. Average CFU of live bacteria per milliliter of spleen homogenate from four mice is depicted.
Figure 14B:
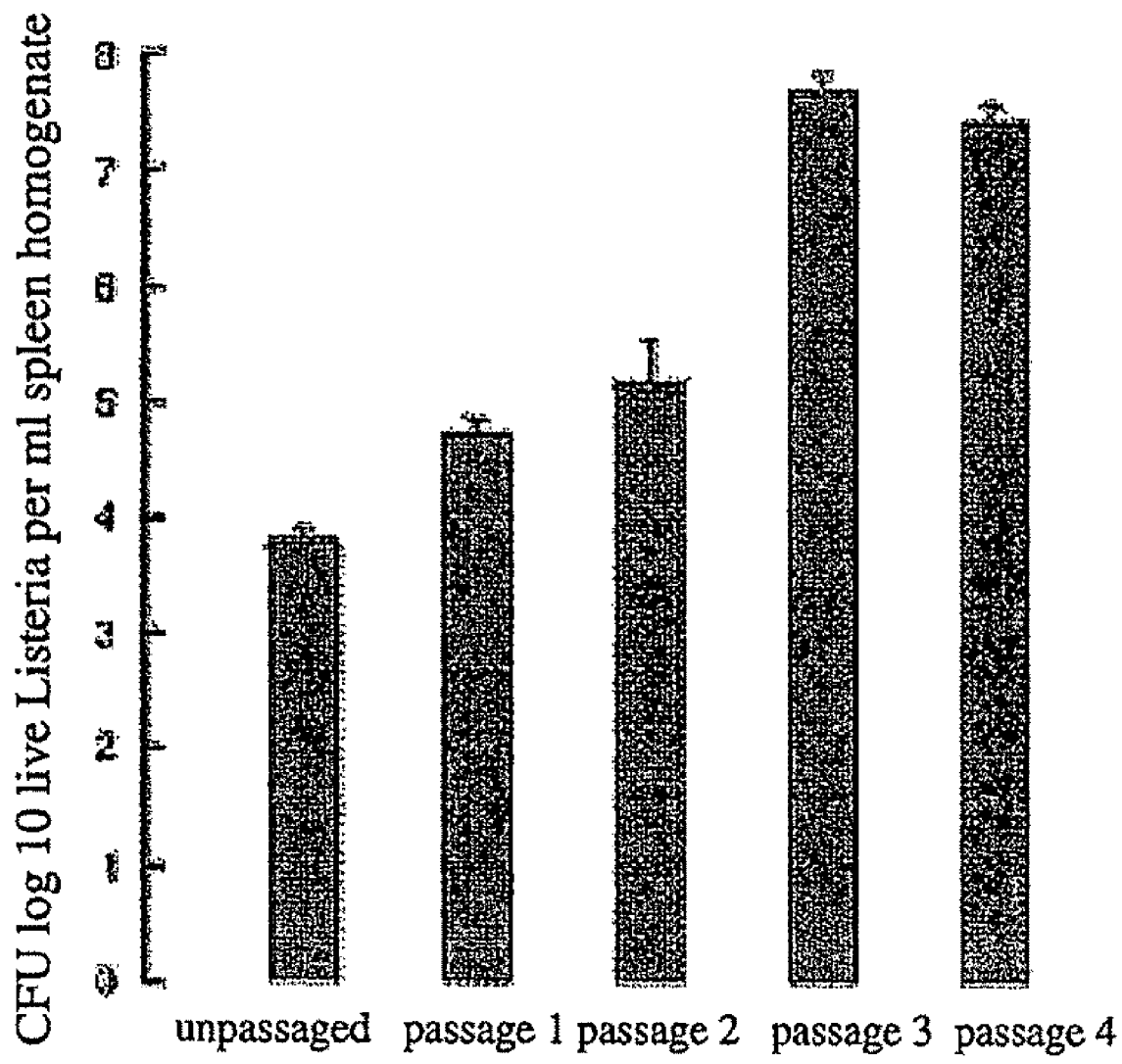

Passaging the bacteria resulted in an increase in bacterial virulence, as measured by numbers of surviving bacteria in the spleen, with each of the first 2 passages. For Lm-Gag and Lm-LLO-E7, virulence increased with each passage up to passage 2 (FIG. 14A). The plasmid-containing construct, Lm-LLO-E7, demonstrated the most dramatic increase in virulence. Prior to passage, the initial immunizing dose of Lm-LLO-E7 had to be increased to $10^7$ bacteria and the spleen had to be harvested on day 2 in order to recover bacteria (whereas an initial dose of $10^5$ bacteria for Lm-Gag was harvested on day 3). After the initial passage, the standard dosage of Lm-LLO-E7 was sufficient to allow harvesting on day 3. For Lm-E7, virulence increased by 1.5 orders of magnitude over unpassaged bacteria (FIG. 14B).

Thus, passage through mice increases the virulence of *Listeria* vaccine strains.

Passaging Increases the Ability of *L. monocytogenes* to Induce CD8+ T Cells

Figure 15:
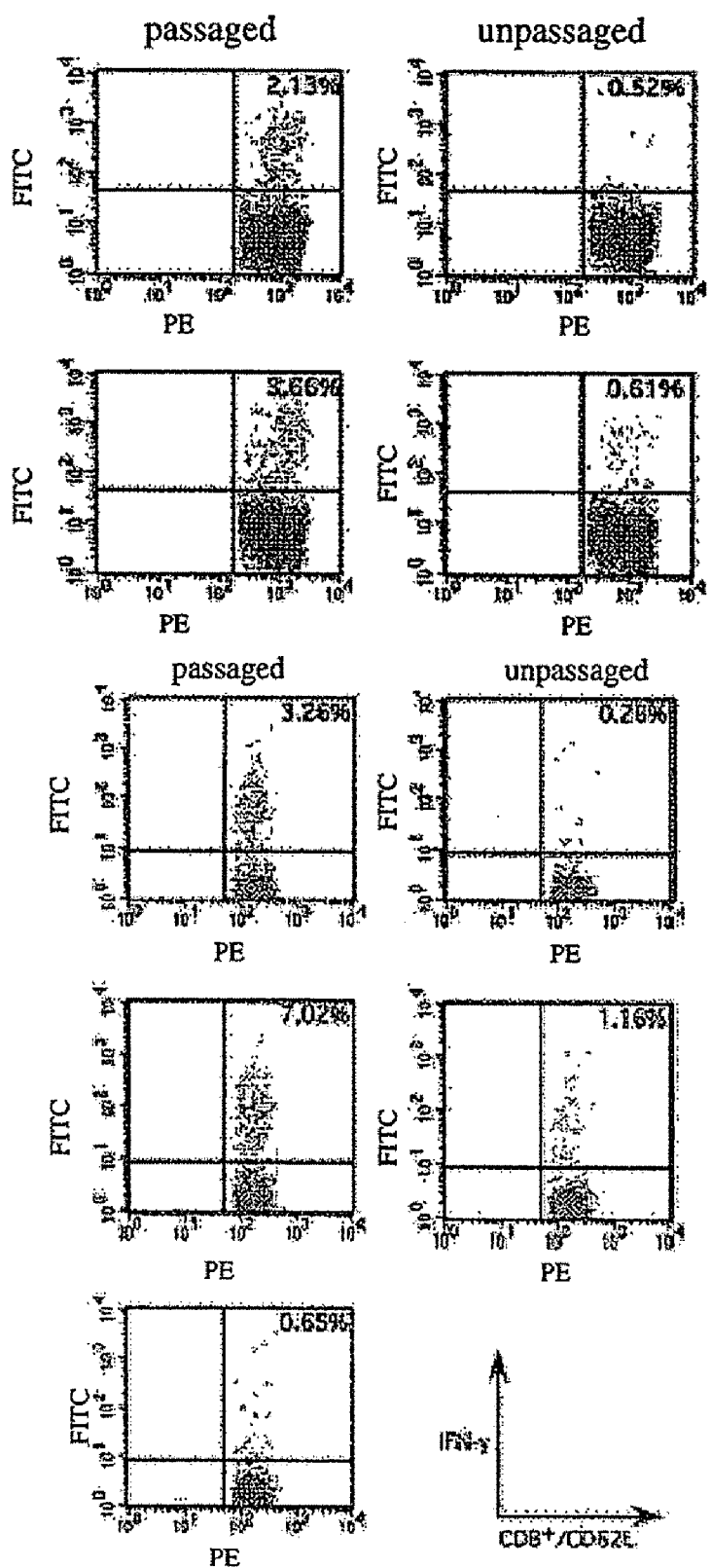
FIG. 15. Induction of antigen-specific $CD8^+$ T-cells for HIV-Gag and LLO after administration of passaged Lm-Gag versus unpassaged Lm-Gag. Mice were immunized with $10^3$ (A, B, E, F) or $10^5$ (C, D, G, H) CFU passaged *Listeria* vaccine vectors, and antigen-specific T-cells were analyzed. B, D, F, H: unpassaged *Listeria* vaccine vectors. A-D immune response to MHC class I HIV-Gag peptide. E-H: immune response to an LLO peptide. I: splenocytes from mice immunized with $10^5$ CFU passaged Lm-Gag stimulated with a control peptide from HPV E7.

Next, the effect of passaging on induction of antigen-specific CD8+ T cells was determined by intracellular cytokine staining with immunodominant peptides specific for MHC-class I using HIV-Gag peptide AMQMLKETI (SEQ ID No: 34) and LLO 91-99 (GYKDGNEYI; SEQ ID No: 35). Injection of $10^3$ CFU passaged bacteria (Lm-Gag) into mice elicited significant numbers of HIV-Gag-specific CD8+ T cells, while the same dose of non-passaged Lm-Gag induced no detectable Gag-specific CD8+ T cells. Even increasing the dose of unpassaged bacteria 100-fold did not compensate for their relative avirulence; in fact, no detectable Gag-specific CD8+ T cells were elicited even at the higher dose. The same dose increase with passaged bacteria increased Gag-specific T cell induction by 50% (FIG. 15). The same pattern of induction of antigen-specific CD8+ T cells was observed with LLO-specific CD8+ T cells, showing that these results were not caused by the properties of the passenger antigen, since they were observed with LLO, an endogenous *Listeria* antigen.

Thus, passage through mice increases the immunogenicity of *Listeria* vaccine strains.

Example 13

A PrfA-Containing Plasmid is Stable in an LM Strain With a PrfA Deletion in the Absence of Antibiotics Materials and Experimental Methods Bacteria

*L. monocytogenes* strain XFL7 contains a 300 base pair deletion in the prfA gene XFL7 carries pGG55 which partially restores virulence and confers CAP resistance, and is described in United States Patent Application Publication No. 200500118184.

Development of Protocol for Plasmid Extraction from *Listeria*

1 mL of *Listeria monocytogenes* Lm-LLO-E7 research working cell bank vial was inoculated into 27 mL BHI medium containing 34 μg/mL CAP and grown for 24 hours at 37° C. and 200 rpm.

Seven 2.5 mL samples of the culture were pelleted (15000 rpm for 5 minutes), and pellets were incubated at 37° C. with 50 μl lysozyme solution for varying amounts of time, from 0-60 minutes.

Lysozyme solution:
29 μl 1 M dibasic Potassium Phosphate
21 μl 1 M monobasic Potassium Phosphate
500 μl 40% Sucrose (filter sterilized through 0.45 μm filter)
450 μl water
60 μl lysozyme (50 mg/mL)

After incubation with the lysozyme, the suspensions were centrifuged as before and the supernatants discarded. Each pellet was then subjected to plasmid extraction by a modified version of the QIAprep Spin Miniprep Kit® (Qiagen, Germantown, Maryland) protocol. The changes to the protocol were as follows:

1. The volumes of buffers P1, P2 and N3 were all increased threefold to allow complete lysis of the increased biomass.
2. 2 mg/mL of lysozyme was added to the resuspended cells before the addition of P2. The lysis solution was then incubated at 37° C. for 15 minutes before neutralization.
3. The plasmid DNA was resuspended in 30 μL rather than 50 μL to increase the concentration.

In other experiments, the cells were incubated for 15 min in P1 buffer+Lysozyme, then incubated with P2 (lysis buffer) and P3 (neutralization buffer) at room temperature.

Equal volumes of the isolated plasmid DNA from each subculture were run on an 0.8% agarose gel stained with ethidium bromide and visualized for any signs of structural or segregation instability.

The results showed that plasmid extraction from *L. monocytogenes* Lm-LLO-E7 increases in efficiency with increasing incubation time with lysozyme, up to an optimum level at approximately 50 minutes incubation.

These results provide an effective method for plasmid extraction from *Listeria* vaccine strains.

Replica Plating

Dilutions of the original culture were plated onto plates containing LB or TB agar in the absence or presence of 34 μg/mL CAP. The differences between the counts on selective and non-selective agar were used to determine whether there was any gross segregational instability of the plasmid.

Results

Figure 16C:
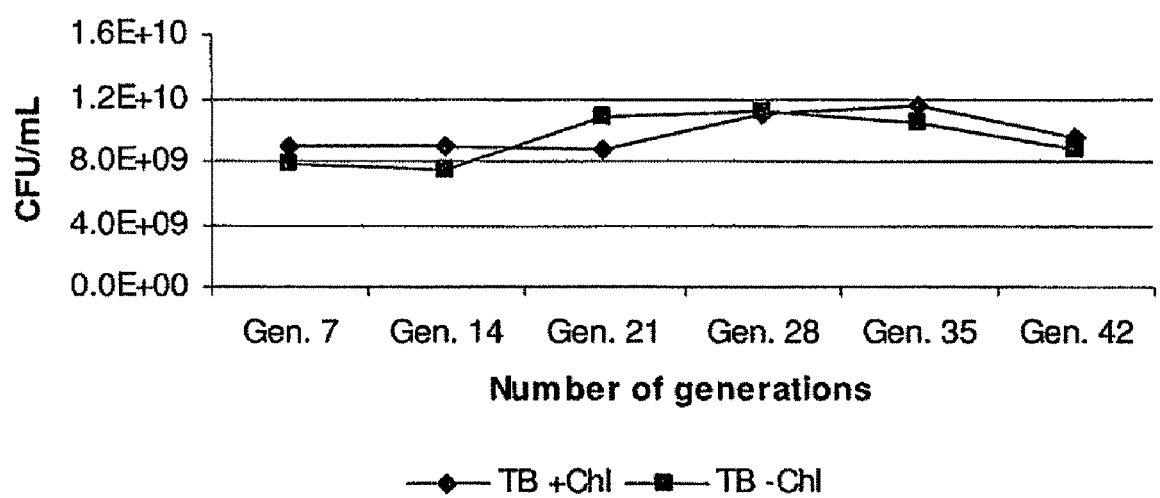
FIG. 16. A. Plasmid isolation throughout LB stability study. B. Plasmid isolation throughout TB stability study. C. Quantitation of TB stability study.

The genetic stability (i.e. the extent to which the plasmid is retained by or remains stably associated with the bacteria in the absence of selection pressure; e.g. antibiotic selection pressure) of the pGG55 plasmid in *L. monocytogenes* strain XFL7 in the absence of antibiotic was assessed by serial sub-culture in both Luria-Bertani media (LB: 5 g/L NaCl, 10 g/ml soy peptone, 5 g/L yeast extract) and Terrific Broth media (TB: 10 g/L glucose, 11.8 g/L soy peptone, 23.6 g/L yeast extract, 2.2 g/L $KH_2PO_4$, 9.4 g/L $K_2HPO_4$), in duplicate cultures. 50 mL of fresh media in a 250 mL baffled shake flask was inoculated with a fixed number of cells (1 ODmL), which was then subcultured at 24 hour intervals. Cultures were incubated in an orbital shaker at 37° C. and 200 rpm. At each subculture the $OD_{600}$ was measured and used to calculate the cell doubling time (or generation) elapsed, until 30 generations were reached in LB and 42 in TB. A known number of cells (15 ODmL) at each subculture stage (approximately every 4 generations) were pelleted by centrifugation, and the plasmid DNA was extracted using the Qiagen QIAprep Spin Miniprep® protocol described above. After purification, plasmid DNA was subjected to agarose gel electrophoresis, followed by ethidium bromide staining. While the amount of plasmid in the preps varied slightly between samples, the overall trend was a constant amount of plasmid with respect to the generational number of the bacteria (FIGS. 16A-B). Thus, pGG55 exhibited stability in strain XFL7, even in the absence of antibiotic.

Figure 17:
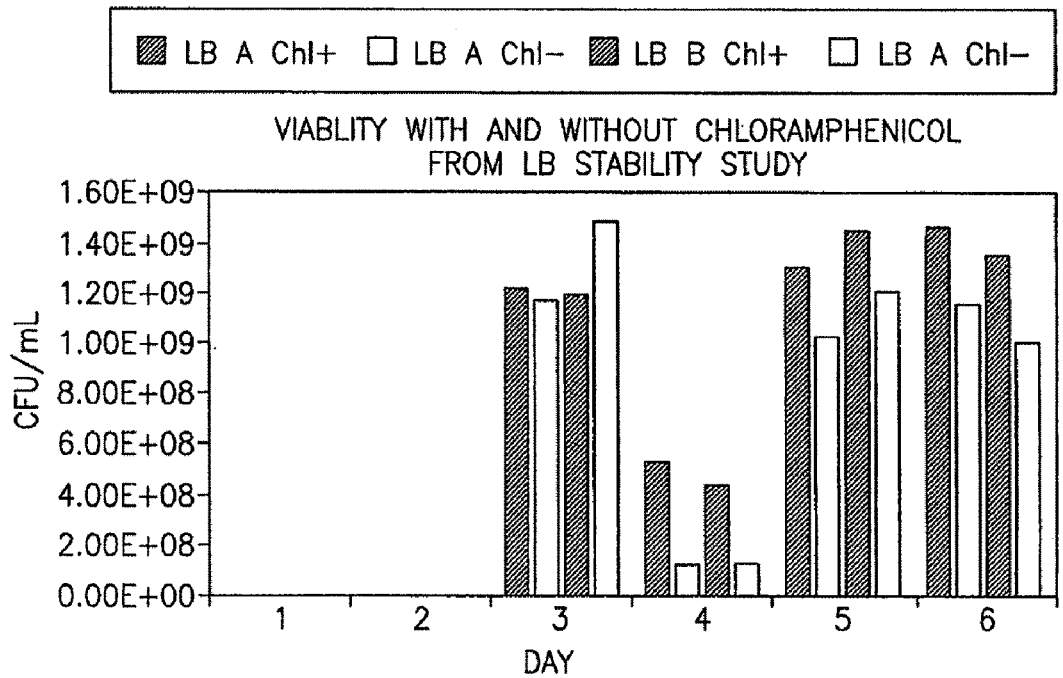
FIG. 17. Numbers of viable bacteria chloramphenicol (CAP)-resistant and CAP-sensitive colony-forming units (CFU) from bacteria grown in LB. Dark bars: $CAP^+$; white bars: $CAP^-$. The two dark bars and two white bars for each time point represent duplicate samples.
Figure 18:
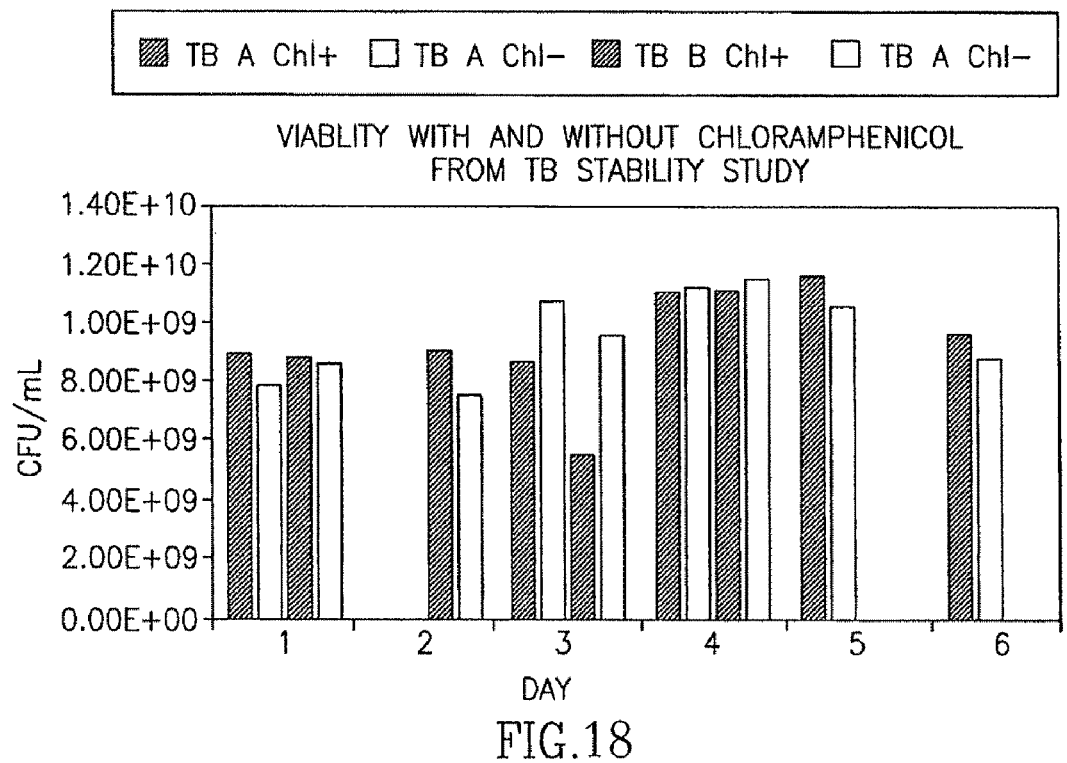
FIG. 18. Numbers of viable bacteria CAP-resistant and CAP-sensitive CFU from bacteria grown in TB. Dark bars: $CAP^+$; white bars: CAP. The two dark bars and two white bars for each time point represent duplicate samples.

Plasmid stability was also monitored during the stability study by replica plating on agar plates at each stage of the subculture. Consistent with the results from the agarose gel electrophoresis, there was no overall change in the number of plasmid-containing cells throughout the study in either LB or TB liquid culture (FIGS. 17 and 18, respectively).

These findings demonstrate that prfA-encoding plasmids exhibit stability in the absence of antibiotic in *Listeria* strains containing mutations in prfA.

Example 14

Optimization of Cryopreservation Conditions for *Listeria* Vaccine Strains

Materials and Experimental Methods

An LB Research Working Cell Bank (RWCB) was produced by the following protocol: 5 ODmL samples were taken from 200 mL cultures grown in LB or TB with 34 μg/mL CAP in 2 L shake flasks at several different $OD_{600}$. The 5 ODmL samples were cryopreserved using 20% v/v glycerol and frozen at less than −70° C. for one day, then were thawed and used to inoculate 50 mL of the same media used for the starter cultures. The initial growth kinetics of these cultures was measured by monitoring the $OD_{600}$ and comparing the growth curves for any sign of lag phase.

An RWCB containing 50 vials of Lm-LLO-E7, cryopreserved in mid-log phase, was produced. Cells from the original glycerol stocks, CTL 2003#0810N, were streaked out onto an LB-agar plate with 34 μg/mL CAP. After a 24-hour incubation, single colonies were selected and grown in 5 mL of LB-CAP for 24 hours at 37° C., which was then used to inoculate 50 mL of LB-CAP. At an $OD_{600}$ of 0.7, cells were cryopreserved after adding glycerol to 20% v/v. The culture was 1-mL aliquots were placed into fifty sterile cry vials and stored below −70° C.

Results

Figure 19:
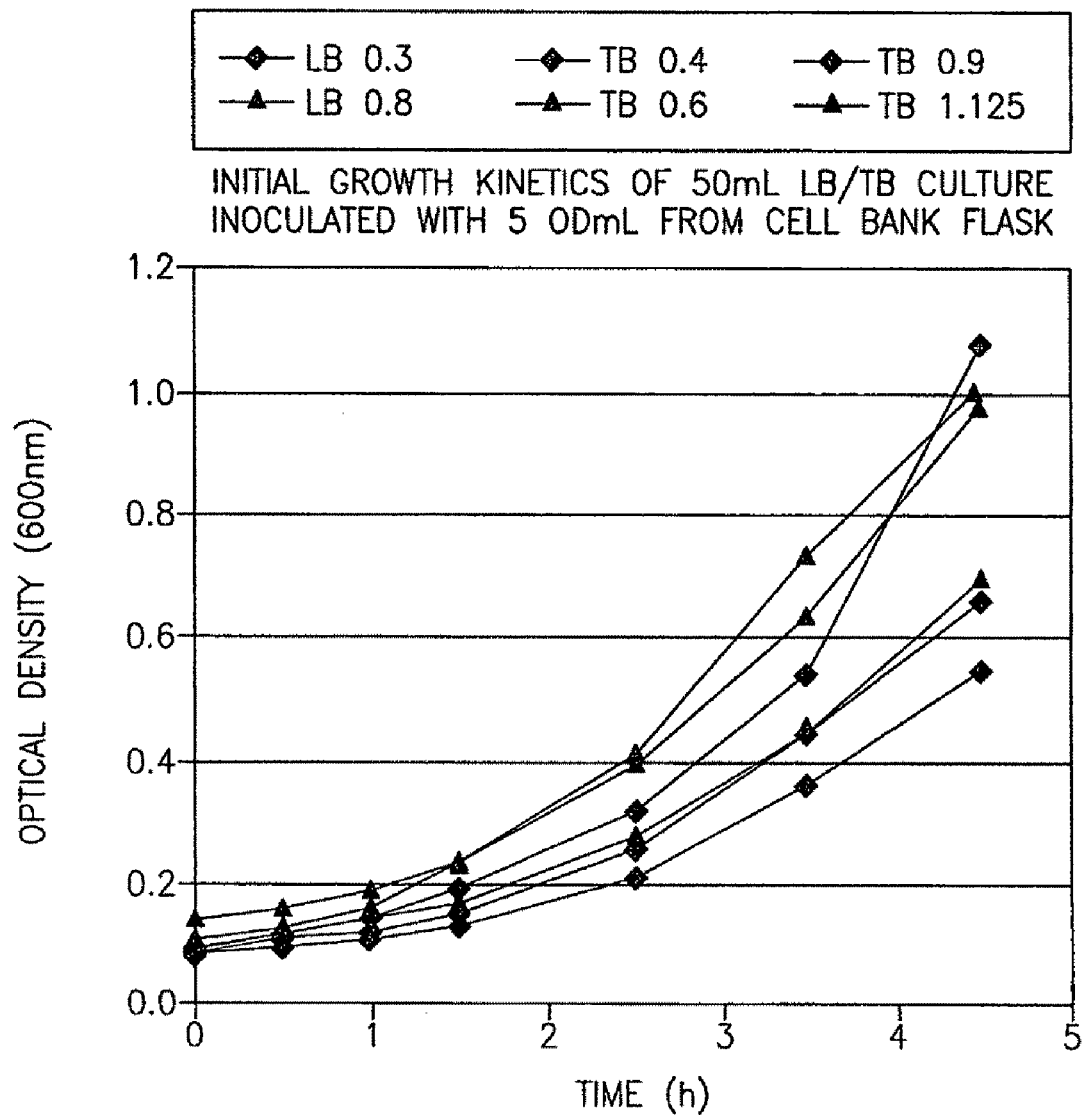
FIG. 19. Growth of L. monocytogenes following short-term cryopreservation.

In order to determine the optimum culture density at which to cry preserve the *L. monocytogenes* strain XFL7 carrying the pGG55 plasmid (which will be referred to as Lm-LLO-E7), bacteria were grown in 200 mL (milliliter) baffled shake flasks in either LB or TB. At various 600 Å optical densities ($OD_{600}$), 5 ODmL (i.e. the product of the $OD_{600}$ reading and the volume of culture in ml) aliquots were removed, glycerol was added to 20% v/v, and the cells were frozen at −70° C. After 24 h (hours) storage at −70° C., the 5 ODmL samples were thawed and used to inoculate 50 mL of fresh media of the same type (LB or TB), and initial growth kinetics of the cultures were monitored. All the cultures immediately entered exponential growth without showing any signs of a lag phase (FIG. 19). Thus, among the $OD_{600}$ utilized, the highest $OD_{600}$ (0.8 for LB and 1.1 for TB) were determined to be optimum for short-term cryopreservation.

Figure 20:
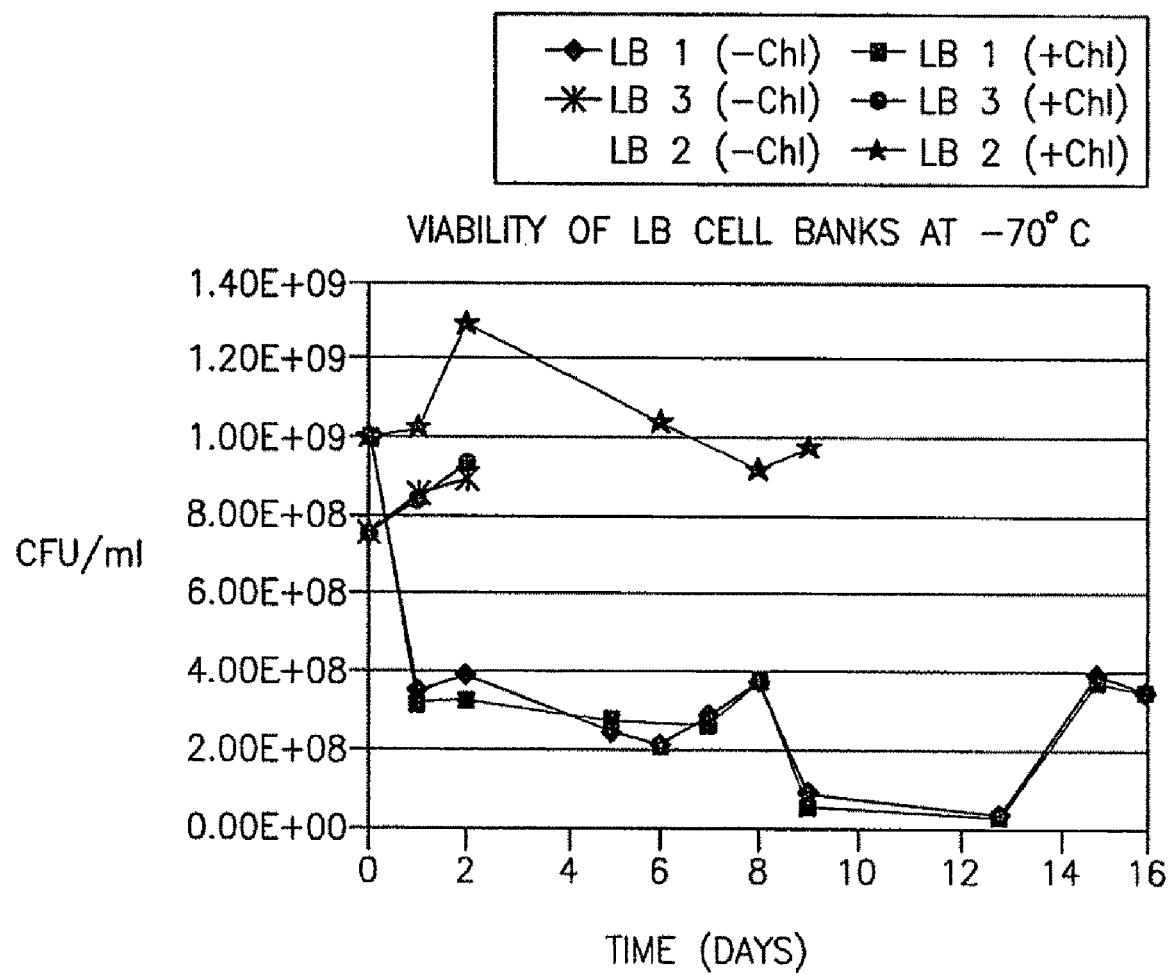
FIG. 20. Viability of LB RWCB following storage at −70° C.

Next, an LB Research Working Cell Bank (RWCB) was produced by adding 20% v/v glycerol to an 0.8 $OD_{600}$ culture and storing below −70° C. (see Materials and Experimental Methods section above). Viability of the RWCB was determined before freezing by replica plating as described for Example 13. Vials of the RWCB were thawed after defined intervals, and viability was determined. As depicted in FIG. 20, the viability in the first LB cell bank appeared to decrease from $1 \times 10^9$ to $3 \times 10^8$ CFU/mL following storage at −70° C.

A second and a third LB RWCB were generated, this time at $OD_{600}$ of 0.72 and 0.74, respectively. These two RWCB exhibited viabilities ranging between 8 and $12 \times 10^8$ CFU/mL, with no decrease in viability, throughout the course of the study. The difference between these RWCB and first are likely due to difference in the $OD_{600}$ at the time of cryopreservation. Thus, an optical density of 0.8 likely corresponds to the end of exponential growth and the beginning of stationary phase of Lm-LLO-E7 in. Consequently, an $OD_{600}$ of 0.7 was used subsequently. The second RWCB was assigned the number 2003#0933A and was utilized to inoculate the cultures used in subsequent experiments.

Figure 21:
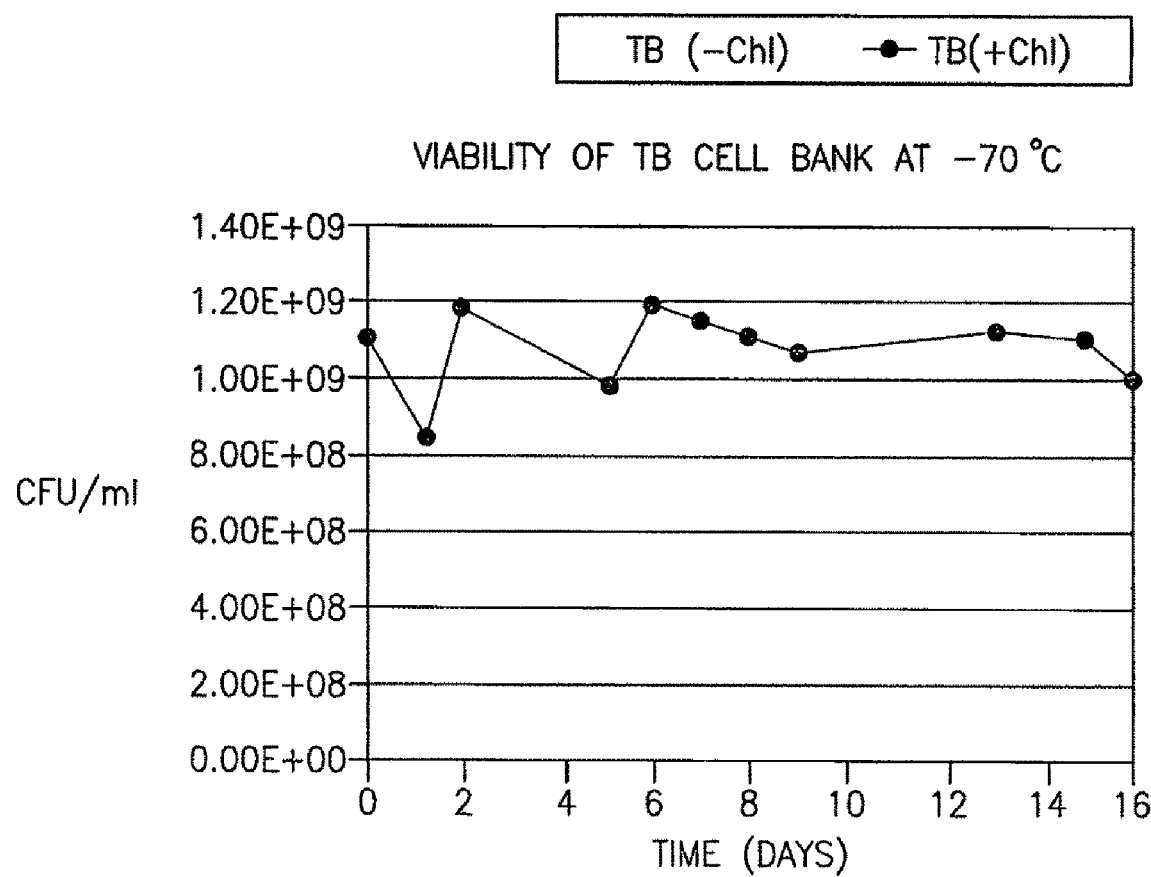
FIG. 21. Viability of TB RWCB following storage at −70° C.

In addition, a TB RWCB was generated from cultures at an $OD_{600}$ of 1.1. The number of viable cells remained stable at $1 \times 10^9$ CFU/mL (FIG. 21).

These findings demonstrate that methods of the present invention (e.g. conditions of 20% glycerol and $OD_{600}$ of 0.7) have utility in generating cryopreserved *Listeria* vaccine strains and stocks with stable long-term viability.

Example 15

Optimization of Media for Growth of *Listeria* Vaccine Strains in Shake Flask Fermentations Materials and Experimental Methods Cultures 50 mL volumes of each of the four different defined media were inoculated with 250 μL aliquots of the LB RWCB and incubated in 250 mL shake flasks at 37° C. overnight. 20 ODmL of the 50 mL culture were then used to inoculate 200 mL of the same media in 2 L shake flasks. This type of cell propagation procedure encourages viability and exponential growth of the bacteria.

Results

Figure 22:
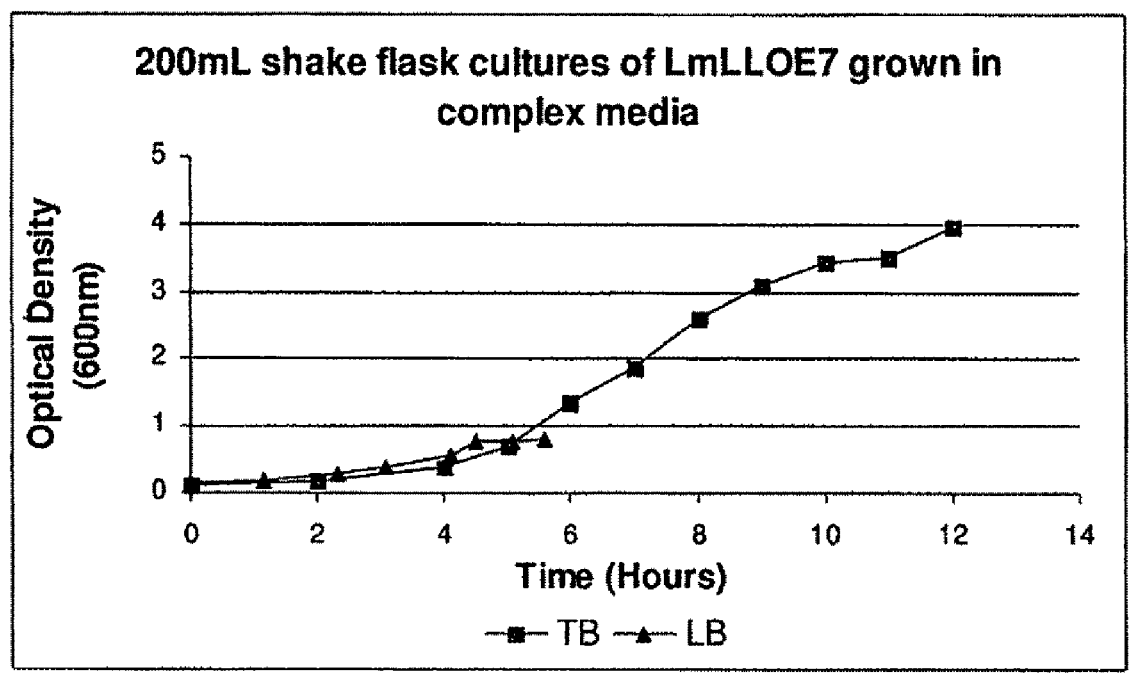
FIG. 22. Growth curve of 200 mL LB and TB cultures of Lm-LLO-E7.

The growth curves of the *Listeria* vaccine strain in LB and TB were investigated in more detail in order to assess its growth potential. The maximum $OD_{600}$ reached in TB and LB were 4 and 0.8 units, which correspond to about $1 \times 10^{10}$ and $9 \times 10^8$ CFU/mL, respectively (FIG. 22).

Experiments were then performed to develop a defined synthetic medium that could support a similar growth to that of TB. A MOPS pH buffer was used instead of a phosphate buffer because its superior buffering capacity would be appropriate for the demands of shake flask growth. The formula outlined in Table 3A below was used as the starting point. In addition to the pH buffer and standard components ("basic components"), the medium contained supplements expected to improve growth of the vaccine strain. These supplements were divided into four groups: essential compounds, amino acids, vitamins and trace elements.

TABLE 3A

Original defined media composition.

| Component | Amount per Liter |
|---|---|
| Basic components | |
| MOPS | 20.93 g |
| $KH_2PO_4$ | 0.656 g |
| $Na_2HPO_4$—$7H_2O$ | 1.639 g |
| Glucose | 10 g |
| $MgSO_4$ | 0.41 g |

TABLE 3A-continued

Original defined media composition.

| Component | Amount per Liter |
|---|---|
| Supplements | |
| Essential components | |
| Ferric Citrate | 0.1 g |
| Methionine | 0.1 g |
| Cysteine | 0.1 g |
| Glutamine | 0.6 g |
| Riboflavin | 5 mg |
| Thioctic acid | 5 µg |
| Amino acids | |
| Leucine | 0.1 g |
| Isoleucine | 0.1 g |
| Valine | 0.1 g |
| Arginine | 0.1 g |
| Histidine | 0.1 g |
| Tryptophan | 0.1 g |
| Phenylalanine | 0.1 g |
| Vitamins | |
| Adenine | 0.25 mg |
| Biotin | 0.5 mg |
| Thiamine HCl | 1 mg |
| Pyridoxal HCl | 1 mg |
| Para-aminobenzoic acid | 1 mg |
| Calcium pantothenate | 1 mg |
| Nicotinamide | 1 mg |
| Trace Elements | |
| Cobalt chloride hexahydrate ($CoCl_2 \cdot 6H_2O$) | 0.02 g |
| Copper (II) chloride dihydrate ($CuCl_2 \cdot 2H_2O$) | 0.019 g |
| Boric acid ($H_3BO_3$) | 0.016 g |
| Manganese sulfate monohydrate ($MnSO_4 \cdot H_2O$) | 0.016 g |
| Sodium molybdate dihydrate ($Na_2MoO_4 \cdot 2H_2O$) | 0.02 g |
| Zinc chloride heptahydrate ($ZnCl_2 \cdot 7H_2O$) | 0.02 g |
| Ferric Sulfate ($Fe_2(SO_4)_3 \times H_2O$) | 0.01 g |
| Calcium Chloride dihydrate ($CaCl_2 \cdot 2H_2O$) | 0.01 g |

In order to determine whether supplementation with the three latter groups (amino acids, vitamins, trace elements) improved the growth of Lm-LLO-E7, bacteria were grown in 50 mL starter cultures, then in 250 mL cultures, of the following media in shake flasks:
1. Bulk medium (i.e. water plus the basic components in Table 3A), essential components, amino acids, vitamins and trace elements.
2. Bulk medium, essential components, amino acids and vitamins.
3. Bulk medium, essential components and amino acids.
4. Bulk medium and essential components.

Figure 23:
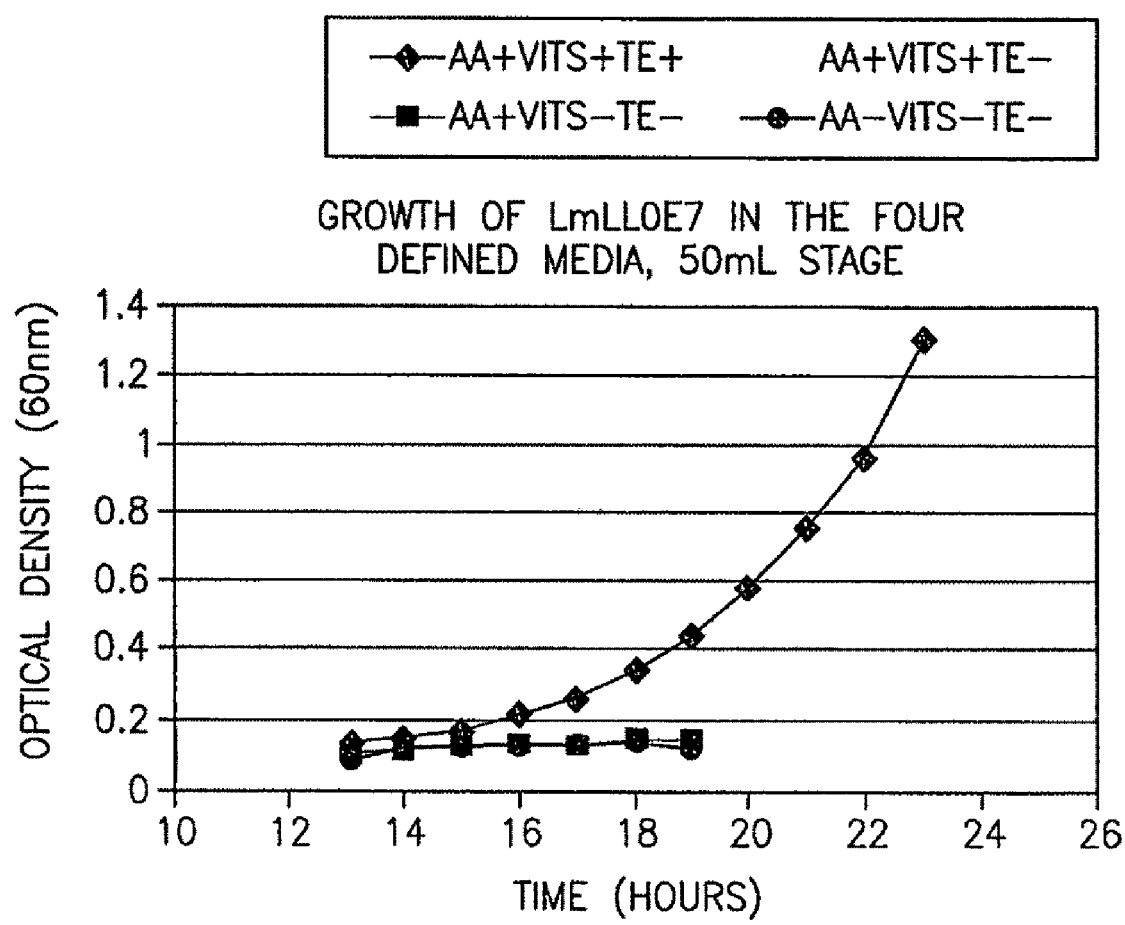
FIG. 23. Growth of Lm-LLO-E7 in 4 defined media with and without AA, vitamins and trace elements, at the 50 mL stage. "AA+Vits+TE+" denotes bulk medium, essential components, AA, vitamins and trace elements; "AA+Vits+TE−" denotes bulk medium, essential components, AA, and vitamins; "AA+Vits−TE−" denotes bulk medium, essential components, and AA; "AA−Vits−TE−" denotes bulk medium and essential components.
Figure 24:
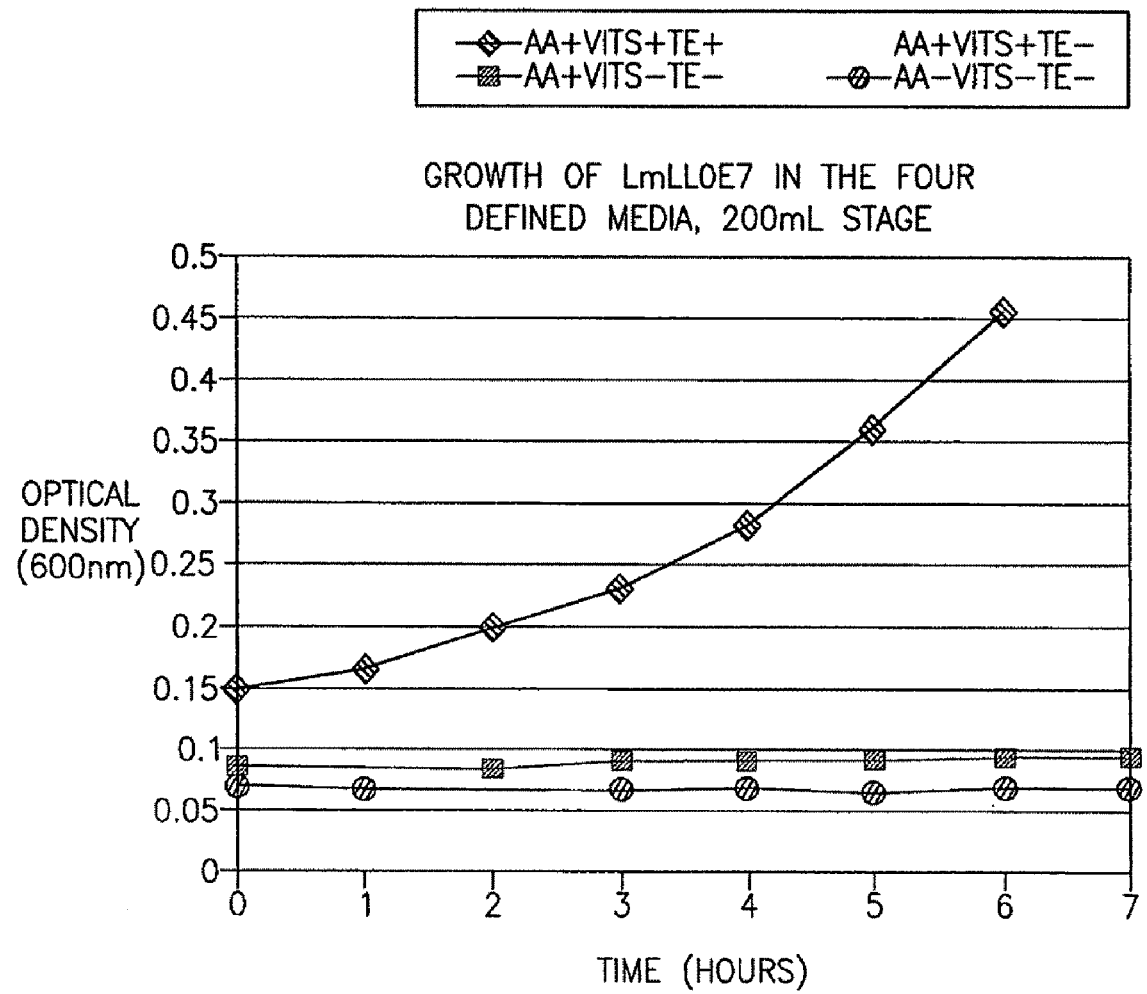
FIG. 24. Growth of Lm-LLO-E7 in 4 defined media with and without amino acids, vitamins and trace elements, at the 200 mL stage. Groups are labeled as for FIG. 23.

Presence of both AA and vitamins was necessary to support significant growth in the 50 mL cultures, and the presence of trace elements enhanced the growth rate (FIG. 23). However, at the 200 mL stage the presence of trace elements did not influence the growth rate (FIG. 24). It is possible that the trace elements supported the adaptation of Lm-LLO-E7 from the LB cell bank into the defined medium at the 50 mL stage. Based on these results, all four of the groups in Table 3A were included in the defined medium in subsequent experiments.

The next experiment investigated the effect of increasing the concentrations of the 4 groups of supplements of Table 3. The concentrations of all the components of these four groups were increased by a factor of 2 or 4 to produce "2×" and "4×" defined media, respectively. In addition, 4× defined media containing 1, 2 or 3 g/L of inorganic nitrogen in the form of $NH_4SO_4$ were tested. The growth of these five cultures was compared to the media of Table 3A ("control") in the 50 mL-200 mL protocol described above.

Figure 25:
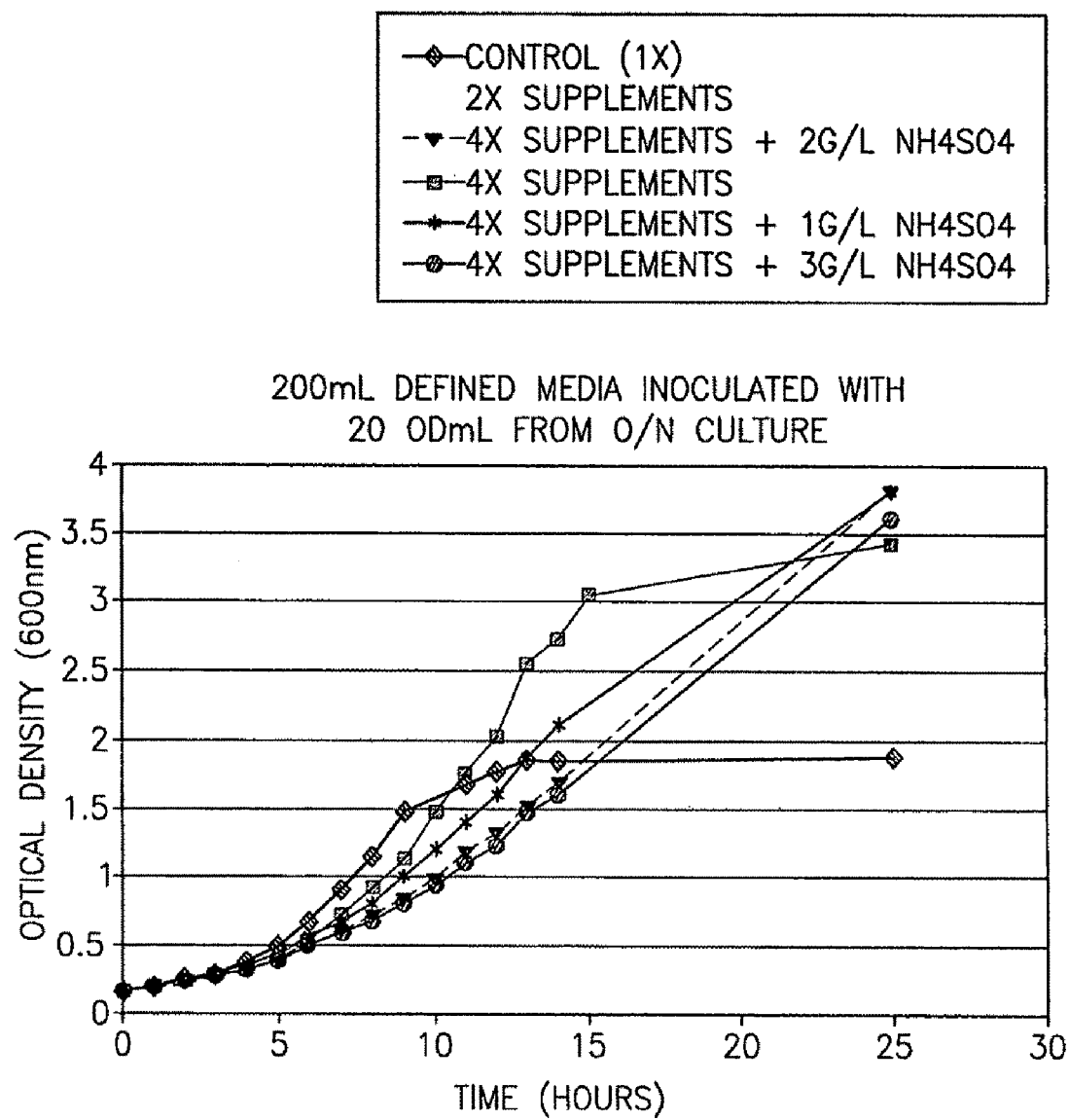
FIG. 25. Growth of Lm-LLO-E7 in 200 mL cultures of defined media with different concentrations of supplements, with and without inorganic nitrogen.

All media tested exhibited similar growth for the first four hours. At this point, the growth in the control media began to decelerate, stopping completely at 13 hours, while the 2× and 4× media continued to support exponential growth (FIG. 25). The flasks containing the 2× and 4× media reached final $OD_{600}$ of 2.5 units and 3.5, respectively. Inclusion of $NH_4SO_4$ slightly increased final biomass concentrations, but considerably decreased the growth rate.

Thus, increasing the nutrient level, but not inclusion of $NH_4SO_4$, significantly improved the growth of the vaccine strain in defined media. Based on these results, $NH_4SO_4$ was not included in subsequent experiments.

Figure 26:
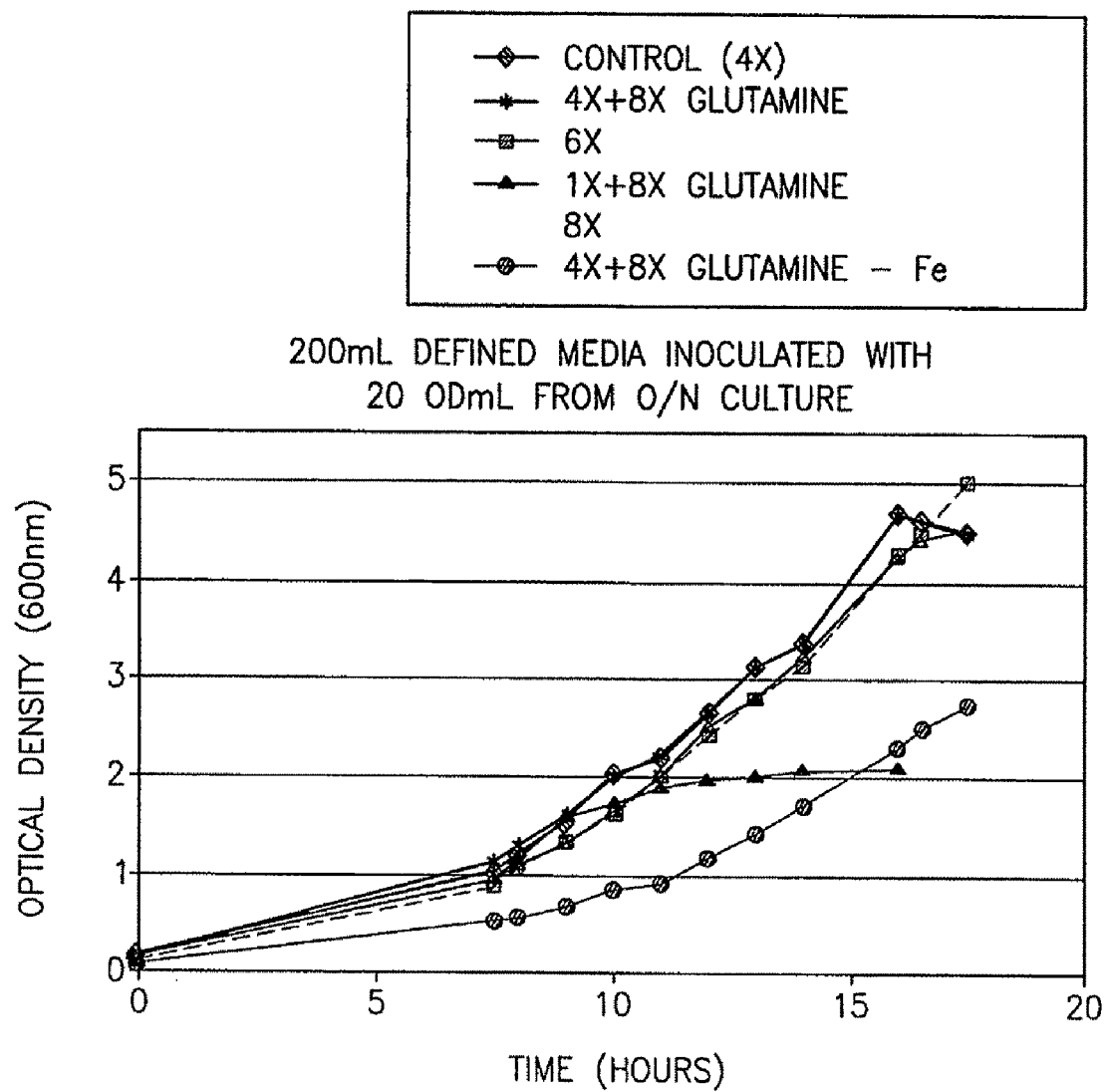
FIG. 26. Growth of Lm-LLO-E7 in 200 mL cultures of defined media supplemented with different concentrations of supplements, with and without glutamine and iron.

Next, the effect in 50 mL and 200 mL cultures of the following additional modifications to the media was examined: 1) further increasing the concentration of the 4 groups of supplements from Table 3A (to 6 and 8 times the original concentration); 2) increasing the concentration of glutamine (a source of organic nitrogen) to 8 times the original concentration; and 3) removing iron from the media. As depicted in FIG. 26 (results from 200 mL cultures), further increasing the concentration of either glutamine or the 4 groups of supplements did not enhance the final biomass concentration of Lm-LLO-E7. Removal of iron, by contrast, reduced the maximum biomass concentration.

The effect of increasing the glucose concentration of the 4× media was examined. Increasing glucose concentration from 10 to 15 g/L significantly improved growth rate and biomass.

The final $OD_{600}$ of each of the 4× supplements was 4.5, which corresponded to $1.1 \times 10^{10}$ CFU/mL, approximately the same as the final biomass obtained with TB. Thus, a defined media was developed that supported growth of a Listeria vaccine strain to the same extent as TB.

In conclusion, media containing 4× the original concentration of the four groups of supplements from Table 3A (referred to henceforth as "4× media") supported optimal growth of Lm-LLO-E7 in 50 mL and 200 mL shake flask cultures. Iron was required for optimal growth. Increasing the glucose from 10 to 15 g/L increased the total biomass achieved. The resulting optimized defined media recipe is depicted in Table 3B.

TABLE 3B

Optimized defined media composition.

| COMPONENT | AMOUNT PER LITER |
|---|---|
| BASIC COMPONENTS | |
| $KH_2PO_4$ | 2.2 g |
| $Na_2HPO_4$—$7H_2O$ | 10.4 g |
| Glucose | 15 g |
| $MgSO_4$ | 0.41 g |
| SUPPLEMENTS | |
| Essential components | |
| Ferric Citrate | 0.4 g |
| Methionine | 0.4 g |
| Cysteine | 0.4 g |
| Glutamine | 2.4 g |
| Riboflavin | 20 mg |
| Thioctic acid | 20 µg |
| Amino acids | |
| Leucine | 0.4 g |
| Isoleucine | 0.4 g |
| Valine | 0.4 g |
| Arginine | 0.4 g |
| Histidine | 0.4 g |
| Tryptophan | 0.4 g |
| Phenylalanine | 0.4 g |

TABLE 3B-continued

Optimized defined media composition.

| COMPONENT | AMOUNT PER LITER |
|---|---|
| Vitamins | |
| Adenine | 0.25 g |
| Biotin | 2 mg |
| Thiamine HCl | 4 mg |
| Pyridoxal HCl | 4 mg |
| Para-aminobenzoic acid | 4 mg |
| Calcium pantothenate | 4 mg |
| Nicotinamide | 4 mg |
| Trace Elements | |
| Cobalt chloride hexahydrate (CoCl$_2$•6H$_2$O) | 0.02 g |
| Copper (II) chloride dihydrate (CuCl$_2$•2H$_2$O) | 0.019 g |
| Boric acid (H$_3$BO$_3$) | 0.016 g |
| Manganese sulfate monohydrate (MnSO$_4$•H$_2$O) | 0.016 g |
| Sodium molybdate dihydrate (Na$_2$MoO$_4$•2H$_2$O) | 0.02 g |
| Zinc chloride heptahydrate (ZnCl$_2$•7H$_2$O) | 0.02 g |
| Ferric Sulfate (Fe$_2$(SO$_4$)$_3$ × H$_2$O) | 0.01 g |
| Calcium Chloride dihydrate (CaCl$_2$•2H$_2$0) | 0.01 g |
| Citric Acid | 0.6 g |

Example 16

Optimization of Media for Growth of *Listeria* Vaccine Strains in Batch Fermentations Materials and Experimental Methods FT Applikon 5/7 L fermenter vessels containing 4500 mL of either TB or defined medium with 34 μg/mL CAP were utilized in this Example. 20 ODmL of Lm-LLO-E7 was used to inoculate a 200 mL starter culture containing CAP, which was grown at 37° C. in an orbital shaker at 200 rpm for 10 hours until it reached mid-log phase; 450 ODmL of this culture was used to inoculate the fermenter vessels. The temperature, pH and dissolved oxygen concentration were continuously monitored and controlled during the fermentation at levels of 37° C., 7.0, and 20% of saturation.

Results

Factors such as dissolved oxygen concentration or pH likely limited the growth of Lm-LLO-E7 in the previous Example, as they are not controlled in shake flasks. Consistent with this possibility, the pH of the cultures in the shake flasks had decreased to approximately 5.5 units. In a batch fermenter, by contrast, pH and dissolved oxygen levels are continuously monitored and controlled. Thus, separate experiments were performed in this Example to optimize the media used for batch fermentations.

Figure 27A:
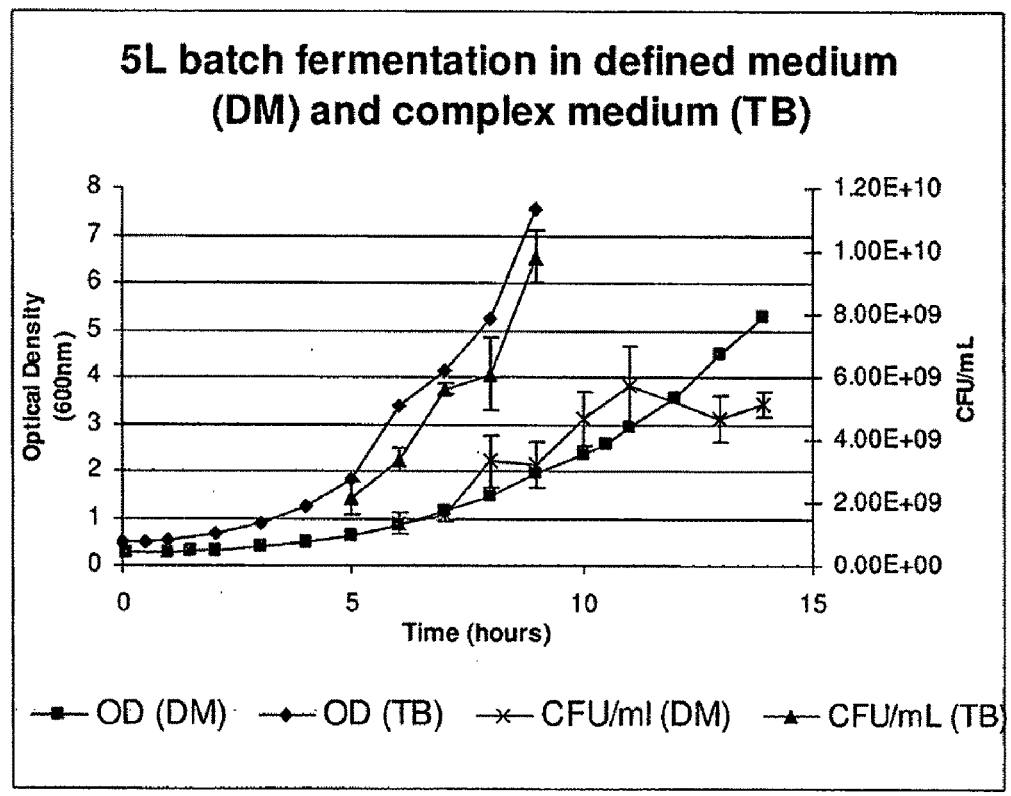
FIG. 27. A. Growth curves of Lm-LLO-E7 in 5 L fermenters in TB and defined media. B. Viability of Lm-LLO-E7 grown in 5 L fermenters in TB to different densities. C. Viability of Lm-LLO-E7 grown in 5 L fermenters in defined media to different densities.

200 mL cultures of Lm-LLO-E7 were grown overnight in either TB or the defined medium from Table 3B until they reached mid-log phase (OD$_{600}$ of 1-2). 450 ODmLs of the starter culture was then used to inoculate 5 L batch fermenters containing the same media. The bacteria grown in the TB culture began to grow exponentially immediately upon innoculation, with a specific growth rate of 0.5 h$^{-1}$, then entered into a deceleration phase about 7 hours after inoculation, reaching stationary phase at a viable cell density of 2.1×10$^{10}$ CFU/mL (FIG. 27A). The bacteria grown in the defined media also exhibited exponential growth; however, the growth rate was 0.25 h$^{-1}$, and the final viable cell density was 1.4×10$^{10}$ CFU/mL. A total yield of 8.9×10$^{13}$ CFR was obtained from the batch fermentation. Both batch fermentations entered into stationary phase as a result of carbon limitation, as evidenced by the finding that the glucose concentration had reached zero at stationary phase. Since LM cannot utilize AA as a carbon source, the cells were unable to grow in the absence of carbohydrate.

Figure 27B:
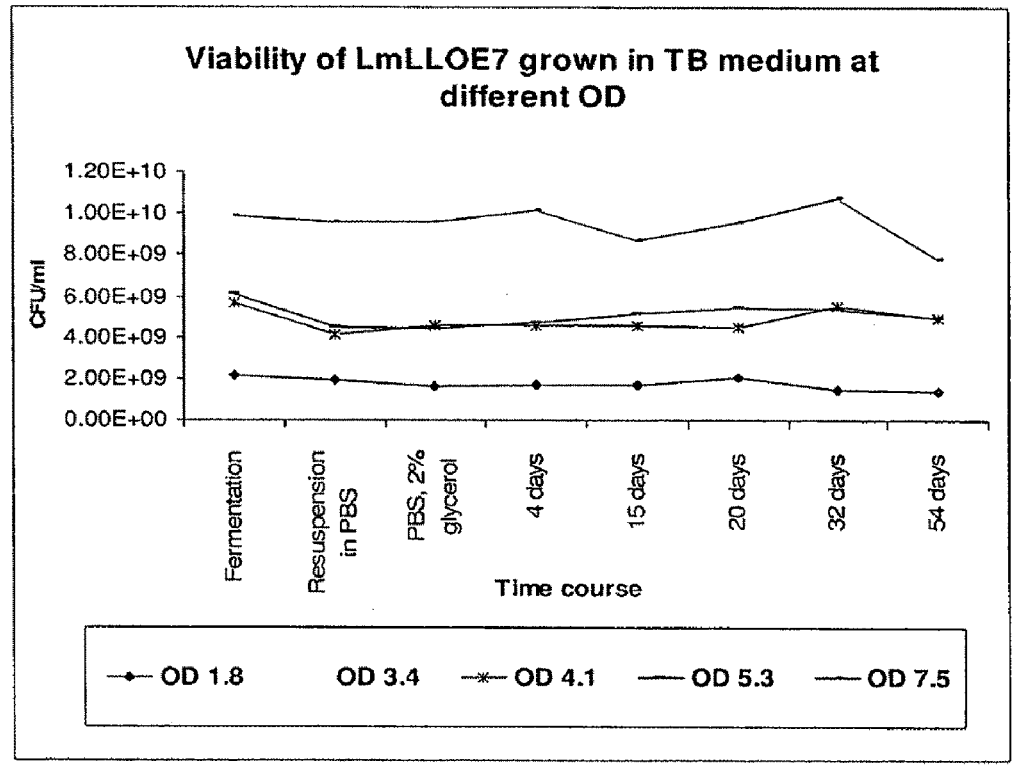
Figure 27C:
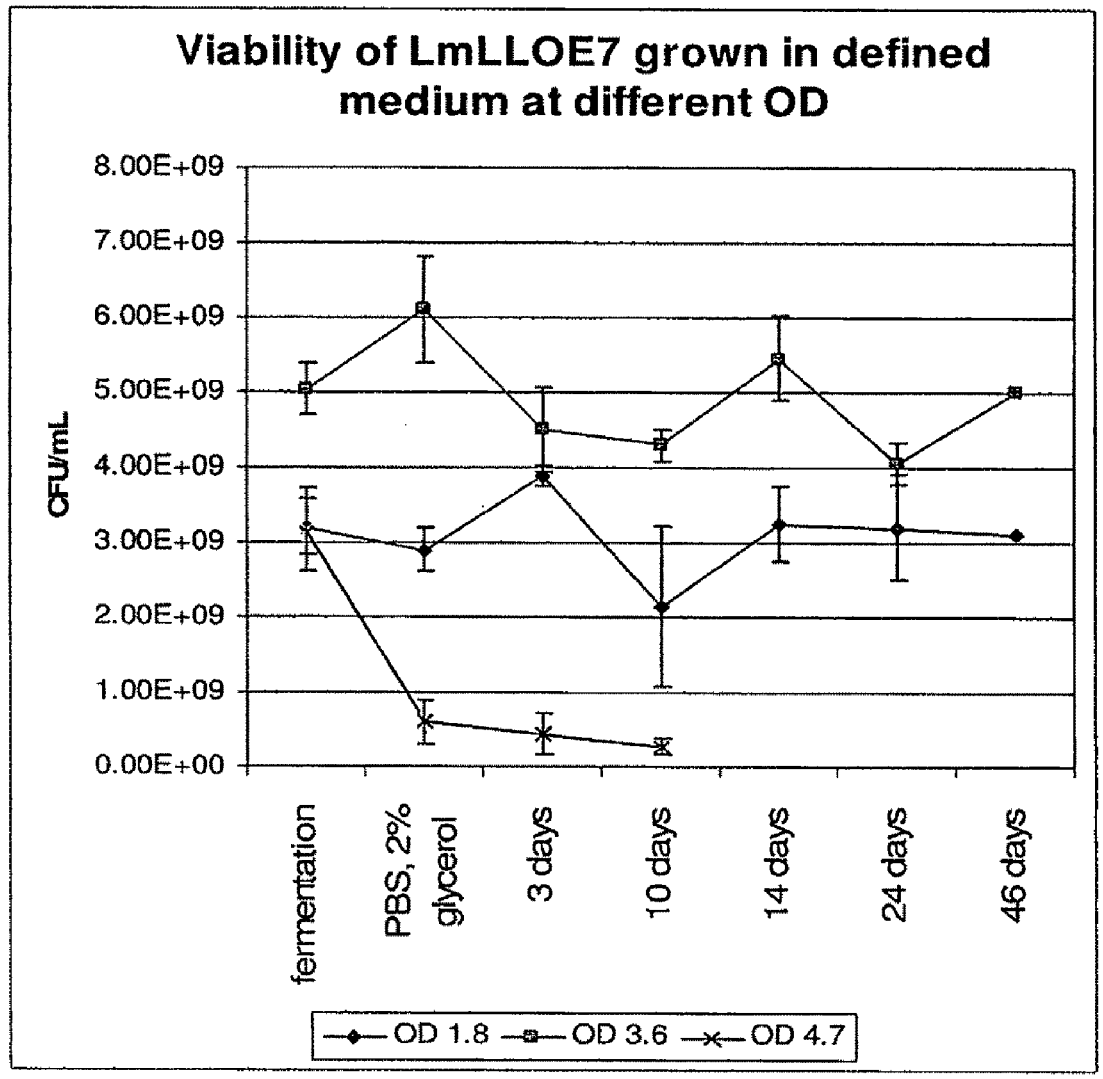

At all densities tested, the bacteria grown in TB retained their viability throughout subsequent steps in the process (FIG. 27B). Bacteria grown in defined media maintained their viability up to an OD of 3-4 (FIG. 27C).

It was further found that, to prevent iron precipitation, the iron and magnesium salts could be dissolved separately in water and heated to 60° C., then filter-sterilized and simultaneously added to the fermenter culture medium.

Example 17

Further Optimization of Cryopreservation Conditions for *Listeria* Vaccine Strains The next experiment examined the viability of cryopreserved Lm-LLO-E7 in the presence of each of 4 different additives: namely, glycerol, mannitol, DMSO and sucrose. PBS was used as a control. In addition, three different storage methods were compared: −20° C., −70° C., and snap freezing in liquid nitrogen followed by storage at −70° C.

Figure 28:
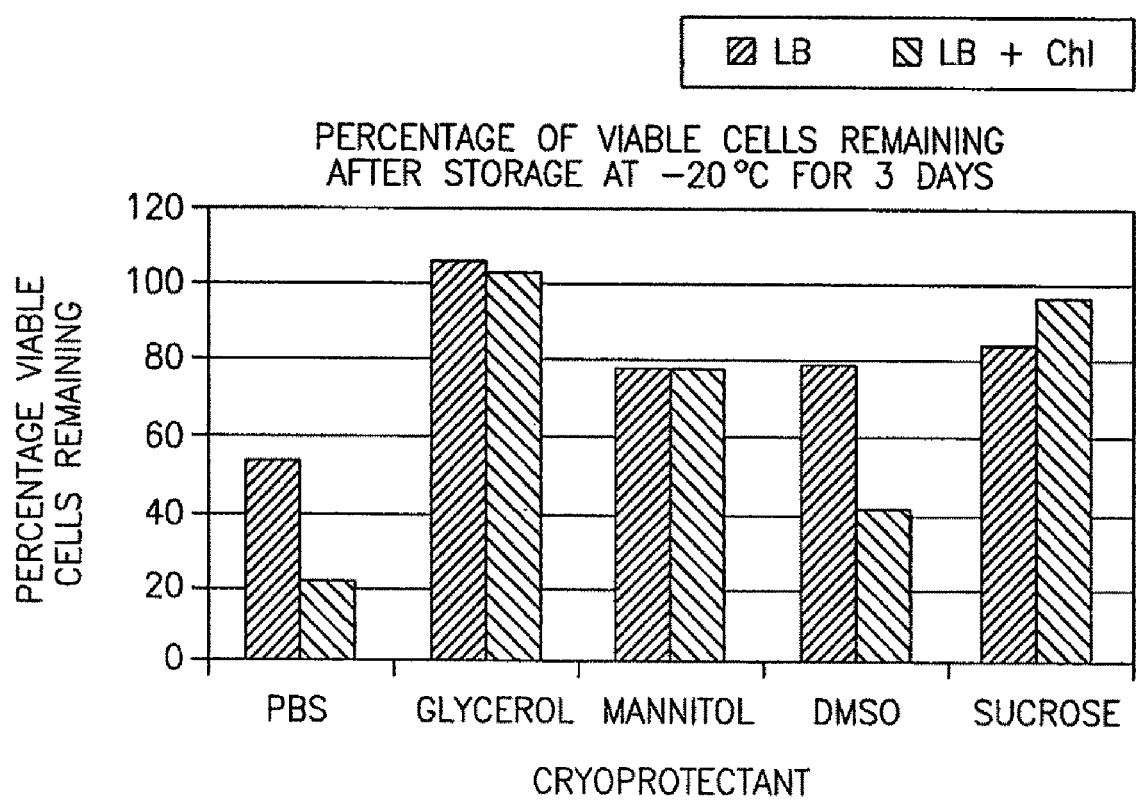
FIG. 28. Percentage of viable cells remaining after storage at −20° C. for 3 days.
Figure 29:
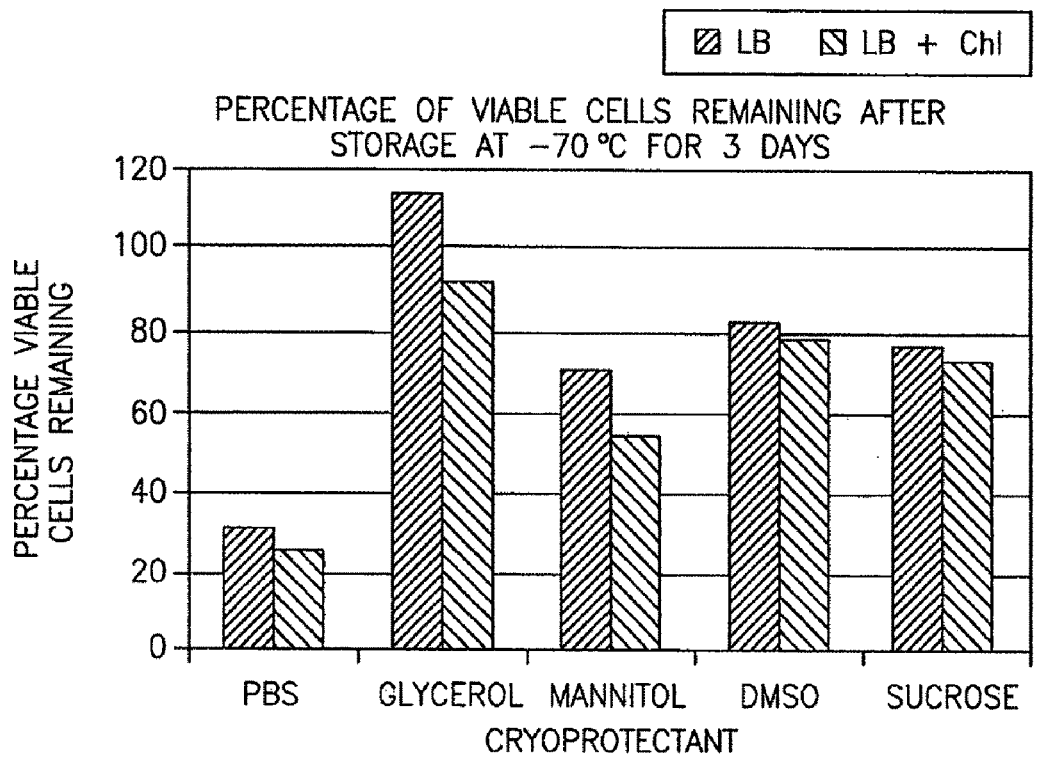
FIG. 29. Percentage of viable cells remaining after storage at −70° C. for 3 days FIG. 30. A. Percentage of viable cells remaining following snap freezing in liquid nitrogen and storage at −70° C. for 3 days. B. Summary of viability studies for several conditions. C. Growth kinetics of cryopreserved samples after thawing.
Figure 30A:
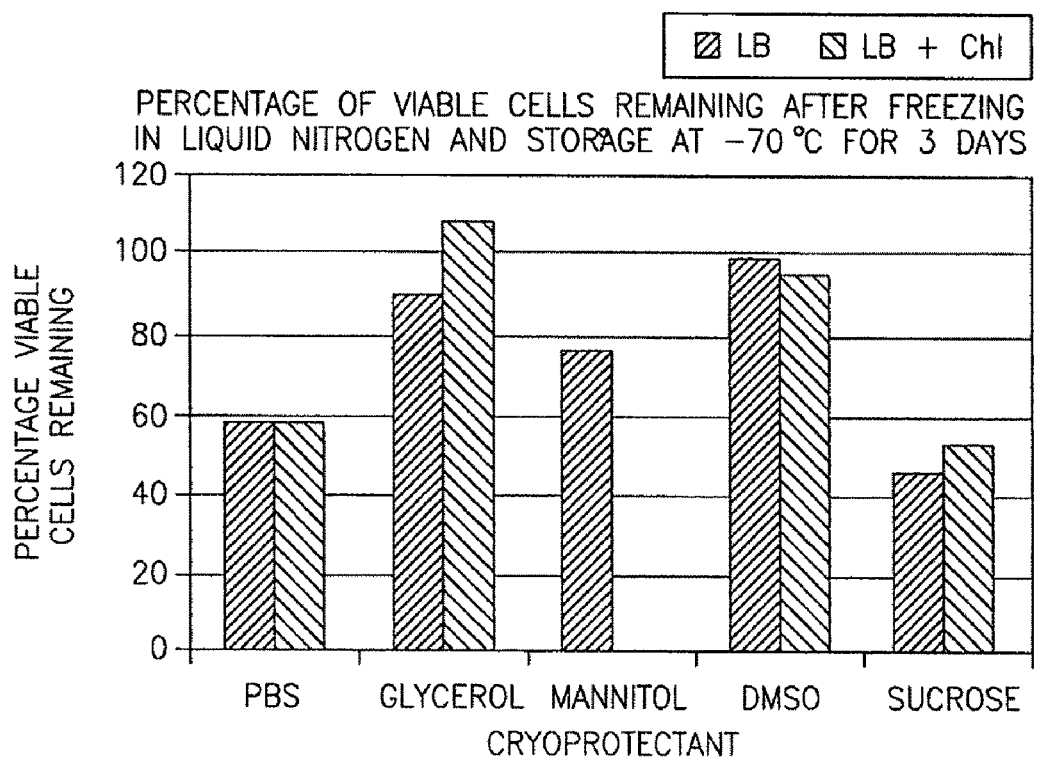
Figure 30B:
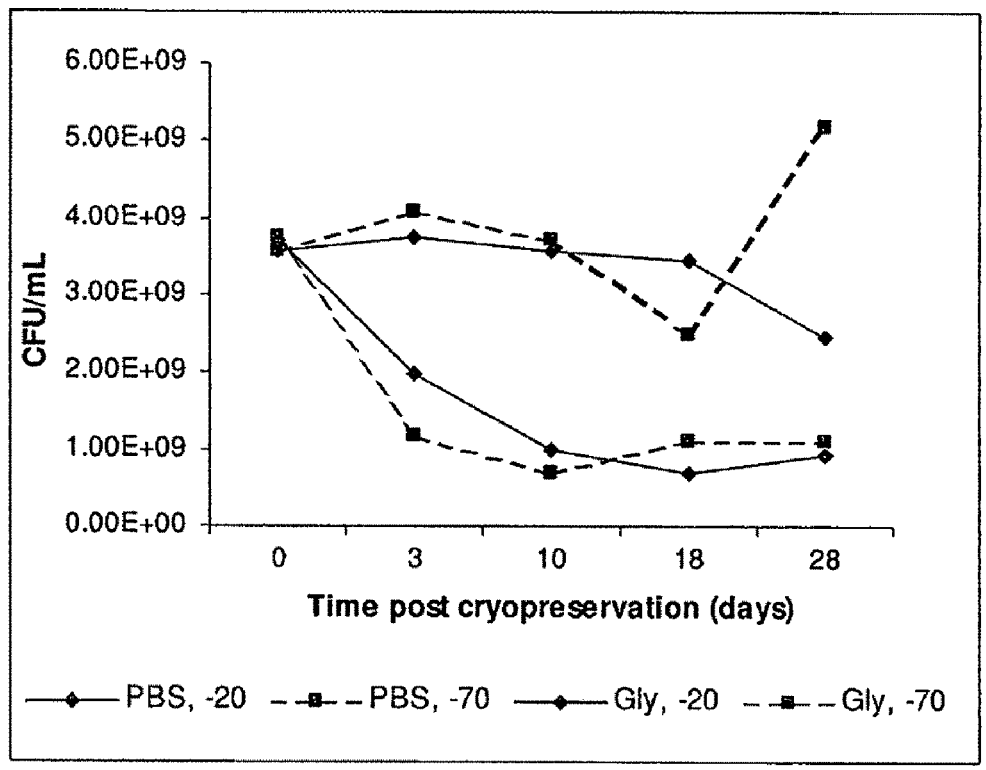
Figure 30C:
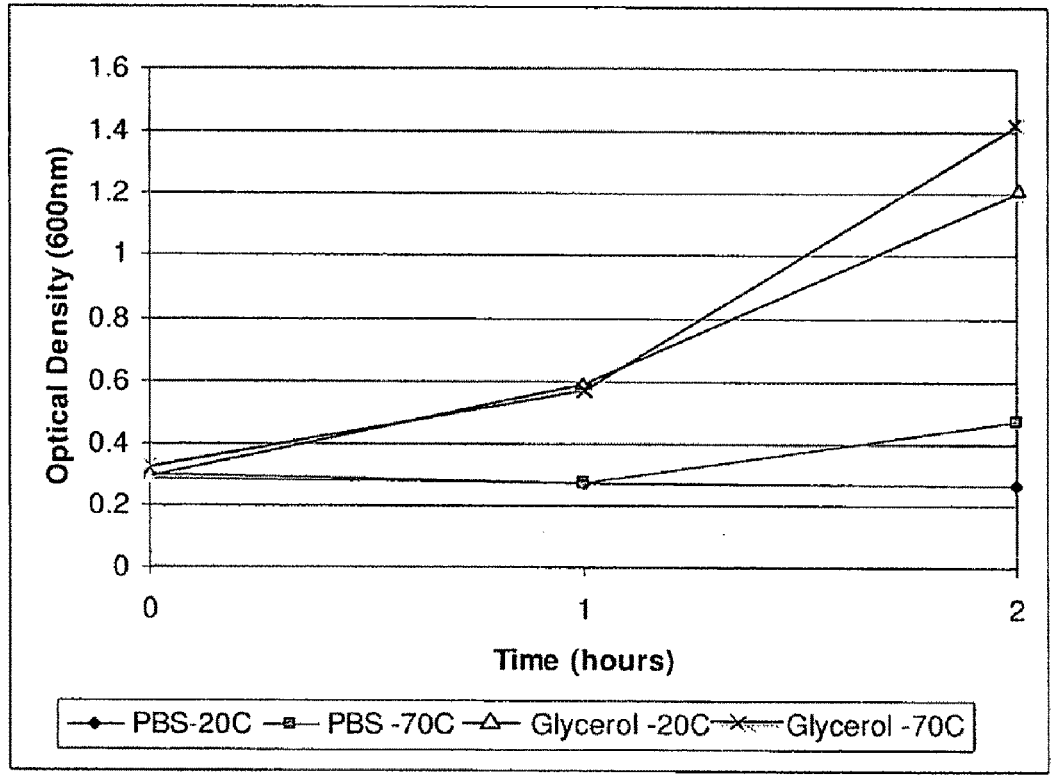
Figure 31:
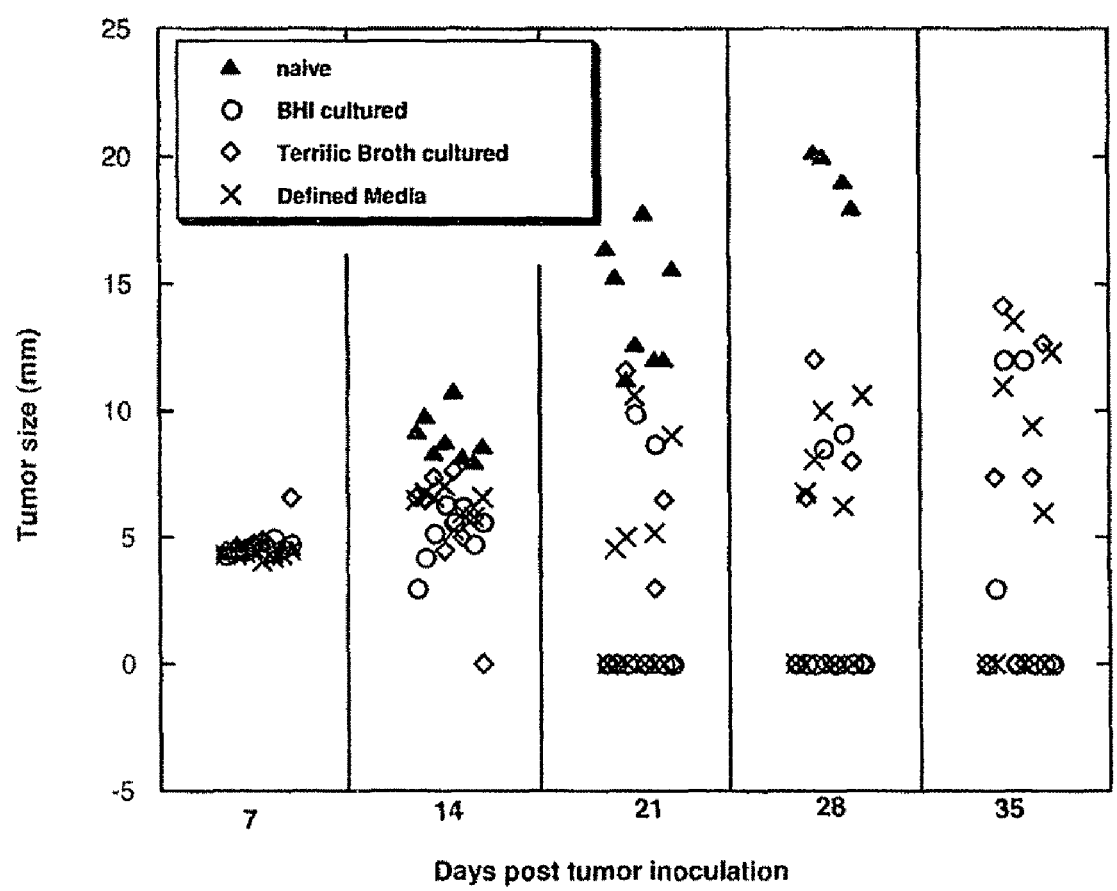
FIG. 31. *Listeria* vaccine vectors grown in defined media effectively protect mice against growth of established tumors. "BHI cultured"—vectors cultured in Brain-Heart Infusion media "Terrific Broth cultured" and "defined media cultured"—vectors cultured in indicated media.

A shake flask containing 200 mL of the 4× media from Table 3B was grown to an OD$_{600}$ of 1.6. Fifteen 10 mL samples were pelleted by centrifugation, the supernatants removed, and the cells resuspended in 10 mL of PBS containing 2% w/v of the appropriate cryoprotectant. One mL aliquots of each resuspended sample were transferred into vials and stored using the appropriate method. Viability was measured by replica plating (with and without CAP) before storage and after 3-28 days or storage, and the percentage of viable cells remaining was calculated. 2% w/v glycerol at −70° C. was found to be the best short-term cryopreservation method; with the bacteria exhibiting approximately 100% viability. The cell viability remained high over the 3-28 days under several of the conditions utilized (FIGS. 28-30).

CONCLUSION

Examples 13-17

The genetic stability of the pGG55 plasmid in Lm-LLO-E7 showed no signs of structural or segregational instability after 35 or 42 cell generations. A RWCB was produced, and the viability of the cells preserved in the RWCB remained constant at approximately 1×10$^9$ CFU/mL after freezing and thawing. The ability of two complex media to support the growth of Lm-LLO-E7 was assessed. LB and TB supported growth to maximum cell densities of approximately 9×10$^8$ and 1×10$^{10}$ CFU/mL, corresponding to OD$_{600}$ of 0.8 and 4.0 units, respectively. A defined media that supported growth to an extent similar to TB was developed and optimized for shake flask cultivations. Lm-LLO-E7 reached a higher biomass concentration in 5 L batch fermenters compared to shake flask cultivation, likely due to the ability to control the pH in fermenters. The optimum method for cryopreservation of the cells was also investigated. Lm-LLO-E7 cryopreserved in PBS containing 2% w/v glycerol exhibited approximately 100% viability following storage at less than −70° C. for 3 days.

TABLE 2

| Subj # | Site 1 | Site 2 | Site 3 | Tumor Site 1- Size | | | | Tumor Site 2 - Size | | | |
|---|---|---|---|---|---|---|---|---|---|---|---|
| | | | | Screening S1 | d43 S1 | d79 S1 | d111 S1 | Screening S2 Size | d43 S2 Size | d79 S2 Size | d111 S2 Size |
| COHORT 1 | | | | | | | | | | | |
| 1 | Paraortal lymph nodes | | | 40 | 40 | 44 | 47 | | | | |
| 2 | Supraclavicular sin | Parahilar right | | 30 | 45 | 70 | | 10 | 35 | 27 | |
| 3 | Pelvis (soft tissue) | | | 50 | 60 | 60 | 65 | | | | |
| 4 | Right, upper lobe | Right, lower lobe | | 20 | 20 | 18 | 18 | 20 | 20 | 14 | 14 |
| 5* | Cervix | Paraortic node | paracaval node* | 65 | 72 | | | 13 | 15 | | |
| mean | | | | 41 | 47.4 | 48 | 43.33 | 14.33 | 23.3 | 20.5 | 14 |
| SE | | | | 7.81 | 8.87 | 11.34 | 13.69 | 2.96 | 6.01 | 6.5 | |
| COHORT 2 | | | | | | | | | | | |
| 03-001-T | Retroperitoneal nodes | Liver tumor | | 90 | | | | 34 | | | |
| 04-002-T | Vagina | Vagina | | 20 | 23 | | | 15 | | | |
| 04-003-T | Uterus | Retrocrural | Iliac Right Region | 13 | 11 | 9.4 | | 14 | 14 | 12 | |
| 04-004-T | Para aortic node | | | 32 | | | | | | | |
| 04-005-T | Uterus | Ovary and salping | Iliac node left | 65 | | | | 38 | | | |
| Mean | | | | 44 | 17 | 9.4 | | 25.25 | 14 | 12 | |
| SITE 3 DATA- COHORT 2 | | | | | | | | | | | |
| 3 | | | | 13 | 13 | 0 | | | | | |
| 5 | | | | 21 | | | | | | | |
| mean | | | | 17 | 13 | 0 | | | | | |

*Patient 5 in cohort 1 had a third tumor site, which changed size from 13 to 14 mm between screening and d43.

---

What is claimed:

1. A method of treating a late stage cervical cancer in a human patient having said late stage cancer, comprising the step of administering to said patient a recombinant *Listeria* strain, said recombinant *Listeria* strain comprising a recombinant polypeptide comprising an N-terminal fragment of an LLO protein fused to a Human Papilloma Virus (HPV) E7 antigen, whereby said recombinant *Listeria* strain induces an immune response against said E7 antigen, thereby treating a late stage cervical cancer in a human patient.

2. The method of claim 1, wherein said N-terminal fragment of an LLO protein comprises SEQ ID No: 1.

3. The method of claim 1, wherein said recombinant *Listeria* strain is administered to said human patient at a dose of $1 \times 10^9 - 3.31 \times 10^{10}$ organisms.

4. The method of claim 1, wherein said recombinant *Listeria* strain is a recombinant *Listeria monocytogenes* strain.

5. The method of claim 1, wherein said recombinant *Listeria* strain has been passaged through an animal host, prior to the step of administering.

6. The method of claim 1, wherein said recombinant polypeptide is expressed by said recombinant *Listeria* strain.

7. The method of claim 1, wherein said recombinant *Listeria* strain comprises a plasmid that encodes said recombinant polypeptide.

8. The method of claim 7, wherein said plasmid comprises a gene encoding a bacterial transcription factor.

9. The method of claim 7, wherein said plasmid further comprises a gene encoding a metabolic enzyme.

10. The method of claim 1, further comprising the step of boosting said human patient with said recombinant *Listeria* strain.

11. The method of claim 1, further comprising the step of inoculating said human patient with an immunogenic composition that comprises or directs expression of said E7 antigen.

12. The method of claim 1, wherein said recombinant *Listeria* strain has been stored in a frozen, dried or lyophilized cell bank.

13. The method of claim 12, wherein said recombinant *Listeria* strain exhibits viability upon thawing or reconstitution of greater than 90%.

14. The method of claim 1, wherein said late stage cervical cancer is stage IV.

15. The method of claim 14, wherein said stage IV is stage IVB.

* * * * *